United States Patent
Tang et al.

(10) Patent No.: US 12,319,703 B2
(45) Date of Patent: *Jun. 3, 2025

(54) MACROCYCLIC FUSED PYRAZOLES AS Mcl-1 INHIBITORS

(71) Applicants: ASCENTAGE PHARMA (SUZHOU) CO., LTD., Suzhou (CN); THE REGENTS OF THE UNIVERSITY OF MICHIGAN, Ann Arbor, MI (US); ASCENTAGE PHARMA GROUP CORP LIMITED, Hong Kong (CN)

(72) Inventors: Guozhi Tang, Suzhou (CN); Dongbo Li, Suzhou (CN); Liugen Li, Suzhou (CN); Xianchan Zha, Suzhou (CN); Wenming Chen, Suzhou (CN); Shaomeng Wang, Superior Township, MI (US); Chao-Yie Yang, Ann Arbor, MI (US)

(73) Assignees: ASCENTAGE PHARMA (SUZHOU) CO., LTD., Suzhou (CN); REGENTS OF THE UNIVERSITY OF MICHIGAN, Ann Arbor, MI (US); ASCENTAGE PHARMA GROUP CORP LIMITED, Hong Kong (CN)

( * ) Notice: Subject to any disclaimer, the term of this patent is extended or adjusted under 35 U.S.C. 154(b) by 588 days.

This patent is subject to a terminal disclaimer.

(21) Appl. No.: 17/048,688

(22) PCT Filed: Jan. 22, 2020

(86) PCT No.: PCT/CN2020/073742
§ 371 (c)(1),
(2) Date: Oct. 19, 2020

(87) PCT Pub. No.: WO2020/151738
PCT Pub. Date: Jul. 30, 2020

(65) Prior Publication Data
US 2022/0396587 A1    Dec. 15, 2022

(30) Foreign Application Priority Data
Jan. 23, 2019  (WO) ................ PCT/CN2019/072801

(51) Int. Cl.
C07D 515/22 (2006.01)
A61P 35/00 (2006.01)
C07D 497/22 (2006.01)

(52) U.S. Cl.
CPC ............ *C07D 515/22* (2013.01); *A61P 35/00* (2018.01); *C07D 497/22* (2013.01)

(58) Field of Classification Search
CPC ...... C07D 515/22; C07D 497/22; A61P 35/00
See application file for complete search history.

(56) References Cited

U.S. PATENT DOCUMENTS 9,840,518 B2    12/2017 Hird et al.
11,691,989 B2 *  7/2023 Chen ................... C07D 403/14
                                                514/229.5
2016/0106731 A1    4/2016 Lee et al.
2017/0305926 A1    10/2017 Hird et al.

FOREIGN PATENT DOCUMENTS

| WO | WO-2008/131000 A2 | 10/2008 |
| WO | WO-2018/178226 A1 | 10/2018 |
| WO | WO-2018/178227 A1 | 10/2018 |
| WO | WO-2018/183418 A1 | 10/2018 |
| WO | WO-2020/185606 A1 | 9/2020 |
| WO | WO-2020/221272 A1 | 11/2020 |

OTHER PUBLICATIONS

Patani et al. Bioisosterism: A Rational Approach in Drug Design. Chem. Rev. 1996, 96, 3147-3176. (Year: 1996).*
Adams et al., The Bcl-2 apoptotic switch in cancer development and therapy, Oncogene, 26(9):1324-37 (2007).
Amundson et al., An informatics approach identifying markers of chemosensitivity in human cancer cell lines, Cancer Res., 60(21):6101-10 (2000).
Beroukhim et al., The landscape of somatic copy-number alteration across human cancers, Nature, 463(7283):899-905 (Feb. 2010).
Bingham et al., Over one hundred solvates of sulfathiazole, Chem. Commun., 603-4 (2001).
Caira et al., Preparation and crystal characterization of a polymorph, a monohydrate, and an ethyl acetate solvate of the antifungal fluconazole, J. Pharm. Sci., 93(3):601-11 (2004).
Danial et al., Cell death: critical control points, Cell, 116(2):205-19 (2004).

(Continued)

*Primary Examiner* — James H Alstrum-Acevedo
*Assistant Examiner* — Lauren Wells

(57) ABSTRACT

Provided are compounds represented by Formula IA: (IA), and the pharmaceutically acceptable salts and solvates thereof, wherein R, $R^{1a}$, $R^{1b}$, $L^1$, $L^2$, $L^3$, X, A, B and C are as defined as set forth in the specification. Also provided compounds of Formula IA for use to treat a condition or disorder responsive to Mcl-1 inhibition such as cancer.

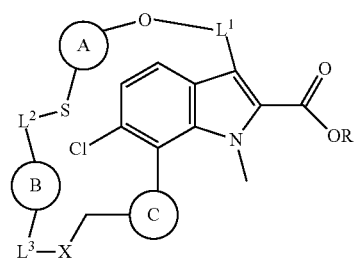

IA

20 Claims, No Drawings

(56) References Cited

OTHER PUBLICATIONS

International Application No. PCT/CN2020/073742, International Search Report and Written Opinion, mailed Apr. 22, 2020.
Johannes et al., Structure Based Design of Non-Natural Peptidic Macrocyclic Mcl-1 Inhibitors, ACS Med. Chem. Lett., 8(2):239-244 (Dec. 2016).
Kirkin et al., The role of Bcl-2 family members in tumorigenesis, Biochim. Biophys. Acta, 1644(2-3):229-49 (2004).
Long et al., Optimization and validation of mitochondria-based functional assay as a useful tool to identify BH3-like molecules selectively targeting anti-apoptotic Bcl-2 proteins, BMC Biotechnol., 13:45 (May 2013).
Mady et al., Discovery of Mcl-1 inhibitors from integrated high throughput and virtual screening, Sci. Rep., 8(1):10210 (Jul. 2018).
Tron et al., Discovery of Mcl-1-specific inhibitor AZD5991 and preclinical activity in multiple myeloma and acute myeloid leukemia, Nat. Commun., 9(1):5341 (Dec. 2018).
vanTonder et al., Preparation and physicochemical characterization of 5 niclosamide solvates and 1 hemisolvate, AAPS PharmSciTech., 5(1):E12 (2004).
Wei et al., Inducing apoptosis and enhancing chemosensitivity to gemcitabine via RNA interference targeting Mcl-1 gene in pancreatic carcinoma cell, Cancer Chemother. Pharmacol., 62(6):1055-64 (Nov. 2008).
Wertz et al., Sensitivity to antitubulin chemotherapeutics is regulated by MCL1 and FBW7, Nature, 471(7336):110-4 (Mar. 2011).
Willis et al., Apoptosis initiated when BH3 ligands engage multiple Bcl-2 homologs, not Bax or Bak, Science, 315(5813):856-9 (2007).
Yang et al., Analysis of Flexibility and Hotspots in Bcl-xL and Mcl-1 Proteins for the Design of Selective Small-Molecule Inhibitors, ACS Med. Chem. Lett., 3(4):308-12 (Feb. 2012).

\* cited by examiner

MACROCYCLIC FUSED PYRAZOLES AS Mcl-1 INHIBITORS

CROSS-REFERENCE TO RELATED APPLICATIONS

This is the U.S. national phase of International Application No. PCT/CN2020/073742, filed Jan. 22, 2020, which claims the benefit of International Application No. PCT/CN2019/072801, filed Jan. 23, 2019.

BACKGROUND OF THE INVENTION

Field of the Invention

The present disclosure provides Mcl-1 inhibitors, synthetic intermediates and methods to prepare Mcl-1 inhibitors, and therapeutic methods of treating conditions and diseases, e.g., cancer, wherein inhibition of Mcl-1 provides a benefit.

Background

Abnormal regulation of apoptosis pays an important role in cancer. The apoptosis pathway can be initiated by various extracellular and intracellular stresses, including growth factor deprivation, DNA damage, oncogene induction, and cytotoxic drugs (Danial and Korsmeyer, Cell 116:205-219 (2004)). The death signal leads to the oligomerization of the pro-apoptotic proteins Bax and Bak. Upon activation, they permeabilize the mitochondrial outer membrane and release apoptogenic factors into the cytoplasm. This process is tightly regulated by both pro-apoptotic (Bax, Bak, Bad, Bid, Bim, Bmf, NOXA, PUMA) and anti-apoptotic (Bcl-2, Bcl-xL, Bcl-w, Bcl2-A1, Mcl-1) members of the Bcl-2 family of proteins. The anti-apoptotic Bcl-2 proteins function to protect the cell from apoptotic insults, primarily by preventing disruption of mitochondrial outer membrane integrity by binding to the pro-apoptotic proteins. Adams and Cory Oncogene 26:1324-1337 (2007); Willis et al., Science 315: 856-859 (2007). Because tumor cells are under stress, alterations in their apoptotic signaling pathways are crucial for their survival.

Down-regulated apoptosis is implicated in the onset of cancer. Research has shown, for example, that anti-apoptotic proteins are over-expressed in many cancer cell types. Beroukhim et al., Nature 463:899-905 (2010); Kirkin et al., Biochimica et Biophysica Acta 1644:229-249 (2004); and Amundson et al., Cancer Research 60:6101-6110 (2000). This dysregulation results in the survival of cells that would otherwise have undergone apoptosis such as cancer cells. This suggests that neutralizing the function of anti-apoptotic Bcl-2 proteins may offer an effective strategy for the elimination of cancer cells. In addition, resistance to chemotherapy can be caused by the upregulation of anti-apoptotic Bcl-2 family proteins. Resistance to chemotherapy is a major cause of treatment failure and poor prognosis in many cancers.

An important anti-apoptotic member of the Bcl-2 family is myeloid cell leukemia-1 protein (Mcl-1) protein. Mcl-1 is one of the most frequently amplified anti-apoptotic genes in human cancers including prostate, lung, pancreatic, breast, ovarian, and cervical cancers, as well as melanoma, B-cell chronic lymphocytic leukemia (B-CLL), acute myeloid leukemia (AML) and acute lymphoblastic leukemia (ALL) Beroukhim et al., Nature 463:899-905 (2010). Moreover, its overexpression is implicated as a resistance factor for multiple therapies including widely prescribed microtubule-targeted agents for breast cancers, such as paclitaxel, vincristine, and gemcitabine. Wei et al., Cancer Chemother Pharmacol 62:1055-1064 (2008) and Wertz et al., Nature 471:110-114 (2011). These data suggest that Mcl-1 is an important target for a wide variety of cancers.

In many cancer cell types, the cancer cell's survival is attributed to the dysregulation of the apoptotic pathway caused by the over-expression of one or more anti-apoptotic Bcl-2 protein family members. Because of the important role for Bcl-2 family of proteins in regulating apoptosis in both cancerous and non-cancerous cells, and the inter-cell variability of Bcl-2 family protein expression, it could be advantageous to have a small molecule inhibitor that selectively targets and preferably binds to one type or a subset of anti-apoptotic Bcl-2 protein(s). A selective compound also may confer certain advantages in the clinical setting, by providing flexibility to select a dosing regimen to reduce on-target toxic effects in normal cells.

Because Mcl-1 protein is an important Bcl-2 family member associated with a number of diseases, there is a need for compounds which bind to and inhibit the activity of Mcl-1 protein.

BRIEF SUMMARY OF THE INVENTION

In one aspect, the present disclosure provides compounds represented by any one of Formulae IA or I-XIII, the S- and R-isomers thereof, see below, and the pharmaceutically acceptable salts and solvates, e.g., hydrates, thereof, collectively referred to as "Compounds of the Disclosure." Compounds of the Disclosure are Mcl-1 inhibitors and/or synthetic intermediates used to prepare Mcl-1 inhibitors. Mcl-1 inhibitors are useful in treating or preventing diseases or conditions such as cancer wherein Mcl-1 inhibition provides a benefit.

In another aspect, the present disclosure provides compounds represented by any one of Formulae XV-XVII, see below, and the salts and solvates, e.g., hydrates, thereof, collectively referred to as "Intermediates of the Disclosure." Intermediates of the Disclosure are synthetic intermediates that can be used to prepare Compounds of the Disclosure.

In another aspect, the present disclosure provides methods of treating or preventing a condition or disease by administering a therapeutically effective amount of a Compound of the Disclosure to a subject, e.g., a human patient, in need thereof. The disease or condition of interest treatable or preventable by inhibition of Mcl-1 is, for example, a cancer, a chronic autoimmune disorder, an inflammatory condition, a proliferative disorder, sepsis, or a viral infection. Also provided are methods of preventing the proliferation of unwanted proliferating cells, such as in cancer, in a subject comprising administering a therapeutically effective amount of a Compound of the Disclosure to a subject at risk of developing a condition characterized by unwanted proliferating cells. In some embodiments, the Compounds of the Disclosure may reduce the proliferation of unwanted cells by inducing apoptosis in those cells.

In another aspect, the present disclosure provides a method of inhibiting Mcl-1 in a subject, comprising administering to the subject a therapeutically effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating or preventing diseases or conditions wherein inhibition of Mcl-1 provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in the treatment or prevention of a disease or condition of interest, e.g., cancer.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides methods of preparing Compounds of the Disclosure and Intermediates of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

I. Compounds of the Disclosure

Compounds of the Disclosure are Mcl-1 inhibitors and/or synthetic intermediates used to prepare Mcl-1 inhibitors. In one embodiment, Compounds of the Disclosure are compounds of Formula IA:

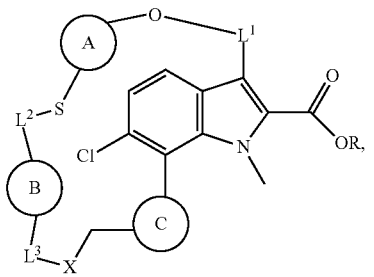

IA wherein:
R is selected from the group consisting of hydrogen and $C_1$-$C_6$ alkyl;
X is selected from the group consisting of —O—, —S—, —S(=O)—, —S(=O)$_2$—, and —N(R$^3$)—;

$R^3$ is selected from the group consisting of hydrogen, $C_1$-$C_4$ alkyl, $C_3$-$C_6$ cycloalkyl, hydroxyalkyl, —C(=O)R$^4$, and —S(=O)$_2$R$^5$;

$R^4$ is selected from the group consisting of $C_1$-$C_4$ alkyl, $C_1$-$C_4$ haloalkyl, optionally substituted $C_3$-$C_6$ cycloalkyl, optionally substituted 4- to 8-membered heterocyclo, optionally substituted $C_6$-$C_{10}$ aryl, optionally substituted 5- to 10-membered heteroaryl, and ($C_6$-$C_{10}$ aryl)$C_1$-$C_4$ alkyl;

$R^5$ is selected from the group consisting of $C_1$-$C_4$ alkyl, $C_1$-$C_4$ haloalkyl, optionally substituted $C_3$-$C_6$ cycloalkyl, optionally substituted 4- to 8-membered heterocyclo, optionally substituted $C_6$-$C_{10}$ aryl, optionally substituted 5- to 10-membered heteroaryl, and ($C_6$-$C_{10}$ aryl)$C_1$-$C_4$ alkyl;

Ⓐ is selected from the group consisting of:

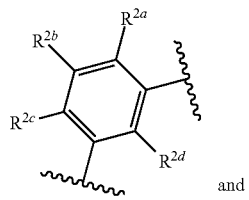

A-1 and

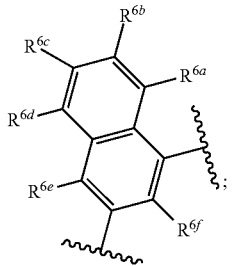

A-2

$R^{2a}$, $R^{2b}$, $R^{2c}$, and $R^{2d}$ are each independently selected from the group consisting of hydrogen, halo, cyano, $C_1$-$C_4$ alkyl, $C_1$-$C_4$ haloalkyl, and $C_1$-$C_4$ alkoxy;

$R^{6a}$, $R^{6b}$, $R^{6c}$, $R^{6d}$, $R^{6e}$, and $R^{6f}$ are each independently selected from the group consisting of hydrogen, halo, cyano, $C_1$-$C_4$ alkyl, $C_1$-$C_4$ haloalkyl, and $C_1$-$C_4$ alkoxy;

Ⓑ is selected from the group consisting of arylenyl and heteroarylenyl;

Ⓒ is selected from the group consisting of:

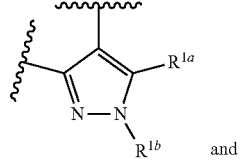

C-1 and

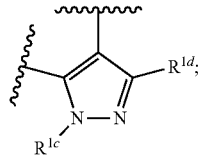

C-2

$R^{1a}$ and $R^{1b}$ are each independently selected from the group consisting of hydrogen, $C_1$-$C_4$ alkyl, $C_1$-$C_4$ haloalkyl, and $C_3$-$C_6$ cycloalkyl; or $R^{1a}$ and $R^{1b}$ taken together with the carbon and nitrogen atoms to which they are attached form an optionally substituted 4- to 8-membered heterocyclo;

$R^{1c}$ and $R^{1d}$ are each independently selected from the group consisting of hydrogen, $C_1$-$C_4$ alkyl, $C_1$-$C_4$ haloalkyl, and $C_3$-$C_6$ cycloalkyl;

$L^1$ is —$(CR^{14a}R^{14b})_s$—;

each $R^{14a}$ and $R^{14b}$ are independently selected from the group consisting of hydrogen and $C_1$-$C_4$ alkyl;

s is 2, 3, 4, 5, or 6;

$L^2$ is —$(CR^{14c}R^{14d})_t$—;

each $R^{14c}$ and $R^{14d}$ are independently selected from the group consisting of hydrogen and $C_1$-$C_4$ alkyl;

t is 1, 2, 3, or 4;

$L^3$ is —$(CR^{14e}R^{14f})_v$—;

each $R^{14e}$ and $R^{14f}$ are independently selected from the group consisting of hydrogen and $C_1$-$C_4$ alkyl; and v is 1, 2, 3, or 4, or a pharmaceutically acceptable salt or solvate thereof.

In another embodiment, Compounds of the Disclosure are compounds of Formula IA, provided that the compound is not a compound of Table A.

TABLE A

| Structure | Name |
|---|---|
| | (Z)-1⁶-chloro-1¹,2¹,2⁵,6¹-tetramethyl-1¹H,2¹H,6¹H-10-oxa-4,8-dithia-1(7,3)-indola-2(4,3),6(3,5)-dipyrazola-9(3,1)-naphthalenacyclotridecaphane-1²-carboxylic acid |
| | (S)-(Z)-1⁶-chloro-1¹,2¹,2⁵,6¹-tetramethyl-1¹H,2¹H,6¹H-10-oxo-4,8-dithia-1(7,3)-indola-2(4,3),6(3,5)-dipyrazola-9(3,1)-naphthalenacyclotridecaphane |

TABLE A-continued

| Structure | Name |
|---|---|
|  | (R)-(Z)-1⁶-chloro-1¹,2¹,2⁵,6¹-tetramethyl-1¹H,2¹H,6¹H-10-oxa-4,8-dithia-1(7,3)-indola-2(4,3),6(3,5)-dipyrazola-9(3,1)-naphthalenacyclotridecaphane |

In another embodiment, Compounds of the Disclosure are compounds of Formula IA, provided that the compound is not a compound of Table B.

TABLE B

| Structure | Name |
|---|---|
|  | (Z)-1⁶-chloro-1¹,2¹,2³,6¹-tetramethyl-1¹H,2¹H,6¹H-10-oxa-4,8-dithia-1(7,3)-indola-2(4,5),6(3,5)-dipyrazola-9(3,1)-naphthalenacyclotridecaphane-1²-carboxylic acid |
|  | (S)-(Z)-1⁶-chloro-1¹,2¹,2³,6¹-tetramethyl-1¹H,2¹H,6¹H-10-oxa-4,8-dithia-1(7,3)-indola-2(4,5),6(3,5)-dipyrazola-9(3,1)-naphthalenacyclotridecaphane-1²-carboxylic acid |

TABLE B-continued

| Structure | Name |
|---|---|
| 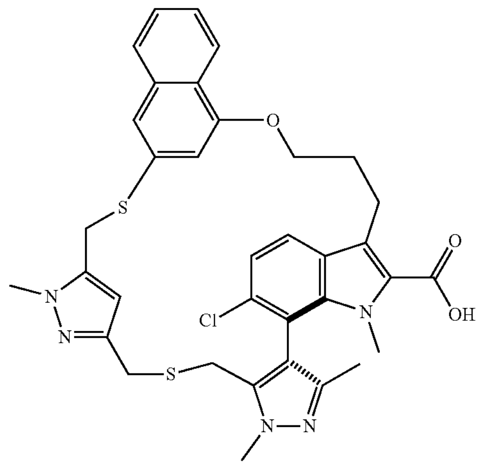 | (R)-(Z)-1$^6$-chloro-1$^1$,2$^1$,2$^3$,6$^1$-tetramethyl-1$^1$H,2$^1$H,6$^1$H-10-oxa-4,8-dithia-1(7,3)-indola-2(4,5),6(3,5)-dipyrazola-9(3,1)-naphthalenacyclotridecaphane-1$^2$-carboxylic acid |
| 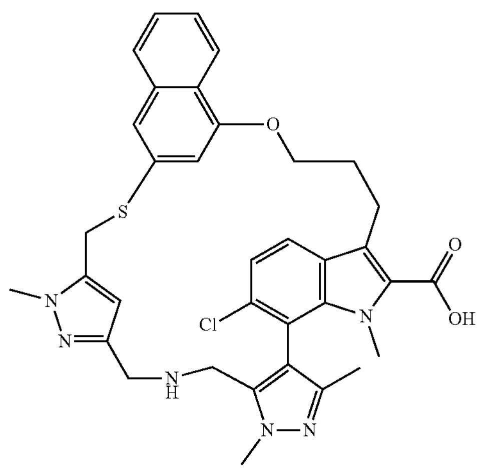 [SMILES: Cc1nn(C)c2c1-c1c(Cl)ccc3c(c(C(=O)O)n(C)c13)CCCOc1cc(cc3ccccc13)SCc1cc(nn1C)CNC2] | (Z)-1$^6$-chloro-1$^1$,2$^1$,2$^3$,6$^1$-tetramethyl-1$^1$H,2$^1$H,6$^1$H-10-oxa-8-thia-4-aza-1(7,3)-indola-2(4,5),6(3,5)-dipyrazola-9(3,1)-naphthalenacyclotridecaphane-1$^2$-carboxylic acid |
| 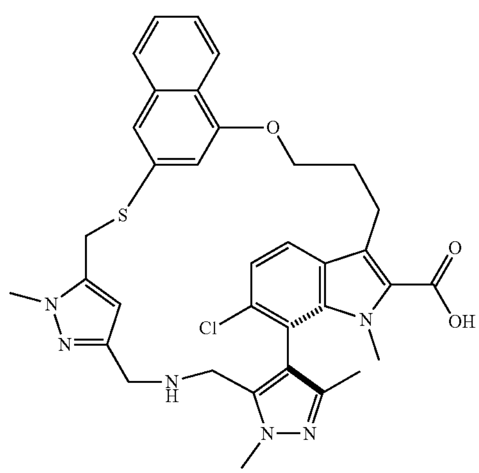 | (S)-(Z)-1$^6$-chloro-1$^1$,2$^1$,2$^3$,6$^1$-tetramethyl-1$^1$H,2$^1$H,6$^1$H-10-oxa-8-thia-4-aza-1(7,3)-indola-2(4,5),6(3,5)-dipyrazola-9(3,1)-naphthalenacyclotridecaphane-1$^2$-carboxylic acid |

TABLE B-continued

| Structure | Name |
|---|---|
| 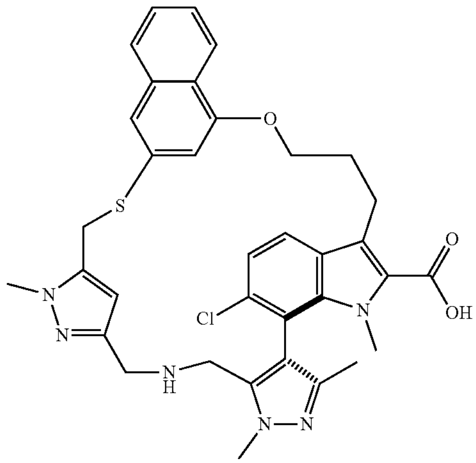 | (R)-(Z)-1$^6$-chloro-1$^1$,2$^1$,2$^3$,6$^1$-tetramethyl-1$^1$H,2$^1$H,6$^1$H-10-oxa-8-thia-4-aza-1(7,3)-indola-2(4,5),6(3,5)-dipyrazola-9(3,1)-naphthalenacyclotridecaphane-1$^2$-carboxylic acid |
| 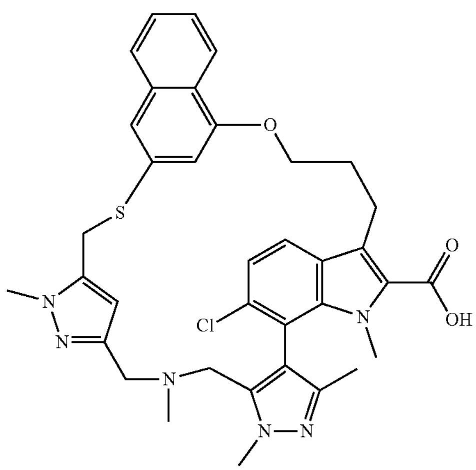 [SMILES: Cc1nn(C)c2c1-c1c(Cl)ccc3c(c(C(=O)O)n(C)c13)CCCOc1cc(cc3ccccc13)SCc1cc(nn1C)CN(C)C2] | (Z)-1$^6$-chloro-1$^1$,2$^1$,2$^3$,6$^1$,4-pentamethyl-1$^1$H,2$^1$H,6$^1$H-10-oxa-8-thia-4-aza-1(7,3)-indola-2(4,5),6(3,5)-dipyrazola-9(3,1)-naphthalenacyclotridecaphane-1$^2$-carboxylic acid |
| 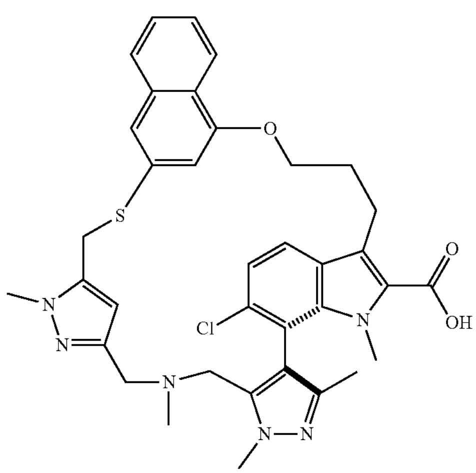 | (S)-(Z)-1$^6$-chloro-1$^1$,2$^1$,2$^3$,6$^1$-,4-pentamethyl-1$^1$H,2$^1$H,6$^1$H-10-oxa-8-thia-4-aza-1(7,3)-indola-2(4,5),6(3,5)-dipyrazola-9(3,1)-naphthalenacyclotridecaphane-1$^2$-carboxylic acid |

TABLE B-continued

| Structure | Name |
|---|---|
| 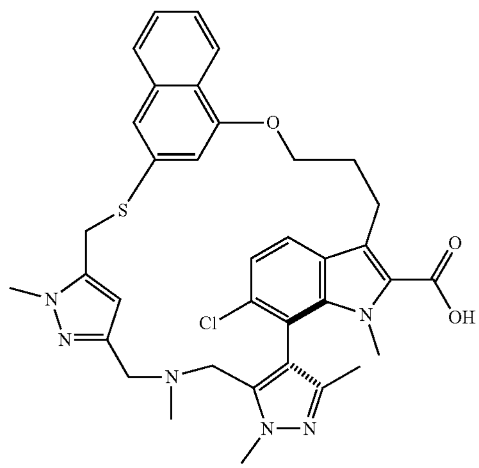 | (R)-(Z)-$1^6$-chloro-$1^1,2^1,2^3,6^1$,4-pentamethyl-$1^1$H,$2^1$H,$6^1$H-10-oxa-8-thia-4-aza-1(7,3)-indola-2(4,5),6(3,5)-dipyrazola-9(3,1)-naphthalenacyclotridecaphane-$1^2$-carboxylic acid |
| 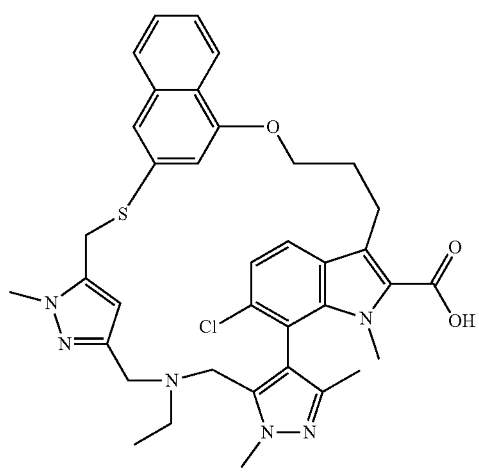 [SMILES: CCN1Cc2cc(n(C)n2)CSc2cc(c3ccccc3c2)OCCCc2c(C(=O)O)n(C)c3c(c(Cl)ccc23)-c2c(C)nn(C)c2C1] | (Z)-$1^6$-chloro-4-ethyl-$1^1,2^1,2^3,6^1$-tetramethyl-$1^1$H,$2^1$H,$6^1$H-10-oxa-8-thia-4-aza-1(7,3)-indola-2(4,5),6(3,5)-dipyrazola-9(3,1)-naphthalenacyclotridecaphane-$1^2$-carboxylic acid |
| 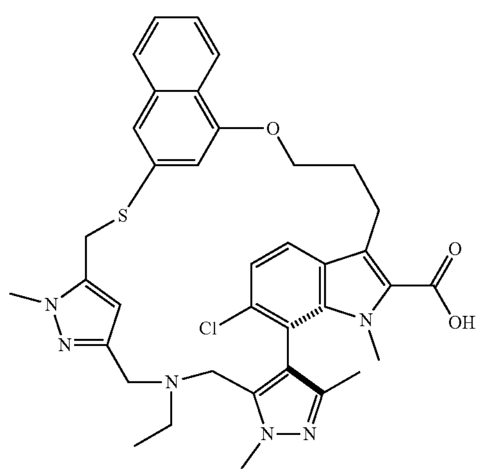 | (S)-(Z)-$1^6$-chloro-4-ethyl-$1^1,2^1,2^3,6^1$-tetramethyl-$1^1$H,$2^1$H,$6^1$H-10-oxa-8-thia-4-aza-1(7,3)-indola-2(4,5),6(3,5)-dipyrazola-9(3,1)-naphthalenacyclotridecaphane-$1^2$-carboxylic acid |

TABLE B-continued

| Structure | Name |
|---|---|
| 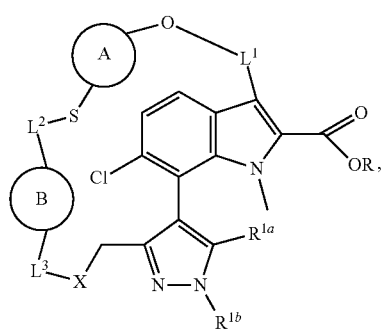 | (R)-(Z)-1⁶-chloro-4-ethyl-1¹,2¹,2³,6¹-tetramethyl-1¹H,2¹H,6¹H-10-oxa-8-thia-4-aza-1(7,3)-indola-2(4,5),6(3,5)-dipyrazola-9(3,1)-naphthalenacyclotridecaphane-1²-carboxylic acid |

In another embodiment, Compounds of the Disclosure are compounds of Formula IA, provided that the compound is not a compound of Table A or Table B.

In another embodiment, Compounds of the Disclosure are compounds of Formula IA, wherein Ⓒ is C-1, or a pharmaceutically acceptable salt or solvate thereof.

In another embodiment, Compounds of the Disclosure are compounds of Formula IA, wherein Ⓒ is C-2, or a pharmaceutically acceptable salt or solvate thereof.

In another embodiment, Compounds of the Disclosure are compounds of Formula IA, wherein:

Ⓒ is C-2; and $R^3$ is selected from the group consisting of $C_3$-$C_6$ cycloalkyl, hydroxyalkyl, —C(=O)R⁴, and —S(=O)₂R⁵, or a pharmaceutically acceptable salt or solvate thereof.

In another embodiment, Compounds of the Disclosure are compounds of Formula I:

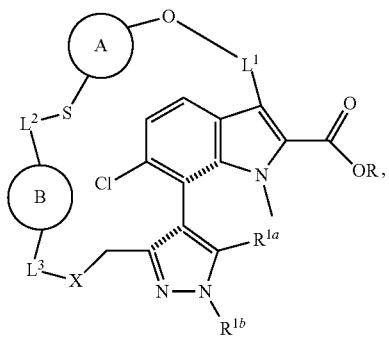

I wherein R, $R^{1a}$, $R^{1b}$, $L^1$, $L^2$, $L^3$, X, Ⓐ, and Ⓑ are as defined in connection with Formula IA, or a pharmaceutically acceptable salt or solvate thereof.

In another embodiment, Compounds of the Disclosure are the S-isomers of a compound of Formula I, i.e., compounds of Formula I-S:

I-S wherein R, $R^{1a}$, $R^{1b}$, $L^1$, $L^2$, $L^3$, X, Ⓐ, and Ⓑ are as defined in connection with Formula IA, or a pharmaceutically acceptable salt or solvate thereof.

In another embodiment, Compounds of the Disclosure are the R-isomers of a compound of Formula I, i.e., compounds of Formula I-R:

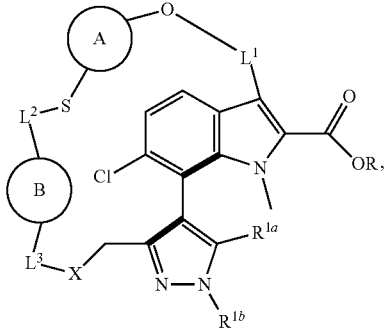

I-R wherein R, $R^{1a}$, $R^{1b}$, $L^1$, $L^2$, $L^3$, X, Ⓐ, and Ⓑ are as defined in connection with Formula IA, or a pharmaceutically acceptable salt or solvate thereof.

In another embodiment, Compounds of the Disclosure are compounds of Formula XII:

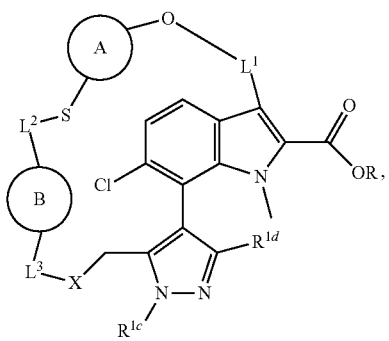

XII wherein R, $R^{1c}$, $R^{1d}$, $L^1$, $L^2$, $L^3$, X, Ⓐ, and Ⓑ are as defined in connection with Formula IA, or a pharmaceutically acceptable salt or solvate thereof.

In another embodiment, Compounds of the Disclosure are the S-isomers of a compound of Formula XII, i.e., compounds of Formula XII-S:

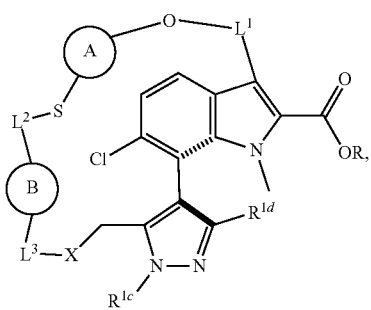

XII-S wherein R, $R^{1c}$, $R^{1d}$, $L^1$, $L^2$, $L^3$, X, Ⓐ, and Ⓑ are as defined in connection with Formula IA, or a pharmaceutically acceptable salt or solvate thereof.

In another embodiment, Compounds of the Disclosure are the R-isomers of a compound of Formula XII, i.e., compounds of Formula XII-R:

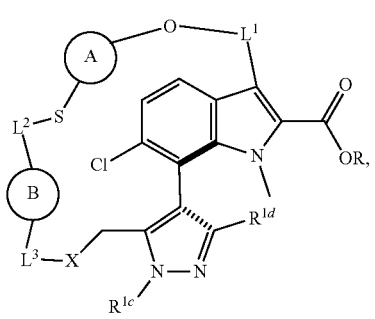

XII-R wherein R, $R^{1c}$, $R^{1d}$, $L^1$, $L^2$, $L^3$, X, Ⓐ, and Ⓑ are as defined in connection with Formula IA, or a pharmaceutically acceptable salt or solvate thereof.

In another embodiment, Compounds of the Disclosure are compounds of any one of Formulae IA, I, I-S, I-R, XII, XII-S, or XII-R, wherein $L^2$ is selected from the group consisting of —CH$_2$— and —CH(CH$_3$)—, or a pharmaceutically acceptable salt or solvate thereof.

In another embodiment, Compounds of the Disclosure are compounds of Formulae IA, I, I-S, I-R, XII, XII-S, or XII-R, wherein $L^3$ is selected from the group consisting of —CH$_2$— and —CH(CH$_3$)—, or a pharmaceutically acceptable salt or solvate thereof.

In another embodiment, Compounds of the Disclosure are compounds of Formulae IA, I, I-S, I-R, XII, XII-S, or XII-R, wherein $L^1$ is selected from the group consisting of —CH$_2$CH$_2$—, —CH$_2$CH$_2$CH$_2$—, and —CH$_2$CH$_2$CH$_2$CH$_2$—, or a pharmaceutically acceptable salt or solvate thereof.

In another embodiment, Compounds of the Disclosure are compounds of Formula II:

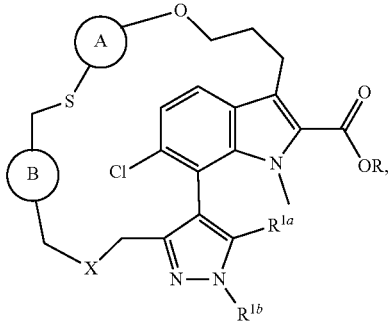

II wherein R, $R^{1a}$, $R^{1b}$, X, Ⓐ, and Ⓑ are as defined in connection with Formula I, or a pharmaceutically acceptable salt or solvate thereof.

In another embodiment, Compounds of the Disclosure are the S-isomers of a compound of Formula II, i.e., compounds of Formula II-S:

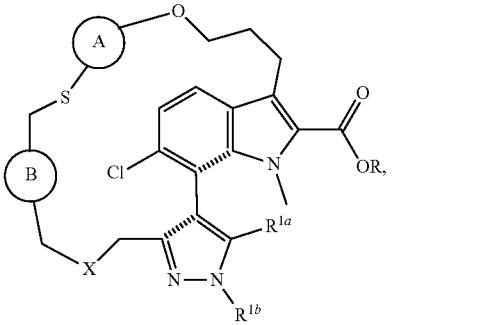

II-S wherein R, $R^{1a}$, $R^{1b}$, X, Ⓐ, and Ⓑ are as defined in connection with Formula II, or a pharmaceutically acceptable salt or solvate thereof.

In another embodiment, Compounds of the Disclosure are the R-isomers of a compound of Formula II, i.e., compounds of Formula II-R:

II-R

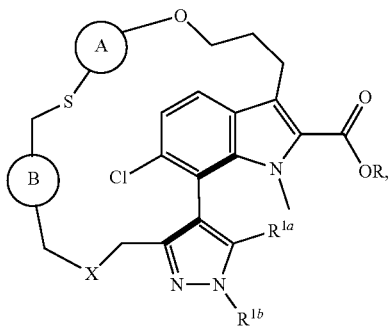

wherein R, R$^{1a}$, R$^{1b}$, X, (A), and (B) are as defined in connection with Formula II, or a pharmaceutically acceptable salt or solvate thereof.

In another embodiment, Compounds of the Disclosure are compounds of any one of Formula I, II, II-S, or II-R, wherein R$^{1a}$ and R$^{1b}$ are each independently selected from the group consisting of hydrogen and C$_1$-C$_4$ alkyl, or a pharmaceutically acceptable salt or solvate thereof.

In another embodiment, Compounds of the Disclosure are compounds of any one of Formula I, II, II-S, or II-R, wherein R$^{1a}$ and R$^{1b}$ are each methyl, or a pharmaceutically acceptable salt or solvate thereof.

In another embodiment, Compounds of the Disclosure are compounds of any one of Formula I, II, II-S, or II-R, wherein R$^{1a}$ and R$^{1b}$ taken together with the atoms to which they are attached form an optionally substituted 4- to 8-membered heterocyclo, or a pharmaceutically acceptable salt or solvate thereof.

In another embodiment, Compounds of the Disclosure are compounds of Formula III:

III

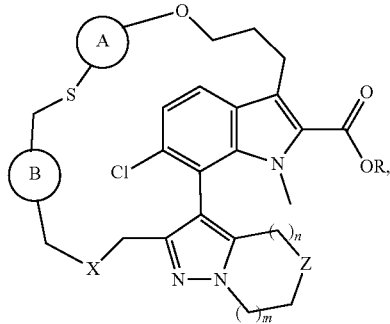

wherein:
m is 0, 1, or 2;
n is 0 or 1;
with the proviso that when m is 0, Z is —CR$^{13a}$R$^{13b}$—;
Z is selected from the group consisting of —CR$^{13a}$R$^{13b}$—, —O—, —S—, S(=O)—, S(=O)$_2$—, and —N(R$^{10}$)—;
R$^{10}$ is selected from the group consisting of hydrogen, C$_1$-C$_4$ alkyl, —C(=O)$_2$R$^{11}$, and —S(=O)$_2$R$^2$;
R$^{11}$ is selected from the group consisting of C$_1$-C$_4$ alkyl, optionally substituted C$_3$-C$_6$ cycloalkyl, optionally substituted C$_6$-C$_{10}$ aryl, and optionally substituted 5- to 10-membered heteroaryl;

R$^{12}$ is selected from the group consisting of C$_1$-C$_4$ alkyl, optionally substituted C$_3$-C$_6$ cycloalkyl, optionally substituted C$_6$-C$_{10}$ aryl, and optionally substituted 5- to 10-membered heteroaryl; and R$^{13a}$ and R$^{13b}$ are independently selected from the group consisting of hydrogen and C$_1$-C$_4$ alkyl; and R, X, (A), and (B) are as defined in connection with Formula I, or a pharmaceutically acceptable salt or solvate thereof.

In another embodiment, Compounds of the Disclosure are the S-isomers of a compound of Formula III, i.e., compounds of Formula III-S:

III-S

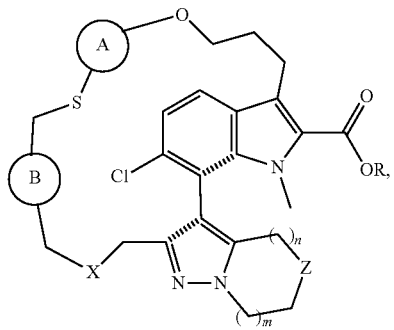

wherein R, X, Z, n, m, (A), and (B) are as defined in connection with Formula III, or a pharmaceutically acceptable salt or solvate thereof.

In another embodiment, Compounds of the Disclosure are the R-isomers of a compound of Formula III, i.e., compounds of Formula III-R:

III-R

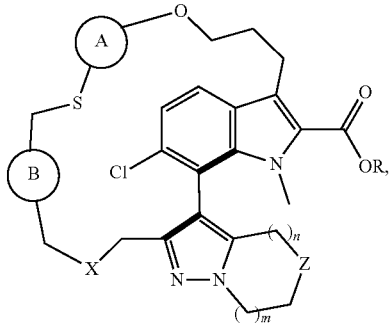

wherein R, X, Z, n, m, (A), and (B) are as defined in connection with Formula III, or a pharmaceutically acceptable salt or solvate thereof.

In another embodiment, Compounds of the Disclosure are compounds of any one of Formula III, III-S, or III-R, wherein Z is —O—, or a pharmaceutically acceptable salt or solvate thereof.

In another embodiment, Compounds of the Disclosure are compounds of any one of Formula III, III-S, or III-R, wherein Z is —CH$_2$—, or a pharmaceutically acceptable salt or solvate thereof.

In another embodiment, Compounds of the Disclosure are of any one of:

Formula IV

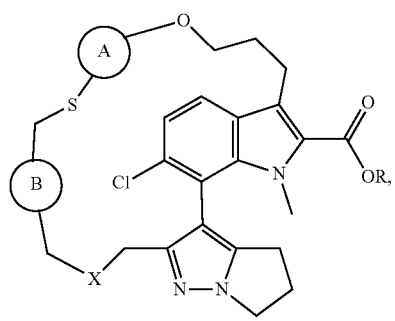

Formula V

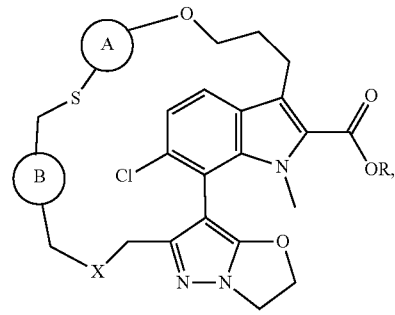

Formula VI

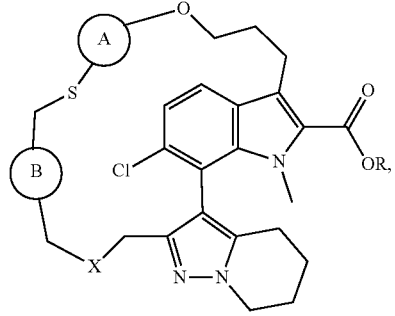

Formula VII

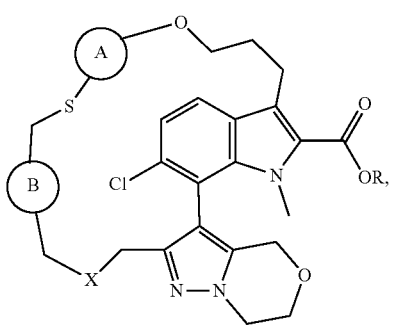

Formula VIII

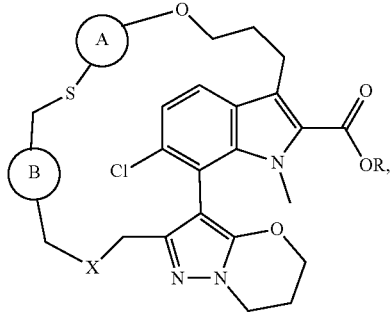

Formula IX

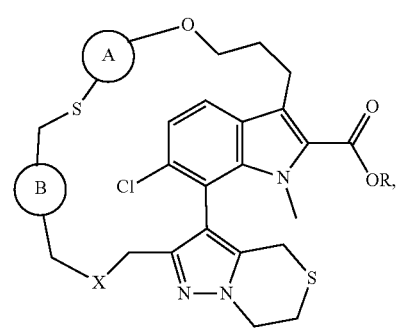

Formula X

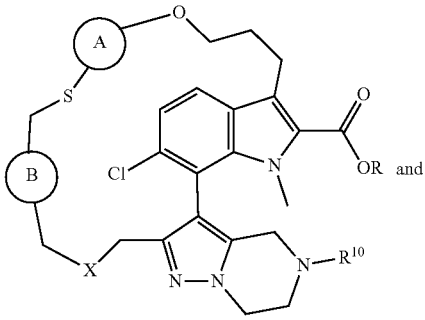

Formula XI

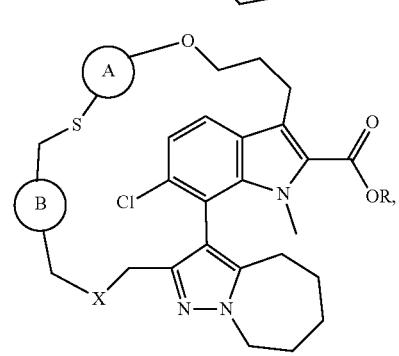

wherein R, X, $R^{10}$, Ⓐ, and Ⓑ are as defined in connection with Formula III, or a pharmaceutically acceptable salt or solvate thereof.

In another embodiment, Compounds of the Disclosure are compounds of Formula IV, or a pharmaceutically acceptable salt or solvate thereof.

In another embodiment, Compounds of the Disclosure are compounds of Formula V, or a pharmaceutically acceptable salt or solvate thereof.

In another embodiment, Compounds of the Disclosure are compounds of Formula VI, or a pharmaceutically acceptable salt or solvate thereof.

In another embodiment, Compounds of the Disclosure are compounds of Formula VII, or a pharmaceutically acceptable salt or solvate thereof.

In another embodiment, Compounds of the Disclosure are compounds of Formula VIII, or a pharmaceutically acceptable salt or solvate thereof.

In another embodiment, Compounds of the Disclosure are compounds of Formula IX, or a pharmaceutically acceptable salt or solvate thereof.

In another embodiment, Compounds of the Disclosure are compounds of Formula X, or a pharmaceutically acceptable salt or solvate thereof.

In another embodiment, Compounds of the Disclosure are compounds of Formula XI, or a pharmaceutically acceptable salt or solvate thereof.

In another embodiment, Compounds of the Disclosure are the S-isomers of a compound of any one of Formula IV-XI, i.e., a compound of any one of:

Formula IV-S

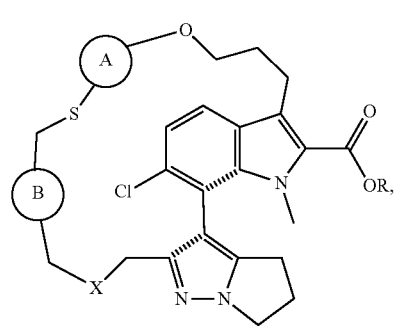

Formula V-S

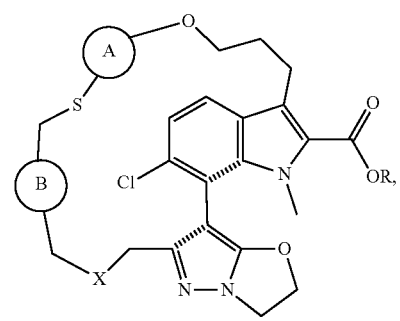

Formula VI-S

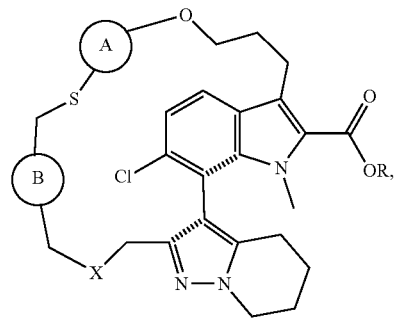

Formula VII-S

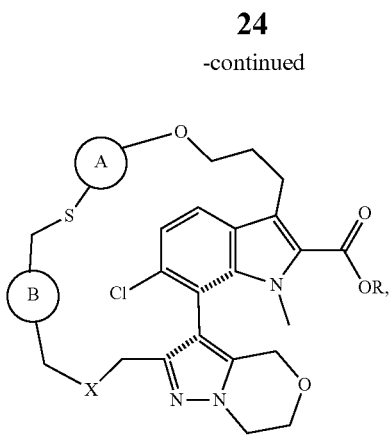

Formula VIII-S

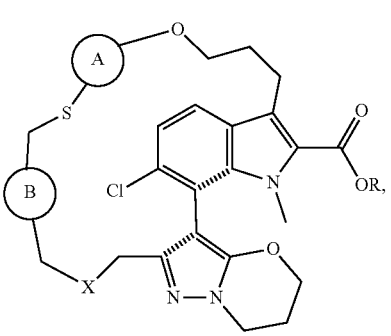

Formula IX-S

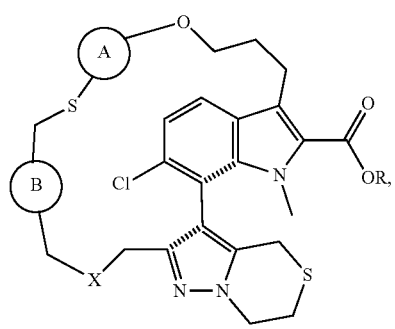

Formula X-S

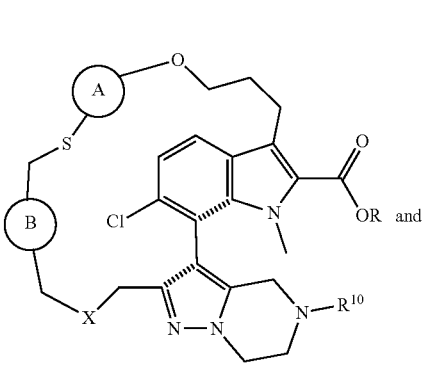

Formula XI-S

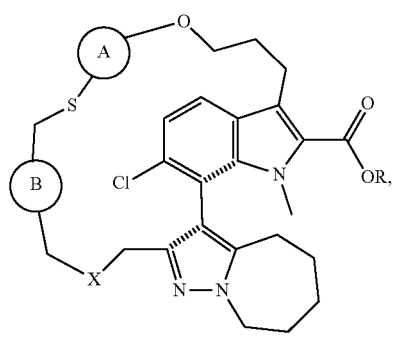

wherein R, X, $R^{10}$, Ⓐ, and Ⓑ are as defined in connection with Formula III, or a pharmaceutically acceptable salt or solvate thereof.

In another embodiment, Compounds of the Disclosure are compounds of Formula IV-S, or a pharmaceutically acceptable salt or solvate thereof.

In another embodiment, Compounds of the Disclosure are compounds of Formula V-S, or a pharmaceutically acceptable salt or solvate thereof.

In another embodiment, Compounds of the Disclosure are compounds of Formula VI-S, or a pharmaceutically acceptable salt or solvate thereof.

In another embodiment, Compounds of the Disclosure are compounds of Formula VII-S, or a pharmaceutically acceptable salt or solvate thereof.

In another embodiment, Compounds of the Disclosure are compounds of Formula VIII-S, or a pharmaceutically acceptable salt or solvate thereof.

In another embodiment, Compounds of the Disclosure are compounds of Formula IX-S, or a pharmaceutically acceptable salt or solvate thereof.

In another embodiment, Compounds of the Disclosure are compounds of Formula X-S, or a pharmaceutically acceptable salt or solvate thereof.

In another embodiment, Compounds of the Disclosure are compounds of Formula XI-S, or a pharmaceutically acceptable salt or solvate thereof.

In another embodiment, Compounds of the Disclosure are the R-isomers of a compound of any one of Formula IV-XI, i.e., a compound of any one of:

Formula IV-R

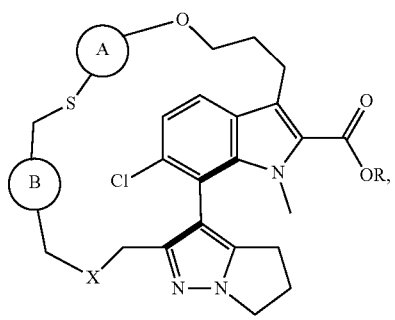

Formula V-R

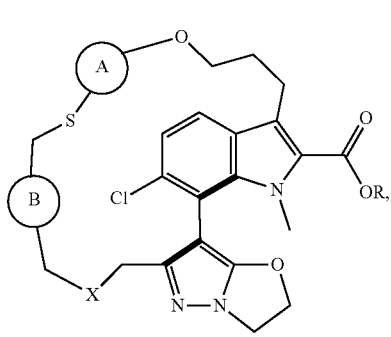

Formula VI-R

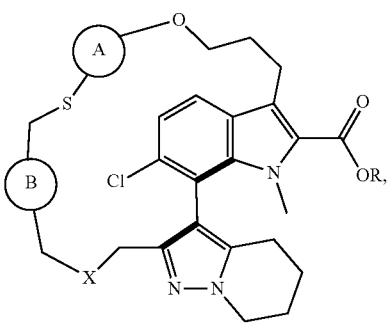

Formula VII-R

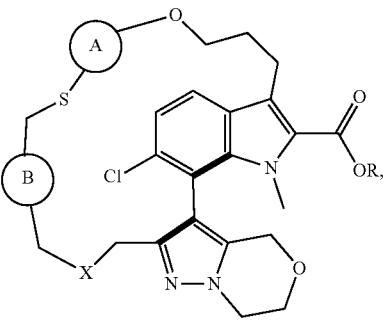

Formula VIII-R

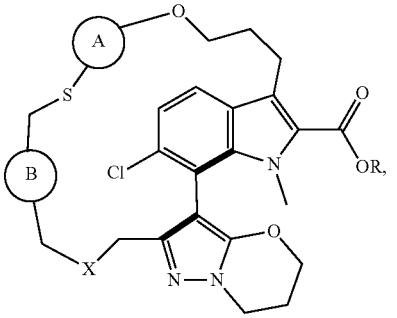

-continued

Formula IX-R

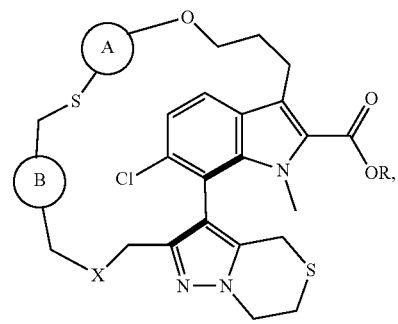

Formula X-R

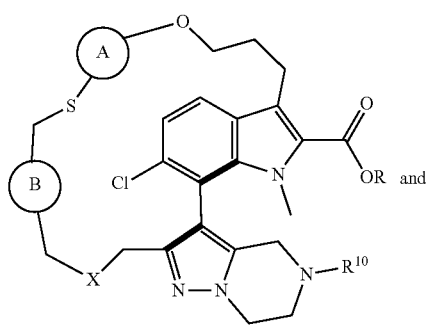

Formula XI-R

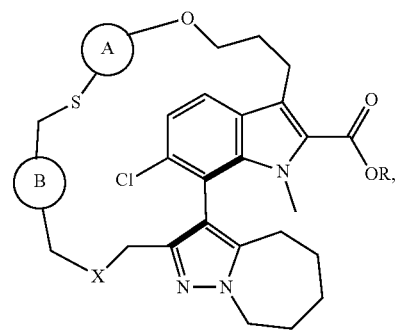

wherein R, X, R$^{10}$, Ⓐ, and Ⓑ are as defined in connection with Formula III, or a pharmaceutically acceptable salt or solvate thereof.

In another embodiment, Compounds of the Disclosure are compounds of Formula IV-R, or a pharmaceutically acceptable salt or solvate thereof.

In another embodiment, Compounds of the Disclosure are compounds of Formula V-R, or a pharmaceutically acceptable salt or solvate thereof.

In another embodiment, Compounds of the Disclosure are compounds of Formula VI-R, or a pharmaceutically acceptable salt or solvate thereof.

In another embodiment, Compounds of the Disclosure are compounds of Formula VII-R, or a pharmaceutically acceptable salt or solvate thereof.

In another embodiment, Compounds of the Disclosure are compounds of Formula VIII-R, or a pharmaceutically acceptable salt or solvate thereof.

In another embodiment, Compounds of the Disclosure are compounds of Formula IX-R, or a pharmaceutically acceptable salt or solvate thereof.

In another embodiment, Compounds of the Disclosure are compounds of Formula X-R, or a pharmaceutically acceptable salt or solvate thereof.

In another embodiment, Compounds of the Disclosure are compounds of Formula XI-R, or a pharmaceutically acceptable salt or solvate thereof.

In another embodiment, Compounds of the Disclosure are compounds of Formula XIII:

XIII

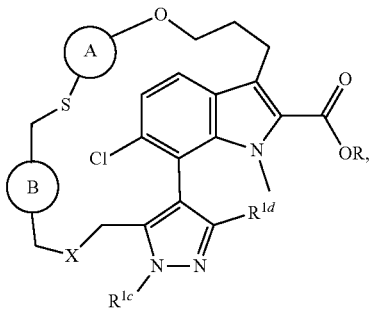

Wherein R, R$^{1c}$, R$^{1d}$, X, Ⓐ, and Ⓑ are as defined in connection with Formula XII, or a pharmaceutically acceptable salt or solvate thereof.

In another embodiment, Compounds of the Disclosure are the S-isomers of a compound of Formula XIII, i.e., compounds of Formula XIII-S:

XIII-S

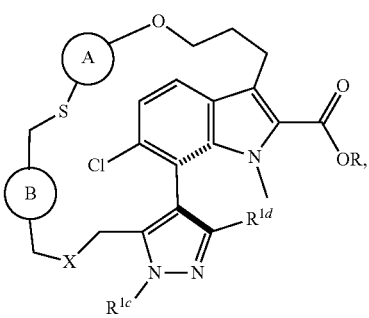

wherein R, R$^{1c}$, R$^{1d}$, X, Ⓐ, and Ⓑ are as defined in connection with Formula XIII, or a pharmaceutically acceptable salt or solvate thereof.

In another embodiment, Compounds of the Disclosure are the R-isomers of a compound of Formula XII, i.e., compounds of Formula XIII-R:

XIII-R

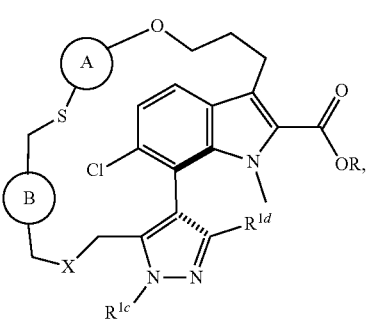

wherein R, $R^{1c}$, $R^{1d}$, X, Ⓐ, and Ⓑ are as defined in connection with Formula XII, or a pharmaceutically acceptable salt or solvate thereof.

In another embodiment, Compounds of the Disclosure are compounds of any one of Formula XIII, XIII-S, or XIII-R, wherein $R^{1c}$ is $C_1$-$C_4$ alkyl; and $R^{1d}$ is $C_1$-$C_4$ haloalkyl, or a pharmaceutically acceptable salt or solvate thereof.

In another embodiment, Compounds of the Disclosure are compounds of any one of Formula XIII, XIII-S, or XIII-R, wherein $R^{1c}$ is $C_1$-$C_4$ alkyl; and $R^{1d}$ is $C_2$-$C_4$ alkyl, or a pharmaceutically acceptable salt or solvate thereof.

In another embodiment, Compounds of the Disclosure are compounds of any one of Formula XIII, XIII-S, or XIII-R, wherein $R^{1c}$ is $C_1$-$C_4$ alkyl; and $R^{1d}$ is $C_3$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein Ⓐ is A-1, or a pharmaceutically acceptable salt or solvate thereof. In another embodiment, $R^{2a}$, $R^{2b}$, and $R^{2c}$ are each independently selected from the group consisting of hydrogen, halo, and $C_1$-$C_4$ alkyl; and $R^{2d}$ is hydrogen, or a pharmaceutically acceptable salt or solvate thereof.

In another embodiment, Compounds of the Disclosure are compounds of any one of Formulae I-XIII (including the S- and R-isomers thereof), wherein Ⓐ is A-2, or a pharmaceutically acceptable salt or solvate thereof. In another embodiment, the 1-position of A-2 is attached to the oxygen atom and the 3-position of A-2 is attached to the sulfur atom. In another embodiment, $R^{6a}$, $R^{6b}$, $R^{6c}$, $R^{6d}$, and $R^{6e}$ are each independently selected from the group consisting of hydrogen, halo, and $C_1$-$C_4$ alkyl; and $R^{6f}$ is hydrogen, or a pharmaceutically acceptable salt or solvate thereof In another embodiment, Compounds of the Disclosure are compounds of any one of Formulae I-XIII (including the S- and R-isomers thereof), wherein Ⓑ is arylenyl, or a pharmaceutically acceptable salt or solvate thereof.

In another embodiment, Compounds of the Disclosure are compounds of any one of Formulae I-XIII (including the S- and R-isomers thereof), wherein:

Ⓑ is selected from the group consisting of:

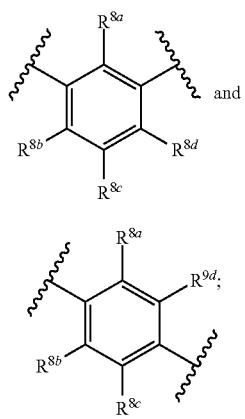

$R^{8a}$, $R^{8b}$, $R^{8c}$, and $R^{8d}$ are each independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl; and $R^{9a}$, $R^{9b}$, $R^{9c}$, and $R^{9d}$ are each independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl, or a pharmaceutically acceptable salt or solvate thereof.

In another embodiment, Compounds of the Disclosure are compounds of any one of Formulae I-XIII (including the S- and R-isomers thereof), wherein Ⓑ is B-1, or a pharmaceutically acceptable salt or solvate thereof. In another embodiment, $R^{8a}$, $R^{8b}$, $R^{8c}$, and $R^{8d}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein Ⓑ is B-2, or a pharmaceutically acceptable salt or solvate thereof. In another embodiment, $R^{9a}$, $R^{9b}$, $R^{9c}$, and $R^{9d}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein Ⓑ is heteroarylenyl, or a pharmaceutically acceptable salt or solvate thereof.

In another embodiment, Compounds of the Disclosure are compounds of any one of Formulae I-XII (including the S- and R-isomers thereof), wherein:

Ⓑ is selected from the group consisting of:

$Z^1$ is selected from the group consisting of —O—, —S—, and —N($R^{7a}$)—;

$R^{7a}$ is selected from the group consisting of hydrogen, $C_1$-$C_4$ alkyl, and $C_3$-$C_6$ cycloalkyl;

$Z^2$ is selected from the group consisting of —C($R^{7b}$)═ and —N═;

$R^{7e}$ is selected from the group consisting of hydrogen, halo, $C_1$-$C_4$ alkyl, and $C_3$-$C_6$ cycloalkyl;

$Z^3$ is selected from the group consisting of —O—, —S—, and —N($R^{7c}$)—;

$R^{7c}$ is selected from the group consisting of hydrogen, $C_1$-$C_4$ alkyl, and $C_3$-$C_6$ cycloalkyl;

$R^{7d}$ is selected from the group consisting of hydrogen, halo, $C_1$-$C_4$ alkyl, and $C_3$-$C_6$ cycloalkyl;

$Z^4$ is selected from the group consisting of —O—, —S—, and —N($R^{7e}$)—;

$R^{7e}$ is selected from the group consisting of hydrogen, $C_1$-$C_4$ alkyl, and $C_3$-$C_6$ cycloalkyl;

$R^{7f}$ is selected from the group consisting of hydrogen, halo, $C_1$-$C_4$ alkyl, and $C_3$-$C_6$ cycloalkyl;

Y is selected from the group consisting of —C($R^{10a}$)═ and —N═;

$Y^1$ is selected from the group consisting of —C($R^{10b}$)═ and —N═;

$Y^2$ is selected from the group consisting of —C($R^{10c}$)═ and —N═;

$Y^3$ is selected from the group consisting of —C($R^{10d}$)═ and —N═;

with proviso that at least one of Y, $Y^1$, $Y^2$, and $Y^3$ is —N═;

$R^{10a}$, $R^{10b}$, $R^{10c}$, and $R^{10d}$ are each independently selected from the group consisting of hydrogen, halo, cyano, $C_1$-$C_4$ alkyl, $C_1$-$C_4$ haloalkyl, and $C_1$-$C_4$ alkoxy;

$Y^4$ is selected from the group consisting of —C($R^{11a}$)═ and —N═;

$Y^5$ is selected from the group consisting of —C($R^{11b}$)═ and —N═;

$Y^6$ is selected from the group consisting of —C($R^{11c}$)═ and —N═;

$Y^7$ is selected from the group consisting of —C($R^{11d}$)═ and —N═;

with proviso that at least one of $Y^4$, $Y^5$, $Y^6$, and $Y^7$ is —N═;

$R^{11a}$, $R^{11b}$, $R^{11c}$, and $R^{11d}$ are each independently selected from the group consisting of hydrogen, halo, cyano, $C_1$-$C_4$ alkyl, $C_1$-$C_4$ haloalkyl, and $C_1$-$C_4$ alkoxy, or a pharmaceutically acceptable salt or solvate thereof.

In another embodiment, Compounds of the Disclosure are compounds of any one of Formulae I-XIII (including the S- and R-isomers thereof), wherein Ⓑ is B-3, or a pharmaceutically acceptable salt or solvate thereof. In another embodiment, $Z^1$ is selected from the group consisting of —O—, —S—, —N(H)—, and —N(CH$_3$)—; and $Z^2$ is selected from the group consisting of —C(H)═, —C(CH$_3$)═, and —N═, or a pharmaceutically acceptable salt or solvate thereof.

In another embodiment, Compounds of the Disclosure are compounds of any one of Formulae I-XIII (including the S- and R-isomers thereof), wherein Ⓑ is B-4, or a pharmaceutically acceptable salt or solvate thereof. In another embodiment, $Z^3$ is selected from the group consisting of —O—, —S—, —N(H)—, and —N(CH$_3$)—; and $R^{7d}$ is selected from the group consisting of hydrogen and methyl, or a pharmaceutically acceptable salt or solvate thereof.

In another embodiment, Compounds of the Disclosure are compounds of an one of Formulae I-XIII (including the S- and R-isomers thereof), wherein Ⓑ is B-5, or a pharmaceutically acceptable salt or solvate thereof. In another embodiment, $Z^4$ is selected from the group consisting of —O—, —S—, —N(H)—, and —N(CH$_3$)—; and $R^{7f}$ is selected from the group consisting of hydrogen and methyl, or a pharmaceutically acceptable salt or solvate thereof.

In another embodiment, Compounds of the Disclosure are compounds of any one of Formulae I-XIII (including the S- and R-isomers thereof), wherein Ⓑ is B-6, or a pharmaceutically acceptable salt or solvate thereof.

In another embodiment, Compounds of the Disclosure are compounds of any one of Formulae I-XIII (including the S- and R-isomers thereof), wherein:

Ⓑ is B-6;

Y is —N═;

$Y^1$ is selected from the group consisting of —C($R^{10b}$)═ and —N═;

$Y^2$ is selected from the group consisting of —C($R^{10c}$)═ and —N═;

$Y^3$ is selected from the group consisting of —C($R^{10d}$)═ and —N═; and $R^{10b}$, $R^{10c}$, and $R^{10d}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein:

Ⓑ is B-6;

Y is selected from the group consisting of —C($R^{10a}$)═ and —N═;

$Y^1$ is —N═;

$Y^2$ is selected from the group consisting of —C($R^{10c}$)═ and —N═;

$Y^3$ is selected from the group consisting of —C($R^{10d}$)═ and —N═; and $R^{10a}$, $R^{10c}$, and $R^{10d}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein:

Ⓑ is B-6;

Y is selected from the group consisting of —C($R^{10a}$)═ and —N═;

$Y^1$ is selected from the group consisting of —C($R^{10b}$)═ and —N═;

$Y^2$ is —N═;

$Y^3$ is selected from the group consisting of —C($R^{10}$)═ and —N═; and $R^{10a}$, $R^{10b}$, and $R^{10d}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein:

Ⓑ is B-6;

Y is selected from the group consisting of —C($R^{10a}$)═ and —N═;

$Y^1$ is selected from the group consisting of —C($R^{10b}$)═ and —N═;

$Y^2$ is selected from the group consisting of —C($R^{10c}$)═ and —N═;

$Y^3$ is —N═; and $R^{10a}$, $R^{10b}$, and $R^{10c}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein Ⓑ is B-7, or a pharmaceutically acceptable salt or solvate thereof.

In another embodiment, Compounds of the Disclosure are compounds of any one of Formulae I-XII (including the S- and R-isomers thereof), wherein:

Ⓑ is B-7;
$Y^4$ is and —N═;
$Y^5$ is selected from the group consisting of —C($R^{11b}$)═ and —N═;
$Y^6$ is selected from the group consisting of —C($R^{11c}$)═ and —N═;
$Y^7$ is selected from the group consisting of —C($R^{11d}$)═ and —N═; and
$R^{11b}$, $R^{11c}$, and $R^{11d}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein:

Ⓑ is B-7;
$Y^4$ is selected from the group consisting of —C($R^{1a}$)═ and —N═;
$Y^5$ is —N═;
$Y^6$ is selected from the group consisting of —C($R^{11c}$)═ and —N═;
$Y^7$ is selected from the group consisting of —C($R^{11d}$)═ and —N═; and
$R^{11a}$, $R^{11c}$, and $R^{11d}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein:

Ⓑ is B-7;
$Y^4$ is selected from the group consisting of —C($R^{11a}$)═ and —N═;
$Y^5$ is selected from the group consisting of —C($R^{11b}$)═ and —N═;
$Y^6$ is —N═;
$Y^7$ is selected from the group consisting of —C($R^{11d}$)═ and —N═; and
$R^{11a}$, $R^{11b}$, and $R^{11d}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein:

Ⓑ is B-7;
$Y^4$ is selected from the group consisting of —C($R^{11a}$)═ and —N═;
$Y^5$ is selected from the group consisting of —C($R^{11b}$)═ and —N═;
$Y^6$ is selected from the group consisting of —C($R^{11c}$)═ and —N═;

$Y^7$ is —N═; and
$R^{11a}$, $R^{11b}$, and $R^{11c}$ are each independently selected from the group consisting of hydrogen, halo, and $C_1$-$C_4$ alkyl, or a pharmaceutically acceptable salt or solvate thereof.

In another embodiment, Compounds of the Disclosure are compounds of any one of Formulae I-XIII (including the S- and R-isomers thereof), wherein Ⓑ is selected from the group consisting of:

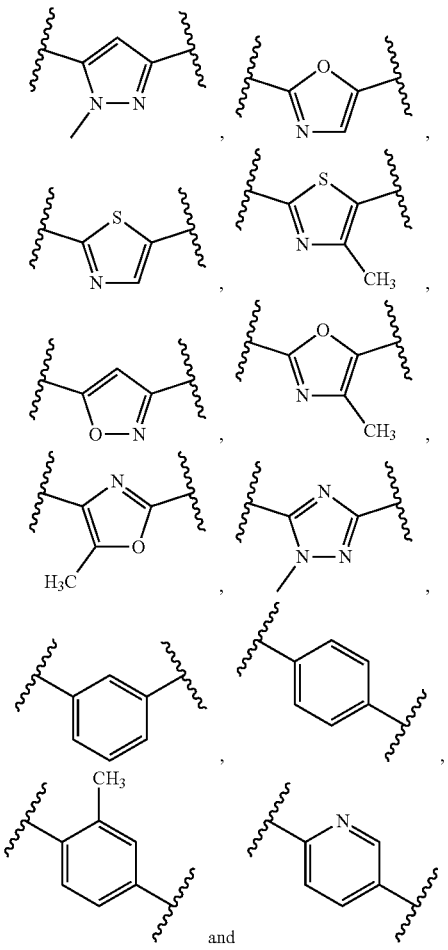

or a pharmaceutically acceptable salt or solvate thereof.

In another embodiment, Compounds of the Disclosure are compounds of any one of Formulae I-XIII (including the S- and R-isomers thereof), wherein X is —O—, or a pharmaceutically acceptable salt or solvate thereof.

In another embodiment, Compounds of the Disclosure are compounds of any one of Formulae I-XIII (including the S- and R-isomers thereof), wherein X is —S— or —S(═O)$_2$—, or a pharmaceutically acceptable salt or solvate thereof.

In another embodiment, Compounds of the Disclosure are compounds of any one of Formulae I-XIII (including the S- and R-isomers thereof), wherein X is —N($R^3$)—, or a pharmaceutically acceptable salt or solvate thereof. In another embodiment, $R^3$ is selected from the group consisting of —C(═O)$R^4$ and —S(═O)$_2R^5$, or a pharmaceutically acceptable salt or solvate thereof. In another embodiment, $R^4$ is $C_1$-$C_4$ alkyl; and $R^5$ is selected from the group consisting of $C_1$-$C_4$ alkyl, optionally substituted 4- to 8-membered heterocyclo, and $(C_6-C_{10}$ aryl)$C_1-C_4$ alkyl, or a pharmaceutically acceptable salt or solvate thereof.

In another embodiment, Compounds of the Disclosure are compounds of any one of Formulae I-XIII (including the S- and R-isomers thereof), wherein R is $C_1-C_6$ alkyl, or a pharmaceutically acceptable salt or solvate thereof. In another embodiment, R is methyl. In another embodiment, R is ethyl.

In another embodiment, Compounds of the Disclosure are compounds of any one of Formulae I-XIII (including the S- and R-isomers thereof), wherein R is hydrogen, or a pharmaceutically acceptable salt or solvate thereof.

In another embodiment, Compounds of the Disclosure are compounds selected from the group consisting of the compounds of Table 1, or a pharmaceutically acceptable salt or solvate thereof.

TABLE 1

| Cpd. No. | Structure | Name |
| --- | --- | --- |
| 1 | 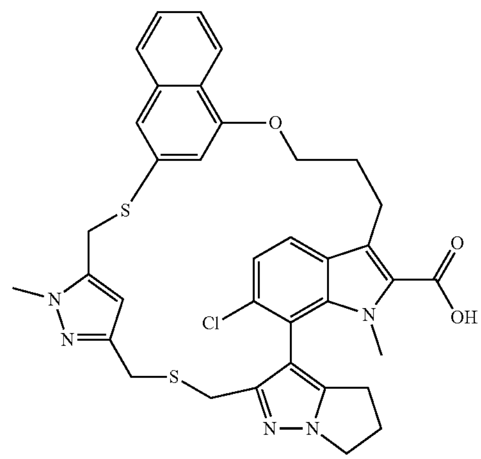 [SMILES: Cn1nc2cc1CSc1cc(c3ccccc3c1)OCCCc1c(C(=O)O)n(C)c3c(c(Cl)ccc13)-c1c(nn3c1CCC3)CSC2] | (Z)-1$^6$-chloro-1$^1$,6$^1$-dimethyl-2$^5$,2$^6$-dihydro-1$^1$H,2$^4$H,6$^1$H-10-oxa-4,8-dithia-1(7,3)-indola-2(3,2)-pyrrolo[1,2-b]pyrazola-6(3,5)-pyrazola-9(3,1)-naphthalenacyclotridecaphane-1$^2$-carboxylic acid |
| 2 | 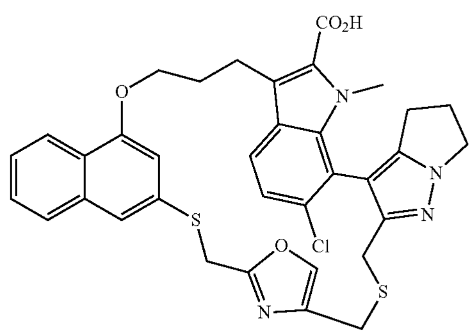 [SMILES: Cn1c(C(=O)O)c2c3ccc(Cl)c(c31)-c1c(nn3c1CCC3)CSCc1coc(n1)CSc1cc(c3ccccc3c1)OCCC2] | (Z)-1$^6$-chloro-1$^1$-methyl-2$^5$,2$^6$-dihydro-1$^1$H,2$^4$H-10-oxa-4,8-dithia-6(4,2)-oxazola-1(7,3)-indola-2(3,2)-pyrrolo[1,2-b]pyrazola-9(3,1)-naphthalenacyclotridecaphane-1$^2$-carboxylic acid |
| 3 | 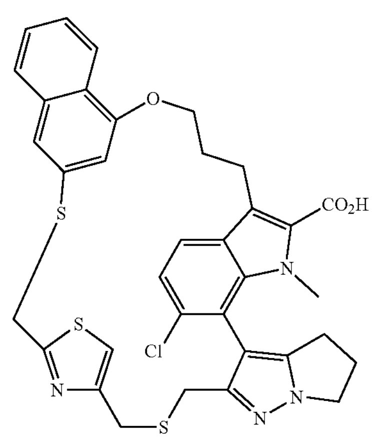 [SMILES: Cn1c(C(=O)O)c2c3ccc(Cl)c(c31)-c1c(nn3c1CCC3)CSCc1csc(n1)CSc1cc(c3ccccc3c1)OCCC2] | (Z)-1$^6$-chloro-1$^1$-methyl-2$^5$,2$^6$-dihydro-1$^1$H,2$^4$H-10-oxa-4,8-dithia-6(4,2)-thiazola-1(7,3)-indola-2(3,2)-pyrrolo[l,2-b]pyrazola-9(3,1)-naphthalenacyclotridecaphane-1$^2$-carboxylic acid |

TABLE 1-continued

| Cpd. No. | Structure | Name |
|---|---|---|
| 4 | 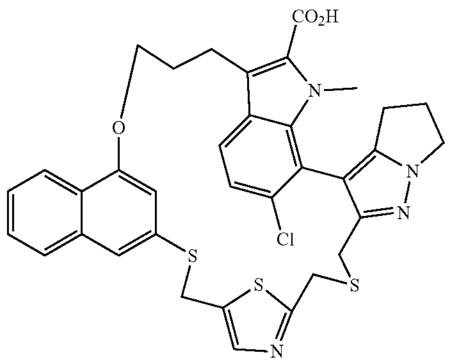 [SMILES: Cn1c(C(=O)O)c2c3ccc(Cl)c(c31)-c1c(nn3c1CCC3)CSCC1=NC=C(CSc3cc(c4ccccc4c3)OCCC2)S1] | $1^6$-chloro-$1^1$methyl-$2^5,2^6$-dihydro-$1^1H,2^4H$-10-oxa-4,8-dithia-6(2,5)-thiazola-1(7,3)-indola-2(3,2)-pyrrolo[1,2-b]pyrazola-9(3,1)-naphthalenacyclotridecaphane-$1^2$-carboxylic acid |
| 5 | 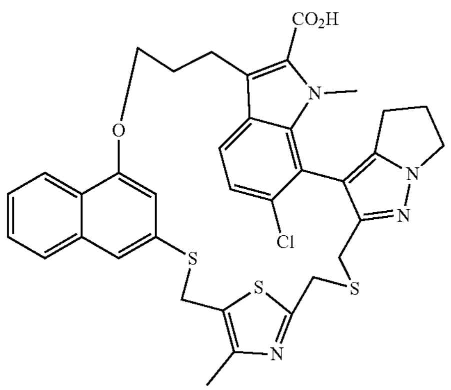 [SMILES: CC1=C2CSc3cc(c4ccccc4c3)OCCCc3c(C(=O)O)n(C)c4c(c(Cl)ccc34)-c3c(nn4c3CCC4)CSCC(=N1)S2] | $1^6$-chloro-$1^1,6^4$-dimethyl-$2^5,2^6$-dihydro-$1^1H,2^4H$-10-oxa-4,8-dithia-6(2,5)-thiazola-1(7,3)-indola-2(3,2)-pyrrolo[1,2-b]pyrazola-9(3,1)-naphthalenacyclotridecaphane-$1^2$-carboxylic acid |
| 6 | 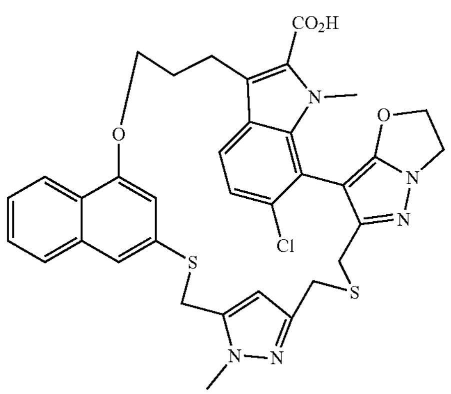 [SMILES: Cn1nc2cc1CSc1cc(c3ccccc3c1)OCCCc1c(C(=O)O)n(C)c3c(c(Cl)ccc13)-c1c(nn3c1OCC3)CSC2] | (Z)-$1^6$-chloro-$1^1,6^1$-dimethyl-$2^2,2^3$-dihydro-$1^1H,6^1H$-10-oxa-4,8-dithia-2(7,6)-pyrazolo[5,1-b]oxazola-1(7,3)-indola-6(3,5)-pyrazola-9(3,1)-naphthalenacyclotridecaphane-$1^2$-carboxylic acid |
| 7 | 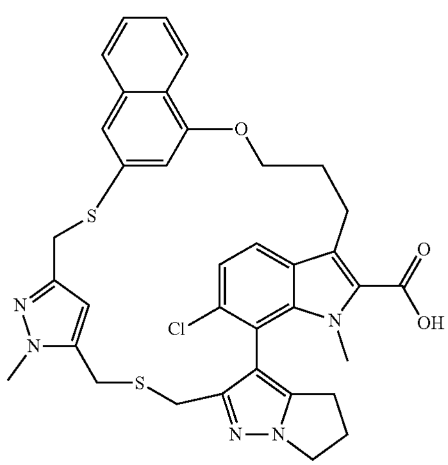 [SMILES: Cn1nc2cc1CSCc1nn3c(c1-c1c(Cl)ccc4c(c(C(=O)O)n(C)c14)CCCOc1cc(cc4ccccc14)SC2)CCC3] | (Z)-$1^6$-chloro-$1^1,6^1$-dimethyl-$2^5,2^6$-dihydro-$1^1H,2^4H,6^1H$-10-oxa-4,8-dithia-1(7,3)-indola-2(3,2)-pyrrolo[1,2-b]pyrazola-6(5,3)-pyrazola-9(3,1)-naphthalenacyclotridecaphane-$1^2$-carboxylic acid |

TABLE 1-continued

| Cpd. No. | Structure | Name |
|---|---|---|
| 8 | 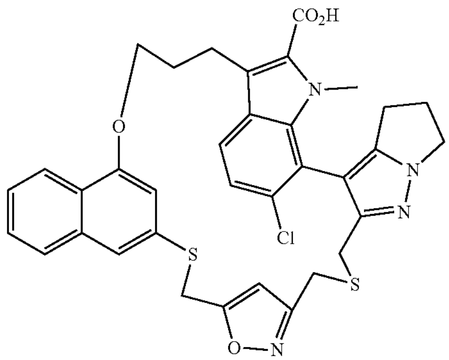 [SMILES: Cn1c(C(=O)O)c2c3ccc(Cl)c(c31)-c1c(nn3c1CCC3)CSCc1cc(on1)CSc1cc(c3ccccc3c1)OCCC2] | (Z)-$1^6$-chloro-$1^1$-methyl-$2^5$,$2^6$-dihydro-$1^1$H,$2^4$H-10-oxa-4,8-dithia-6(3,5)-isoxazola-1(7,3)-indola-2(3,2)-pyrrolo[1,2-b]pyrazola-9(3,1)-naphthalenacyclotridecaphane-$1^2$-carboxylic acid |
| 9 | 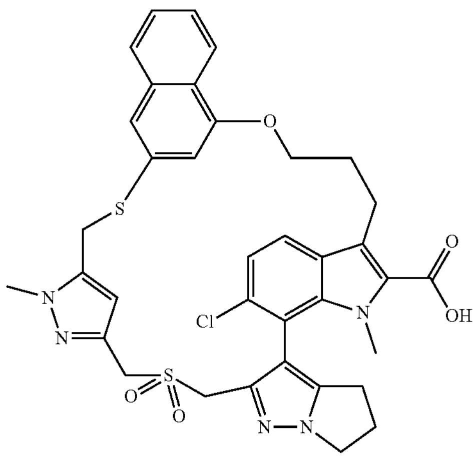 [SMILES: Cn1nc2cc1CSc1cc(c3ccccc3c1)OCCCc1c(C(=O)O)n(C)c3c(c(Cl)ccc13)-c1c(nn3c1CCC3)CS(=O)(=O)C2] | (Z)-$1^6$-chloro-$1^1$,$6^1$-dimethyl-$2^5$,$2^6$-dihydro-$1^1$H,$2^4$H,$6^1$H-10-oxa-4,8-dithia-1(7,3)-indola-2(3,2)-pyrrolo[1,2-b]pyrazola-6(3,5)-pyrazola-9(3,1)-naphthalenacyclotridecaphane-$1^2$-carboxylic acid 4,4-dioxide |
| 10 | 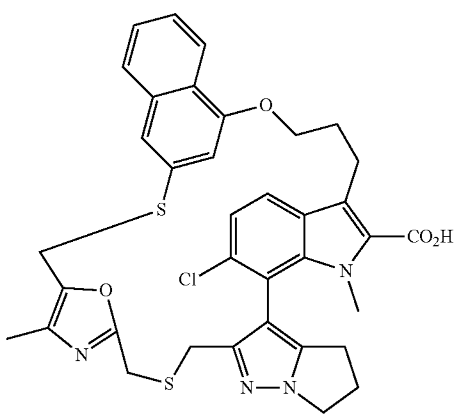 [SMILES: CC1=C2CSc3cc(c4ccccc4c3)OCCCc3c(C(=O)O)n(C)c4c(c(Cl)ccc34)-c3c(nn4c3CCC4)CSCC(=N1)O2] | $1^6$-chloro-$1^1$,$6^4$-dimethyl-$2^5$,$2^6$-dihydro-$1^1$H,$2^4$H-10-oxa-4,8-dithia-6(2,5)-oxazola-1(7,3)-indola-2(3,2)-pyrrolo[1,2-b]pyrazola-9(3,1)-naphthalenacyclotridecaphane-$1^2$-carboxylic acid |
| 11 | 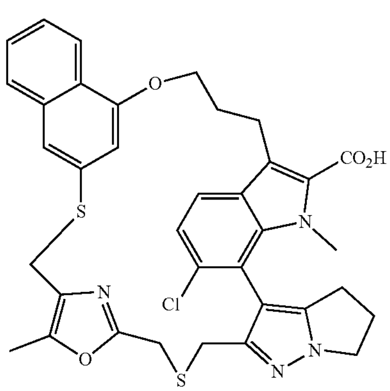 [SMILES: Cc1oc2nc1CSc1cc(c3ccccc3c1)OCCCc1c(C(=O)O)n(C)c3c(c(Cl)ccc13)-c1c(nn3c1CCC3)CSC2] | (Z)-$1^6$-chloro-$1^1$,$6^5$-dimethyl-$2^5$,$2^6$-dihydro-$1^1$H,$2^4$H-10-oxa-4,8-dithia-6(2,4)-oxazola-1(7,3)-indola-2(3,2)-pyrrolo[1,2-b]pyrazola-9(3,1)-naphthalenacyclotridecaphane-$1^2$-carboxylic acid |

TABLE 1-continued

| Cpd. No. | Structure | Name |
| --- | --- | --- |
| 12 | 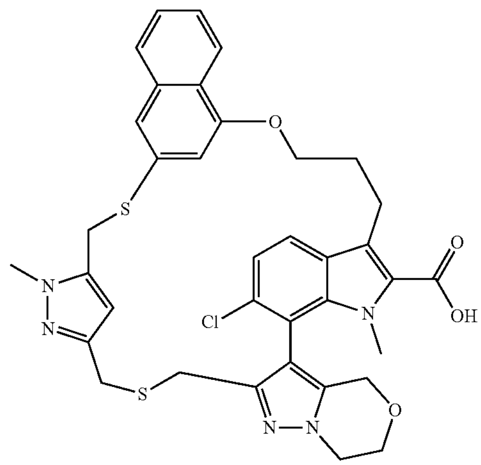 [SMILES: Cn1nc2cc1CSc1cc(c3ccccc3c1)OCCCc1c(C(=O)O)n(C)c3c(c(Cl)ccc13)-c1c(nn3c1COCC3)CSC2] | (Z)-1$^6$-chloro-1$^1$,6$^1$-dimethyl-2$^6$,2$^7$-dihydro-1$^1$H,2$^4$H,6$^1$H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-1$^2$-carboxylic acid |
| 13 | 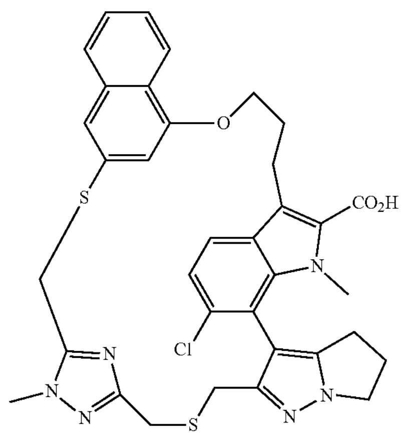 [SMILES: Cn1nc2nc1CSc1cc(c3ccccc3c1)OCCCc1c(C(=O)O)n(C)c3c(c(Cl)ccc13)-c1c(nn3c1CCC3)CSC2] | (Z)-1$^6$-chloro-1$^1$,6$^1$-dimethyl-2$^5$,2$^6$-dihydro-1$^1$H,2$^4$H,6$^1$H-10-oxa-4,8-dithia-1(7,3)-indola-2(3,2)-pyrrolo[1,2-b]pyrazola-6(3,5)-triazola-9(3,1)-naphthalenacyclotridecaphane-1$^2$-carboxylic acid |
| 16 | 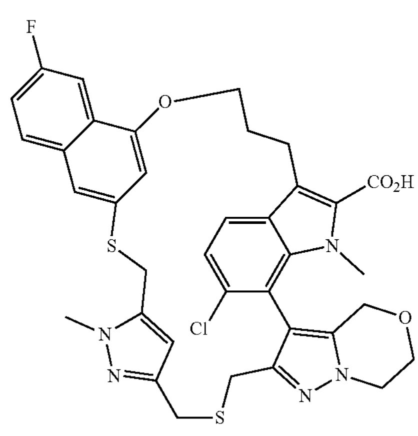 [SMILES: Cn1nc2cc1CSc1cc(c3cc(F)ccc3c1)OCCCc1c(C(=O)O)n(C)c3c(c(Cl)ccc13)-c1c(nn3c1COCC3)CSC2] | (Z)-1$^6$-chloro-9$^7$-fluoro-1$^1$,6$^1$-dimethyl-2$^6$,2$^7$-dihydro-1$^1$H,2$^4$H,6$^1$H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-1$^2$-carboxylic acid |

TABLE 1-continued

| Cpd. No. | Structure | Name |
|---|---|---|
| 17 | 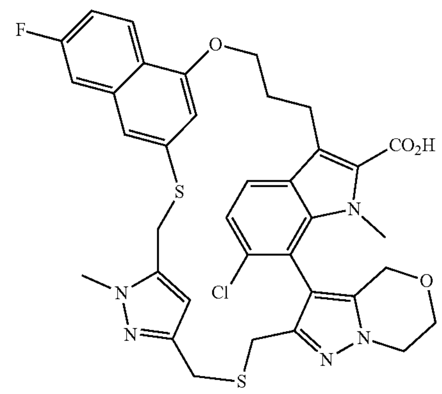 [SMILES: Cn1nc2cc1CSc1cc(c3ccc(F)cc3c1)OCCCc1c(C(=O)O)n(C)c3c(c(Cl)ccc13)-c1c(nn3c1COCC3)CSC2] | (Z)-16-chloro-96-fluoro-11,61-dimethyl-26,27-dihydro-11H,24H,61H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-$1^2$-carboxylic acid |
| 18 | 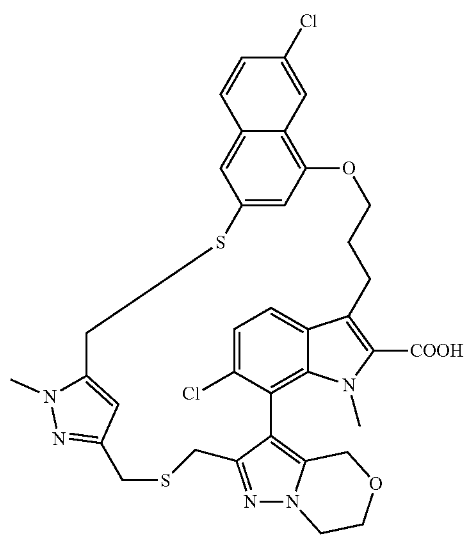 [SMILES: Cn1nc2cc1CSc1cc(c3cc(Cl)ccc3c1)OCCCc1c(C(=O)O)n(C)c3c(c(Cl)ccc13)-c1c(nn3c1COCC3)CSC2] | (Z)-$1^6,9^7$-dichloro-$1^1,6^1$-dimethyl-$2^6,2^7$-dihydro-$1^1$H,$2^4$H,$6^1$H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-$1^2$-carboxylic acid |
| 19 | 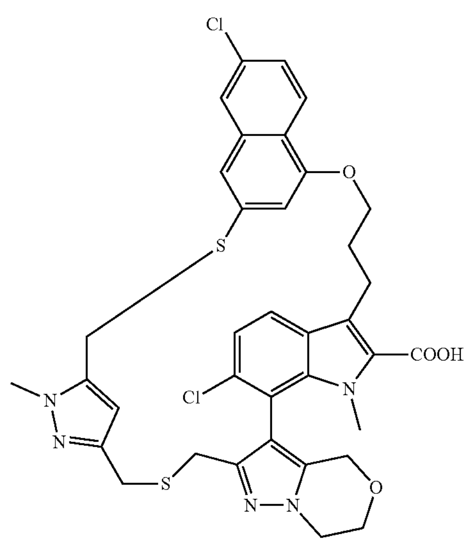 [SMILES: Cn1nc2cc1CSc1cc(c3ccc(Cl)cc3c1)OCCCc1c(C(=O)O)n(C)c3c(c(Cl)ccc13)-c1c(nn3c1COCC3)CSC2] | (Z)-$1^6,9^6$-dichloro-$1^1,6^1$-dimethyl-$2^6,2^7$-dihydro-$1^1$H,$2^4$H,$6^1$H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-$1^2$-carboxylic acid |

TABLE 1-continued

| Cpd. No. | Structure | Name |
|---|---|---|
| 20 | 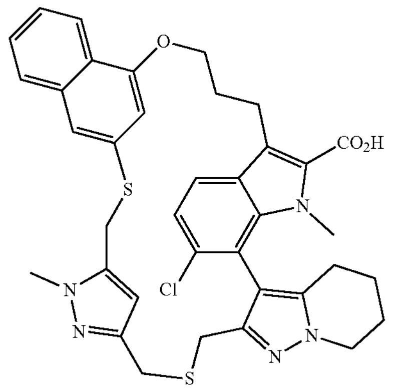 [SMILES: Cn1nc2cc1CSc1cc(c3ccccc3c1)OCCCc1c(C(=O)O)n(C)c3c(c(Cl)ccc13)-c1c(nn3c1CCCC3)CSC2] | (Z)-1$^6$-chloro-1$^1$,6$^1$-dimethyl-2$^4$,2$^5$,2$^6$,2$^7$-tetrahydro-1$^1$H,6$^1$H-10-oxa-4,8-dithia-2(3,2)-pyrazolo[1,5-a]pyridina-1(7,3)-indola-6(3,5)-pyrazola-9(3,1)-naphthalenacyclotridecaphane-1$^2$-carboxylic acid |
| 21 | 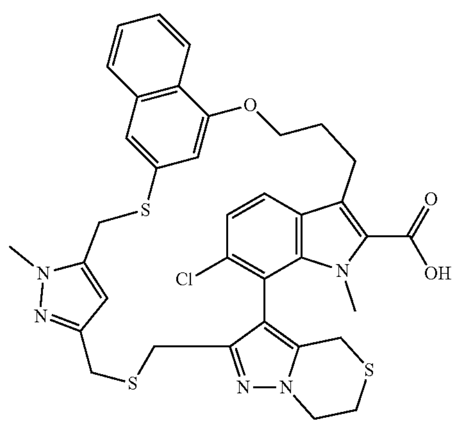 [SMILES: Cn1nc2cc1CSc1cc(c3ccccc3c1)OCCCc1c(C(=O)O)n(C)c3c(c(Cl)ccc13)-c1c(nn3c1CSCC3)CSC2] | (Z)-1$^6$-chloro-1$^1$,6$^1$-dimethyl-2$^6$,2$^7$-dihydro-1$^1$H,2$^4$H,6$^1$H-10-oxa-4,8-dithia-2(3,2)-pyrazolo[5,1-c][1,4]thiazina-1(7,3)-indola-6(3,5)-pyrazola-9(3,1)-naphthalenacyclotridecaphane-1$^2$-carboxylic acid |
| 22 | 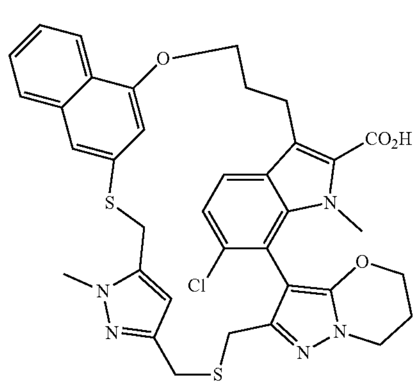 [SMILES: Cn1nc2cc1CSc1cc(c3ccccc3c1)OCCCc1c(C(=O)O)n(C)c3c(c(Cl)ccc13)-c1c(nn3c1OCCC3)CSC2] | (Z)-1$^6$-chloro-1$^1$,6$_1$-dimethyl-2$^6$,2$^7$-dihydro-1$^1$H,2$^5$H,6$^1$H-10-oxa-4,8-dithia-2(3,2)-pyrazolo[5,1-b][1,3]oxazina-1(7,3)-indola-6(3,5)-pyrazola-9(3,1)-naphthalenacyclotridecaphane-1$^2$-carboxylic acid |

TABLE 1-continued

| Cpd. No. | Structure | Name |
|---|---|---|
| 23 | 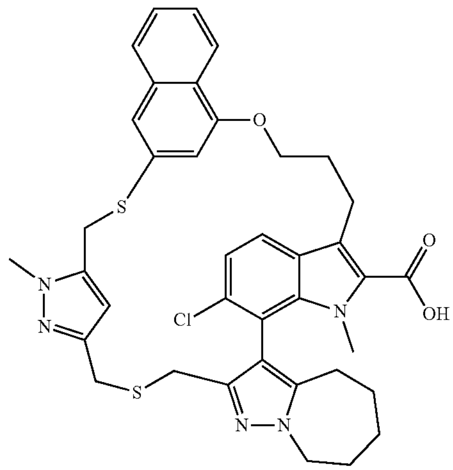 [SMILES: Cn1nc2cc1CSc1cc(c3ccccc3c1)OCCCc1c(C(=O)O)n(C)c3c(c(Cl)ccc13)-c1c(nn3c1CCCCC3)CSC2] | (Z)-1$^6$-chloro-1$^1$,6$^1$-dimethyl-2$^5$,2$^6$,2$^7$,2$^8$-tetrahydro-1$^1$H,2$^4$H,6$^1$H-10-oxa-4,8-dithia-2(3,2)-pyrazolo[1,5-a]azepina-1(7,3)-indola-6(3,5)-pyrazola-9(3,1)-naphthalenacyclotridecaphane-1$^2$-carboxylic acid |
| 24 | 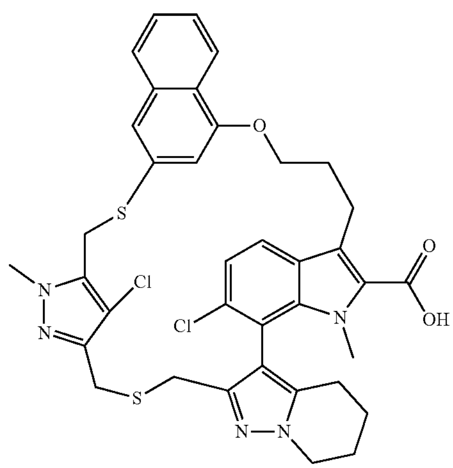 [SMILES: Cn1nc2c(Cl)c1CSc1cc(c3ccccc3c1)OCCCc1c(C(=O)O)n(C)c3c(c(Cl)ccc13)-c1c(nn3c1CCCC3)CSC2] | (E)-1$^6$,6$^4$-dichloro-1$^1$,6$^1$-dimethyl-2$^4$,2$^5$,2$^6$,2$^7$-tetrahydro-1$^1$H,6$^1$H-10-oxa-4,8-dithia-2(3,2)-pyrazolo[1,5-a]pyridina-1(7,3)-indola-6(3,5)-pyrazola-9(3,1)-naphthalenacyclotridecaphane-1$^2$-carboxylic acid |
| 25 | 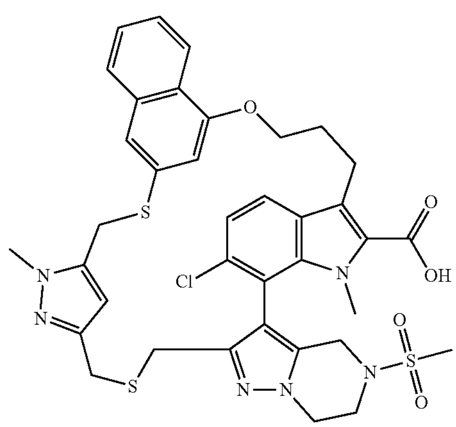 | (Z)-1$^6$-chloro-1$^1$,6$^1$-dimethyl-2$^5$-(methylsulfonyl)-2$^4$,2$^5$,2$^6$,2$^7$-tetrahydro-1$^1$H,6$^1$H-10-oxa-4,8-dithia-2(3,2)-pyrazolo[1,5-a]pyrazina-1(7,3)-indola-6(3,5)-pyrazola-9(3,1)-naphthalenacyclotridecaphane-1$^2$-carboxylic acid |

TABLE 1-continued

| Cpd. No. | Structure | Name |
|---|---|---|
| 26 | 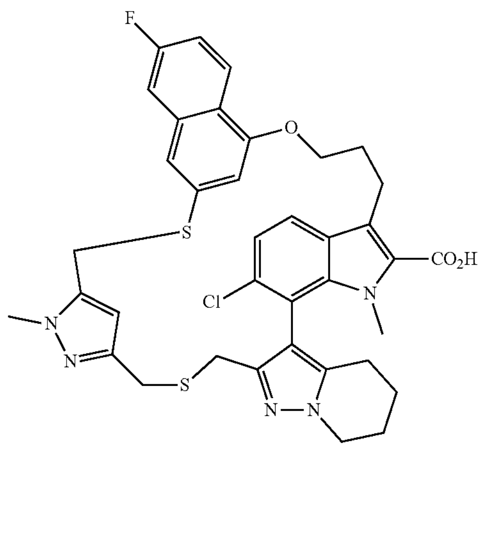 [SMILES: Cn1nc2cc1CSc1cc(c3ccc(F)cc3c1)OCCCc1c(C(=O)O)n(C)c3c(c(Cl)ccc13)-c1c(nn3c1CCCC3)CSC2] | (Z)-1$^6$-chloro-96-fluoro-1$^1$,6$^1$-dimethyl-2$^4$,2$^5$,2$^6$,2$^7$-tetrahydro-1$^1$H,6$^1$H-10-oxa-4,8-dithia-2(3,2)-pyrazolo[1,5-a]pyridina-1(7,3)-indola-6(3,5)-pyrazola-9(3,1)-naphthalenacyclotridecaphane-1$^2$-carboxylic acid |
| 27 | 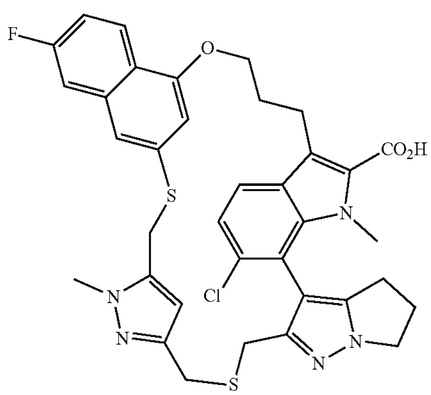 [SMILES: Cn1nc2cc1CSc1cc(c3ccc(F)cc3c1)OCCCc1c(C(=O)O)n(C)c3c(c(Cl)ccc13)-c1c(nn3c1CCC3)CSC2] | (Z)-1$^6$-chloro-9$^6$-fluoro-1$^1$,6$^1$-dimethyl-2$^5$,2$^6$-dihydro-1$^1$H,2$^4$H,6$^1$H-10-oxa-4,8-dithia-1(7,3)-indola-2(3,2)-pyrrolo[1,2-b]pyrazola-6(3,5)-pyrazola-9(3,1)-naphthalenacyclotridecaphane-1$^2$-carboxylic acid |
| 28 | 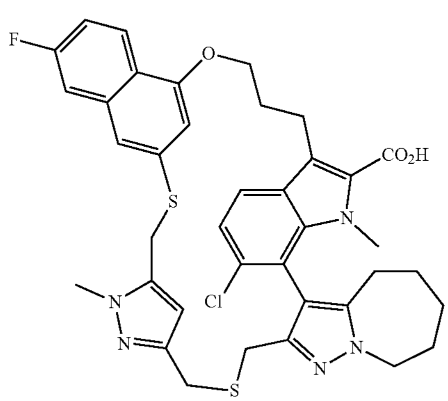 [SMILES: Cn1nc2cc1CSc1cc(c3ccc(F)cc3c1)OCCCc1c(C(=O)O)n(C)c3c(c(Cl)ccc13)-c1c(nn3c1CCCCC3)CSC2] | (Z)-1$^6$-chloro-9$^6$-fluoro-1$^1$,6$^1$dimethyl-2$^5$,2$^6$,2$^7$,2$^8$-tetrahydro-1$^1$H,2$^4$H,6$^1$H-10-oxa-4,8-dithia-2(3,2)-pyrazolo[1,5-a]azepina-1(7,3)-indola-6(3,5)-pyrazola-9(3,1)-naphthalenacyclotridecaphane-1$^2$-carboxylic acid |

TABLE 1-continued

| Cpd. No. | Structure | Name |
| --- | --- | --- |
| 29 | 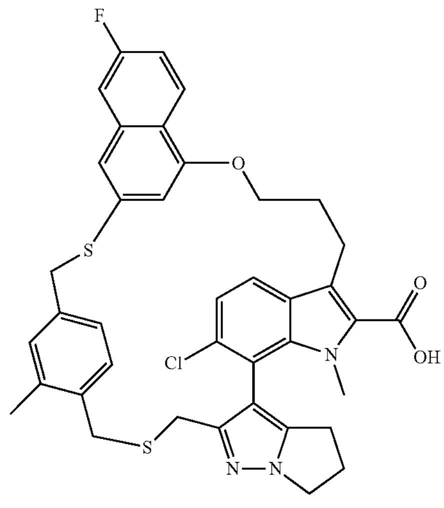 [SMILES: Cc1cc2ccc1CSCc1nn3c(c1-c1c(Cl)ccc4c(c(C(=O)O)n(C)c14)CCCOc1cc(cc4cc(F)ccc14)SC2)CCC3] | $1^6$-chloro-$9^6$-fluoro-$1^1$,$6^2$-dimethyl-$2^5$,$2^6$-dihydro-$1^1$H,$2^4$H-10-oxa-4,8-dithia-1(7,3)-indola-2(3,2)-pyrrolo[1,2-b]pyrazola-9(3,1)-naphthalena-6(1,4)-benzenacyclotridecaphane-$1^2$-carboxylic acid |
| 30 | 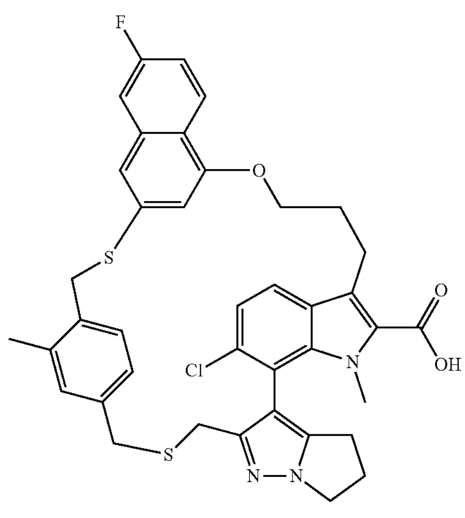 [SMILES: Cc1cc2ccc1CSc1cc(c3ccc(F)cc3c1)OCCCc1c(C(=O)O)n(C)c3c(c(Cl)ccc13)-c1c(nn3c1CCC3)CSC2] | $1^6$-chloro-$9^6$-fluoro-$1^1$,$6^3$-dimethyl-$2^5$,$2^6$-dihydro-$1^1$H,$2^4$H-10-oxa-4,8-dithia-1(7,3)-indola-2(3,2)-pyrrolo[1,2-b]pyrazola-9(3,1)-naphthalena-6(1,4)-benzenacyclotridecaphane-$1^2$-carboxylic acid |
| 31 | 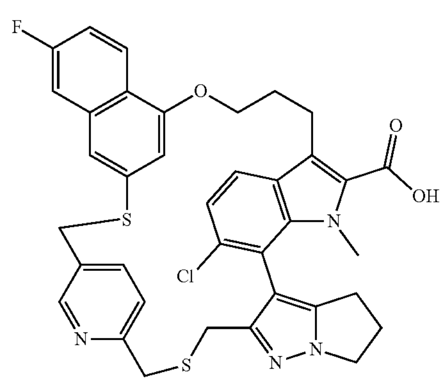 [SMILES: Cn1c(C(=O)O)c2c3ccc(Cl)c(c31)-c1c(nn3c1CCC3)CSCc1ccc(cn1)CSc1cc(c3ccc(F)cc3c1)OCCC2] | $1^6$-chloro-$9^6$-fluoro-$1^1$-methyl-$2^5$,$2^6$-dihydro-$1^1$H,$2^4$H-10-oxa-4,8-dithia-1(7,3)-indola-2(3,2)-pyrrolo[1,2-b]pyrazola-6(2,5)-pyridina-9(3,1)-naphthalenacyclotridecaphane-$1^2$-carboxylic acid |

TABLE 1-continued

| Cpd. No. | Structure | Name |
|---|---|---|
| 32 | 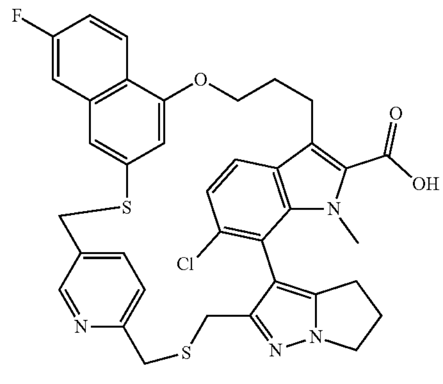 [SMILES: Cn1c(C(=O)O)c2c3ccc(Cl)c(c31)-c1c(nn3c1CCC3)CSCc1ccc(cn1)CSc1cc(c3ccc(F)cc3c1)OCCC2] | $1^6$-chloro-$9^6$-fluoro-$1^1$-methyl-$2^5$,$2^6$-dihydro-$1^1$H,$2^4$H-10-oxa-4,8-dithia-1(7,3)-indola-2(3,2)-pyrrolo[1,2-b]pyrazola-6(5,2)-pyridina-9(3,1)-naphthalenacyclotridecaphane-$1^2$-carboxylic acid |
| 33 | 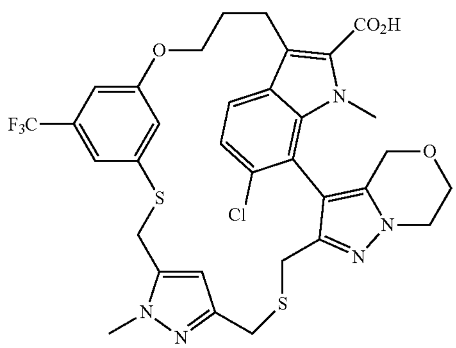 [SMILES: Cn1nc2cc1CSc1cc(cc(C(F)(F)F)c1)OCCCc1c(C(=O)O)n(C)c3c(c(Cl)ccc13)-c1c(nn3c1COCC3)CSC2] | (Z)-$1^6$-chloro-$1^1$,$6^1$-dimethyl-$9^5$-(trifluoromethyl)-$2^6$,$2^7$-dihydro-$1^1$H,$2^4$H,$6^1$H-10-oxa-4,8-dithia-2(3,2)-pyrazolo[5,1-c][1,4]oxazina-1(7,3)-indola-6(3,5)-pyrazola-9(l,3)-benzenacyclotridecaphane-$1^2$-carboxylic acid |
| 35 | 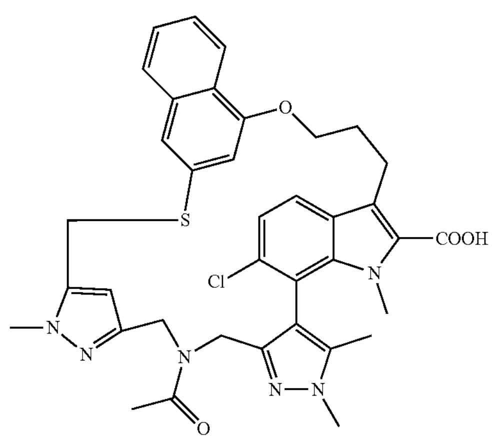 [SMILES: CC(=O)N1Cc2cc(n(C)n2)CSc2cc(c3ccccc3c2)OCCCc2c(C(=O)O)n(C)c3c(c(Cl)ccc23)-c2c(nn(C)c2C)C1] | (Z)-4-acetyl-$1^6$-chloro-$1^1$,$2^1$,$2^5$,$6^1$-tetramethyl-$1^1$H,$2^1$H,$6^1$H-10-oxa-8-thia-4-aza-1(7,3)-indola-2(4,3),6(3,5)-dipyrazola-9(3,1)-naphthalenacyclotridecaphane-$1^2$-carboxylic acid |

TABLE 1-continued

| Cpd. No. | Structure | Name |
|---|---|---|
| 36 | 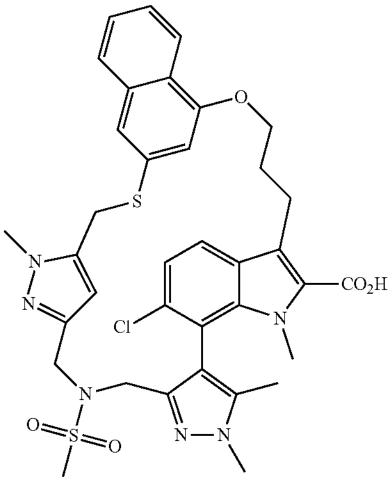 [SMILES: Cc1c2c(nn1C)CN(S(C)(=O)=O)Cc1cc(n(C)n1)CSc1cc(c3ccccc3c1)OCCCc1c(C(=O)O)n(C)c3c-2c(Cl)ccc13] | (Z)-1⁶-chloro-1¹,2¹,2⁵,6¹-tetramethyl-4-(methylsulfonyl)-1¹H,2¹H,6¹H-10-oxa-8-thia-4-aza-1(7,3)-indola-2(4,3),6(3,5)-dipyrazola-9(3,1)-naphthalenacyclotridecaphane-1²-carboxylic acid |
| 37 | 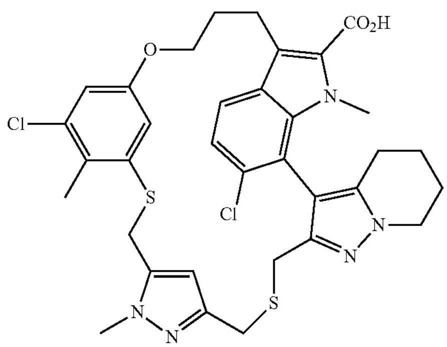 [SMILES: Cc1c(Cl)cc2cc1SCc1cc(nn1C)CSCc1nn3c(c1-c1c(Cl)ccc4c(c(C(=O)O)n(C)c14)CCCO2)CCCC3] | (Z)-1⁶,9⁵-dichloro-1¹,6¹,9⁶-trimethyl-2⁴,2⁵,2⁶,2⁷-tetrahydro-1¹H,6¹H-10-oxa-4,8-dithia-2(3,2)-pyrazolo[1,5-a]pyridina-1(7,3)-indola-6(3,5)-pyrazola-9(1,3)-benzenacyclotridecaphane-1²-carboxylic acid |
| 38 | 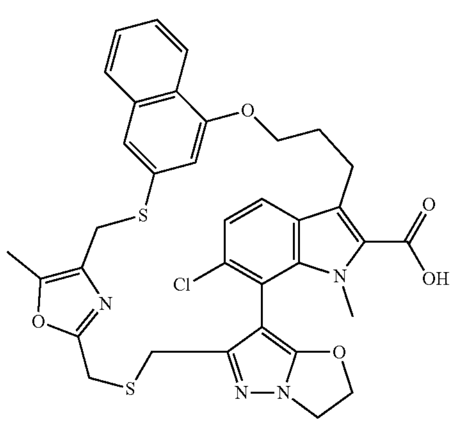 [SMILES: Cc1oc2nc1CSc1cc(c3ccccc3c1)OCCCc1c(C(=O)O)n(C)c3c(c(Cl)ccc13)-c1c(nn3c1OCC3)CSC2] | (Z)-1⁶-chloro-1¹,6⁵-dimethyl-2²,2³-dihydro-1¹H-10-oxa-4,8-dithia-2(7,6)-pyrazolo[5,1-b]oxazola-6(2,4)-oxazola-1(7,3)-indola-9(3,1)-naphthalenacyclotridecaphane-1²-carboxylic acid |

TABLE 1-continued

| Cpd. No. | Structure | Name |
|---|---|---|
| 39 | 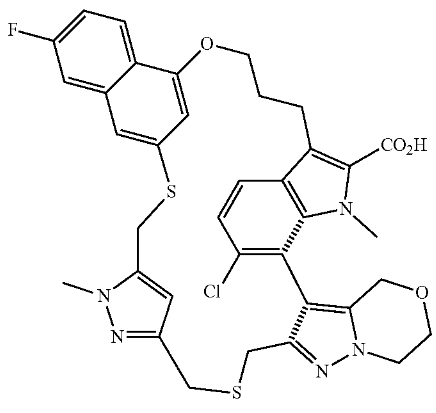 | (S)-(Z)-1⁶-chloro-9⁶-fluoro-1¹,6¹-dimethyl-26,27-dihydro-1¹H,2⁴H,6¹H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-1²-carboxylic acid |
| 40 | 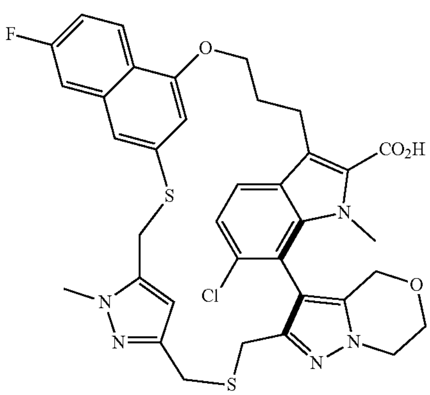 | (R)-(Z)-1⁶-chloro-9⁶-fluoro-1¹,6¹-dimethyl-26,27-dihydro-1¹H,2⁴H,6¹H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-1²-carboxylic acid |
| 41 | 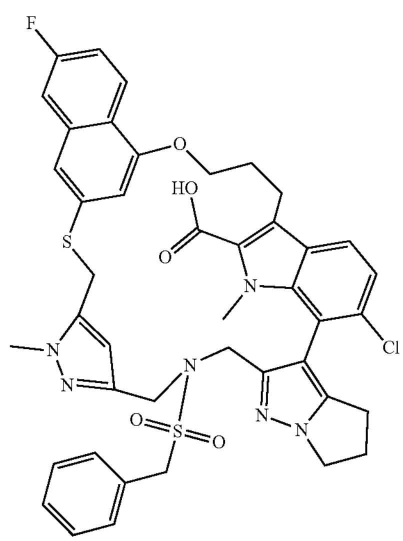 [SMILES: Cn1nc2cc1CSc1cc(c3ccc(F)cc3c1)OCCCc1c(C(=O)O)n(C)c3c(c(Cl)ccc13)-c1c(nn3c1CCC3)CN(S(=O)(=O)Cc1ccccc1)C2] | (Z)-4-(benzylsulfonyl)-1⁶-chloro-9⁶-fluoro-1,6¹-dimethyl-2⁵,2⁶-dihydro-1¹H,2⁴H,6¹H-10-oxa-8-thia-4-aza-1(7,3)-indola-2(3,2)-pyrrolo[1,2-b]pyrazola-6(3,5)-pyrazola-9(3,1)-naphthalenacyclotridecaphane-1²-carboxylic acid |

TABLE 1-continued

| Cpd. No. | Structure | Name |
|---|---|---|
| 42 | 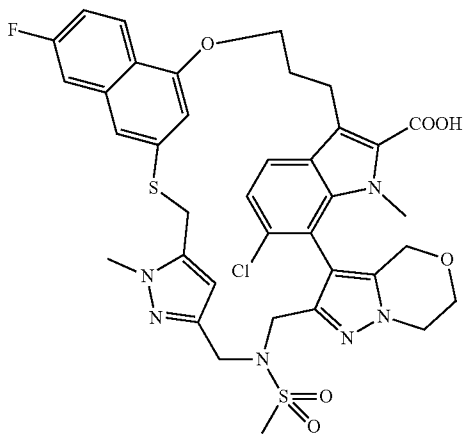 [SMILES: Cn1nc2cc1CSc1cc(c3ccc(F)cc3c1)OCCCc1c(C(=O)O)n(C)c3c(c(Cl)ccc13)-c1c(nn3c1COCC3)CN(S(C)(=O)=O)C2] | (Z)-1⁶-chloro-9⁶-fluoro-1¹,6¹-dimethyl-4-(methylsulfonyl)-2⁶,2⁷-dihydro-1¹H,2⁴H,6¹H-10-oxa-8-thia-4-aza-2(3,2)-pyrazolo[5,1-c][1,4]oxazina-1(7,3)-indola-6(3,5)-pyrazola-9(3,1)-naphthalenacyclotridecaphane-1²-carboxylic acid |
| 43 | 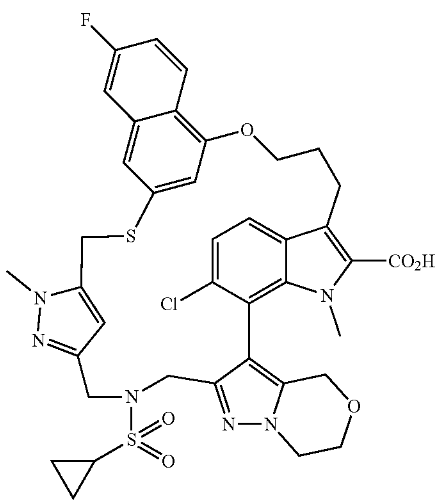 [SMILES: Cn1nc2cc1CSc1cc(c3ccc(F)cc3c1)OCCCc1c(C(=O)O)n(C)c3c(c(Cl)ccc13)-c1c(nn3c1COCC3)CN(S(=O)(=O)C1CC1)C2] | (Z)-1⁶-chloro-4-(cyclopropylsulfonyl)-9⁶-fluoro-1¹,6¹-dimethyl-2⁶,2⁷-dihydro-1¹H,2⁴H,6¹H-10-oxa-8-thia-4-aza-2(3,2)-pyrazolo[5,1-c][1,4]oxazina-1(7,3)-indola-6(3,5)-pyrazola-9(3,1)-naphthalenacyclotridecaphane-1²-carboxylic acid |
| 44 | 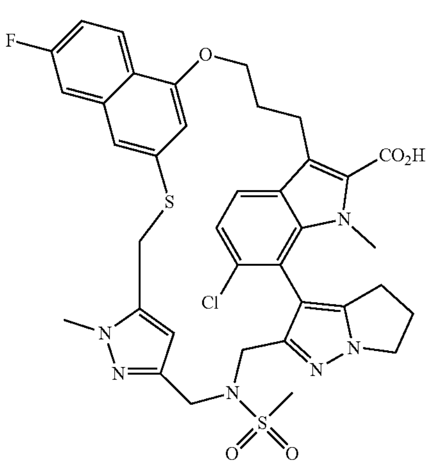 [SMILES: Cn1nc2cc1CSc1cc(c3ccc(F)cc3c1)OCCCc1c(C(=O)O)n(C)c3c(c(Cl)ccc13)-c1c(nn3c1CCC3)CN(S(C)(=O)=O)C2] | (Z)-1⁶-chloro-9⁶-fluoro-1¹,6¹-dimethyl-4-(methylsulfonyl)-2⁵,2⁶-dihydro-1¹H,2⁴H,6¹H-10-oxa-8-thia-4-aza-1(7,3)-indola-2(3,2)-pyrrolo[1,2-b]pyrazola-6(3,5)-pyrazola-9(3,1)-naphthalenacyclotridecaphane-1²-carboxylic acid |

TABLE 1-continued

| Cpd. No. | Structure | Name |
|---|---|---|
| 45 | 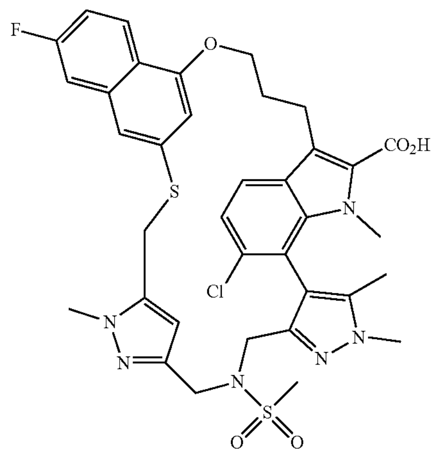 [SMILES: Cc1c2c(nn1C)CN(S(C)(=O)=O)Cc1cc(n(C)n1)CSc1cc(c3ccc(F)cc3c1)OCCCc1c(C(=O)O)n(C)c3c-2c(Cl)ccc13] | (Z)-$1^6$-chloro-$9^6$-fluoro-$1^1,2^1,2^5,6^1$-tetramethyl-4-(methylsulfonyl)-$1^1H,2^1H,6^1H$-10-oxa-8-thia-4-aza-1(7,3)-indola-2(4,3),6(3,5)-dipyrazola-9(3,1)-naphthalenacyclotridecaphane-$1^2$-carboxylic acid |
| 46 | 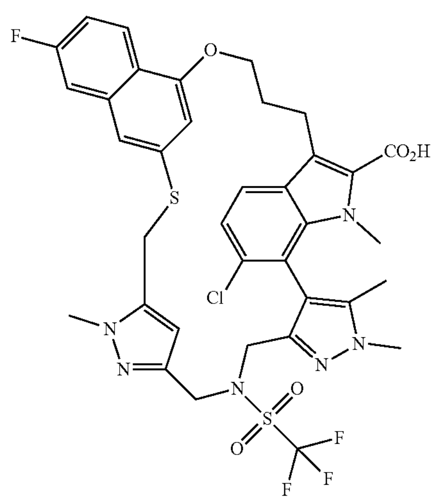 [SMILES: Cc1c2c(nn1C)CN(S(=O)(=O)C(F)(F)F)Cc1cc(n(C)n1)CSc1cc(c3ccc(F)cc3c1)OCCCc1c(C(=O)O)n(C)c3c-2c(Cl)ccc13] | (Z)-$1^6$-chloro-$9^6$-fluoro-$1^1,2^1,2^5,6^1$-tetramethyl-4-((trifluoromethyl)sulfonyl)-$1^1H,2^1H,6^1H$-10-oxa-8-thia-4-aza-1(7,3)-indola-2(4,3),6(3,5)-dipyrazola-9(3,1)-naphthalenacyclotridecaphane-$1^2$-carboxylic acid |
| 47 | 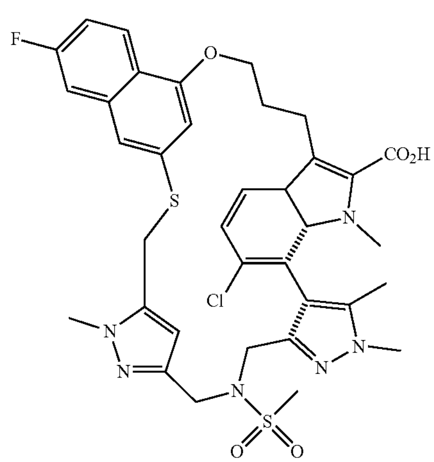 | (S)-(Z)-$1^6$-chloro-$9^6$-fluoro-$1^1,2^1,2^5,6^1$-tetramethyl-4-(methylsulfonyl)-$1^1H,2^1H,6^1H$-10-oxa-8-thia-4-aza-1(7,3)-indola-2(4,3),6(3,5)-dipyrazola-9(3,1)-naphthalenacyclotridecaphane-$1^2$-carboxylic acid |

TABLE 1-continued

| Cpd. No. | Structure | Name |
|---|---|---|
| 48 | 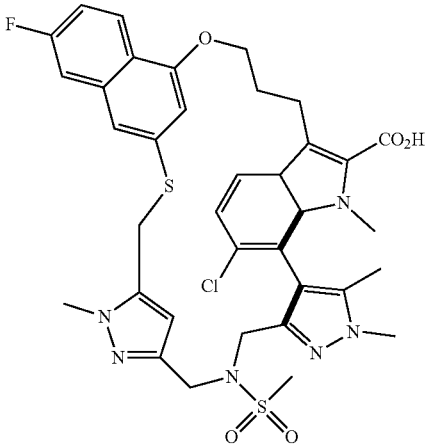 | (R)-(Z)-1⁶-chloro-9⁶-fluoro-1¹,2¹,2⁵,6¹-tetramethyl-4-(methylsulfonyl)-1¹H,2¹H,6¹H-10-oxa-8-thia-4-aza-1(7,3)-indola-2(4,3),6(3,5)-dipyrazola-9(3,1)-naphthalenacyclotridecaphane-1²-carboxylic acid |
| 49 | 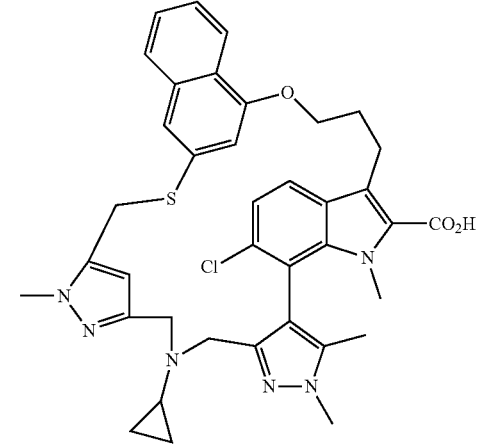 [SMILES: Cc1c2c(nn1C)CN(C1CC1)Cc1cc(n(C)n1)CSc1cc(c3ccccc3c1)OCCCc1c(C(=O)O)n(C)c3c-2c(Cl)ccc13] | (Z)-1⁶-chloro-4-cyclopropyl-1¹,2¹,2⁵,6¹-tetramethyl-1¹H,2¹H,6¹H-10-oxa-8-thia-4-aza-1(7,3)-indola-2(4,3),6(3,5)-dipyrazola-9(3,1)-naphthalenacyclotridecaphane-1²-carboxylic acid |
| 50 | 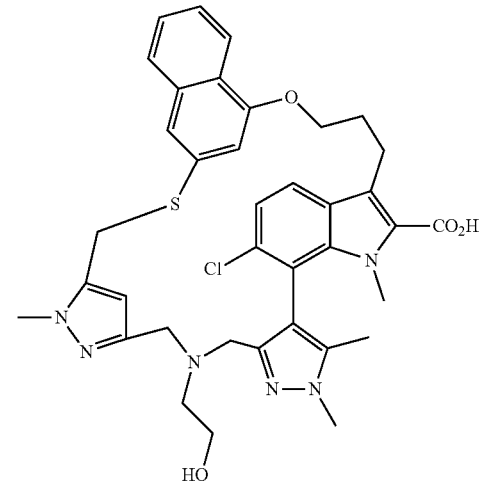 [SMILES: Cc1c2c(nn1C)CN(CCO)Cc1cc(n(C)n1)CSc1cc(c3ccccc3c1)OCCCc1c(C(=O)O)n(C)c3c-2c(Cl)ccc13] | (Z)-1⁶-chloro-4-(2-hydroxyethyl)-1¹,2¹,2⁵,6¹-tetramethyl-1¹H,2¹H,6¹H-10-oxa-8-thia-4-aza-1(7,3)-indola-2(4,3), 6(3,5)-dipyrazola-9(3,1)-naphthalenacyclotridecaphane-1²-carboxylic acid |

TABLE 1-continued

| Cpd. No. | Structure | Name |
|---|---|---|
| 51 | 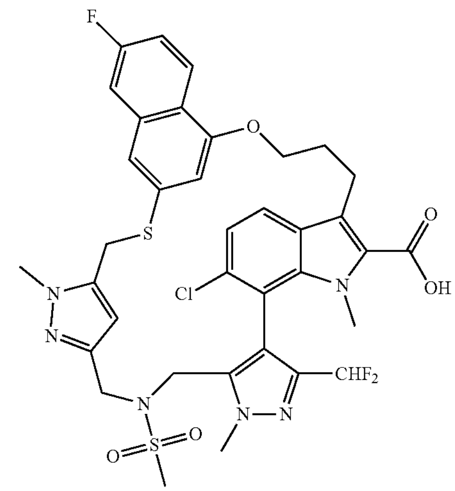 [SMILES: Cn1nc2cc1CSc1cc(c3ccc(F)cc3c1)OCCCc1c(C(=O)O)n(C)c3c(c(Cl)ccc13)-c1c(C(F)F)nn(C)c1CN(S(C)(=O)=O)C2] | (Z)-1$^6$-chloro-2$^3$-(difluoromethyl)-9$^6$-fluoro-1$^1$,2$^1$,6$^1$-trimethyl-4-(methylsulfonyl)-1$^1$H,2$^1$H,6$^1$H-10-oxa-8-thia-4-aza-1(7,3)-indola-2(4,5),6(3,5)-dipyrazola-9(3,1)-naphthalenacyclotridecaphane-1$^2$-carboxylic acid |
| 52 | 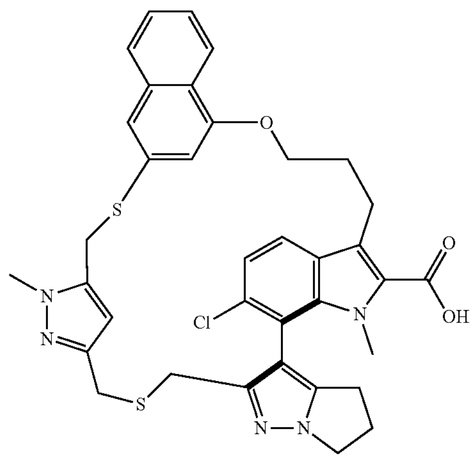 | (R)-(Z)-1$^6$-chloro-1$^1$,6$^1$-dimethyl-2$^5$,2$^6$-dihydro-1$^1$H,2$^4$H,6$^1$H-10-oxa-4,8-dithia-1(7,3)-indola-2(3,2)-pyrrolo[1,2-b]pyrazola-6(3,5)-pyrazola-9(3,1)-naphthalenacyclotridecaphane-1$^2$-carboxylic acid |
| 53 | 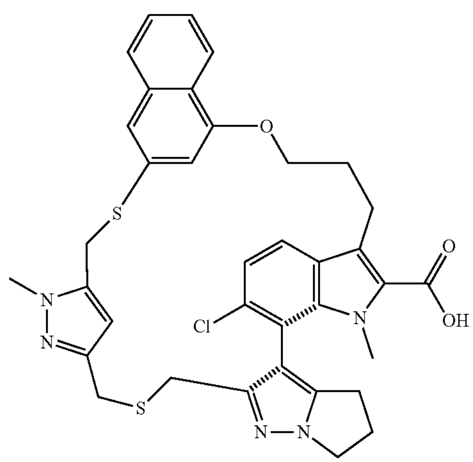 | (S)-(Z)-1$^6$-chloro-1$^1$,6$^1$-dimethyl-2$^5$,2$^6$-dihydro-1$^1$H,2$^4$H,6$^1$H-10-oxa-4,8-dithia-1(7,3)-indola-2(3,2)-pyrrolo[1,2-b]pyrazola-6(3,5)-pyrazola-9(3,1)-naphthalenacyclotridecaphane-1$^2$-carboxylic acid |

In another embodiment, the disclosure provides a pharmaceutical composition comprising a Compound of the Disclosure and a pharmaceutically acceptable carrier.

In another embodiment, Compounds of the Disclosure are enantiomerically enriched, e.g., the enantiomeric excess or "ee" of the compound is about 5% or more as measured by chiral HPLC. In another embodiment, the ee is about 10%. In another embodiment, the ee is about 20%. In another embodiment, the ee is about 30%. In another embodiment, the ee is about 40%. In another embodiment, the ee is about 50%. In another embodiment, the ee is about 60%. In another embodiment, the ee is about 70%. In another embodiment, the ee is about 80%. In another embodiment, the ee is about 85%. In another embodiment, the ee is about 90%. In another embodiment, the ee is about 91%. In another embodiment, the ee is about 92%. In another embodiment, the ee is about 93%. In another embodiment, the ee is about 94%. In another embodiment, the ee is about 95%. In another embodiment, the ee is about 96%. In another embodiment, the ee is about 97%. In another embodiment, the ee is about 98%. In another embodiment, the ee is about 99%.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with a suitable acid. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Non-limiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate, or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, and ethanol, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

II. Intermediates of the Disclosure

The disclosure also provides synthetic intermediates, collectively referred to as "Intermediates of the Disclosure," that can be used to prepare Compounds of the Disclosure. The following particular embodiments are drawn to Intermediates of the Disclosure.

Embodiment I1. A compound of Formula XV:

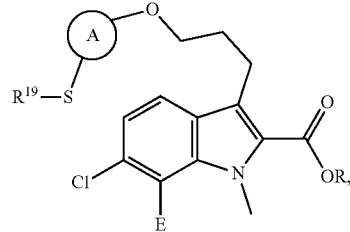

XV wherein:

R is selected from the group consisting of hydrogen and $C_1$-$C_6$ alkyl;

Ⓐ is selected from the group consisting of:

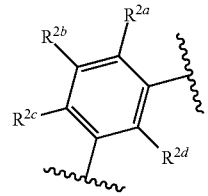

A-1 and

-continued

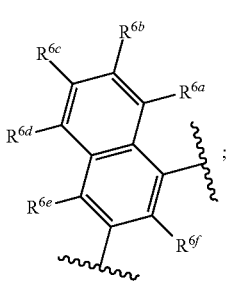

A-2

$R^{2a}$, $R^{2b}$, $R^{2c}$, and $R^{2d}$ are each independently selected from the group consisting of hydrogen, halo, cyano, $C_1$-$C_4$ alkyl, $C_1$-$C_4$ haloalkyl, and $C_1$-$C_4$ alkoxy;

$R^{6a}$, $R^{6b}$, $R^{6c}$, $R^{6d}$, $R^{6e}$, and $R^{6f}$ are each independently selected from the group consisting of hydrogen, halo, cyano, $C_1$-$C_4$ alkyl, $C_1$-$C_4$ haloalkyl, and $C_1$-$C_4$ alkoxy;

$R^{19}$ is selected from the group consisting of hydrogen and a protecting group;

E is selected from the group consisting of:

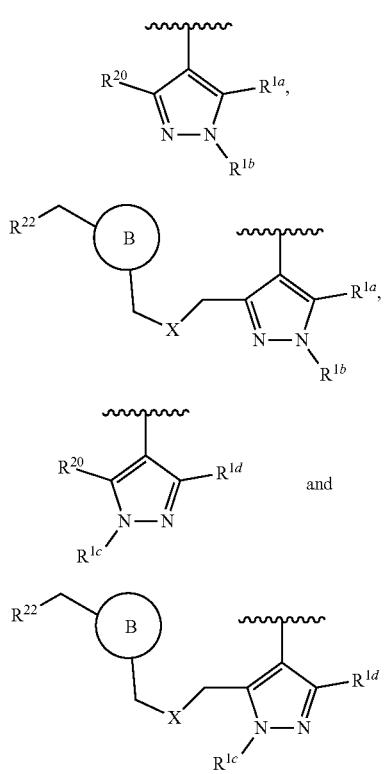

$R^{1a}$ and $R^{1b}$ are each independently selected from the group consisting of hydrogen, $C_1$-$C_4$ alkyl, $C_1$-$C_4$ haloalkyl, and $C_3$-$C_6$ cycloalkyl; or $R^{1a}$ and $R^{1b}$ taken together with the carbon and nitrogen atoms to which they are attached form an optionally substituted 4- to 8-membered heterocyclo;

$R^{1c}$ and $R^{1d}$ are each independently selected from the group consisting of hydrogen, $C_1$-$C_4$ alkyl, $C_1$-$C_4$ haloalkyl, and $C_3$-$C_6$ cycloalkyl;

X is selected from the group consisting of —O—, —S—, —S(=O)—, —S(=O)$_2$—, and —N($R^3$)—;

$R^3$ is selected from the group consisting of hydrogen, $C_1$-$C_4$ alkyl, $C_3$-$C_6$ cycloalkyl, hydroxyalkyl, —C(=O)$R^4$, and —S(=O)$_2R^5$;

$R^4$ is selected from the group consisting of $C_1$-$C_4$ alkyl, $C_1$-$C_4$ haloalkyl, optionally substituted $C_3$-$C_6$ cycloalkyl, optionally substituted 4- to 8-membered heterocyclo, optionally substituted $C_6$-$C_{10}$ aryl, optionally substituted 5- to 10-membered heteroaryl, and ($C_6$-$C_{10}$ aryl)$C_1$-$C_4$ alkyl;

$R^5$ is selected from the group consisting of $C_1$-$C_4$ alkyl, $C_1$-$C_4$ haloalkyl, optionally substituted $C_3$-$C_6$ cycloalkyl, optionally substituted 4- to 8-membered heterocyclo, optionally substituted $C_6$-$C_{10}$ aryl, optionally substituted 5- to 10-membered heteroaryl, and ($C_6$-$C_{10}$ aryl)$C_1$-$C_4$ alkyl;

$R^{20}$ is selected from the group consisting of —C(=O)H, —CH$_2$-LG, and —CH$_2$X$R^{21}$;

LG is a leaving group;

X is selected from the group consisting of —O—, —S—, and —N(H)—;

$R^{21}$ is selected from the group consisting of hydrogen, $C_1$-$C_4$ alkyl, $C_1$-$C_4$ hydroxyalkyl, optionally substituted $C_3$-$C_6$ cycloalkyl, optionally substituted $C_6$-$C_{10}$ aryl, ($C_6$-$C_{10}$ aryl)$C_1$-$C_4$ alkyl, optionally substituted 5- to 10-membered heteroaryl, (5- to 10-membered heteroaryl)$C_1$-$C_4$ alkyl, ($C_1$-$C_4$ alkoxy)$C_1$-$C_4$ alkyl, and a protecting group;

Ⓑ is selected from the group consisting of arylenyl and heteroarylenyl;

$R^{22}$ is selected from the group consisting of —O$R^{23}$ and a leaving group; and $R^{23}$ is selected from the group consisting of hydrogen and a protecting group, or a salt or solvate thereof.

Embodiment I2. The compound of Embodiment I1, wherein E is E-1.

Embodiment I3. The compound of Embodiment I1, wherein E is E-2.

Embodiment I4. The compound of Embodiment I2 of Formula XVI:

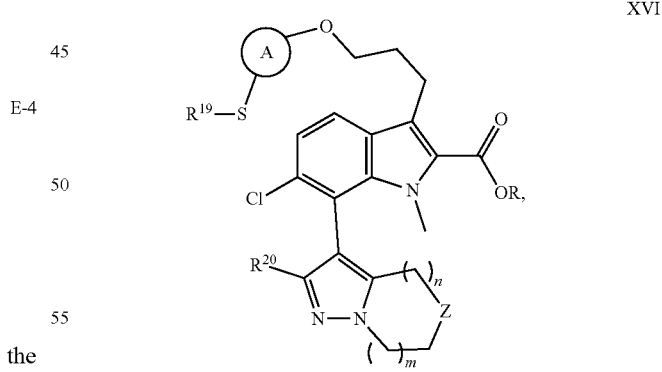

XVI wherein:

m is 0, 1, or 2;

n is 0 or 1;

with the proviso that when m is 0, Z is —CR$^{13a}$R$^{13b}$—;

Z is selected from the group consisting of —CR$^{13a}$R$^{13b}$—, —O—, —S—, S(=O)—, S(=O)$_2$—, and —N($R^{10}$)—;

$R^{10}$ is selected from the group consisting of hydrogen, $C_1$-$C_4$ alkyl, —C(=O)$_2R^{11}$, and —S(=O)$_2R^2$;

$R^{11}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl;

$R^{12}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl; and $R^{13a}$ and $R^{13b}$ are independently selected from the group consisting of hydrogen and $C_1$-$C_4$ alkyl.

Embodiment I5. The compound of Embodiment I4, wherein $R^{20}$ is selected from the group consisting of —C(=O)H, —CH$_2$Br, —CH$_2$OH, and —CH$_2$NH$_2$.

Embodiment I6. The compound of Embodiment I3 of Formula XVII:

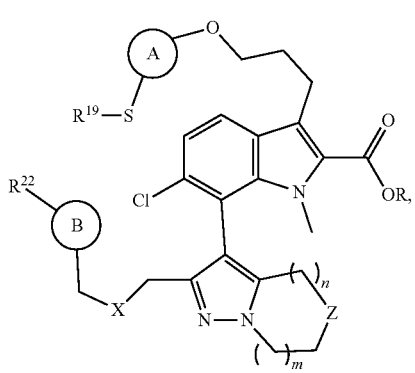

XVII wherein:
m is 0, 1, or 2;
n is 0 or 1;
with the proviso that when m is 0, Z is —CR$^{13a}$R$^{13b}$—;
Z is selected from the group consisting of —CR$^{13a}$R$^{13b}$—, —O—, —S—, S(=O)—, S(=O)$_2$—, and —N(R$^{10}$)—;
$R^{10}$ is selected from the group consisting of hydrogen, $C_1$-$C_4$ alkyl, —C(=O)$_2$R$^{11}$, and —S(=O)$_2$R$^{12}$;
$R^{11}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl;
$R^{12}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl; and
$R^{13a}$ and $R^{13b}$ are independently selected from the group consisting of hydrogen and $C_1$-$C_4$ alkyl.

Embodiment I7. The compound of Embodiment I6, wherein $R^{22}$ is selected from the group consisting of —OH and —Br.

Embodiment I8. The compound of any one of Embodiments I4-I7, wherein Z is —O—.

Embodiment I9. The compound of Embodiments I4-I7, wherein Z is —CH$_2$—.

Embodiment I10. The compound of Embodiments I4-I7, wherein Z is —S—.

Embodiment I11. The compound of Embodiments I4-I7, wherein o is 1.

Embodiment I12. The compound of any one of Embodiments I1-I11, wherein Ⓐ is A-1.

Embodiment I13. The compound of Embodiment I12, wherein:
$R^{2a}$, $R^{2b}$, and $R^{2c}$ are each independently selected from the group consisting of hydrogen halo, and $C_1$-$C_4$ alkyl; and
$R^{2d}$ is hydrogen.

Embodiment I14. The compound of any one of Embodiments I1-I11, wherein Ⓐ is A-2.

Embodiment I15. The compound or process of Embodiment I14, wherein the 1-position of A-2 is attached to the oxygen atom and the 3-position of A-2 is attached to the sulfur atom.

Embodiment I16. The compound or process of Embodiments I14 or I15, wherein:
$R^{6a}$, $R^{6b}$, $R^{6c}$, $R^{6d}$, and $R^{6e}$ are each independently selected from the group consisting of hydrogen, halo, and $C_1$-$C_4$ alkyl; and
$R^{6f}$ is hydrogen.

Embodiment I17. The compound of any one of Embodiments I1, I3, or I6-I16, wherein Ⓑ is arylenyl.

Embodiment I18. The compound of Embodiment I17, wherein:

Ⓑ is selected from the group consisting of:

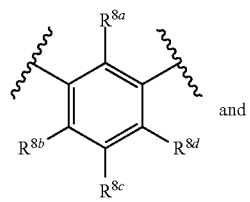

B-1 and

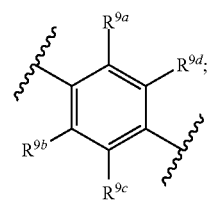

B-2

$R^{8a}$, $R^{8b}$, $R^{8c}$, and $R^{8d}$ are each independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl; and $R^{9a}$, $R^{9b}$, $R^{9c}$, and $R^{9d}$ are each independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl.

Embodiment I19. The compound of Embodiment I18, wherein Ⓑ is B-1, or a pharmaceutically acceptable salt or solvate thereof.

Embodiment I20. The compound of Embodiment I19, wherein $R^{8a}$, $R^{8b}$, $R^{8c}$, and $R^{8d}$ are each independently selected from the group consisting of hydrogen, halo, and $C_1$-$C_4$ alkyl.

Embodiment I21. The compound of Embodiment I18, wherein Ⓑ is B-2.

Embodiment I22. The compound of Embodiment I21, wherein $R^{9a}$, $R^{9b}$, $R^{9c}$, and $R^{9d}$ are each independently selected from the group consisting of hydrogen, halo, and $C_1$-$C_4$ alkyl.

Embodiment I23. The compound of any one of Embodiments I1, I3, or I6-I16, wherein Ⓑ is heteroarylenyl.

Embodiment I24. The compound of Embodiment I23, wherein:

Ⓑ is selected from the group consisting of:

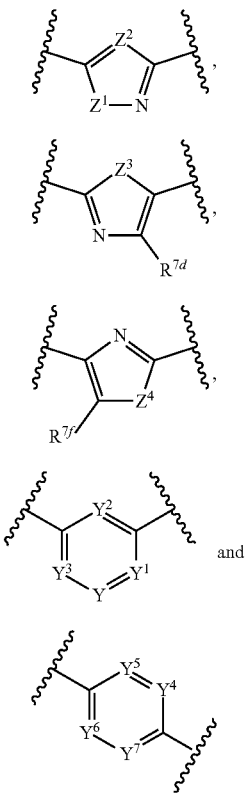

B-3, B-4, B-5, B-6, B-7

$Z^1$ is selected from the group consisting of —O—, —S—, and —N($R^{7a}$)—;
$R^{7a}$ is selected from the group consisting of hydrogen, $C_1$-$C_4$ alkyl, and $C_3$-$C_6$ cycloalkyl;
$Z^2$ is selected from the group consisting of —C($R^{7b}$)═ and —N═;
$R^{7b}$ is selected from the group consisting of hydrogen, halo, $C_1$-$C_4$ alkyl, and $C_3$-$C_6$ cycloalkyl;
$Z^3$ is selected from the group consisting of —O—, —S—, and —N($R^{7c}$)—;
$R^{7c}$ is selected from the group consisting of hydrogen, $C_1$-$C_4$ alkyl, and $C_3$-$C_6$ cycloalkyl;
$R^{7d}$ is selected from the group consisting of hydrogen, halo, $C_1$-$C_4$ alkyl, and $C_3$-$C_6$ cycloalkyl;
$Z^4$ is selected from the group consisting of —O—, —S—, and —N($R^{7e}$)—;
$R^{7e}$ is selected from the group consisting of hydrogen, $C_1$-$C_4$ alkyl, and $C_3$-$C_6$ cycloalkyl;
$R^{7f}$ is selected from the group consisting of hydrogen, halo, $C_1$-$C_4$ alkyl, and $C_3$-$C_6$ cycloalkyl;
Y is selected from the group consisting of —C($R^{10a}$)═ and —N═;
$Y^1$ is selected from the group consisting of —C($R^{10b}$)═ and —N═;
$Y^2$ is selected from the group consisting of —C($R^{10c}$)═ and —N═;
$Y^3$ is selected from the group consisting of —C($R^{10d}$)═ and —N═;
with proviso that at least one of Y, $Y^1$, $Y^2$, and $Y^3$ is —N═;
$R^{10a}$, $R^{10b}$, $R^{10c}$, and $R^{10d}$ are each independently selected from the group consisting of hydrogen, halo, cyano, $C_1$-$C_4$ alkyl, $C_1$-$C_4$ haloalkyl, and $C_1$-$C_4$ alkoxy;
$Y^4$ is selected from the group consisting of —C($R^{11a}$)═ and —N═;
$Y^5$ is selected from the group consisting of —C($R^{11b}$)═ and —N═;
$Y^6$ is selected from the group consisting of —C($R^{11c}$)═ and —N═;
$Y^7$ is selected from the group consisting of —C($R^{11d}$)═ and —N═;
with proviso that at least one of $Y^4$, $Y^5$, $Y^6$, and $Y^7$ is —N═; and
$R^{11a}$, $R^{11b}$, $R^{11c}$, and $R^{11d}$ are each independently selected from the group consisting of hydrogen, halo, cyano, $C_1$-$C_4$ alkyl, $C_1$-$C_4$ haloalkyl, and $C_1$-$C_4$ alkoxy.

Embodiment I25. The compound of Embodiment I24, wherein Ⓑ is B-3, or a salt or solvate thereof.

Embodiment I26. The compound of Embodiment I25, wherein:
$Z^1$ is selected from the group consisting of —O—, —S—, —N(H)—, and —N($CH_3$)—; and
$Z^2$ is selected from the group consisting of —C(H)═, —C($CH_3$)═, and —N═.

Embodiment I27. The compound of Embodiment I24, wherein Ⓑ is B-4.

Embodiment I28. The compound of Embodiment I27, wherein:
$Z^3$ is selected from the group consisting of —O—, —S—, —N(H)—, and —N($CH_3$)—;
$R^{7d}$ is selected from the group consisting of hydrogen and methyl.

Embodiment I29. The compound of Embodiment I24, wherein Ⓑ is B-5, or a pharmaceutically acceptable salt or solvate thereof.

Embodiment I30. The compound of Embodiment I29, wherein:
$Z^4$ is selected from the group consisting of —O—, —S—, —N(H)—, and —N($CH_3$)—;
$R^{7f}$ is selected from the group consisting of hydrogen and methyl.

Embodiment I31. The compound of Embodiment I24, wherein Ⓑ is B-6.

Embodiment I32. The compound of Embodiment I31, wherein:
Y is —N═;
$Y^1$ is selected from the group consisting of —C($R^{10b}$)═ and —N═;
$Y^2$ is selected from the group consisting of —C($R^{10c}$)═ and —N═;
$Y^3$ is selected from the group consisting of —C($R^{10d}$)═ and —N═; and
$R^{10b}$, $R^{10c}$, and $R^{10d}$ are each independently selected from the group consisting of hydrogen, halo, and $C_1$-$C_4$ alkyl.

Embodiment I33. The compound of Embodiment I31, wherein:
Y is selected from the group consisting of —C($R^{10a}$)═ and —N═;
$Y^1$ is —N═;

Y² is selected from the group consisting of —C(R¹⁰ᶜ)= and —N=;
Y³ is selected from the group consisting of —C(R¹⁰ᵈ)= and —N=; and
R¹⁰ᵃ, R¹⁰ᶜ, and R¹⁰ᵈ are each independently selected from the group consisting of hydrogen, halo, and C₁-C₄ alkyl.

Embodiment I34. The compound of Embodiment I31, wherein:
Y is selected from the group consisting of —C(R¹⁰ᵃ)= and —N=;
Y¹ is selected from the group consisting of —C(R¹⁰ᵇ)= and —N=;
Y² is —N=;
Y³ is selected from the group consisting of —C(R¹⁰ᵈ)= and —N=; and
R¹⁰ᵃ, R¹⁰ᵇ, and R¹⁰ᵈ are each independently selected from the group consisting of hydrogen, halo, and C₁-C₄ alkyl.

Embodiment I35. The compound of Embodiment I31, wherein:
Y is selected from the group consisting of —C(R¹⁰ᵃ)= and —N=;
Y¹ is selected from the group consisting of —C(R¹⁰ᵇ)= and —N=;
Y² is selected from the group consisting of —C(R¹⁰ᶜ)= and —N=;
Y³ is —N=; and
R¹⁰ᵃ, R¹⁰ᵇ, and R¹⁰ᶜ are each independently selected from the group consisting of hydrogen, halo, and C₁-C₄ alkyl.

Embodiment I36. The compound of Embodiment I24, wherein Ⓑ is B-7.

Embodiment I37. The compound of Embodiment I36, wherein:
Y⁴ is and —N=;
Y⁵ is selected from the group consisting of —C(R¹¹ᵇ)= and —N=;
Y⁶ is selected from the group consisting of —C(R¹¹ᶜ)= and —N=;
Y⁷ is selected from the group consisting of —C(R¹¹ᵈ)= and —N=; and
R¹¹ᵇ, R¹¹ᶜ, and R¹¹ᵈ are each independently selected from the group consisting of hydrogen, halo, and C₁-C₄ alkyl.

Embodiment I38. The compound of Embodiment I36, wherein:
Y⁴ is selected from the group consisting of —C(R¹¹ᵃ)= and —N=;
Y⁵ is —N=;
Y⁶ is selected from the group consisting of —C(R¹¹ᶜ)= and —N=;
Y⁷ is selected from the group consisting of —C(R¹¹ᵈ)= and —N=; and
R¹¹ᵃ, R¹¹ᶜ, and R¹¹ᵈ are each independently selected from the group consisting of hydrogen, halo, and C₁-C₄ alkyl.

Embodiment I39. The compound of Embodiment I36, wherein:
Y⁴ is selected from the group consisting of —C(R¹¹ᵃ)= and —N=;
Y⁵ is selected from the group consisting of —C(R¹¹ᵇ)= and —N=;
Y⁶ is —N=;
Y⁷ is selected from the group consisting of —C(R¹¹ᵈ)= and —N=; and
R¹¹ᵃ, R¹¹ᵇ, and R¹¹ᵈ are each independently selected from the group consisting of hydrogen, halo, and C₁-C₄ alkyl.

Embodiment I40. The compound of Embodiment I36, wherein:
Y⁴ is selected from the group consisting of —C(R¹¹ᵃ)= and —N=;
Y⁵ is selected from the group consisting of —C(R¹¹ᵇ)= and —N=;
Y⁶ is selected from the group consisting of —C(R¹¹ᶜ)= and —N=;
Y⁷ is —N=; and
R¹¹ᵃ, R¹¹ᵇ, and R¹¹ᶜ are each independently selected from the group consisting of hydrogen, halo, and C₁-C₄ alkyl.

Embodiment I41. The compound of any one of Embodiments I1, I3, or I6-I16, wherein Ⓑ is selected from the group consisting of:

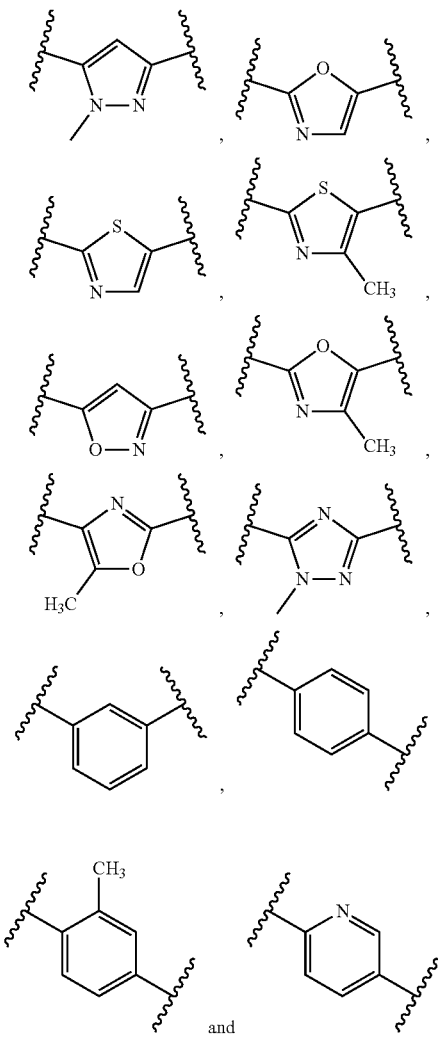

and

Embodiment I42. The compound of Embodiment I21, wherein Ⓑ is:

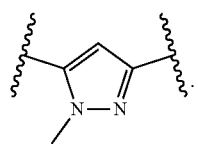 [SMILES: *c1cc(*)n(C)n1]

Embodiment I43. The compound of any one of Embodiments I1-I42, wherein R is selected from the group consisting of methyl and ethyl.

Embodiment I44. The compound of any one of Embodiments I1-I43, wherein $R^{19}$ is a protecting group.

Embodiment I45. The compound of Embodiment I44, wherein $R^{19}$ is p-methoxybenzyl (PMB).

Embodiment I46. The compound of any one of Embodiments I1-I43, wherein $R^{19}$ is hydrogen.

Embodiment I47. In another embodiment, Intermediates of the Disclosure are compounds of Formula XV selected from group consisting of the compounds of Table 2.

TABLE 2

| Intermediate No. | Structure |
|---|---|
| 1 | 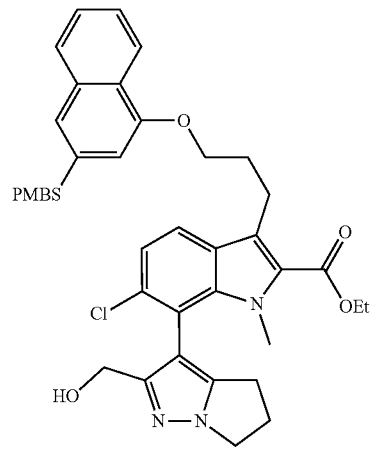 |
| 2 | 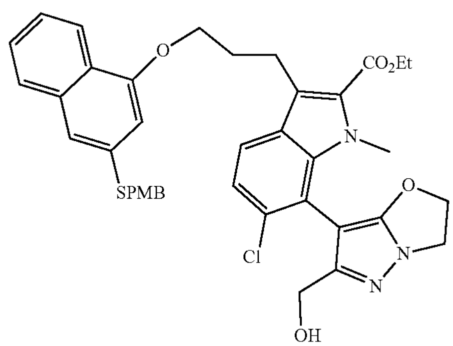 |
| 3 | 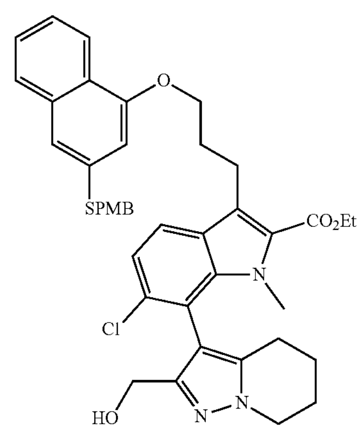 |

TABLE 2-continued
| Intermediate No. | Structure |
|---|---|
| 4 | 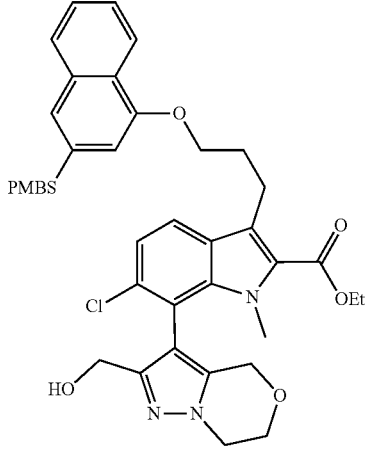 |
| 5 | 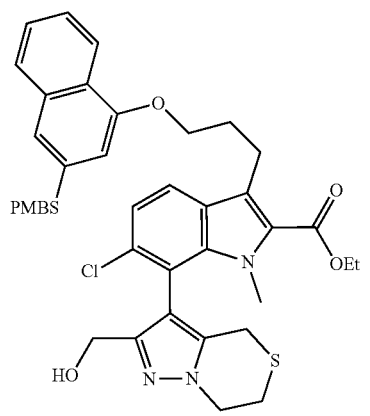 |
| 6 | 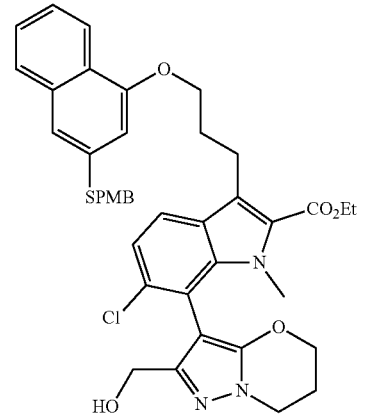 |

TABLE 2-continued
| Intermediate No. | Structure |
| --- | --- |
| 7 | 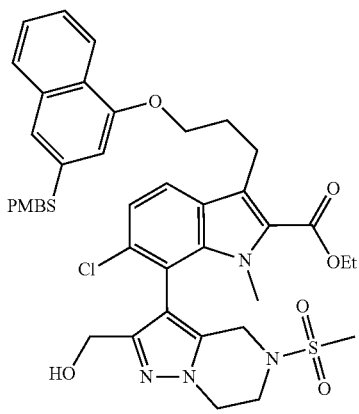 |
| 8 | 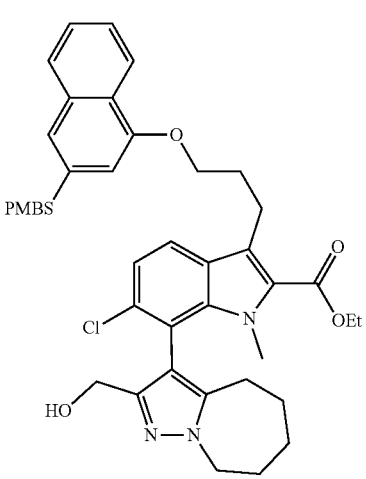 |
| 9 | 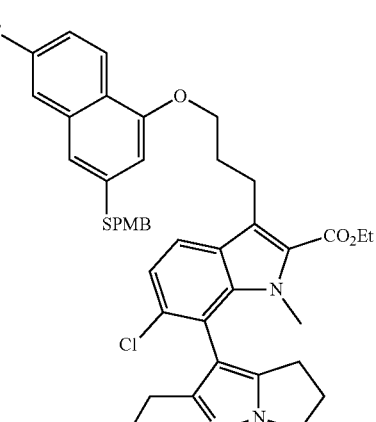 |

TABLE 2-continued
| Intermediate No. | Structure |
| --- | --- |
| 10 | 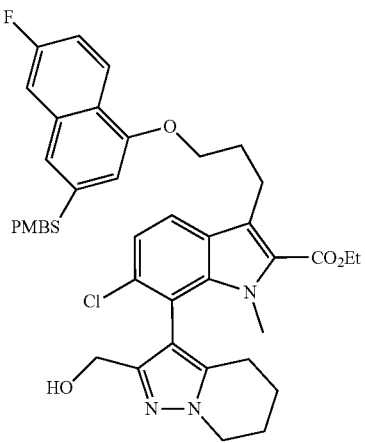 |
| 11 | 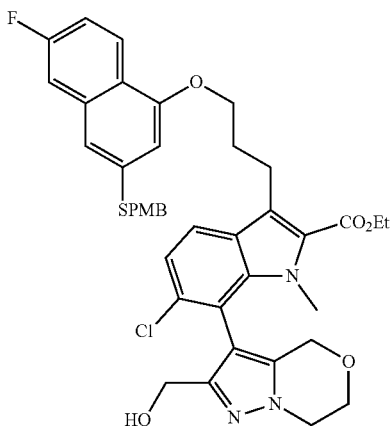 |
| 12 | 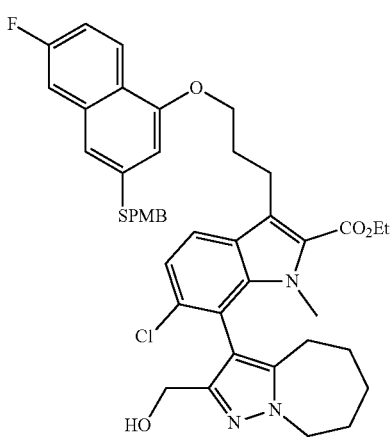 |

TABLE 2-continued
| Intermediate No. | Structure |
|---|---|
| 13 | 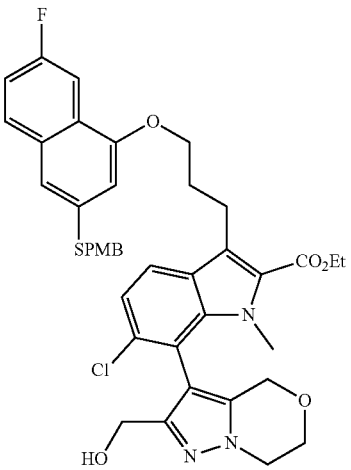 |
| 14 | 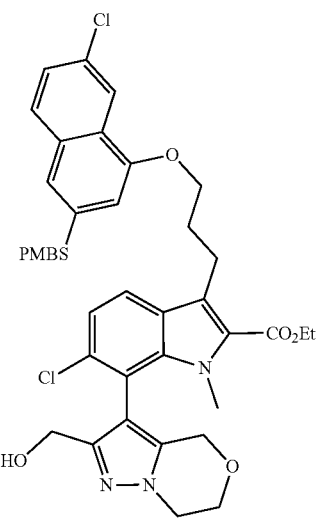 |
| 15 | 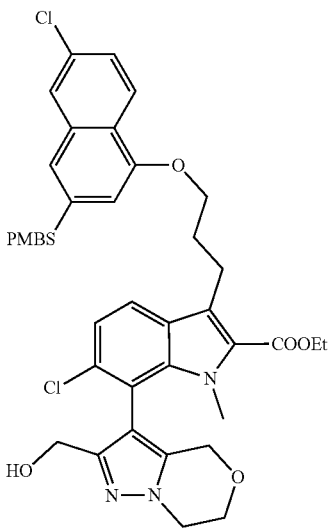 |

TABLE 2-continued
| Intermediate No. | Structure |
|---|---|
| 16 | 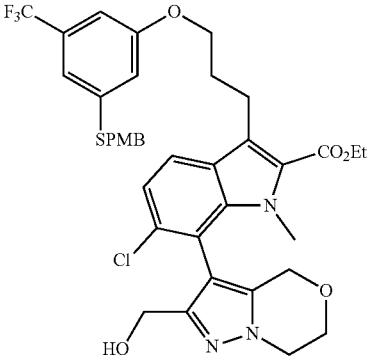 |
| 17 | 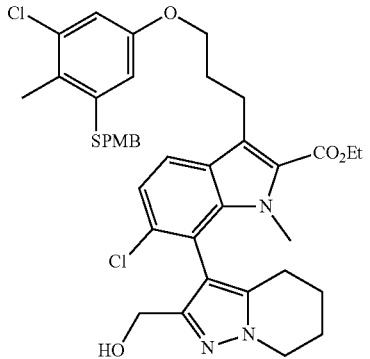 |
| 18 | 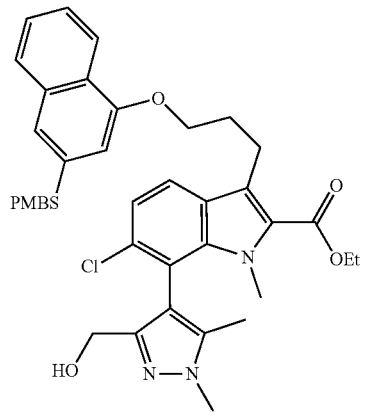 |
| 19 | 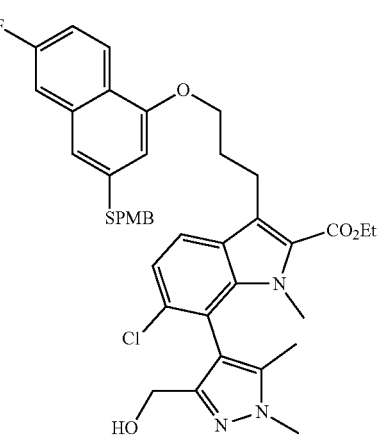 |

TABLE 2-continued
| Intermediate No. | Structure |
| --- | --- |
| 20 | 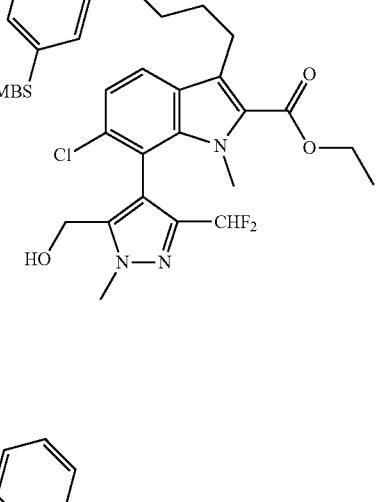 |
| 21 | 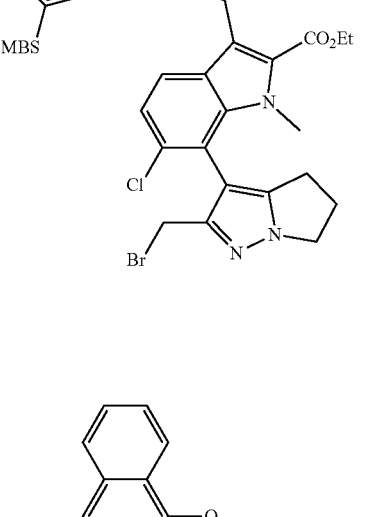 |
| 22 | 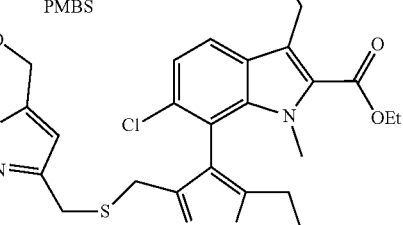 |

TABLE 2-continued
| Intermediate No. | Structure |
| --- | --- |
| 23 | 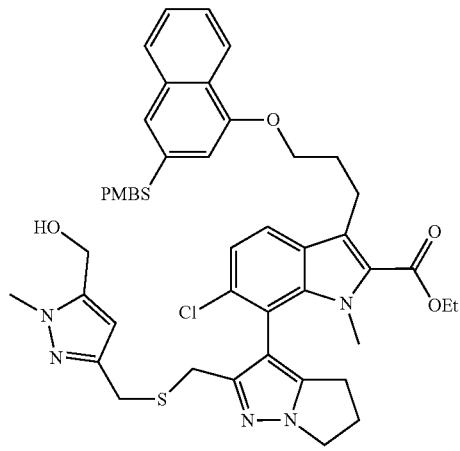 |
| 24 | 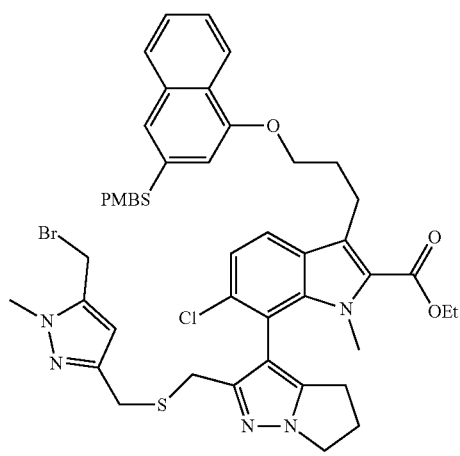 |
| 25 | 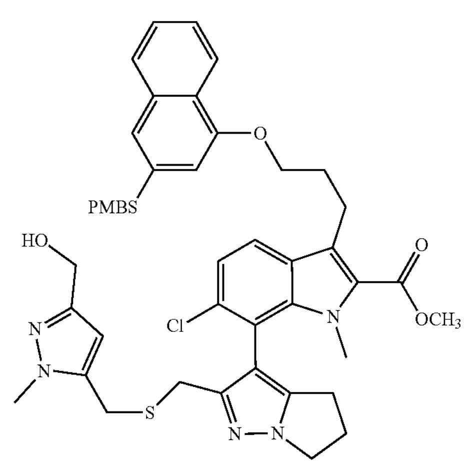 |

TABLE 2-continued
| Intermediate No. | Structure |
| --- | --- |
| 26 | 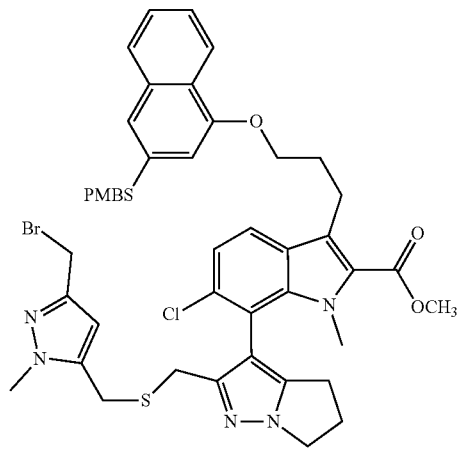 |
| 27 | 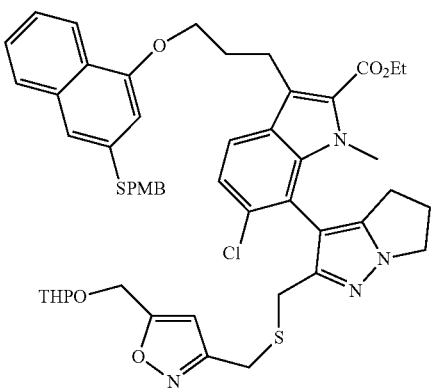 |
| 28 | 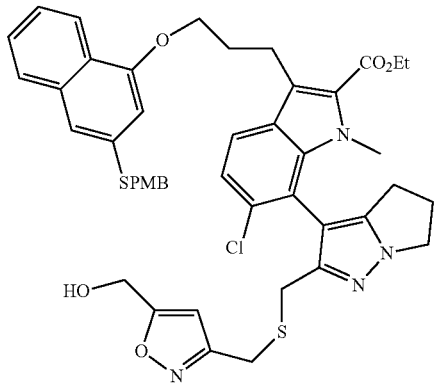 |

TABLE 2-continued
| Intermediate No. | Structure |
|---|---|
| 29 | 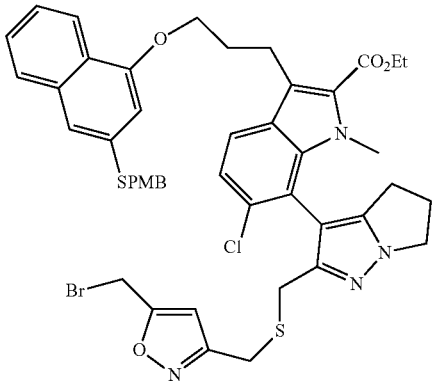 |
| 30 | 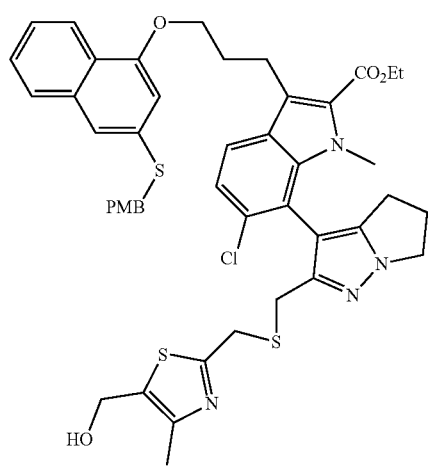 |
| 31 | 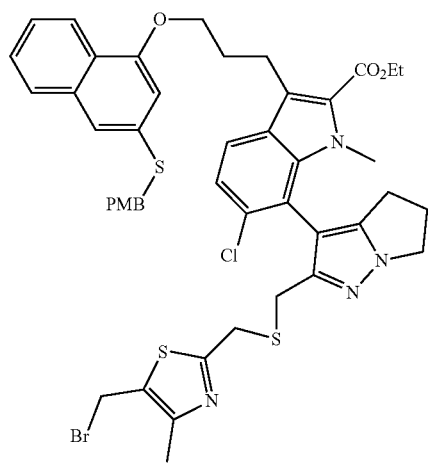 |

TABLE 2-continued
| Intermediate No. | Structure |
| --- | --- |
| 32 | 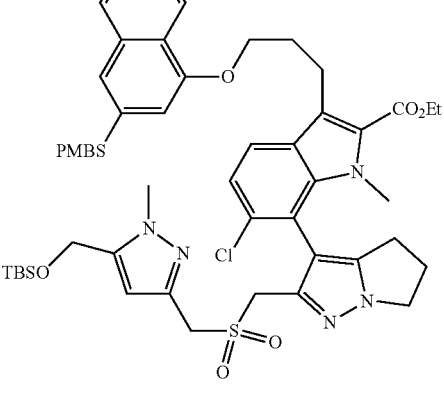 |
| 33 | 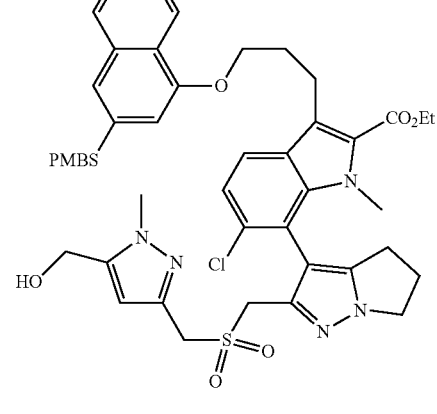 |
| 34 | 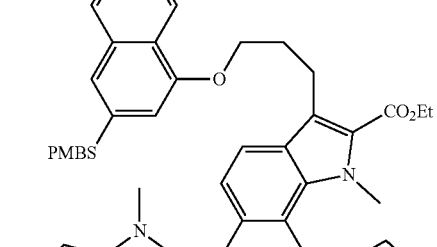 |

TABLE 2-continued
| Intermediate No. | Structure |
|---|---|
| 35 | 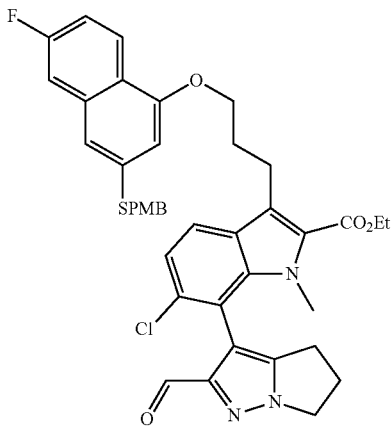 |
| 36 | 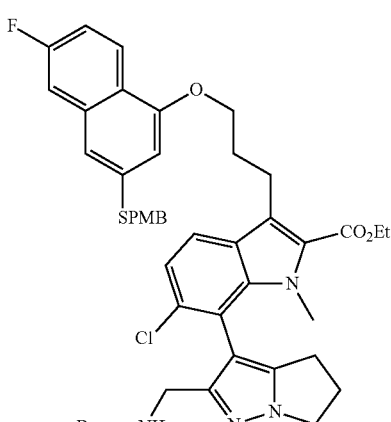 |
| 37 | 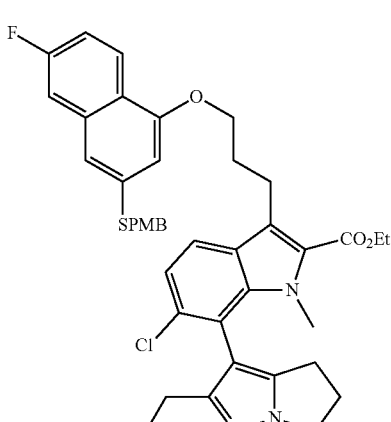 |

TABLE 2-continued

| Intermediate No. | Structure |
| --- | --- |
| 38 | *chemical structure* |
| 39 | *chemical structure* |
| 40 | *chemical structure* |

TABLE 2-continued
| Intermediate No. | Structure |
| --- | --- |
| 41 | 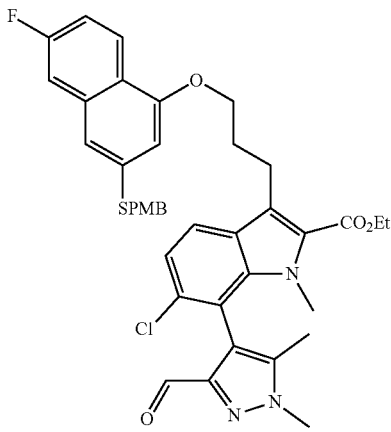 |
| 42 | 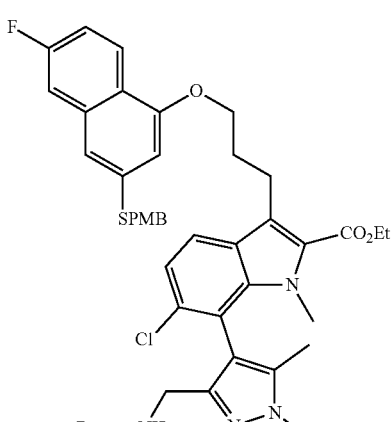 |
| 43 | 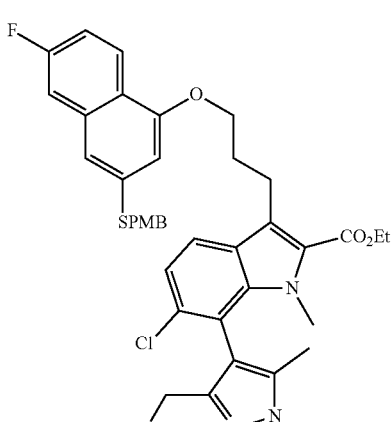 |

TABLE 2-continued
| Intermediate No. | Structure |
| --- | --- |
| 44 | 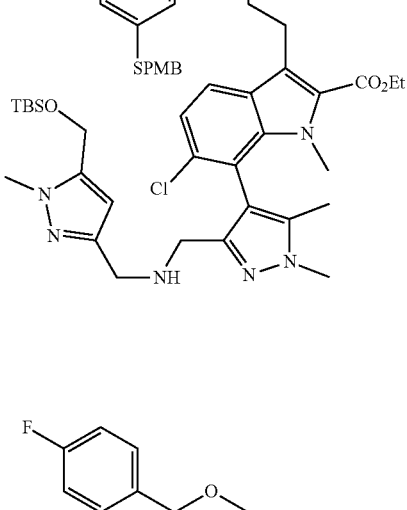 |
| 45 | 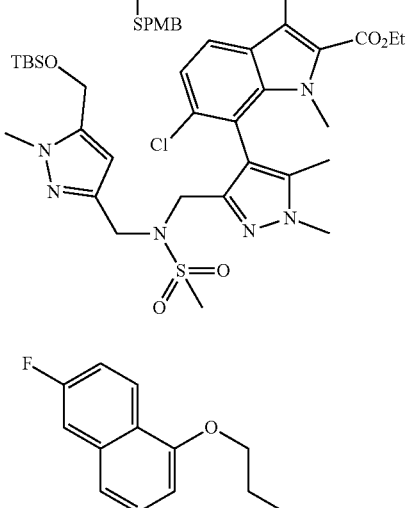 |
| 46 | 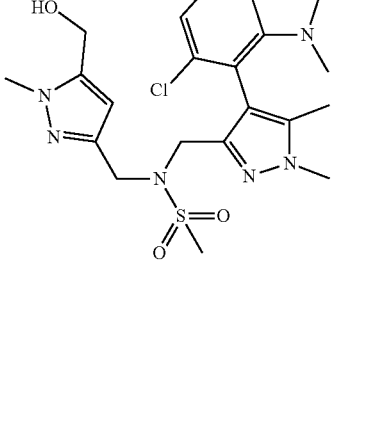 |

TABLE 2-continued
| Intermediate No. | Structure |
|---|---|
| 47 | 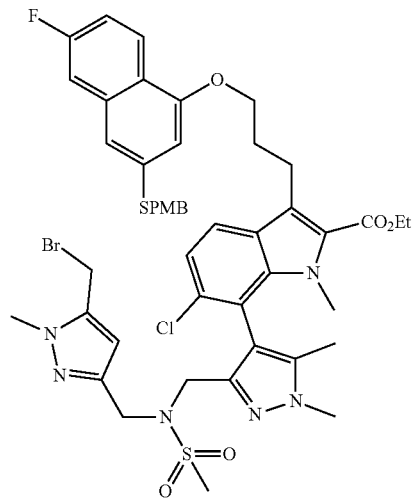 |
| 48 | 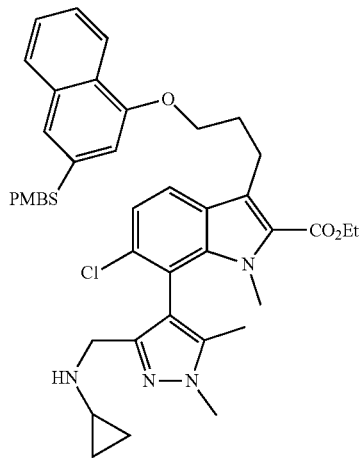 |
| 49 | 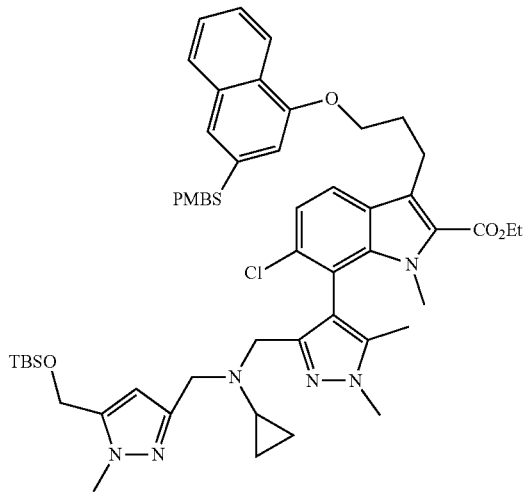 |

TABLE 2-continued
| Intermediate No. | Structure |
|---|---|
| 50 | 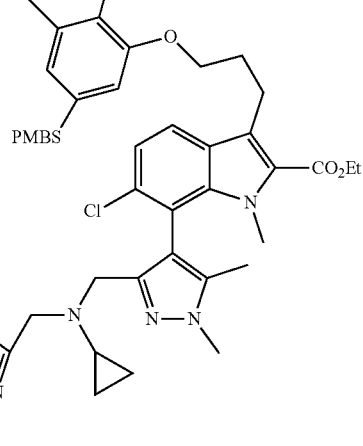 |
| 51 | 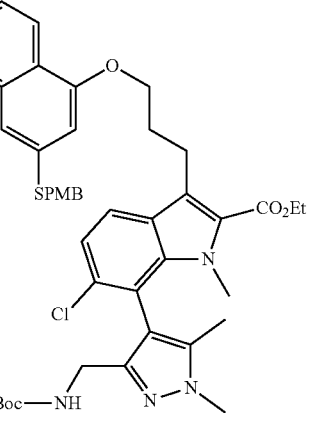 |
| 52 | 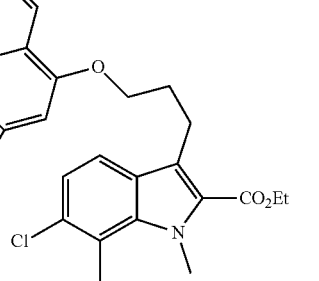 |

TABLE 2-continued
| Intermediate No. | Structure |
|---|---|
| 53 | 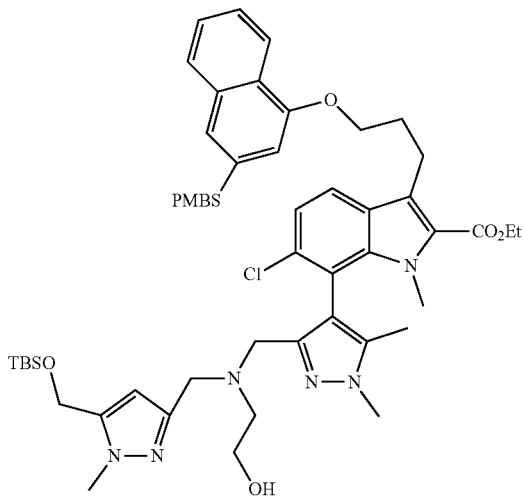 |
| 54 | 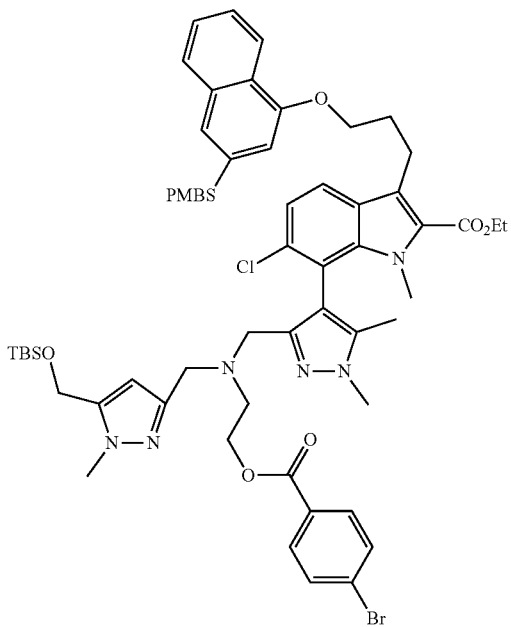 |

TABLE 2-continued

| Intermediate No. | Structure |
|---|---|
| 55 | 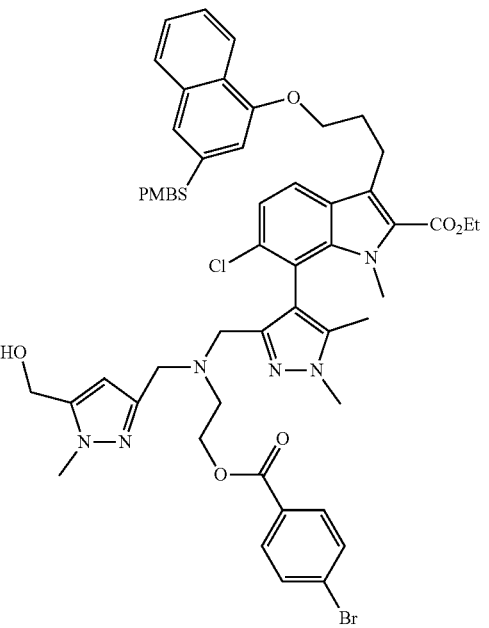 |
| 56 | 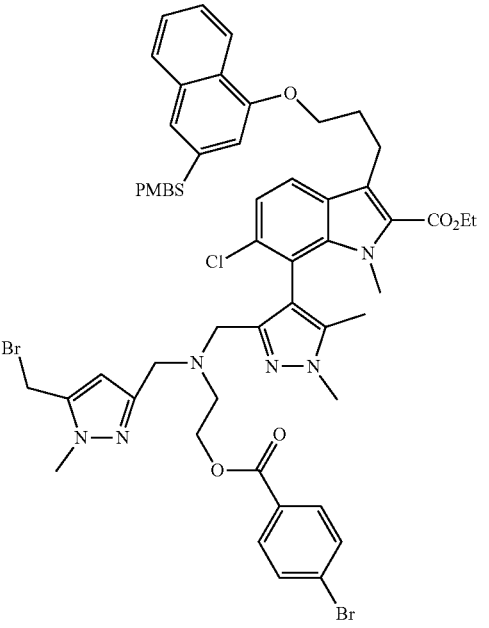 |

III. Methods of Preparing Compounds and Intermediates of the Disclosure

The disclosure also provides methods of preparing Compounds of the Disclosure and/or Intermediates of the Disclosure. The following particular embodiments are drawn to methods of preparing Compounds of the Disclosure and/or Intermediates of the Disclosure.

Embodiment P1. A process for preparing a compound of Formula III:

III

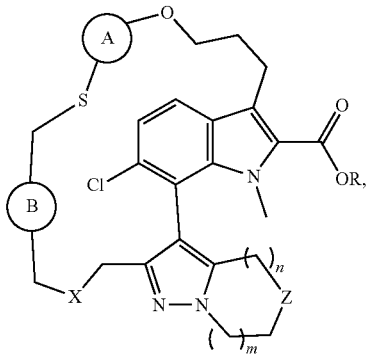

wherein:
R is $C_1$-$C_6$ alkyl;

Ⓐ is selected from the group consisting of:

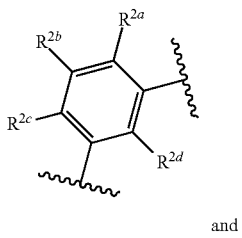

and

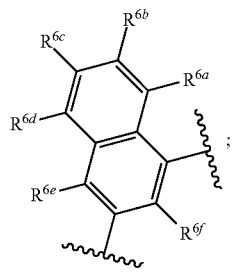

;

$R^{2a}$, $R^{2b}$, $R^{2c}$, and $R^{2d}$ are each independently selected from the group consisting of hydrogen, halo, cyano, $C_1$-$C_4$ alkyl, $C_1$-$C_4$ haloalkyl, and $C_1$-$C_4$ alkoxy;

$R^{6a}$, $R^{6b}$, $R^{6c}$, $R^{6d}$, $R^{6e}$, and $R^{6f}$ are each independently selected from the group consisting of hydrogen, halo, cyano, $C_1$-$C_4$ alkyl, $C_1$-$C_4$ haloalkyl, and $C_1$-$C_4$ alkoxy;

Ⓑ is selected from the group consisting of arylenyl and heteroarylenyl;

m is 0, 1, or 2;
n is 0 or 1;
with the proviso that when m is 0, Z is —$CR^{13a}R^{13b}$—;
Z is selected from the group consisting of —$CR^{13a}R^{13b}$—, —O—, —S—, S(═O)—, S(═O)$_2$—, and —N($R^{10}$)—;
$R^{10}$ is selected from the group consisting of hydrogen, $C_1$-$C_4$ alkyl, —C(═O)$_2R^{11}$, and —S(═O)$_2R^2$;
$R^{11}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl;
$R^{12}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl; and
$R^{13a}$ and $R^{13b}$ are independently selected from the group consisting of hydrogen and $C_1$-$C_4$ alkyl,
the process comprising cyclizing a compound of Formula XVII:

XVII

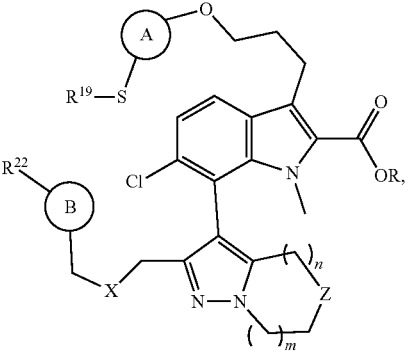

wherein:
R is $C_1$-$C_6$ alkyl;

Ⓐ is selected from the group consisting of:

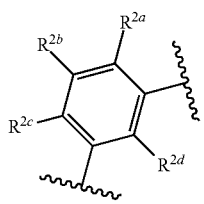

and

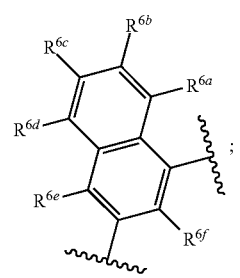

;

$R^{2a}$, $R^{2b}$, $R^{2c}$, and $R^{2d}$ are each independently selected from the group consisting of hydrogen, halo, cyano, $C_1$-$C_4$ alkyl, $C_1$-$C_4$ haloalkyl, and $C_1$-$C_4$ alkoxy;

$R^{6a}$, $R^{6b}$, $R^{6c}$, $R^{6d}$, $R^{6e}$, and $R^{6f}$ are each independently selected from the group consisting of hydrogen, halo, cyano, $C_1$-$C_4$ alkyl, $C_1$-$C_4$ haloalkyl, and $C_1$-$C_4$ alkoxy;

Ⓑ is selected from the group consisting of arylenyl and heteroarylenyl;

m is 0, 1, or 2;
n is 0 or 1;
with the proviso that when m is 0, Z is —$CR^{13a}R^{13b}$—;
Z is selected from the group consisting of —$CR^{13a}R^{13b}$—, —O—, —S—, S(═O)—, S(═O)$_2$—, and —N($R^{10}$)—;
$R^{10}$ is selected from the group consisting of hydrogen, $C_1$-$C_4$ alkyl, —C(═O)$_2R^{11}$, and —S(═O)$_2R^2$;

$R^{11}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl;

$R^{12}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl; and $R^{13a}$ and $R^{13b}$ are independently selected from the group consisting of hydrogen and $C_1$-$C_4$ alkyl, $R^{19}$ is hydrogen; and and $R^{22}$ is a leaving group, e.g., —Br, in a solvent in the presence of a base, e.g., $K_2CO_3$.

Embodiment P2. The compound of P1, wherein Z is —O—.

Embodiment P3. The compound of Embodiment P1, wherein Z is —CH$_2$—.

Embodiment P4. The compound of Embodiment P1, wherein Z is —S—.

Embodiment P5. The compound of Embodiment P1, wherein o is 1.

Embodiment P6. The compound of any one of Embodiments P1-P5, wherein Ⓐ is A-1.

Embodiment P7. The compound of Embodiment P6, wherein:

$R^{2a}$, $R^{2b}$, and $R^{2c}$ are each independently selected from the group consisting of hydrogen halo, and $C_1$-$C_4$ alkyl; and $R^{2d}$ is hydrogen.

Embodiment P8. The compound of any one of Embodiments P1-P5, wherein Ⓐ is A-2.

Embodiment P9. The compound or process of Embodiment P8, wherein the 1-position of A-2 is attached to the oxygen atom and the 3-position of A-2 is attached to the sulfur atom.

Embodiment P10. The compound or process of Embodiments P8 or P9, wherein:

$R^{6a}$, $R^{6b}$, $R^{6c}$, $R^{6d}$, and $R^{6e}$ are each independently selected from the group consisting of hydrogen, halo, and $C_1$-$C_4$ alkyl; and $R^{6f}$ is hydrogen.

Embodiment P11. The compound of any one of Embodiments P1-P10, wherein Ⓑ is arylenyl.

Embodiment P12. The compound of Embodiment P11, wherein:

Ⓑ is selected from the group consisting of:

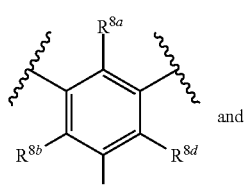

B-1

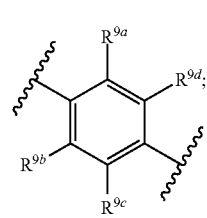

B-2

$R^{8a}$, $R^{8b}$, $R^{8c}$, and $R^{8d}$ are each independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl; and $R^{9a}$, $R^{9b}$, $R^{9c}$, and $R^{9d}$ are each independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl.

Embodiment P13. The compound of Embodiment P12, wherein Ⓑ is B-1, or a pharmaceutically acceptable salt or solvate thereof.

Embodiment P14. The compound of Embodiment P13, wherein $R^{8a}$, $R^{8b}$, $R^{8c}$, and $R^{8d}$ are each independently selected from the group consisting of hydrogen, halo, and $C_1$-$C_4$ alkyl.

Embodiment P15. The compound of Embodiment P12, wherein Ⓑ is B-2.

Embodiment P16. The compound of Embodiment P15, wherein $R^{9a}$, $R^{9b}$, $R^{9c}$, and $R^{9d}$ are each independently selected from the group consisting of hydrogen, halo, and $C_1$-$C_4$ alkyl.

Embodiment P17. The compound of any one of Embodiments P1-P10, wherein Ⓑ is heteroarylenyl.

Embodiment P18. The compound of Embodiment P17, wherein:

Ⓑ is selected from the group consisting of:

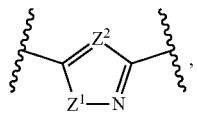

B-3

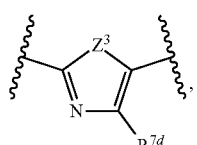

B-4

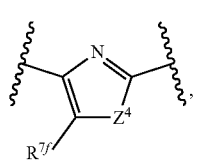

B-5

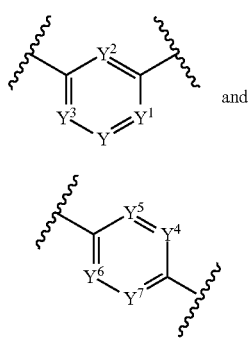

B-6 and

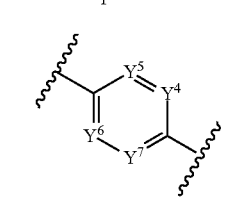

B-7

$Z^1$ is selected from the group consisting of —O—, —S—, and —N($R^{7a}$)—;

$R^{7a}$ is selected from the group consisting of hydrogen, $C_1$-$C_4$ alkyl, and $C_3$-$C_6$ cycloalkyl;

$Z^2$ is selected from the group consisting of —C($R^{7b}$)= and —N=;

$R^{7b}$ is selected from the group consisting of hydrogen, halo, $C_1$-$C_4$ alkyl, and $C_3$-$C_6$ cycloalkyl;

$Z^3$ is selected from the group consisting of —O—, —S—, and —N($R^{7c}$)—;

$R^{7c}$ is selected from the group consisting of hydrogen, $C_1$-$C_4$ alkyl, and $C_3$-$C_6$ cycloalkyl;

$R^{7d}$ is selected from the group consisting of hydrogen, halo, $C_1$-$C_4$ alkyl, and $C_3$-$C_6$ cycloalkyl;

$Z^4$ is selected from the group consisting of —O—, —S—, and —N($R^{7e}$)—;

$R^{7e}$ is selected from the group consisting of hydrogen, $C_1$-$C_4$ alkyl, and $C_3$-$C_6$ cycloalkyl;

$R^{7f}$ is selected from the group consisting of hydrogen, halo, $C_1$-$C_4$ alkyl, and $C_3$-$C_6$ cycloalkyl;

Y is selected from the group consisting of —C($R^{10a}$)= and —N=;

$Y^1$ is selected from the group consisting of —C($R^{10b}$)= and —N=;

$Y^2$ is selected from the group consisting of —C($R^{10c}$)= and —N=;

$Y^3$ is selected from the group consisting of —C($R^{10d}$)= and —N=;

with proviso that at least one of Y, $Y^1$, $Y^2$, and $Y^3$ is —N=;

$R^{10a}$, $R^{10b}$, $R^{10c}$, and $R^{10d}$ are each independently selected from the group consisting of hydrogen, halo, cyano, $C_1$-$C_4$ alkyl, $C_1$-$C_4$ haloalkyl, and $C_1$-$C_4$ alkoxy;

$Y^4$ is selected from the group consisting of —C($R^{11a}$)= and —N=;

$Y^5$ is selected from the group consisting of —C($R^{11b}$)= and —N=;

$Y^6$ is selected from the group consisting of —C($R^{11c}$)= and —N=;

$Y^7$ is selected from the group consisting of —C($R^{11d}$)= and —N=;

with proviso that at least one of $Y^4$, $Y^5$, $Y^6$, and $Y^7$ is —N=; and $R^{11a}$, $R^{11b}$, $R^{11c}$, and $R^{11d}$ are each independently selected from the group consisting of hydrogen, halo, cyano, $C_1$-$C_4$ alkyl, $C_1$-$C_4$ haloalkyl, and $C_1$-$C_4$ alkoxy.

Embodiment P19. The compound of Embodiment P18, wherein Ⓑ is B-3, or a pharmaceutically acceptable salt or solvate thereof.

Embodiment P20. The compound of Embodiment P19, wherein:

$Z^1$ is selected from the group consisting of —O—, —S—, —N(H)—, and —N(CH$_3$)—; and $Z^2$ is selected from the group consisting of —C(H)=, —C(CH$_3$)=, and —N=.

Embodiment P21. The compound of Embodiment I24, wherein Ⓑ is B-4.

Embodiment P22. The compound of Embodiment P21, wherein:

$Z^3$ is selected from the group consisting of —O—, —S—, —N(H)—, and —N(CH$_3$)—;

$R^{7d}$ is selected from the group consisting of hydrogen and methyl.

Embodiment P23. The compound of Embodiment P18, wherein Ⓑ is B-5, or a pharmaceutically acceptable salt or solvate thereof.

Embodiment P24. The compound of Embodiment P23, wherein:

$Z^4$ is selected from the group consisting of —O—, —S—, —N(H)—, and —N(CH$_3$)—;

$R^{7f}$ is selected from the group consisting of hydrogen and methyl.

Embodiment P25. The compound of Embodiment P18, wherein Ⓑ is B-6.

Embodiment P26. The compound of Embodiment P25, wherein:

Y is —N=;

Y is selected from the group consisting of —C($R^{10b}$)= and —N=;

$Y^2$ is selected from the group consisting of —C($R^{10c}$)= and —N=;

$Y^3$ is selected from the group consisting of —C($R^{10d}$)= and —N=; and $R^{10b}$, $R^{10c}$, and $R^{10d}$ are each independently selected from the group consisting of hydrogen, halo, and $C_1$-$C_4$ alkyl.

Embodiment P27. The compound of Embodiment P25, wherein:

Y is selected from the group consisting of —C($R^{10a}$)= and —N=;

Y is —N=;

$Y^2$ is selected from the group consisting of —C($R^{10c}$)= and —N=;

$Y^3$ is selected from the group consisting of —C($R^{10d}$)= and —N=; and $R^{10a}$, $R^{10c}$, and $R^{10d}$ are each independently selected from the group consisting of hydrogen, halo, and $C_1$-$C_4$ alkyl.

Embodiment P28. The compound of Embodiment P25, wherein:

Y is selected from the group consisting of —C($R^{10a}$)= and —N=;

Y is selected from the group consisting of —C($R^{10b}$)= and —N=;

$Y^2$ is —N=;

$Y^3$ is selected from the group consisting of —C($R^{10d}$)= and —N=; and $R^{10a}$, $R^{10b}$, and $R^{10d}$ are each independently selected from the group consisting of hydrogen, halo, and $C_1$-$C_4$ alkyl.

Embodiment P29. The compound of Embodiment P25, wherein:

Y is selected from the group consisting of —C($R^{10a}$)= and —N=;

$Y^1$ is selected from the group consisting of —C($R^{10b}$)= and —N=;

$Y^2$ is selected from the group consisting of —C($R^{10c}$)= and —N=;

$Y^3$ is —N=; and $R^{10a}$, $R^{10b}$, and $R^{10c}$ are each independently selected from the group consisting of hydrogen, halo, and $C_1$-$C_4$ alkyl.

Embodiment P30. The compound of Embodiment P18, wherein Ⓑ is B-7.

Embodiment P31. The compound of Embodiment P30, wherein:

$Y^4$ is and —N=;

$Y^5$ is selected from the group consisting of —C($R^{11b}$)= and —N=;

$Y^6$ is selected from the group consisting of —C($R^{11c}$)= and —N=;

$Y^7$ is selected from the group consisting of —C($R^{11d}$)= and —N=; and $R^{11b}$, $R^{11c}$, and $R^{11d}$ are each independently selected from the group consisting of hydrogen, halo, and $C_1$-$C_4$ alkyl.

Embodiment P32. The compound of Embodiment P30, wherein:
$Y^4$ is selected from the group consisting of —C($R^{11a}$)═ and —N═;
$Y^5$ is —N═;
$Y^6$ is selected from the group consisting of —C($R^{11c}$)═ and —N═;
$Y^7$ is selected from the group consisting of —C($R^{11d}$)═ and —N═; and
$R^{11a}$, $R^{11c}$, and $R^{11d}$ are each independently selected from the group consisting of hydrogen, halo, and $C_1$-$C_4$ alkyl.

Embodiment P33. The compound of Embodiment P30, wherein:
$Y^4$ is selected from the group consisting of —C($R^{11a}$)═ and —N═;
$Y^5$ is selected from the group consisting of —C($R^{11b}$)═ and —N═;
$Y^6$ is —N═;
$Y^7$ is selected from the group consisting of —C($R^{11d}$)═ and —N═; and
$R^{11a}$, $R^{11b}$, and $R^{11d}$ are each independently selected from the group consisting of hydrogen, halo, and $C_1$-$C_4$ alkyl.

Embodiment P34. The compound of Embodiment P31, wherein:
$Y^4$ is selected from the group consisting of —C($R^{11a}$)═ and —N═;
$Y^5$ is selected from the group consisting of —C($R^{11b}$)═ and —N═;
$Y^6$ is selected from the group consisting of —C($R^{11c}$)═ and —N═;
$Y^7$ is —N═; and
$R^{11a}$, $R^{11b}$, and $R^{11c}$ are each independently selected from the group consisting of hydrogen, halo, and $C_1$-$C_4$ alkyl.

Embodiment P35. The compound of any one of Embodiments P1-P10, wherein Ⓑ is selected from the group consisting of:

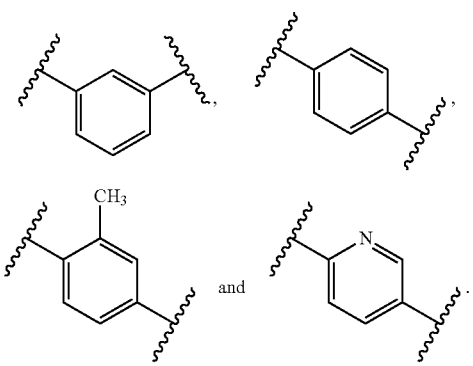

-continued

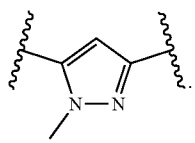 [SMILES: *c1cc(*)n(C)n1]

Embodiment P36. The compound of Embodiment P35, wherein Ⓑ is:

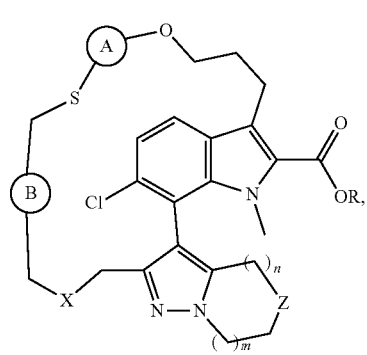

Embodiment P37. The compound of any one of Embodiments P1-P36, wherein R is selected from the group consisting of methyl and ethyl.

Embodiment P38. A process for preparing a compound of Formula III:

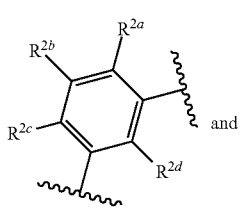

III wherein:

R is hydrogen;

Ⓐ is selected from the group consisting of:

A-1

-continued

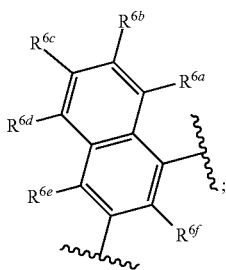
A-2

$R^{2a}$, $R^{2b}$, $R^{2c}$, and $R^{2d}$ are each independently selected from the group consisting of hydrogen, halo, cyano, $C_1$-$C_4$ alkyl, $C_1$-$C_4$ haloalkyl, and $C_1$-$C_4$ alkoxy;

$R^{6a}$, $R^{6b}$, $R^{6c}$, $R^{6d}$, $R^{6e}$, and $R^{6f}$ are each independently selected from the group consisting of hydrogen, halo, cyano, $C_1$-$C_4$ alkyl, $C_1$-$C_4$ haloalkyl, and $C_1$-$C_4$ alkoxy;

Ⓑ is selected from the group consisting of arylenyl and heteroarylenyl;

m is 0, 1, or 2;

n is 0 or 1;

with the proviso that when m is 0, Z is —$CR^{13a}R^{13b}$—;

Z is selected from the group consisting of —$CR^{13a}R^{13b}$—, —O—, —S—, S(=O)—, S(=O)$_2$—, and —N($R^{10}$)—;

$R^{10}$ is selected from the group consisting of hydrogen, $C_1$-$C_4$ alkyl, —C(=O)$_2R^{11}$, and —S(=O)$_2R^{12}$;

$R^{11}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl;

$R^{12}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl; and $R^{13a}$ and $R^{13b}$ are independently selected from the group consisting of hydrogen and $C_1$-$C_4$ alkyl, the process comprising:

(a) hydrolyzing a compound having Formula III:

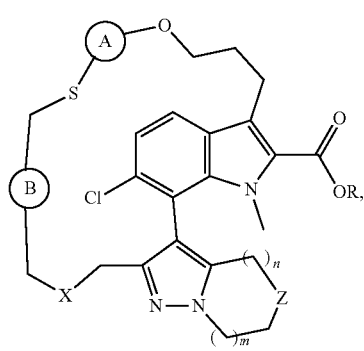
III wherein:

R is $C_1$-$C_6$ alkyl;

Ⓐ is selected from the group consisting of:

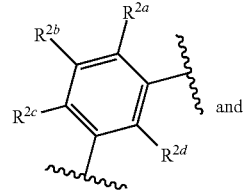
A-1 and

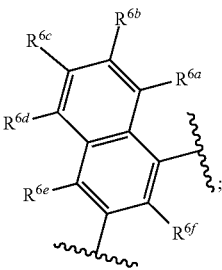
A-2

$R^{2a}$, $R^{2b}$, $R^{2c}$, and $R^{2d}$ are each independently selected from the group consisting of hydrogen, halo, cyano, $C_1$-$C_4$ alkyl, $C_1$-$C_4$ haloalkyl, and $C_1$-$C_4$ alkoxy;

$R^{6a}$, $R^{6b}$, $R^{6c}$, $R^{6d}$, $R^{6e}$, and $R^{6f}$ are each independently selected from the group consisting of hydrogen, halo, cyano, $C_1$-$C_4$ alkyl, $C_1$-$C_4$ haloalkyl, and $C_1$-$C_4$ alkoxy;

Ⓑ is selected from the group consisting of arylenyl and heteroarylenyl;

m is 0, 1, or 2;

n is 0 or 1;

with the proviso that when m is 0, Z is —$CR^{13a}R^{13b}$—;

Z is selected from the group consisting of —$CR^{13a}R^{13b}$—, —O—, —S—, S(=O)—, S(=O)$_2$—, and —N($R^{10}$)—;

$R^{10}$ is selected from the group consisting of hydrogen, $C_1$-$C_4$ alkyl, —C(=O)$_2R^{11}$, and —S(=O)$_2R^{12}$;

$R^{11}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl;

$R^{12}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl; and $R^{13a}$ and $R^{13b}$ are independently selected from the group consisting of hydrogen and $C_1$-$C_4$ alkyl, in the presence of a base, e.g., NaOH or KOH; and (b) acidifying the product in the presence of an acid, e.g., HCl.

IV. Methods of Treating Disease with Compounds of the Disclosure

Compounds of the Disclosure inhibit Mcl-1 and are useful in the treatment or prevention of a variety of diseases and conditions. In particular, Compounds of the Disclosure are useful in methods of treating or preventing a disease or condition wherein inhibition of Mcl-1 provides a benefit, for example, cancers and proliferative diseases. In one embodiment, such a cancer is referred to as a "Mcl-1 mediated cancer." Cancers responsive to Mcl-1 inhibition are known in the art. The therapeutic methods of this disclosure comprise administering a therapeutically effective amount of a Compound of the Disclosure to a subject in need thereof. The present methods also encompass administering a second therapeutic agent to the subject in addition to the Compound of the Disclosure. The second therapeutic agent is selected from drugs known as useful in treating the disease or condition afflicting the subject in need thereof, e.g., a chemotherapeutic agent and/or radiation known as useful in treating a particular cancer.

The present disclosure provides Compounds of the Disclosure as Mcl-1 inhibitors for the treatment of diseases and conditions wherein inhibition of Mcl-1 has a beneficial effect. Compounds of the Disclosure typically have a half maximal inhibitory concentration ($IC_{50}$) for inhibiting Mcl-1 of less than 100 µM, e.g., less than 50 µM, less than 25 µM, and less than 5 µM, less than about 1 µM, less than about 0.5 µM, less than about 0.1 µM, less than about 0.05 µM, or less than about 0.01 µM. In one embodiment, the present disclosure relates to a method of treating an individual suffering from a disease or condition wherein inhibition of Mcl-1 provides a benefit comprising administering a therapeutically effective amount of a Compound of the Disclosure to an individual in need thereof.

Since Compounds of the Disclosure are inhibitors of Mcl-1 protein, a number of diseases and conditions mediated by Mcl-1 can be treated by employing these compounds. The present disclosure is thus directed generally to a method for treating a condition or disorder responsive to Mcl-1 inhibition in an animal, e.g., a human, suffering from, or at risk of suffering from, the condition or disorder, the method comprising administering to the animal an effective amount of one or more Compounds of the Disclosure.

The present disclosure is further directed to a method of inhibiting Mcl-1 in a subject in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent, packaged separately or together, and an insert having instructions for using these active agents.

In one embodiment, a Compound of the Disclosure is administered in conjunction with a second therapeutic agent useful in the treatment of a disease or condition wherein inhibition of Mcl-1 provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to inhibit Mcl-1 activity in the patient.

In another aspect, the present disclosure provides a method of treating cancer in a subject comprising administering a therapeutically effective amount of a Compound of the Disclosure. While not being limited to a specific mechanism, in some embodiments, Compounds of the Disclosure treat cancer by inhibiting Mcl-1. Examples of treatable cancers include, but are not limited to, any one or more of the cancers of Table 3.

TABLE 3

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryoblastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blastoma | bone cancer | Brenner tumor |
| Brown tumor | Burkitt's lymphoma | breast cancer | brain cancer |

TABLE 3-continued

| | | | |
|---|---|---|---|
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |
| glial tumor | glioblastoma multiforme | glioma | gliomatosis cerebri |
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological cancer | hepatoblastoma |
| hepatosplenic T-cell lymphoma | Hodgkin's lymphoma | non-Hodgkin's lymphoma | invasive lobular carcinoma |
| intestinal cancer | kidney cancer | laryngeal cancer | lentigo maligna |
| lethal midline carcinoma | leukemia | leydig cell tumor | liposarcoma |
| lung cancer | lymphangioma | lymphangiosarcoma | lymphoepithelioma |
| lymphoma | acute lymphocytic leukemia | acute myelogeous leukemia | chronic lymphocytic leukemia |
| liver cancer | small cell lung cancer | non-small cell lung cancer | MALT lymphoma |
| malignant fibrous histiocytoma | malignant peripheral nerve sheath tumor | malignant triton tumor | mantle cell lymphoma |
| marginal zone B-cell lymphoma | mast cell leukemia | mediastinal germ cell tumor | medullary carcinoma of the breast |
| medullary thyroid cancer | medulloblastoma | melanoma | meningioma |
| merkel cell cancer | mesothelioma | metastatic urothelial carcinoma | mixed Mullerian tumor |
| mucinous tumor | multiple myeloma | muscle tissue neoplasm | mycosis fungoides |
| myxoid liposarcoma | myxoma | myxosarcoma | nasopharyngeal carcinoma |
| neurinoma | neuroblastoma | neurofibroma | neuroma |
| nodular melanoma | ocular cancer | oligoastrocytoma | oligodendroglioma |
| oncocytoma | optic nerve sheath meningioma | optic nerve tumor | oral cancer |
| osteosarcoma | ovarian cancer | Pancoast tumor | papillary thyroid cancer |
| paraganglioma | pinealoblastoma | pineocytoma | pituicytoma |
| pituitary adenoma | pituitary tumor | plasmacytoma | polyembryoma |
| precursor T-lymphoblastic lymphoma | primary central nervous system lymphoma | primary effusion lymphoma | preimary peritoneal cancer |
| prostate cancer | pancreatic cancer | pharyngeal cancer | pseudomyxoma periotonei |
| renal cell carcinoma | renal medullary carcinoma | retinoblastoma | rhabdomyoma |
| rhabdomyosarcoma | Richter's transformation | rectal cancer | sarcoma |
| Schwannomatosis | seminoma | Sertoli cell tumor | sex cord-gonadal stromal tumor |
| signet ring cell carcinoma | skin cancer | small blue round cell tumors | small cell carcinoma |
| soft tissue sarcoma | somatostatinoma | soot wart | spinal tumor |
| splenic marginal zone lymphoma | squamous cell carcinoma | synovial sarcoma | Sezary's disease |
| small intestine cancer | squamous carcinoma | stomach cancer | T-cell lymphoma |
| testicular cancer | thecoma | thyroid cancer | transitional cell carcinoma |
| throat cancer | urachal cancer | urogenital cancer | urothelial carcinoma |
| uveal melanoma | uterine cancer | verrucous carcinoma | visual pathway glioma |

TABLE 3-continued

| | | | |
|---|---|---|---|
| vulvar cancer | vaginal cancer | Waldenstrom's macroglobulinemia | Warthin's tumor |
| Wilms' tumor | | | |

In another embodiment, the cancer is a solid tumor. In another embodiment, the cancer a hematological cancer. Exemplary hematological cancers include, but are not limited to, the cancers listed in Table 4. In another embodiment, the hematological cancer is acute lymphocytic leukemia, chronic lymphocytic leukemia (including B-cell chronic lymphocytic leukemia), or acute myeloid leukemia.

TABLE 4

| | |
|---|---|
| acute lymphocytic leukemia (ALL) | acute eosinophilic leukemia |
| acute myeloid leukemia (AML) | acute erythroid leukemia |
| chronic lymphocytic leukemia (CLL) | acute lymphoblastic leukemia |
| small lymphocytic lymphoma (SLL) | acute megakaryoblastic leukemia |
| multiple myeloma (MM) | acute monocytic leukemia |
| Hodgkins lymphoma (HL) | acute promyelocytic leukemia |
| non-Hodgkin's lymphoma (NHL) | acute myelogeous leukemia |
| mantle cell lymphoma (MCL) | B-cell prolymphocytic leukemia |
| marginal zone B-cell lymphoma | B-cell lymphoma |
| splenic marginal zone lymphoma | MALT lymphoma |
| follicular lymphoma (FL) | precursor T-lymphoblastic lymphoma |
| Waldenstrom's macroglobulinemia (WM) | T-cell lymphoma |
| diffuse large B-cell lymphoma (DLBCL) | mast cell leukemia |
| marginal zone lymphoma (MZL) | adult T cell leukemia/lymphoma |
| hairy cell leukemia (HCL) | aggressive NK-cell leukemia |
| Burkitt's lymphoma (BL) | angioimmunoblastic T-cell lymphoma |
| Richter's transformation | |

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatitis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the Mcl-1 inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, about 0.05, about 0.5, about 5, about 10, about 20, about 30, about 40, about 50, about 100, about 150, about 200, about 250, about 300, about 350, about 400, about 450, or about 500 milligrams, including all doses between 0.005 and 500 milligrams.

The dosage of a composition containing a Compound of the Disclosure, or a composition containing the same, can be from about 1 ng/kg to about 200 mg/kg, about 1 g/kg to about 100 mg/kg, or about 1 mg/kg to about 50 mg/kg. The dosage of a composition can be at any dosage including, but not limited to, about 1 μg/kg. The dosage of a composition may be at any dosage including, but not limited to, about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor;

an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketoconazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DMI, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransyl-cytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU101, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, Cl-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a Compound of the Disclosure, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxypro-gesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a Compound of the Disclosure also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon (e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compounds of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, PA, 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

The disclosure provides the following particular embodiments in connection with treating a disease in a subject.

Embodiment I. A method of treating a subject, the method comprising administering to the subject a therapeutically effective amount of a Compound of the Disclosure, wherein the subject has cancer, a chronic autoimmune disorder, an inflammatory condition, a proliferative disorder, sepsis, or a viral infection.

Embodiment II. The method Embodiment I, wherein the subject has cancer.

Embodiment III. The method of Embodiment II, wherein the cancer is any one or more of the cancers of Table 3.

Embodiment IV. The method of Embodiment II, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment V. The method of Embodiment II, wherein the cancer is any one or more of the cancers of Table 4.

Embodiment VI. The method of any one of Embodiments I-V further comprising administering a therapeutically effective amount of a second therapeutic agent useful in the treatment of the disease or condition.

Embodiment VII. A pharmaceutical composition comprising a Compound of the Disclosure and a pharmaceutically acceptable excipient for use in treating cancer, a chronic autoimmune disorder, an inflammatory condition, a proliferative disorder, sepsis, or a viral infection.

Embodiment VIII. The pharmaceutical composition of Embodiment VII for use in treating cancer.

Embodiment IX. The pharmaceutical composition of Embodiment VIII, wherein the cancer is any one or more of the cancers of Table 3.

Embodiment X. The pharmaceutical composition of Embodiment IX, wherein the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XI. The pharmaceutical composition of Embodiment VIII, wherein the cancer is any one or more of the cancers of Table 4.

Embodiment XII. A Compound of the Disclosure for use in treatment of cancer, a chronic autoimmune disorder, an inflammatory condition, a proliferative disorder, sepsis, or a viral infection.

Embodiment XIII. The compound of Embodiment XII for use in treating cancer.

Embodiment XIV. The compound of Embodiment XIII, wherein the cancer is any one or more of the cancers of Table 3.

Embodiment XV. The compound of Embodiment XIII, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XVI. The compound of Embodiment XIII, wherein the cancer is any one or more of the cancers of Table 4.

Embodiment XVII. Use of a Compound of the Disclosure for the manufacture of a medicament for treatment of cancer, a chronic autoimmune disorder, an inflammatory condition, a proliferative disorder, sepsis, or a viral infection.

Embodiment XVIII. The use of Embodiment XVII for the treatment of cancer.

Embodiment XIX. The use of Embodiment XVIII, wherein the cancer is any one or more of the cancers of Table 3.

Embodiment XX. The use of Embodiment XVIII, wherein the cancer is selected from the group consisting of acute monocytic leukemia, acute myelogenous leukemia, chronic myelogenous leukemia, chronic lymphocytic leukemia mixed lineage leukemia, NUT midline carcinoma, multiple myeloma, small cell lung cancer, non-small cell lung cancer, neuroblastoma, Burkitt's lymphoma, cervical cancer, esophageal cancer, ovarian cancer, colorectal cancer, prostate cancer, breast cancer, bladder cancer, ovary cancer, glioma, sarcoma, esophageal squamous cell carcinoma, and papillary thyroid carcinoma.

Embodiment XXI. The use of Embodiment XVIII, wherein the cancer is any one or more of the cancers of Table 4.

V. Kits of the Disclosure

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure, e.g., the method of any one of Embodiments I-VI. In one embodiment, the compound or composition is packaged in a unit dosage form. The kit further can include a device suitable for administering the composition according to the intended route of administration.

VI. Definitions

The term "a disease or condition wherein inhibition of Mcl-1 provides a benefit" pertains to a disease or condition in which Mcl-1, is important or necessary, e.g., for the onset, progress, expression of that disease or condition, or a disease or a condition which is known to be treated by an Mcl-1 inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a Mcl-1 inhibitor for any particular cell type, for example, by assays which conveniently can be used to assess the activity of particular compounds.

The terms "Mcl-1" or "Myeloid Cell Leukemia Sequence 1" refer to a protein in humans encoded by the MCLI gene. The term Mcl-1 includes isoforms and mutants of Mcl-1. Mcl-1 belongs to the Bcl-2 family. Alternative splicing occurs at this locus and two transcript variants encoding distinct isoforms have been identified. The longer gene product (isoform 1) enhances cell survival by inhibiting apoptosis while the alternatively spliced shorter gene product (isoform 2) promotes apoptosis and is death-inducing.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, Compounds of the Disclosure are inhibitors of Mcl-1 and can be used in treating or preventing diseases and conditions wherein inhibition of Mcl-1 provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. The term "treat" and synonyms contemplate administering a therapeutically effective amount of a Compound of the Disclosure to a subject in need of such treatment. The treatment can be orientated symptomatically, for example, to suppress symptoms. It can be effected over a short period, be oriented over a medium term, or can be a long-term treatment, for example within the context of a maintenance therapy.

As used herein, the terms "prevent," "preventing," and "prevention" refer to a method of preventing the onset of a disease or condition and/or its attendant symptoms or barring a subject from acquiring a disease. As used herein, "prevent," "preventing," and "prevention" also include delaying the onset of a disease and/or its attendant symptoms and reducing a subject's risk of acquiring a disease. The terms "prevent," "preventing" and "prevention" may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to a subject in need thereof. In the case of a cancer or other proliferation disorder, the therapeutically effective amount of the agent may reduce (i.e., retard to some extent or stop) unwanted cellular proliferation; reduce the number of cancer cells; reduce the tumor size; inhibit (i.e., retard to some extent or stop) cancer cell infiltration into peripheral organs; inhibit (i.e., retard to some extent or stop) tumor metastasis; inhibit, to some extent, tumor growth; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to a subject in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to a subject in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

In the present disclosure, the term "protecting group" as used herein refers to group that blocks, i.e., protects, an amine or hydroxy functionality while reactions are carried out on other functional groups or parts of the molecule. Those skilled in the art will be familiar with the selection, attachment, and cleavage of protecting groups, and will appreciate that different protective groups are known in the art, the suitability of one protective group or another being dependent on the particular the synthetic scheme planned. Treatises on the subject are available for consultation, such as Wuts, "Greene's Protective Groups in Organic Synthesis", 5th Ed., J. Wiley & Sons, Inc., NY, 2014. Suitable amine protecting groups include, but are not limited to, carbobenzyloxy (Cbz), tert-butyloxycarbonyl (BOC), 9-fluorenylmethyloxycarbonyl (FMOC), and benzyl (Bn) groups. Suitable hydroxy protecting groups include, but are not limited to, tetrahydropyran (THP), —C(=O)CH$_3$ (Ac), and —C(=O)Ph (Bz), and silyl-based protecting groups such as -TMS and -TBS.

In the present disclosure, the term "leaving group" refers to an atom or group of atoms that becomes detached from an atom or group of atoms in what is considered to be the residual or main part of the molecule in a specified reaction. Non-limiting exemplary leaving groups include —Cl, —I, —Br, —OTf, —OMs, and —OTs.

In the present disclosure, the term "halo" as used by itself or as part of another group refers to —Cl, —F, —Br, or —I.

In the present disclosure, the term "nitro" as used by itself or as part of another group refers to —NO$_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., C$_{1-12}$ alkyl, or the number of carbon atoms designated, e.g., a C$_1$ alkyl such as methyl, a C$_2$ alkyl such as ethyl, a C$_3$ alkyl such as propyl or isopropyl, a C$_{1-3}$ alkyl such as methyl, ethyl, propyl, or isopropyl, and so on. In one embodiment, the alkyl is a C$_{1-10}$ alkyl. In another embodiment, the alkyl is a C$_{1-6}$ alkyl. In another embodiment, the alkyl is a C$_{1-4}$ alkyl. In another embodiment, the alkyl is a straight chain C$_{1-10}$ alkyl. In another embodiment, the alkyl is a branched chain C$_{3-10}$ alkyl. In another embodiment, the alkyl is a straight chain C$_{1-6}$ alkyl. In another embodiment, the alkyl is a branched chain C$_{3-6}$ alkyl. In another embodiment, the alkyl is a straight chain C$_{1-4}$ alkyl. In another embodiment, the alkyl is a branched chain C$_{3-4}$ alkyl. In another embodiment, the alkyl is a straight or branched chain C$_{3-4}$ alkyl. Non-limiting exemplary C$_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary C$_{1-4}$ alkyl groups include methyl, ethyl, propyl, isopropyl, butyl, sec-butyl, tert-butyl, and iso-butyl.

In the present disclosure, the term "optionally substituted alkyl" as used by itself or as part of another group means that the alkyl as defined above is either unsubstituted or substituted with one, two, or three substituents independently selected from the group consisting of nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, and cycloalkyl. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$SO$_2$CH$_3$, CH$_2$CH$_2$CO$_2$H, —CH$_2$CH$_2$SO$_2$CH$_3$, —CH$_2$CH$_2$COPh, and —CH$_2$C$_6$H$_{11}$.

In the present disclosure, the term "cycloalkyl" as used by itself or as part of another group refers to saturated and partially unsaturated (containing one or two double bonds) cyclic aliphatic hydrocarbons containing one, two, or three rings having from three to twelve carbon atoms, i.e., C$_{3-12}$ cycloalkyl, or the number of carbons designated. In one embodiment, the cycloalkyl group has two rings. In one embodiment, the cycloalkyl group has one ring. In another embodiment, the cycloalkyl group is a C$_{3-8}$ cycloalkyl group. In another embodiment, the cycloalkyl group is a C$_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, and cyclohexenyl.

In the present disclosure, the term "optionally substituted cycloalkyl" as used by itself or as part of another group means that the cycloalkyl as defined above is either unsubstituted or substituted with one, two, or three substituents independently selected from the group consisting of from halo, nitro, cyano, hydroxy, amino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent. In another embodiment, the optionally substituted cycloalkyl is substituted with one amino or (amino)alkyl substituent. Non-limiting exemplary optionally substituted cycloalkyl groups include:

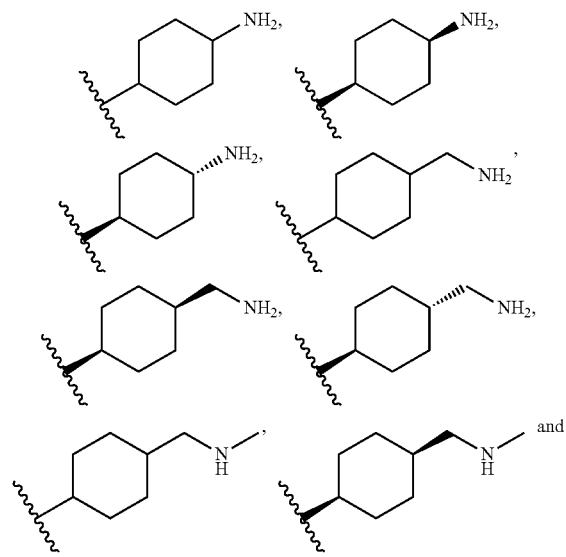

-continued

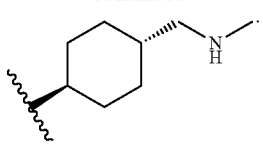

In the present disclosure, the term "alkenyl" as used by itself or as part of another group refers to an alkyl group as defined above containing one, two, or three carbon-to-carbon double bonds. In one embodiment, the alkenyl group is a C$_{2-6}$ alkenyl group. In another embodiment, the alkenyl group is a C$_{2-4}$ alkenyl group. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group means the alkenyl as defined above is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, optionally substituted aryl, optionally substituted heteroaryl, and optionally substituted heterocyclo.

In the present disclosure, the term "alkynyl" as used by itself or as part of another group refers to an alkyl group as defined above containing one, two, or three carbon-to-carbon triple bonds. In one embodiment, the alkynyl has one carbon-to-carbon triple bond. In one embodiment, the alkynyl group is a C$_{2-6}$ alkynyl group. In another embodiment, the alkynyl group is a C$_{2-4}$ alkynyl group. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part of another group means the alkynyl as defined above is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, optionally substituted aryl, optionally substituted heteroaryl, and optionally substituted heterocyclo.

In the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is a C$_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "hydroxyalkyl" as used by itself or as part of another group refers to an alkyl group substituted with one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups.

In another embodiment, the hydroxyalkyl group is a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

In the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is a $C_{1-4}$ alkoxy group. In another embodiment, the alkoxy group is a $C_{1-4}$ alkyl attached to a terminal oxygen atom, e.g., methoxy, ethoxy, and tert-butoxy.

In the present disclosure, the term "alkylthio" as used by itself or as part of another group refers to a sulfur atom substituted by an optionally substituted alkyl group. In one embodiment, the alkylthio group is a $C_{1-4}$ alkylthio group. Non-limiting exemplary alkylthio groups include —$SCH_3$ and —$SCH_2CH_3$.

In the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

In the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to a monocyclic or bicyclic aromatic ring system having from six to fourteen carbon atoms, i.e., $C_6$-$C_{14}$ aryl, or the number of carbon atoms designated. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is phenyl or naphthyl. In another embodiment, the aryl group is phenyl.

In the present disclosure, the term "optionally substituted aryl" as used herein by itself or as part of another group means that the aryl as defined above is either unsubstituted or substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Non-limiting examples include:

In the present disclosure, the term "arylenyl" as used by itself or part of another group refers to a divalent form of an optionally substituted aryl group. In one embodiment, the arylenyl is a divalent form of an optionally substituted phenyl. In one embodiment, the arylenyl is a divalent form of phenyl. Non-limiting exemplary alkylenyl groups include:

In the present disclosure, the term "aryloxy" as used by itself or as part of another group refers to an optionally substituted aryl attached to a terminal oxygen atom. A non-limiting exemplary aryloxy group is PhO—.

In the present disclosure, the term "aralkyloxy" as used by itself or as part of another group refers to an aralkyl group attached to a terminal oxygen atom. A non-limiting exemplary aralkyloxy group is $PhCH_2O$—.

In the present disclosure, the term "heteroaryl" or "heteroaromatic" refers to monocyclic and bicyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), or indazolyl (e.g., 1H-indazol-3-yl). The term "heteroaryl" is also meant to include possible N-oxides. A non-limiting exemplary N-oxide is pyridyl N-oxide. The heteroaryl can be attached to the remained of the molecule through any available carbon or nitrogen atom.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group means that the heteroaryl as defined above is either unsubstituted or substituted with one to four substituents, e.g., one or two substituents, independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, and (heterocyclo)alkyl. In one embodiment, the optionally substituted heteroaryl has one substituent. Any available carbon or nitrogen atom can be substituted.

The term optionally substituted heteroaryl is also meant to include groups having fused optionally substituted cycloalkyl and fused optionally substituted heterocyclo rings. Non-limiting examples include:

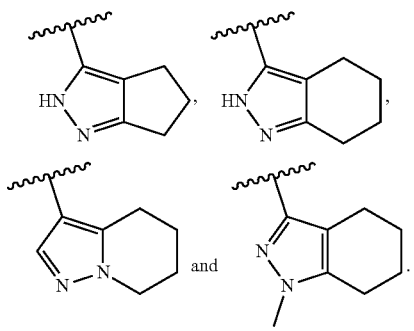

In another embodiment, the heteroaryl is an optionally substituted 9- to 14-membered bicyclic aromatic ring system, wherein at least one carbon atom of one of the rings is replaced with a heteroatom independently selected from the group consisting of oxygen, nitrogen, and sulfur. In another embodiment, the heteroaryl is an optionally substituted 9-membered bicyclic aromatic ring system, wherein one or two carbon atoms of one of the rings is replaced with a heteroatom independently selected from the group consisting of oxygen, nitrogen, and sulfur. Non-limiting exemplary 9- to 14-membered bicyclic aromatic ring systems include:

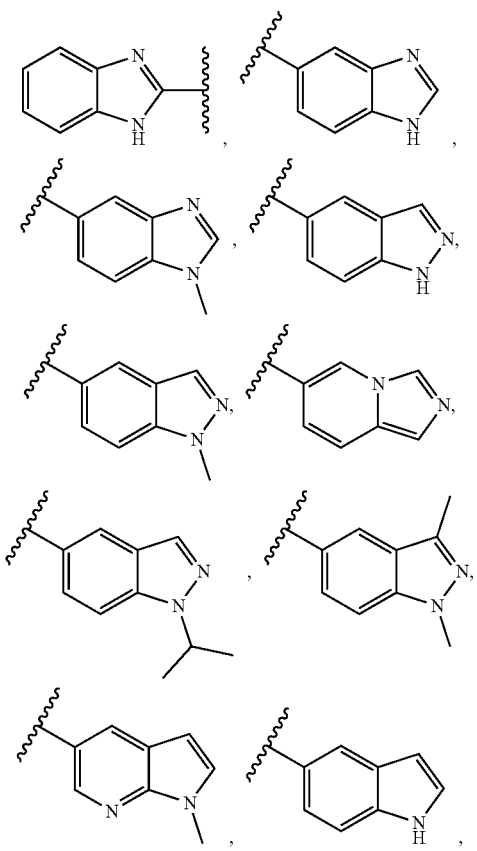

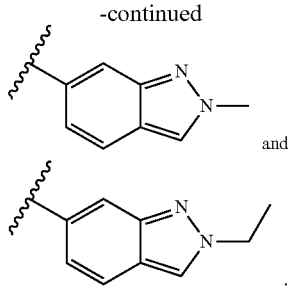

In the present disclosure, the term "heteroarylenyl" as used herein by itself or part of another group refers to a divalent form of an optionally substituted heteroaryl group. In one embodiment, the heteroarylenyl is a 5-membered heteroarylenyl. Non-limiting examples of a 5-membered heteroarylenyl include:

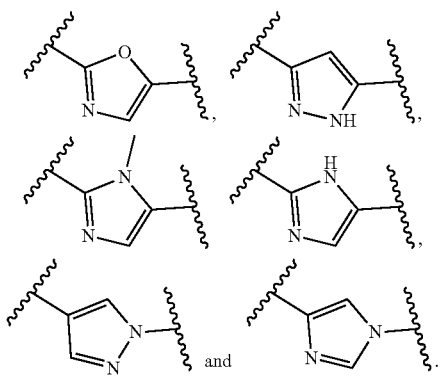

In one embodiment, the heteroarylenyl is a 6-membered heteroarylenyl. Non-limiting examples of a 6-membered heteroarylenyl include:

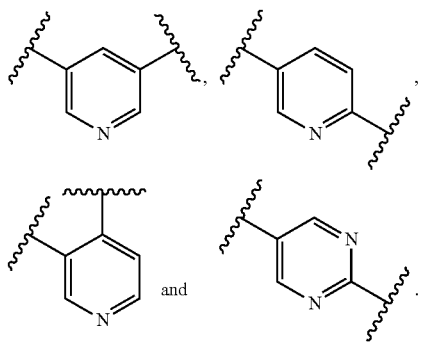

In the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members, i.e., a 3- to 14-membered heterocyclo, wherein at least one carbon atom of one of the rings is replaced with a heteroatom. In one embodiment, the heterocyclo is a 4- to 8-membered heterocyclo. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring —CH$_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" is also meant to include groups having fused optionally substituted aryl groups, e.g., indolinyl, chroman-4-yl. In one embodiment, the heterocyclo group is a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

In the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, amido, carboxamido, sulfonamido, alkylcarbonyl, alkoxycarbonyl, CF$_3$C(=O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. Substitution may occur on any available carbon or nitrogen atom, or both. Non-limiting exemplary optionally substituted heterocylo groups include:

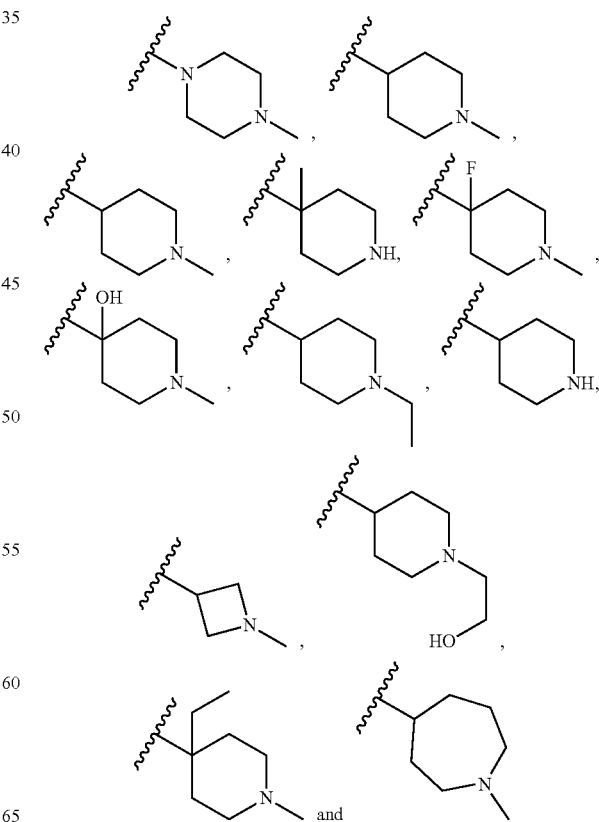

In the present disclosure, the term "amino" as used by itself or as part of another group refers to a radical of the formula —NR$^{30a}$R$^{30b}$, wherein R$^{30a}$ and R$^{30b}$ are independently hydrogen, alkyl, hydroxyalkyl, optionally substituted cycloalkyl, optionally substituted aryl, optionally substituted heterocyclo, or optionally substituted heteroaryl, or R$^{30a}$ and R$^{30b}$ are taken together to form a 3- to 8-membered optionally substituted heterocyclo. In one embodiment, R$^{30a}$ and R$^{30b}$ are independently hydrogen or C$_{1-4}$ alkyl. Non-limiting exemplary amino groups include —NH$_2$ and —N(H)(CH$_3$).

In the present disclosure, the term "(amino)alkyl" as used by itself or as part of another group refers to an alkyl group substituted with an amino group. In one embodiment, the (amino)alkyl is a C$_{1-6}$ alkyl substituted with an amino group, i.e., an (amino)C$_{1-6}$ alkyl. In another embodiment, the (amino)alkyl is an (amino)C$_{1-4}$ alkyl. Non-limiting exemplary (amino)alkyl groups include —CH$_2$NH$_2$, —CH$_2$CH$_2$NH$_2$, —CH$_2$CH$_2$N(H)CH$_3$, —CH$_2$CH$_2$N(CH$_3$)$_2$, and —CH$_2$N(H)cyclopropyl.

In the present disclosure, the term "carboxamido" as used by itself or as part of another group refers to a radical of formula —C(=O)NR$^{31a}$R$^{31b}$, wherein R$^{31a}$ and R$^{31b}$ are each independently hydrogen, optionally substituted alkyl, hydroxyalkyl, optionally substituted cycloalkyl, optionally substituted aryl, optionally substituted heterocyclo, or optionally substituted heteroaryl, or R$^{31a}$ and R$^{31b}$ taken together with the nitrogen to which they are attached form a 3- to 8-membered optionally substituted heterocyclo group. In one embodiment, R$^{31a}$ and R$^{31b}$ are each independently hydrogen or optionally substituted alkyl. In one embodiment, R$^{31a}$ and R$^{31b}$ are taken together to taken together with the nitrogen to which they are attached form a 3- to 8-membered optionally substituted heterocyclo group. Non-limiting exemplary carboxamido groups include —CONH$_2$, —CON(H)CH$_3$, —CON(CH$_3$)$_2$, and —CON(H)Ph.

In the present disclosure, the term "amido" as used by itself or as part of another group refers to a radical of formula —N(R$^{32a}$)C(=O)R$^{32b}$, wherein R$^{32a}$ is hydrogen or C$_{1-4}$ alkyl; and R$^{32b}$ is C$_{1-6}$ alkyl, optionally substituted cycloalkyl, optionally substituted aryl, C$_{1-4}$ alkoxy, or amino. In one embodiment, R$^{32a}$ is hydrogen. In another embodiment, R$^{32b}$ is C$_{1-4}$ alkyl, C$_{1-4}$ alkoxy, or amino. Non-limiting exemplary amido groups include —N(H)C(=O)CH$_3$, —N(H)C(=O)OCH$_3$, and —N(H)C(=O)N(H)CH$_3$.

In the present disclosure, the term "sulfonamido" as used by itself or as part of another group refers to a radical of the formula —SO$_2$NR$^{8a}$R$^{8b}$, wherein R$^{8a}$ and R$^{8b}$ are each independently hydrogen, optionally substituted alkyl, or optionally substituted aryl, or R$^{8a}$ and R$^{8b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

In the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

In the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

In the present disclosure, the term "alkoxycarbonyl" as used by itself or as part of another group refers to a carbonyl group, i.e., —C(=O)—, substituted by an alkoxy group. Non-limiting exemplary alkoxycarbonyl groups include —C(=O)OMe, —C(=O)OEt, and —C(=O)OtBu.

In the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

In the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

In the present disclosure, the term "mercaptoalkyl" as used by itself or as part of another group refers to any of the above-mentioned alkyl groups substituted by a —SH group.

In the present disclosure, the term "carboxy" as used by itself or as part of another group refers to a radical of the formula —COOH.

In the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

In the present disclosure, the terms "aralkyl" or "arylalkyl" as used by themselves or as part of another group refers to an alkyl group substituted with one, two, or three optionally substituted aryl groups. In one embodiment, the optionally substituted aralkyl group is a C$_{1-4}$ alkyl substituted with one optionally substituted aryl group. In one embodiment, the optionally substituted aralkyl group is a C$_1$ or C$_2$ alkyl substituted with one optionally substituted aryl group. In one embodiment, the optionally substituted aralkyl group is a C$_1$ or C$_2$ alkyl substituted with one optionally substituted phenyl group. Non-limiting exemplary optionally substituted aralkyl groups include benzyl, phenethyl, —CHPh$_2$, —CH$_2$(4-F-Ph), —CH$_2$(4-Me-Ph), —CH$_2$(4-CF$_3$-Ph), and —CH(4-F-Ph)$_2$.

In the present disclosure, the terms "(heterocyclo)alkyl" as used by itself or part of another group refers to an alkyl group substituted with one or two optionally substituted heterocyclo groups. In one embodiment, the (heterocyclo)alkyl is a C$_{1-4}$ alkyl substituted with one optionally substituted heterocyclo group, i.e., a (heterocyclo)C$_{1-4}$ alkyl. In another embodiment, the (heterocyclo)alkyl is a C$_{1-4}$ alkyl substituted with one optionally substituted 4- to 8-membered heterocyclo group, i.e., a (4- to 8-membered heterocyclo)C$_1$. 4 alkyl. In another embodiment, the (heterocyclo)alkyl is a C$_1$ alkyl substituted with one optionally substituted 4- to 8-membered heterocyclo group, i.e., (4- to 8-membered heterocyclo)-CH$_2$—. Non-limiting exemplary (heterocyclo)alkyl groups include:

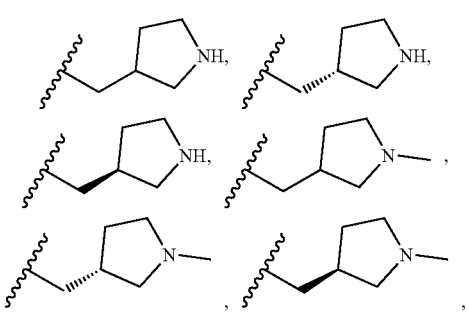

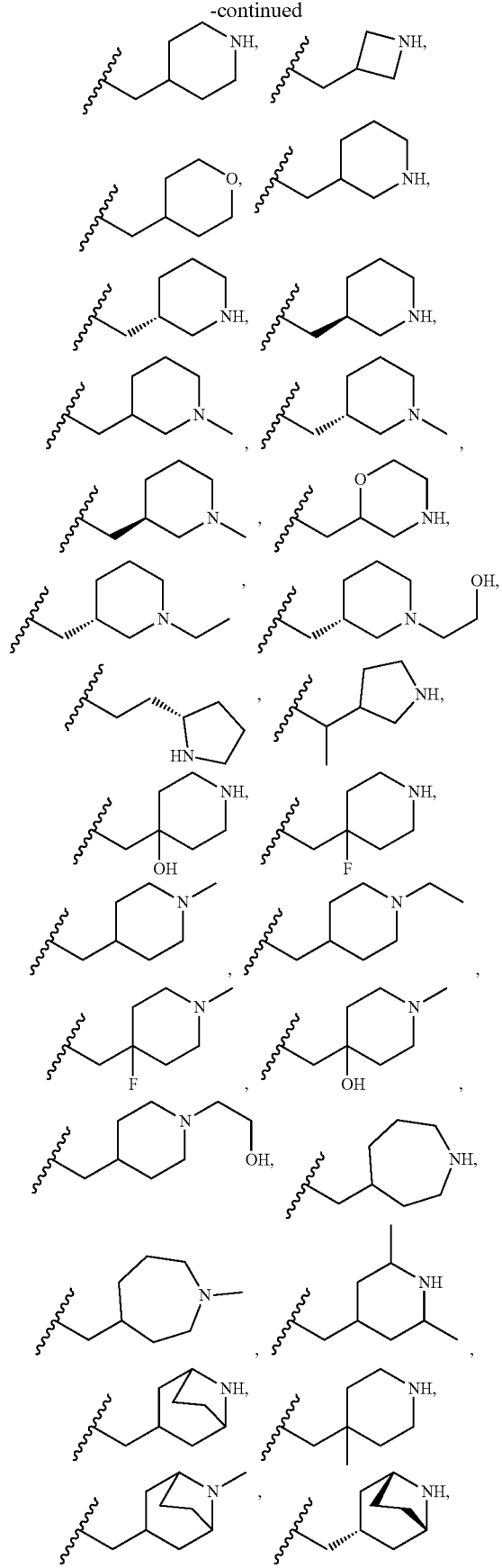

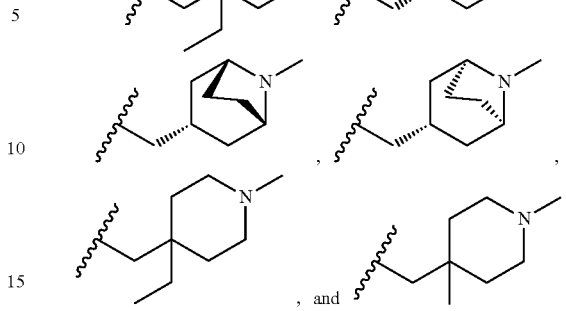

In the present disclosure, the terms "(cycloalkyl)alkyl" as used by itself or part of another group refers to an alkyl group substituted with one or two optionally substituted cycloalky groups. In one embodiment, the (cycloalkyl)alkyl is a $C_{1-4}$ alkyl substituted with one optionally substituted cycloalkyl group, i.e., a (cycloalkyl)$C_{1-4}$ alkyl. In another embodiment, the (cycloalkyl)alkyl is a $C_{1-4}$ alkyl substituted with one amino- or (alkyl)amino-substituted cycloalkyl. Non-limiting exemplary (cycloalkyl)alkyl groups include:

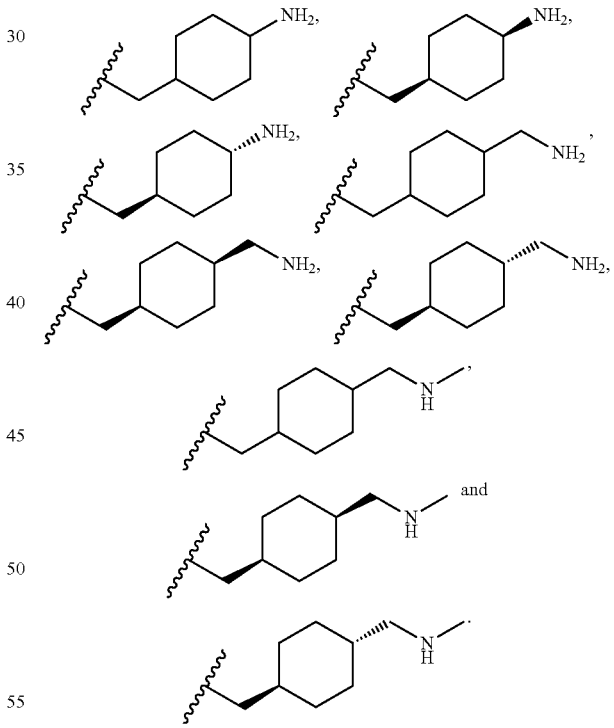

In the present disclosure, the terms "(heteroaryl)alkyl" as used by itself or part of another group refers to an alkyl group substituted with one or two optionally substituted heteroaryl groups. In one embodiment, the (heteroaryl)alkyl is a $C_{1-4}$ alkyl substituted with one optionally substituted heteroaryl group, i.e., a (heteroaryl)$C_{1-4}$ alkyl. In another embodiment, the (heteroaryl)alkyl is a $C_{1-4}$ alkyl substituted with one optionally substituted 5- or 6-membered heteroaryl group, i.e., a (5- or 6-membered heteroaryl)$C_{1-4}$ alkyl. Non-limiting exemplary (heteroaryl)alkyl groups include:

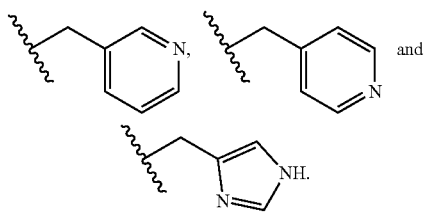

Compounds of the Disclosure and certain Intermediates of the Disclosure exist as stereoisomers, i.e., isomers that differ only in the spatial arrangement of atoms, including optical isomers and conformational isomers (or conformers) and tautomers. The disclosure includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

As used herein, the term "stereoisomers" is a general term for all isomers of individual molecules that differ only in the orientation of their atoms in space. It includes enantiomers, atropisomers, and isomers of compounds with more than one chiral center that are not mirror images of one another (diastereomers).

The term "chiral center" or "asymmetric carbon atom" refers to a carbon atom to which four different groups are attached.

The term "atropisomer" refers to a stereoisomer arising because of hindered rotation about a single bond. Atropisomers display axial chirality.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction. Enantiomers may be separated by chiral chromatography using methods well known in the art.

The term "racemic" or "racemate" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography, or optical polarimetry. Compounds of the Disclosure or Intermediates of the Disclosure that are racemic can be separated by chiral HPLC, e.g., using a CHIRALPAK IE column. In one embodiment, Compounds of the Disclosure or Intermediates of the Disclosure have an ee of about 70% or more, e.g., about 80% or more, about 90% or more, about 91% or more, about 92% or more, about 93% or more, about 94% or more, about 95% or more, about 96% or more, about 97% or more, about 98% or more, or about 99% or more.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure. Certain compounds of the Disclosure are enantioenriched.

The term "about," as used herein, includes the recited number ±10%. Thus, "about 10" means 9 to 11.

EXAMPLES

General Schemes

Compounds of the Disclosure and Intermediates of the Disclosure can be prepared according to the following General Schemes.

General Scheme 1 describes exemplary reaction steps and conditions for the preparation of compounds of Formula III, wherein Ⓐ is A-2 (and $R^{6e}$ and $R^{6f}$ are hydrogen) and X is —S—.

In step 1, a compound of Formula XVI, wherein R is $C_1$-$C_6$ alkyl, Ⓐ is A-2, $R^{19}$ is a protecting group, i.e., PMB, and $R^{20}$ is —$CH_2XR^2$, X is —O—, and $R^{21}$ is hydrogen, i.e., $R^{20}$ is —$CH_2OH$, is reacted with $CBr_4$ to give a compound of Formula XVI, wherein $R^{20}$ is —$CH_2$-LG, and the leaving group is —Br, i.e., $R^{20}$ is —$CH_2Br$. Other methods to convert an alcohol to an alkyl halide are known in the art.

In steps 2, the alkyl bromide of Formula XVI is reacted with a compound of Formula A to give a compound of Formula XVII, wherein X is —S— and $R^{22}$ is —$OR^{23}$ and $R^{23}$ is a protecting group, i.e., $R^{22}$ is —OTBS or —OBz. The compound is deprotected to give a compound of Formula XVII, wherein X is —S— and R is —OH.

In step 3, the compound of Formula XVII, wherein $R^{22}$ is —OH is converted to a compound of Formula XVII, wherein $R^{22}$ is a leaving group, i.e., $R^{22}$ is —Br.

In step 4, the protecting group, i.e., PMB, is removed and the resulting compound, i.e., a compound of Formula XVII, wherein $R^{19}$ is hydrogen, is cyclized to give a compound of Formula III, wherein R is $C_1$-$C_6$ alkyl.

In step 5, the ester is hydrolyzed to give a compound of Formula III, wherein R is hydrogen.

General Scheme 1
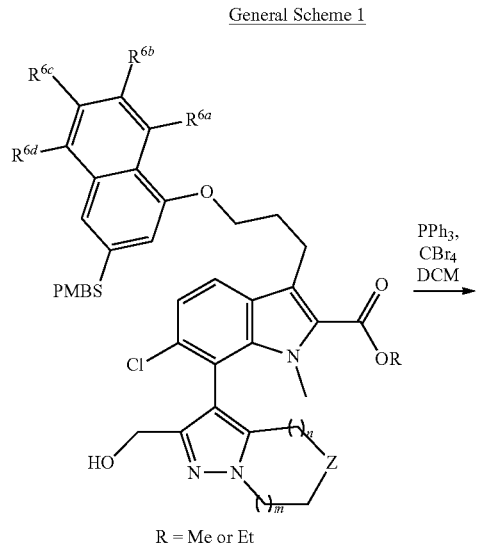
R = Me or Et
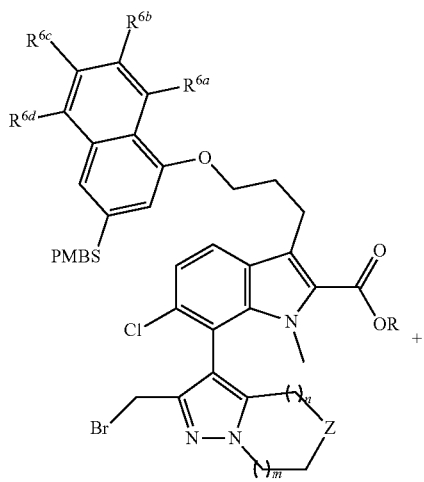
R' = TBS, Bz
Formula A
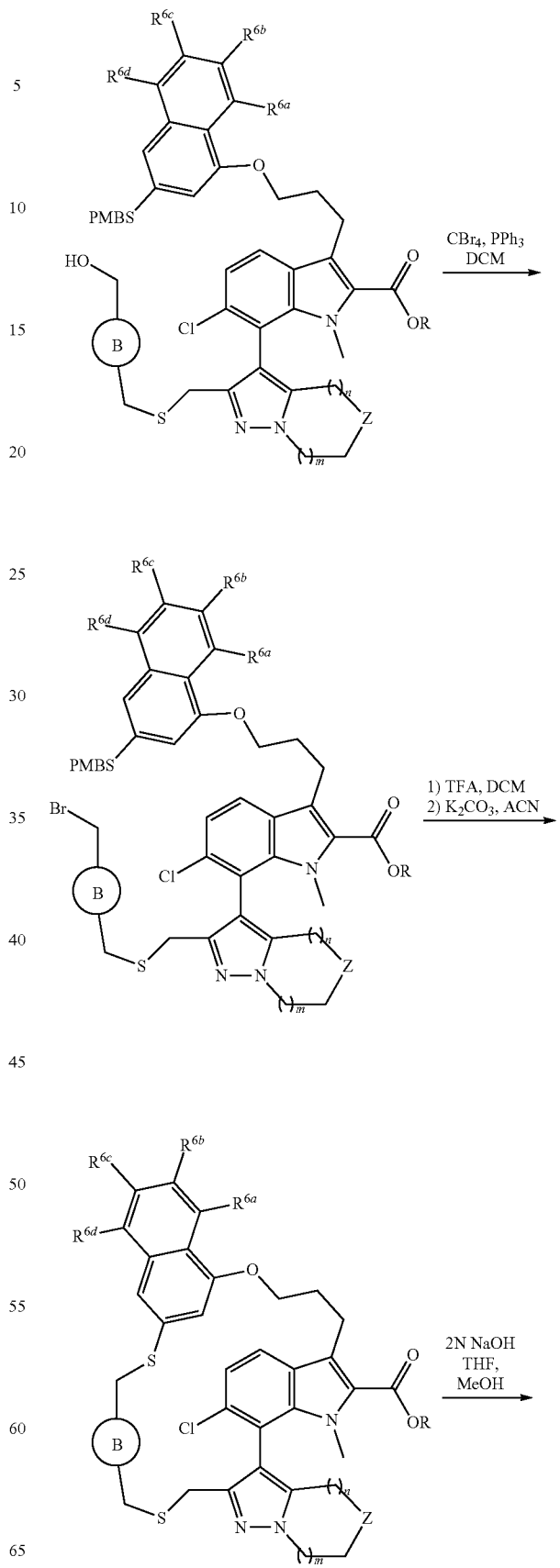

-continued

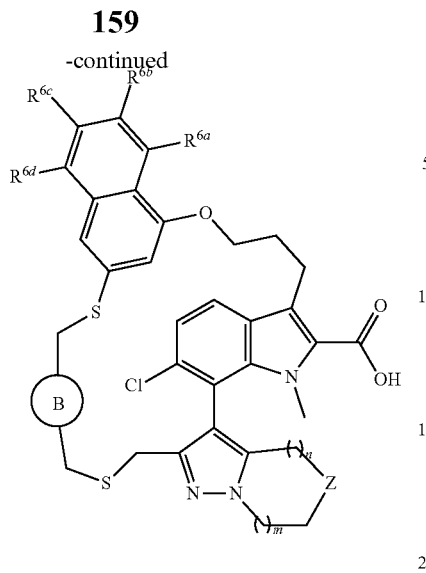

General Scheme 2

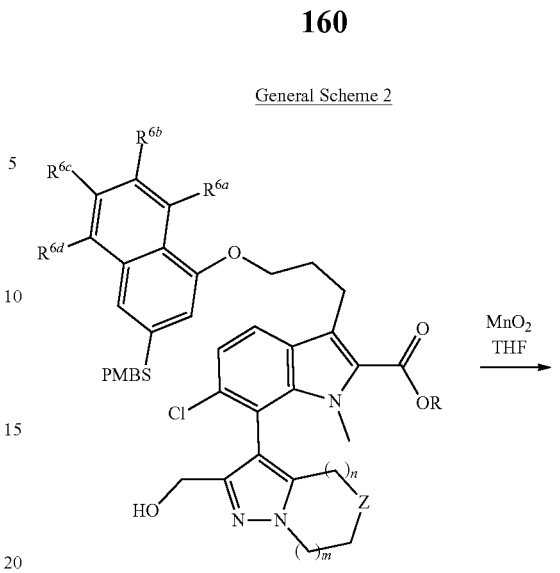

General Scheme 2 describes exemplary reaction steps and conditions for the preparation of compounds of Formula III, wherein Ⓐ is A-2 (and $R^{6e}$ and $R^{6f}$ are hydrogen) and X is —N($R^3$)—.

In step 1, a compound of Formula XVI, wherein R is $C_1$-$C_6$ alkyl, Ⓐ is A-2, $R^{19}$ is a protecting group, i.e., PMB, and $R^{20}$ is —$CH_2XR^{21}$, X is —O—, and $R^{21}$ is hydrogen, i.e., $R^{20}$ is —$CH_2OH$, is oxidized to give a compound of Formula XVI, wherein $R^{20}$ is —C(=O)H.

In steps 2/3, compound of Formula XVI, wherein $R^{20}$ is —C(=O)H, is made to undergo reductive amination of a with $BocNH_2$. The resulting compound is deprotected to give a compound of Formula XVI, wherein $R^{20}$ is —$CH_2XR^2$, X is —N(H)—, $R^{21}$ is hydrogen, i.e., $R^{20}$ is —$CH_2NH_2$.

In step 4, another reductive amination with a compound of Formula B, to give a compound of Formula XVII, wherein X is —N(H)— and $R^{22}$ is —$OR^{23}$ and $R^{23}$ is a protecting group, i.e., R is —OTBS.

In step 5, the amino group of Formula XVII is reacted with, e.g., $R^3Cl$, to give a compound of Formula XVII, wherein —N($R^3$)—.

In steps 6/7, the compound of Formula XVII is deprotected and converted to a compound of Formula XVII, wherein $R^{22}$ is a leaving group, i.e., $R^{22}$ is —Br.

In step 8, the protecting group, i.e., PMB, is removed and the resulting compound, i.e., a compound of Formula XVII, wherein $R^{19}$ is hydrogen, is cyclized to give a compound of Formula III, wherein R is $C_1$-$C_6$ alkyl.

In step 9, the ester is hydrolyzed to give a compound of Formula III, wherein R is hydrogen.

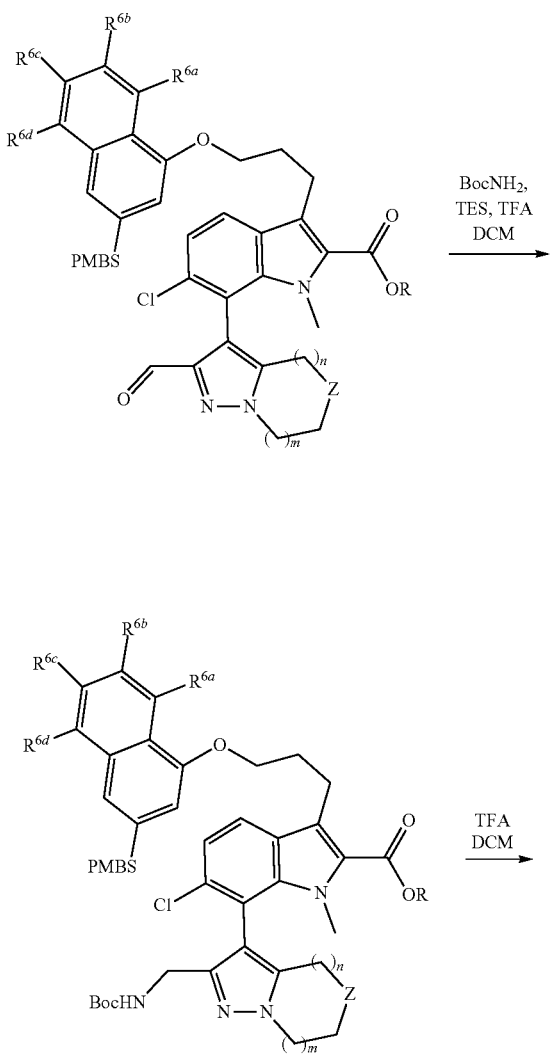

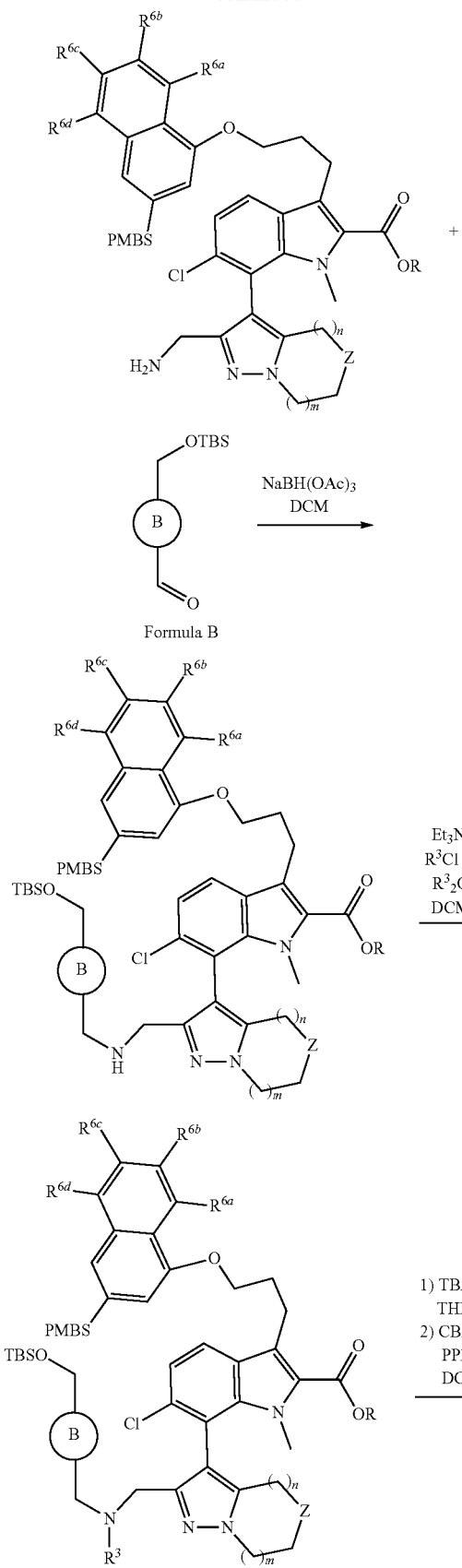
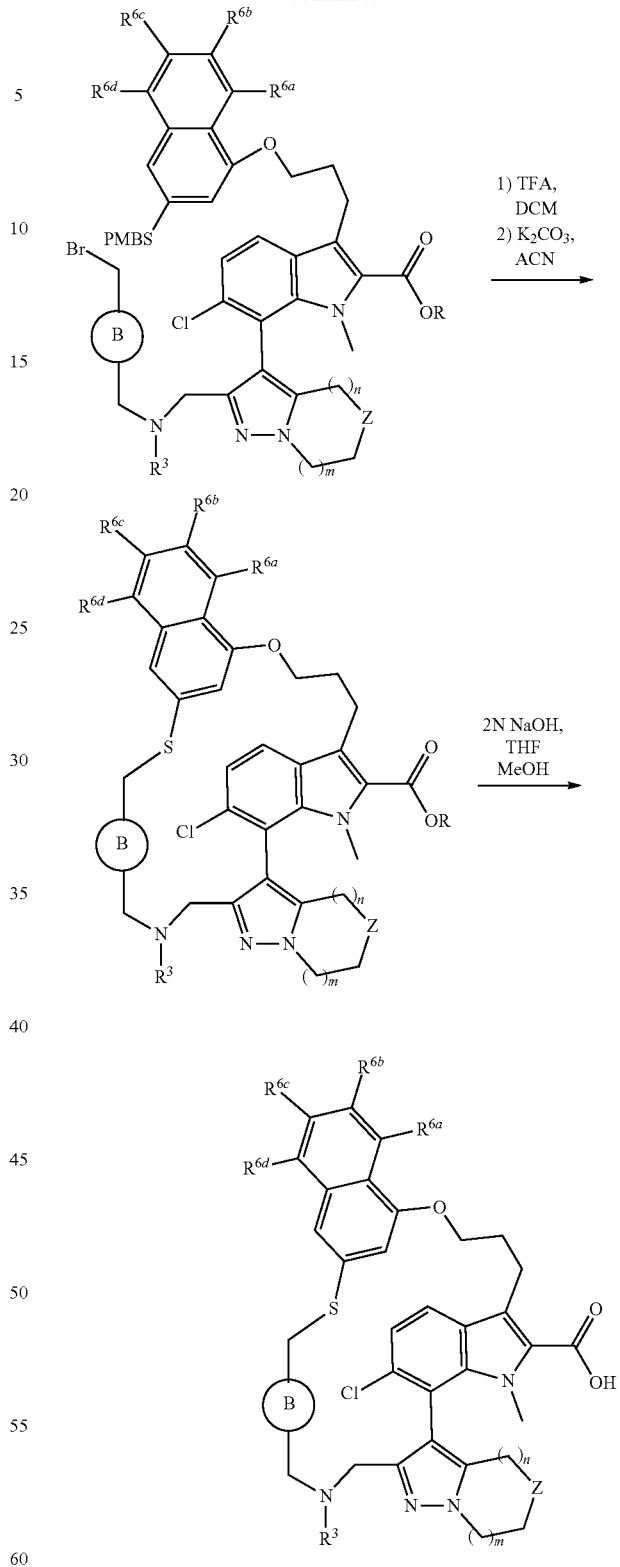
General Scheme 3 describes exemplary reaction steps and conditions for the preparation of compounds of Formula XII, wherein Ⓐ is A-2 (and $R^{6e}$ and $R^{6f}$ are hydrogen) and X is —N($R^3$)—. These reaction steps and conditions are similar to those described in General Scheme 2.

General Scheme 3
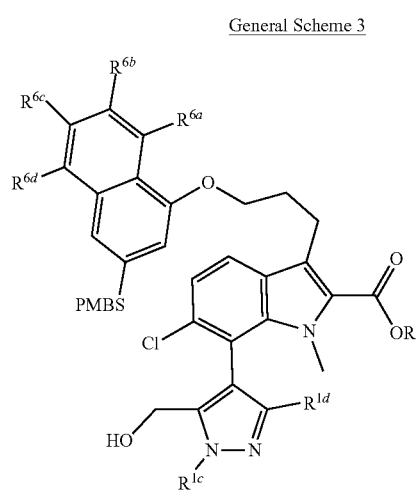
MnO₂
THF
→
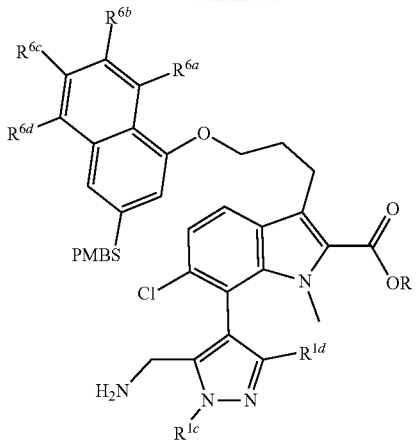 +
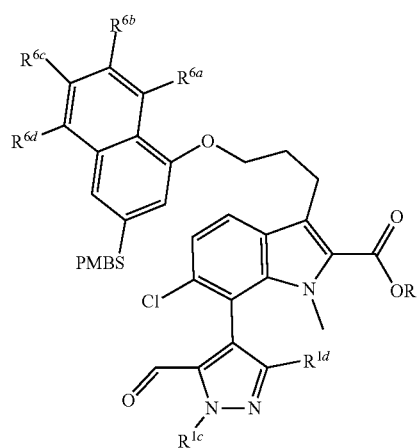
BocNH₂,
TES, TFA
DCM
→
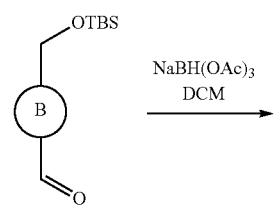
NaBH(OAc)₃
DCM
→
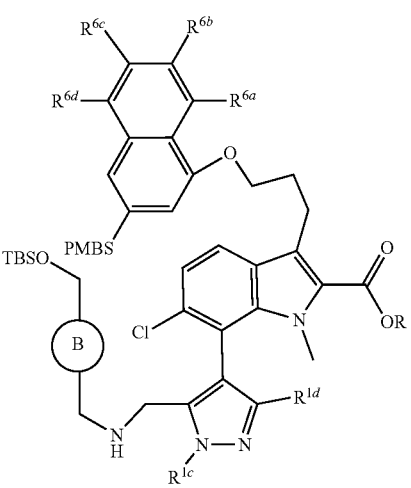
Et₃N,
R³Cl or
R³₂O
DCM
→
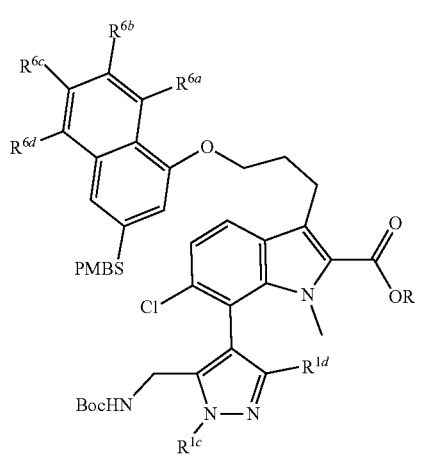
TFA
DCM
→
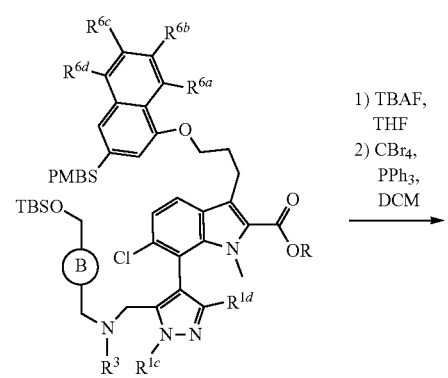
1) TBAF, THF
2) CBr₄, PPh₃, DCM
→

165
-continued

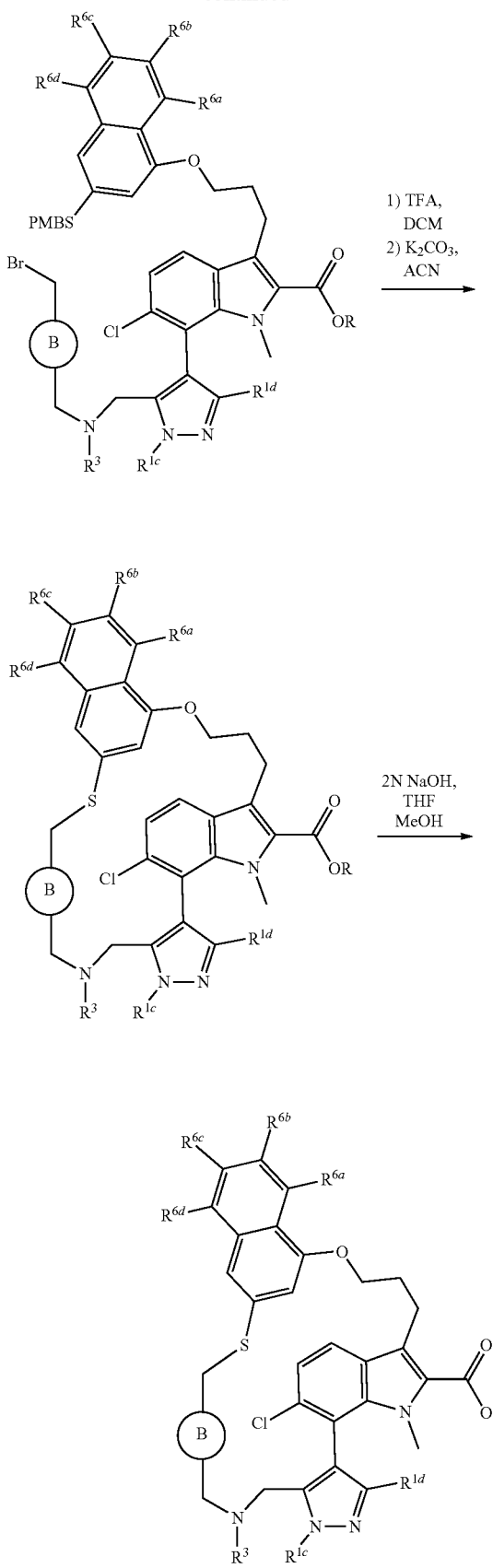

166

Example 1

Synthesis of (Z)-$1^6$-chloro-$1^1$,$6^1$-dimethyl-$2^5$,$2^6$-dihydro-$1^1$H,$2^4$H,$6^1$H-10-oxa-4,8-dithia-1(7,3)-indola-2(3,2)-pyrrolo[1,2-b]pyrazola-6(3,5)-pyrazola-9 (3,1)-naphthalenacyclotridecaphane-$1^2$-carboxylic acid (Cpd. No. 1)

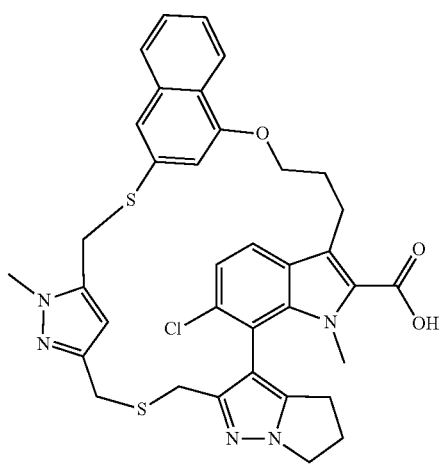 [SMILES: Cn1nc2cc1CSc1cc(c3ccccc3c1)OCCCc1c(C(=O)O)n(C)c3c(c(Cl)ccc13)-c1c(nn3c1CCC3)CSC2]

Step A: Ethyl 7-(2-(bromomethyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate

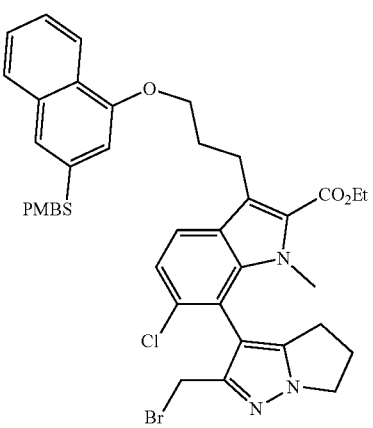

Under Ar, to a solution of ethyl 6-chloro-7-(2-(hydroxymethyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate (Intermediate E1, 1.0 g, 1.41 mmol) and Ph$_3$P (0.74 g, 2.82 mmol) in dry DCM (25 mL) was added CBr$_4$ (0.93 g, 2.82 mmol) at 0° C., then the reaction mixture was stirred at room temperature for 16 h. After removal of volatiles under reduced pressure, the residue was purified by silica gel column (DCM:MeOH, 10:1) to afford the title compound (1.02 g, 94%) as a yellow oil. MS: 774.1 (M+H$^+$).

Step B: Ethyl 7-(2-(((((5-(((tert-butyldimethylsilyl)oxy)methyl)-1-methyl-1H-pyrazol-3-yl)methyl)thio)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate

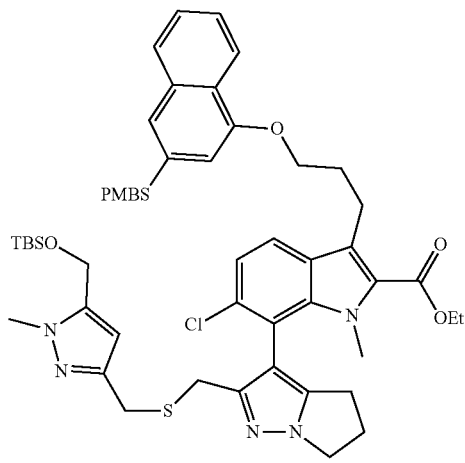

Under Ar, to a solution of S-((5-(((tert-butyldimethylsilyl)oxy)methyl)-1-methyl-1H-pyrazol-3-yl)methyl) ethanethioate (Intermediate D1, 100 mg, 0.32 mmol) and the crude ethyl 7-(2-(bromomethyl)-5,6-dihydro-4H-pyrrolo[1,2-b]pyrazol-3-yl)-6-chloro-3-(3-((3-((4-methoxy benzyl)thio)naphthalen-1-yl)oxy)propyl)-1-methyl-1H-indole-2-carboxylate (Step A, 393 mg) in a mixed solution of dry MeOH (10 mL) and dry THF (10 mL) was added $K_2CO_3$ (220 mg, 1.59 mmol), then the reaction mixture was stirred at room temperature for 1 h. After filtration and removal of volatiles under reduced pressure, the residue was concentrated under reduced pressure to give the crude title compound as a brown oil, which was directly used without purification. MS: 964.3 (M+H$^+$); 986.4 (M+Na$^+$).

Step C: Ethyl 6-chloro-7-(2-((((5-(hydroxymethyl)-1-methyl-1H-pyrazol-3-yl)methyl)thio)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate

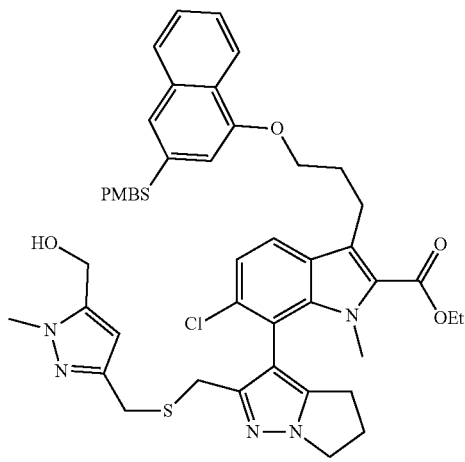

Under Ar, to a solution of the above brown oil (Step B, 480 mg) in dry THF (10 mL) was added TBAF·3H$_2$O (784 mg, 3.00 mmol), then the reaction was stirred at room temperature for 2 h. After removal of volatiles under reduced pressure, the residue was purified by silica gel column (DCM:MeOH, 20:1) to afford the crude title compound (110 mg) as a yellow oil, which was used for the next step without further purification. MS: 851.4 (M+H$^+$); 872.3 (M+Na$^+$).

Step D: Ethyl 7-(2-((((5-(bromomethyl)-1-methyl-1H-pyrazol-3-yl)methyl)thio)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate

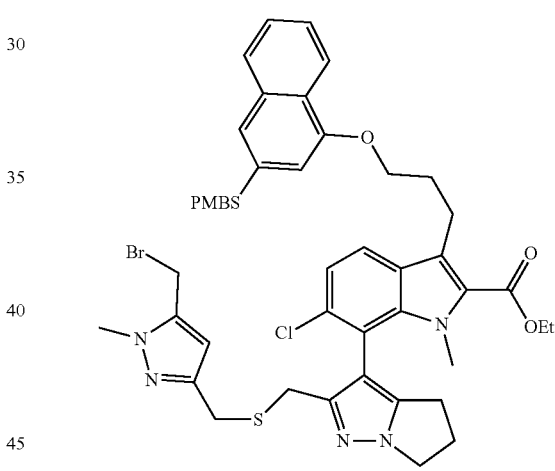

Under Ar, to a solution of the crude ethyl 6-chloro-7-(2-((((5-(hydroxymethyl)-1-methyl-1H-pyrazol-3-yl)methyl)thio)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate (Step C, 110 mg) in dry DCM (15 mL) was added PPh$_3$ (136 mg, 0.52 mmol) and CBr$_4$ (172 mg, 0.52 mmol) subsequently, then the reaction solution was stirred at room temperature for 3 h. After removal of volatiles under reduced pressure, the residue was purified by silica gel column (DCM:MeOH, 60:1) to afford the crude title compound (200 mg) as a brown oil, which was used for the next step without further purification. MS: 914.0 (M+H$^+$); 935.9 (M+Na$^+$).

Step E: Ethyl (Z)-1⁶-chloro-1¹,6¹-dimethyl-2⁵,2⁶-dihydro-1¹H,2⁴H,6¹H-10-oxa-4,8-dithia-1(7,3)-indola-2(3,2)-pyrrolo[1,2-b]pyrazola-6(3,5)-pyrazola-9(3,1)-naphthalenacyclotridecaphane-1²-carboxylate

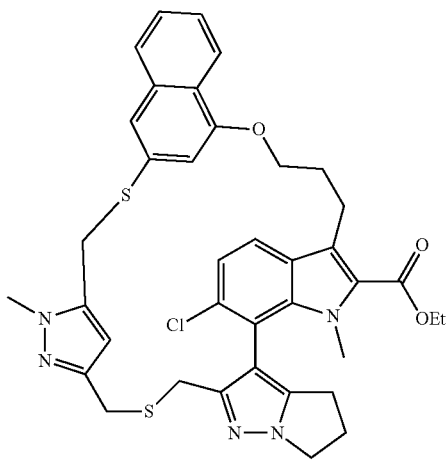 [SMILES: CCOC(=O)c1c2c3ccc(Cl)c(c3n1C)-c1c(nn3c1CCC3)CSCc1cc(n(C)n1)CSc1cc(c3ccccc3c1)OCCC2]

Under Ar, to a solution of the crude ethyl 7-(2-((((5-(bromomethyl)-1-methyl-1H-pyrazol-3-yl)methyl)thio)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate (Step D, 40 mg) in DCM (2 mL) was added TFA (6.0 mL) and TES (2.0 mL), then the reaction mixture was stirred at room temperature for overnight. After removal of volatiles under reduced pressure, the resulting yellow oil was directly used for the next step without purification. MS: 794.0 (M+H⁺), 816.0 (M+Na⁺).

Under Ar, to a solution of the above yellow oil (35 mg, 0.044 mmol) in dry acetonitrile (14 mL) was added K₂CO₃ (183 mg, 1.32 mmol), then the reaction mixture was stirred at room temperature for 3 h. After filtration and removal of volatiles under reduced pressure, the crude title compound as a brown oil was directly used for the next step without purification. MS: 712.2 (M+H⁺); 734.2 (M+Na⁺).

Step F: (Z)-1⁶-Chloro-1¹,6¹-dimethyl-2⁵,2⁶-dihydro-1¹H,2⁴H,6¹H-10-oxa-4,8-dithia-1(7,3)-indola-2(3,2)-pyrrolo[1,2-b]pyrazola-6(3,5)-pyrazola-9(3,1)-naphthalenacyclotridecaphane-1²-carboxylic acid To a solution of the above brown oil in a mixed solution of THF (12 mL) and MeOH (4 mL) was added 2N NaOH (4 mL) at room temperature, then the reaction was stirred for overnight. After removal of volatiles under reduced pressure, the residue was adjusted to pH to 2-3 with 1 N HCl. The resulting mixture was extracted with DCM twice. The combined DCM layer was concentrated under reduced pressure to give a brown oil, which was purified by C18 prep-HPLC column to afford the title compound (5 mg, 3% over 6 steps) as a white solid. ¹H NMR (500 MHz, DMSO-d₆) δ 8.12 (d, J=8.2 Hz, 1H), 7.90 (d, J=8.6 Hz, 1H), 7.75 (d, J=7.9 Hz, 1H), 7.53-7.47 (m, 2H), 7.40 (s, 1H), 7.15 (d, J=8.5 Hz, 1H), 6.72 (s, 1H), 4.76 (s, 1H), 4.31 (s, 2H), 4.19-4.10 (m, 4H), 3.90-3.85 (m, 1H), 3.74 (s, 3H), 3.57 (s, 3H), 3.26 (d, J=12.2 Hz, 2H), 3.16-3.08 (m, 2H), 2.93 (d, J=15 Hz, 1H), 2.72-2.57 (m, 4H), 2.42-2.37 (m, 1H), 2.29-2.20 (m, 1H). MS: 684.3 (M+H⁺); 706.2 (M+Na⁺).

Example 2

Synthesis of (Z)-1⁶-chloro-1¹,6¹-dimethyl-2⁵,2⁶-dihydro-1¹H,2⁴H,6¹H-10-oxa-4,8-dithia-1(7,3)-indola-2(3,2)-pyrrolo[1,2-b]pyrazola-6(5,3)-pyrazola-9(3,1)-naphthalenacyclotridecaphane-1²-carboxylic acid (Cpd. No. 7)

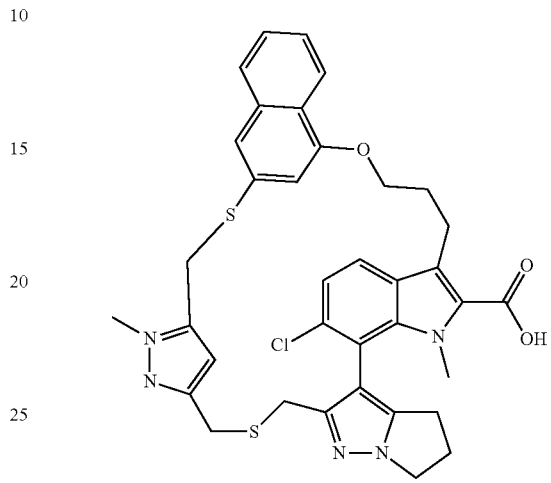

Step A: Methyl 6-chloro-7-(2-((((3-(hydroxymethyl)-1-methyl-1H-pyrazol-5-yl)methyl)thio)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate

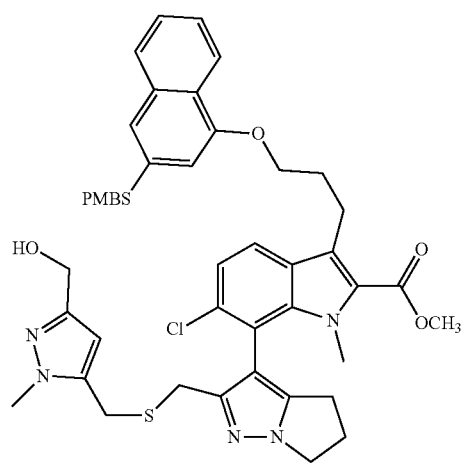

Under Ar, to a solution of (5-((acetylthio)methyl)-1-methyl-1H-pyrazol-3-yl)methyl benzoate (Intermediate D2, 54 mg, 0.18 mmol) and ethyl 7-(2-(bromomethyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate (Step A of EXAMPLE 1, 137 mg, 0.18 mmol) in a mixed solvent of dry MeOH (2 mL) and dry THF (2 mL) was added K₂CO₃ (123 mg, 0.89 mmol), then the reaction mixture was stirred at room temperature for overnight. After removal of volatiles under reduced pressure, the residue was purified by silica gel column (DCM:MeOH, 10:1) to afford the title compound as a light yellow foam (40 mg, 27%). MS: 836.1 (M+H$^+$).

Step B: Methyl 7-(2-((((3-(bromomethyl)-1-methyl-1H-pyrazol-5-yl)methyl)thio)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate

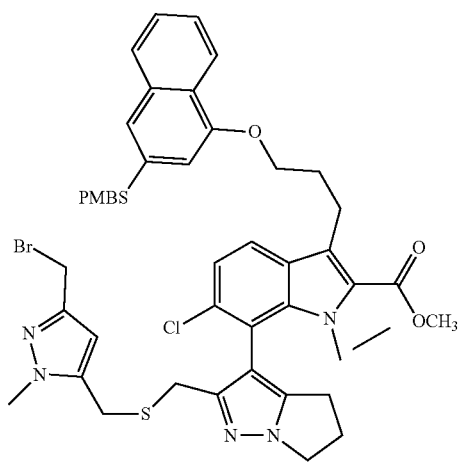

Under Ar, to a solution of ethyl 6-chloro-7-(2-((((3-(hydroxymethyl)-1-methyl-1H-pyrazol-5-yl)methyl)thio)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate (Step A, 40 mg, 0.05 mmol) in dry DCM (10 mL) was added PPh$_3$ (24.7 mg, 0.10 mmol) and CBr$_4$ (31.2 mg, 0.10 mmol), then the reaction mixture was stirred at room temperature for 1 h. After removal of volatiles under reduced pressure, the residue was purified by silica gel column (DCM:MeOH, 20:1) to afford the crude title compound as a yellow solid, which was used for the next step without further purification. MS: 899.9 (M+H$^+$), 921.9 (M+Na$^+$).

Step C: (Z)-1$^6$-chloro-1$^1$,6$^1$-dimethyl-2$^5$,2$^6$-dihydro-1$^1$H,2$^4$H,6$^1$H-10-oxa-4,8-dithia-1(7,3)-indola-2(3,2)-pyrrolo[1,2-b]pyrazola-6(5,3)-pyrazola-9(3,1)-naphthalenacyclotridecaphane-1$^2$-carboxylic acid Under Ar, to a solution of methyl 7-(2-((((3-(bromomethyl)-1-methyl-1H-pyrazol-5-yl)methyl)thio)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate (Step B, 30 mg) in DCM (2 mL) was added TES (2 mL) and TFA (6 mL), then the reaction mixture was stirred at room temperature for overnight. After removal of volatiles under reduced pressure, the residue was concentrated under reduced pressure to give a brown oil, which was directly used without further purification. MS: 780.7 (M+H$^+$), 801.9 (M+Na$^+$).

Under Ar, to a solution of the above brown oil (26 mg, 0.03 mmol) in dry acetonitrile (10 mL) was added K$_2$CO$_3$ (41 mg, 0.3 mmol), then the reaction mixture was stirred at room temperature for 3 h. After filtration, the filtrate was concentrated under reduced pressure to give a brown oil, which was directly used without purification. MS: 698.1 (M+H$^+$), 720.1 (M+Na$^+$).

Under Ar, to a solution of the above brown oil (26 mg) in a mixed solution of THF (10 mL) and MeOH (4 mL) was added 2N NaOH (10 mL), then the reaction mixture was stirred at room temperature for 5 h. After removal of volatiles under reduced pressure, the residue was adjusted to pH value to 2-3 with 1 N HCl. The resulting mixture was extracted with DCM twice, the combined DCM layer was concentrated under reduced pressure to give a brown oil, which was purified by C18 prep-HPLC column to afford the title compound (1.9 mg, 9% over 4 steps) as a white solid. $^1$H NMR (500 MHz, DMSO-d$_6$) δ 8.18 (d, J=6.6 Hz, 1H), 7.76 (d, J=7.3 Hz, 1H), 7.59 (d, J=8.4 Hz, 1H), 7.52-7.47 (m, 2H), 7.39 (s, 1H), 6.87 (d, J=8.4 Hz, 1H), 6.66 (s, 1H), 4.95 (s, 1H), 4.11-4.03 (m, 2H), 4.01-3.90 (m, 4H), 3.55 (s, 3H), 3.31 (s, 3H), 3.18 (d, J=15 Hz, 2H), 3.08 (d, J=15 Hz, 2H), 2.63 (brs, 2H), 2.58-2.53 (m, 4H), 2.36 (brs, 1H), 2.23-2.16 (m, 1H). MS: 684.1 (M+H$^+$).

Example 3

Synthesis of (Z)-1$^6$-chloro-1'-methyl-2$^5$,2$^6$-dihydro-1$^1$H,2$^4$H-10-oxa-4,8-dithia-6(4,2)-oxazola-1(7,3)-indola-2(3,2)-pyrrolo[1,2-b]pyrazola-9(3,1)-naphthalenacyclotridecaphane-1$^2$-carboxylic acid (Cpd, No. 2)

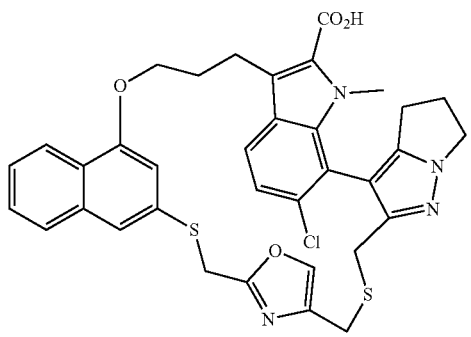 [SMILES: Cn1c(C(=O)O)c2c3ccc(Cl)c(c31)-c1c(nn3c1CCC3)CSCc1coc(n1)CSc1cc(c3ccccc3c1)OCCC2]

Essentially the same synthetic protocol described in EXAMPLE 1 was used to afford Cpd, No. 2 (9.4 mg) as a white solid. $^1$H NMR (500 MHz, DMSO-d$_6$): δ 8.24 (d, J=7.4 Hz, 1H), 7.80 (d, J=7.6 Hz, 1H), 7.57-7.49 (m, 4H), 6.88 (d, J=8.8 Hz, 1H), 6.73 (s, 1H), 6.47 (s, 1H), 4.32 (d, J=15.5 Hz, 1H), 4.20 (d, J=15.5 Hz, 1H), 4.14-4.09 (m, 2H), 4.01-3.97 (m, 1H), 3.93-3.88 (m, 1H), 3.53 (s, 3H), 3.41-3.34 (m, 4H), 3.19-3.14 (m, 1H), 3.08 (d, J=16.0 Hz, 1H), 2.96 (d, J=15.5 Hz, 1H), 2.72-2.62 (m, 1H), 2.57-2.53 (m, 2H), 2.36-2.29 (m, 1H), 2.26-2.21 (m, 1H). MS: 671.3 (M+H$^+$).

Example 4

Synthesis of 1⁶-chloro-1¹,6⁴-dimethyl-2⁵,2⁶-dihydro-1¹H,2⁴H-10-oxa-4,8-dithia-6(2,5)-oxazola-1(7,3)-indola-2(3,2)-pyrrolo[1,2-b]pyrazola-9(3,1)-naphthalenacyclotridecaphane-12-carboxylic acid (Cpd. No. 10)

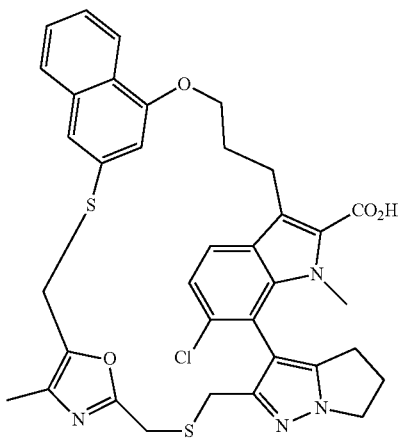 [SMILES: CC1=C2CSc3cc(c4ccccc4c3)OCCCc3c(C(=O)O)n(C)c4c(c(Cl)ccc34)-c3c(nn4c3CCC4)CSCC(=N1)O2]

Essentially the same synthetic protocol described in EXAMPLE 1 was used to afford Cpd. No. 10 (10 mg) as a white solid. $^1$H NMR (500 MHz, DMSO-d$_6$) δ 8.18 (d, J=7.3 Hz, 1H), 7.79 (d, J=7.3 Hz, 1H), 7.61 (d, J=8.7 Hz, 1H), 7.58-7.44 (m, 3H), 6.89 (d, J=7.4 Hz, 1H), 6.36 (s, 1H), 4.27-4.08 (m, 4H), 3.90-3.75 (m, 2H), 3.63-3.48 (m, 7H), 3.20-3.05 (m, 2H), 2.75-2.54 (m, 4H), 2.43-2.14 (m, 2H), 1.70 (s, 3H). MS: 686.9 (M+H⁺).

Example 5

Synthesis of (Z)-1⁶-chloro-1¹-methyl-2⁵,2⁶-dihydro-1¹H,2⁴H-10-oxa-4,8-dithia-6(4,2)-thiazola-1(7,3)-indola-2(3,2)-pyrrolo[1,2-b]pyrazola-9(3,1)-naphthalenacyclotridecaphane-12-carboxylic acid (Cpd. No. 3)

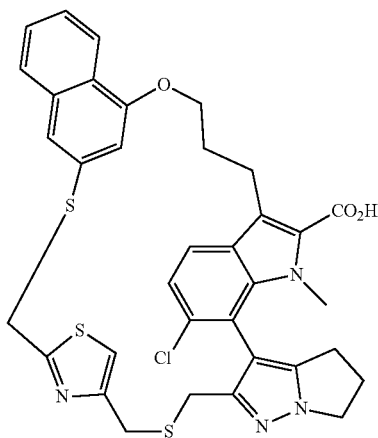 [SMILES: Cn1c(C(=O)O)c2c3ccc(Cl)c(c31)-c1c(nn3c1CCC3)CSCc1csc(n1)CSc1cc(c3ccccc3c1)OCCC2]

Essentially the same synthetic protocol described in EXAMPLE 1 was used to afford this example (9 mg) as a white solid. $^1$H NMR (500 MHz, DMSO-d$_6$) δ 13.35 (s, 1H), 8.20 (d, J=7.8 Hz, 1H), 7.80 (d, J=7.6 Hz, 1H), 7.61-7.44 (m, 4H), 6.89 (d, J=8.5 Hz, 1H), 6.80 (s, 1H), 6.75 (s, 1H), 4.60 (d, J=16.2 Hz, 1H), 4.40 (d, J=16.4 Hz, 1H), 4.22-4.08 (m, 2H), 4.06-3.93 (m, 1H), 3.90-3.75 (m, 1H), 3.57-3.47 (m, 5H), 3.34-3.20 (m, 3H), 3.18-3.07 (m, 1H), 2.76-2.61 (m, 2H), 2.60-2.53 (m, 2H), 2.32-2.09 (m, 2H). MS: 688.6 (M+H⁺).

Example 6

Synthesis of (Z)-1⁶-chloro-1¹,6¹-dimethyl-2⁵,2⁶-dihydro-1¹H,2⁴H,6¹H-10-oxa-4,8-dithia-1(7,3)-indola-2(3,2)-pyrrolo[1,2-b]pyrazola-6(3,5)-triazola-9(3,1)-naphthalenacyclotridecaphane-1²-carboxylic acid (Cpd. No. 13)

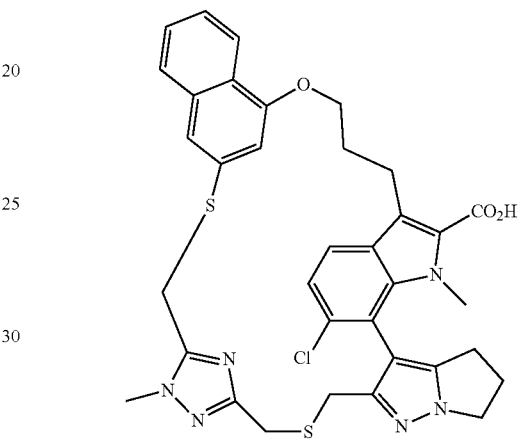

Essentially the same synthetic protocol described in EXAMPLE 1 was used to afford Cpd. No. 13 (12.5 mg) as a white solid. $^1$H NMR (500 MHz, DMSO-d$_6$) δ 8.19 (d, J=7.9 Hz, 1H), 7.75 (d, J=7.9 Hz, 1H), 7.56-7.42 (m, 3H), 7.37 (s, 1H), 7.09 (s, 1H), 6.81 (d, J=8.5 Hz, 1H), 4.20-3.92 (m, 6H), 3.63-3.47 (m, 6H), 3.46-3.40 (m, 2H), 3.33-3.25 (m, 4H), 3.15-3.04 (m, 1H), 2.69-2.54 (m, 4H), 2.43-2.18 (m, 1H). MS: 686.9 (M+H⁺).

Example 7

Synthesis of (Z)-1⁶-chloro-1¹,6¹-dimethyl-2²,2³-dihydro-1¹H,6¹H-10-oxa-4,8-dithia-2(7,6)-pyrazolo[5,1-b]oxazola-1(7,3)-indola-6(3,5)-pyrazola-9(3,1)-naphthalenacyclotridecaphane-1²-carboxylic acid (Cpd. No. 6)

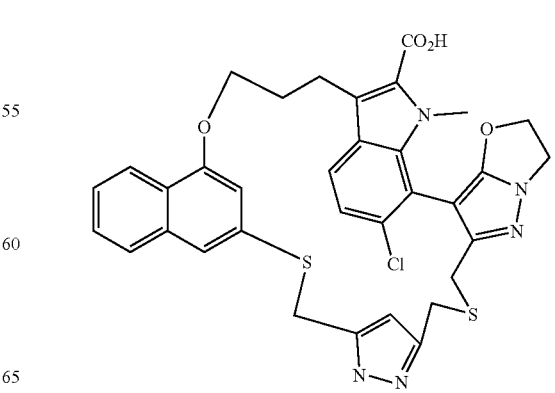

Essentially the same synthetic protocol described in EXAMPLE 1 was used to afford t Cpd. No. 6 (6 mg) as a white solid. $^1$H NMR (500 MHz, DMSO-d$_6$): δ 8.08 (d, J=8.0 Hz, 1H), 7.91 (d, J=8.0 Hz, 1H), 7.70 (d, J=8.0 Hz, 1H), 7.49-7.43 (m, 2H), 7.36 (s, 1H), 7.14 (d, J=8.5 Hz, 1H), 6.71 (s, 1H), 5.13-5.04 (m, 2H), 4.68 (s, 1H), 4.34-4.24 (m, 4H), 4.19-4.14 (m, 1H), 3.72 (s, 3H), 3.67 (s, 3H), 3.44-3.40 (m, 3H), 3.23-3.15 (m, 2H), 3.08-3.04 (m, 1H), 2.92 (d, J=14.5 Hz, 1H), 2.39-2.34 (m, 1H), 2.21-2.19 (m, 1H). MS: 686.1, 687.9 (M+H$^+$).

Example 8

Synthesis of (Z)-1$^6$-chloro-1$^1$,6$^5$-dimethyl-2$^2$,2$^3$-dihydro-1$^1$H-10-oxa-4,8-dithia-2(7,6)-pyrazolo[5,1-b]oxazola-6(2,4)-oxazola-1(7,3)-indola-9(3,1)-naphthalenacyclotridecaphane-1$^2$-carboxylic acid (Cpd. No. 38)

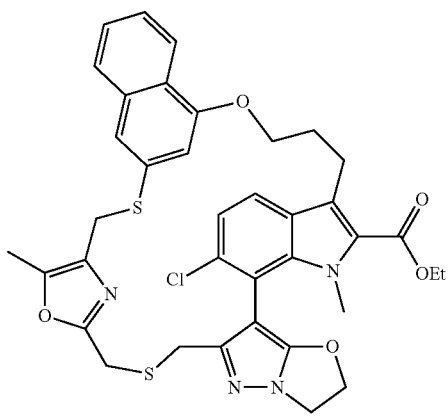 [SMILES: CCOC(=O)c1c2c3ccc(Cl)c(c3n1C)-c1c(nn3c1OCC3)CSCc1nc(c(C)o1)CSc1cc(c3ccccc3c1)OCCC2]

Essentially the same synthetic protocol described in EXAMPLE 1 was used to afford Cpd. No. 38 (2 mg) as a white solid. $^1$H NMR (500 MHz, DMSO-d$_6$) δ 8.30 (d, J=7.7 Hz, 1H), 7.85 (d, J=7.4 Hz, 1H), 7.63 (s, 1H), 7.58 (m, 3H), 6.81 (d, J=8.6 Hz, 1H), 6.34 (s, 1H), 5.10-5.16 (m, 2H), 4.35-4.40 (m, 2H), 3.98-3.88 (m, 2H), 3.80-3.77 (m, 1H), 3.71 (s, 3H), 3.66-3.56 (m, 2H), 3.31 (d, J=14.5 Hz, 1H), 3.24-3.16 (m, 1H), 3.15-3.12 (m, 1H), 3.00 (d, J=14.6 Hz, 1H), 2.38-2.30 (m, 1H), 2.28-2.18 (m, 1H), 2.05-2.00 (m, 1H), 1.78 (s, 3H). MS: 687.0 (M+H$^+$).

Example 9

Synthesis of (Z)-1$^6$-chloro-1$^1$,6$^1$-dimethyl-2$^4$,2$^5$,2$^6$,2$^7$-tetrahydro-1$^1$H,6$^1$H-10-oxa-4,8-dithia-2(3,2)-pyrazolo[1,5-a]pyridina-1(7,3)-indola-6(3,5)-pyrazola-9(3,1)-naphthalenacyclotridecaphane-1$^2$-carboxylic acid (Cpd. No. 20)

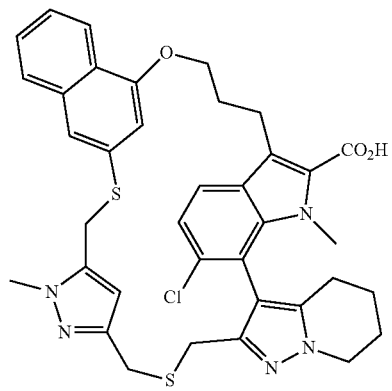 [SMILES: Cn1nc2cc1CSc1cc(c3ccccc3c1)OCCCc1c(C(=O)O)n(C)c3c(c(Cl)ccc13)-c1c(nn3c1CCCC3)CSC2]

Essentially the same synthetic protocol described in EXAMPLE 1 was used to afford Cpd. No. 20 (59 mg) as a white solid. $^1$H NMR (500 MHz, DMSO-d$_6$): δ 8.08 (d, J=8.5 Hz, 1H), 7.86 (d, J=8.0 Hz, 1H), 7.71 (d, J=8.0 Hz, 1H), 7.50-7.44 (m, 2H), 7.37 (s, 1H), 7.12 (d, J=9.0 Hz, 1H), 6.67 (s, 1H), 4.72 (s, 1H), 4.26 (s, 2H), 4.14-4.02 (m, 3H), 4.86-4.82 (m, 1H), 3.71 (s, 3H), 3.54 (s, 3H), 3.50-3.44 (m, 2H), 3.21-3.06 (m, 3H), 2.90 (d, J=14.5 Hz, 1H), 2.38-2.21 (m, 4H), 1.98-1.94 (m, 2H), 1.77-1.69 (m, 2H). MS: 699.4 (M+H$^+$).

Example 10

Synthesis of (E)-1$^6$,6$^4$-dichloro-1$^1$,6$^1$-dimethyl-2$^4$,2$^5$,2$^6$,2$^7$-tetrahydro-1$^1$H,6$^1$H-10-oxa-4,8-dithia-2(3,2)-pyrazolo[1,5-a]pyridina-1(7,3)-indola-6(3,5)-pyrazola-9(3,1)-naphthalenacyclotridecaphane-1$^2$-carboxylic acid (Cpd. No. 24)

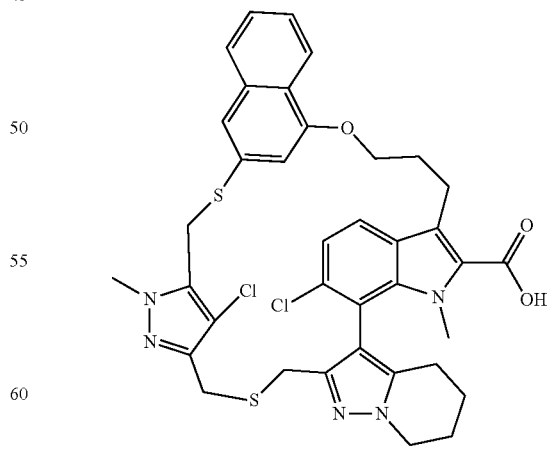

Essentially the same synthetic protocol described in Example 2 was used to afford Cpd. No. 24 (30 mg) as a white solid. $^1$H NMR (500 MHz, DMSO-d$_6$) δ 13.29 (s, 1H), 8.23 (d, J=5.3 Hz, 1H), 7.91-7.76 (m, 1H), 7.71-7.60 (m, 2H), 7.60-7.50 (m, 2H), 6.94 (d, J=8.5 Hz, 1H), 6.22 (s, 1H), 4.16 (d, J=15.1 Hz, 1H), 4.13-4.00 (m, 3H), 3.87-3.82 (m, 1H), 3.59 (s, 3H), 3.54 (s, 3H), 3.45-3.40 (m, 4H), 3.23-3.17 (m, 1H), 2.83-2.67 (m, 2H), 2.40 (d, J=4.0 Hz, 2H), 2.32-2.25 (m, 2H), 2.04-1.91 (m, 2H), 1.80-1.74 (m, 2H). MS: 733.9 (M+H⁺).

Example 11

Synthesis of (Z)-1⁶-chloro-1¹,6¹-dimethyl-2⁶,2⁷-dihydro-1¹H,2⁵H,6¹H-10-oxa-4,8-dithia-2(3,2)-pyrazolo[5,1-b][1,3]oxazina-1(7,3)-indola-6(3,5)-pyrazola-9(3,1)-naphthalenacyclotridecaphane-1²-carboxylic acid (Cpd. No. 22)

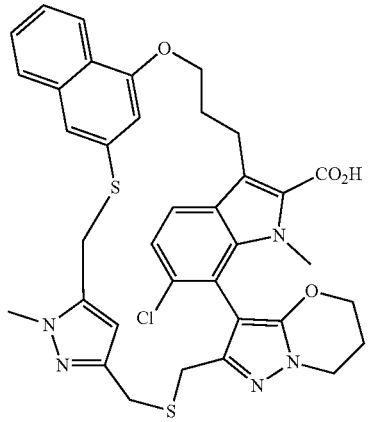 [SMILES: Cn1nc2cc1CSc1cc(c3ccccc3c1)OCCCc1c(C(=O)O)n(C)c3c(c(Cl)ccc13)-c1c(nn3c1OCCC3)CSC2]

Essentially the same synthetic protocol described in EXAMPLE 1 was used to afford Cpd. No. 22 (6.8 mg) as a white solid. ¹H NMR (500 MHz, DMSO-d₆): δ 8.07 (d, J=8.5 Hz, 1H), 7.89 (d, J=8.5 Hz, 1H), 7.71 (d, J=7.5 Hz, 1H), 7.48-7.44 (m, 2H), 7.36 (s, 1H), 7.12 (d, J=9.0 Hz, 1H), 6.70 (s, 1H), 4.67 (s, 1H), 4.32-4.07 (m, 6H), 3.82-3.78 (m, 1H), 3.72 (s, 3H), 3.65 (s, 3H), 3.44-3.40 (m, 4H), 3.20-3.15 (m, 2H), 3.39-3.34 (m, 1H), 2.91 (d, J=15 Hz, 1H), 2.22-2.15 (m, 3H). MS: 700.2 (M+H⁺).

Example 12

Synthesis of (Z)-1⁶-chloro-1¹,6¹-dimethyl-2⁶,2⁷-dihydro-1¹H,2⁴H,6¹H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-1²-carboxylic acid (Cpd. No. 12)

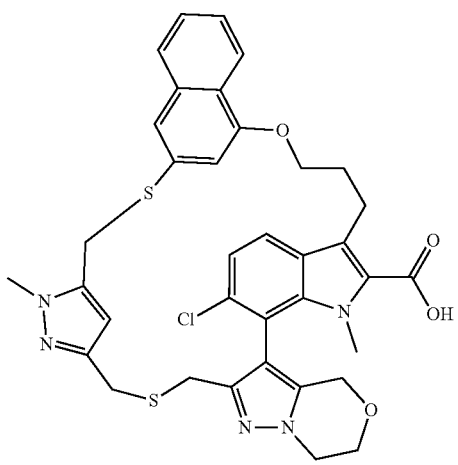 [SMILES: Cn1nc2cc1CSc1cc(c3ccccc3c1)OCCCc1c(C(=O)O)n(C)c3c(c(Cl)ccc13)-c1c(nn3c1COCC3)CSC2]

Essentially the same synthetic protocol described in EXAMPLE 1 was used to afford Cpd. No. 12 (15 mg) as a white solid. ¹H NMR (500 MHz, DMSO-d₆) δ 13.38 (br, 1H), 8.10 (d, J=6.5 Hz, 1H), 7.89 (d, J=6.5 Hz, 1H), 7.72 (d, J=5.5 Hz, 1H), 7.43 (d, J=9.0 Hz, 2H), 7.38 (s, 1H), 7.14 (d, J=7.5 Hz, 1H), 6.66 (s, 1H), 4.74 (s, 1H), 4.50 (d, J=15.1 Hz, 1H), 4.43 (d, J=15.0 Hz, 1H), 4.26 (s, 2H), 4.11-4.07 (m, 5H), 3.85 (brs, 1H), 3.71 (s, 3H), 3.54 (s, 3H), 3.49-3.40 (m, 2H), 3.22 (d, J=11.7 Hz, 1H), 3.12-3.09 (m, 2H), 2.90 (d, J=14.7 Hz, 1H), 2.36-2.34 (m, 1H), 2.21-2.18 (m, 1H). MS: 700.1 (M+H⁺).

Example 13

Synthesis of (Z)-1⁶-chloro-1¹,6¹-dimethyl-2⁶,2⁷-dihydro-1¹H,2⁴H,6¹H-10-oxa-4,8-dithia-2(3,2)-pyrazolo[5,1-c][1,4]thiazina-1(7,3)-indola-6(3,5)-pyrazola-9(3,1)-naphthalenacyclotridecaphane-1²-carboxylic acid (Cpd. No. 21)

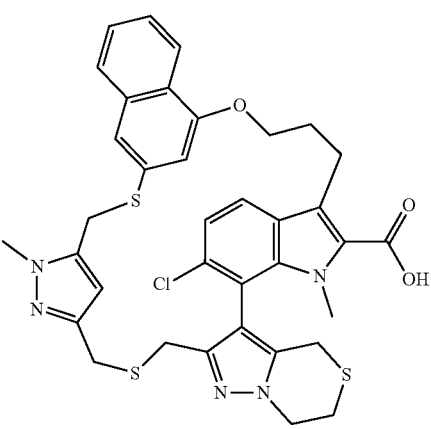 [SMILES: Cn1nc2cc1CSc1cc(c3ccccc3c1)OCCCc1c(C(=O)O)n(C)c3c(c(Cl)ccc13)-c1c(nn3c1CSCC3)CSC2]

Essentially the same synthetic protocol described in EXAMPLE 1 was used to afford Cpd. No. 21 (25 mg) as a white solid. ¹H NMR (500 MHz, DMSO-d₆) δ 8.13 (d, J=8.0 Hz, 1H), 7.92 (d, J=8.6 Hz, 1H), 7.75 (d, J=7.9 Hz, 1H), 7.55-7.46 (m, 2H), 7.41 (s, 1H), 7.17 (d, J=8.5 Hz, 1H), 6.69 (s, 1H), 4.78 (s, 1H), 4.36-4.30 (m, 1H), 4.29 (brs, 3H), 4.16-4.12 (m, 2H), 3.92-3.85 (m, 2H), 3.74 (s, 3H), 3.56-3.54 (m, 2H), 3.52-3.43 (m, 3H), 3.25-3.10 (m, 5H), 2.93 (d, J=14.1 Hz, 1H), 2.45-2.35 (m, 1H), 2.30-2.20 (m, 1H). MS: 716.3 (M+H⁺).

Example 14

Synthesis of (Z)-1⁶-chloro-1¹,6¹-dimethyl-2⁵-(methylsulfonyl)-2⁴,2⁵,2⁶,2⁷-tetrahydro-1¹H,6¹H-10-oxa-4,8-dithia-2(3,2)-pyrazolo[1,5-a]pyrazina-1(7,3)-indola-6(3,5)-pyrazola-9(3,1)-naphthalenacyclotridecaphane-1²-carboxylic acid (Cpd. No. 25)

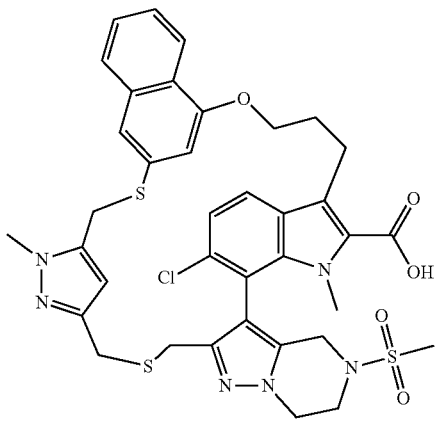

Essentially the same synthetic protocol described in EXAMPLE 1 was used to afford Cpd. No. 25 (36 mg) as a white solid. ¹H NMR (500 MHz, DMSO-d₆) δ 8.13 (d, J=8.0 Hz, 1H), 7.93 (d, J=8.6 Hz, 1H), 7.76 (d, J=7.7 Hz, 1H), 7.54-7.48 (m, 2H), 7.42 (s, 1H), 7.18 (d, J=8.6 Hz, 1H), 6.67 (s, 1H), 4.79 (s, 1H), 4.29-4.27 (m, 3H), 4.21-4.18 (m, 1H), 4.23-4.07 (m, 3H), 3.90-3.87 (m, 1H), 3.81-3.74 (m, 2H), 3.74 (s, 3H), 3.59 (s, 3H), 3.50 (d, J=12.9 Hz, 2H), 3.25 (d, J=12.9 Hz, 1H), 3.17-3.10 (m, 2H), 3.02 (s, 3H), 2.93 (d, J=14.1 Hz, 1H), 2.45-2.35 (m, 1H), 2.30-2.20 (m, 1H). MS: 777.2 (M+H⁺).

Example 15

Synthesis of (Z)-1⁶-chloro-1¹,6¹-dimethyl-2⁵,2⁶,2⁷,2⁸-tetrahydro-1¹H,2⁴H,6¹H-10-oxa-4,8-dithia-2(3,2)-pyrazolo[1,5-a]azepina-1(7,3)-indola-6(3,5)-pyrazola-9(3,1)-naphthalenacyclotridecaphane-1²-carboxylic acid (Cpd. No. 23)

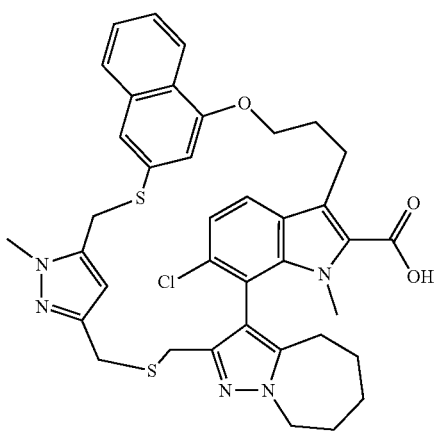 [SMILES: Cn1nc2cc1CSc1cc(c3ccccc3c1)OCCCc1c(C(=O)O)n(C)c3c(c(Cl)ccc13)-c1c(nn3c1CCCCC3)CSC2]

Essentially the same synthetic protocol described in EXAMPLE 1 was used to afford Cpd. No. 23 (2.6 mg) as a white solid. ¹H NMR (500 MHz, DMSO-d₆) δ 13.39 (s, 1H), 8.10 (d, J=8.1 Hz, 1H), 7.87 (d, J=8.6 Hz, 1H), 7.72 (d, J=7.9 Hz, 1H), 7.53-7.44 (m, 2H), 7.38 (s, 1H), 7.13 (d, J=8.5 Hz, 1H), 6.65 (s, 1H), 4.74 (s, 1H), 4.25-4.24 (m, 4H), 4.10 (dd, J=16.1, 8.6 Hz, 1H), 3.86 (dd, J=8.5, 3.8 Hz, 1H), 3.71 (s, 3H), 3.53 (s, 3H), 3.19-3.04 (m, 3H), 2.88 (d, J=14.0 Hz, 1H), 2.45-2.29 (m, 3H), 2.25-2.18 (m, 1H), 1.86-1.71 (m, 3H), 1.68-1.52 (m, 2H), 1.48-1.37 (m, 1H), 1.23 (s, 2H). MS: 712.5 (M+H⁺).

Example 16

Synthesis of (Z)-1⁶,9⁷-dichloro-1¹,6¹-dimethyl-2⁶,2⁷-dihydro-1¹H,2⁴H,6¹H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-1²-carboxylic acid (Cpd. No. 18)

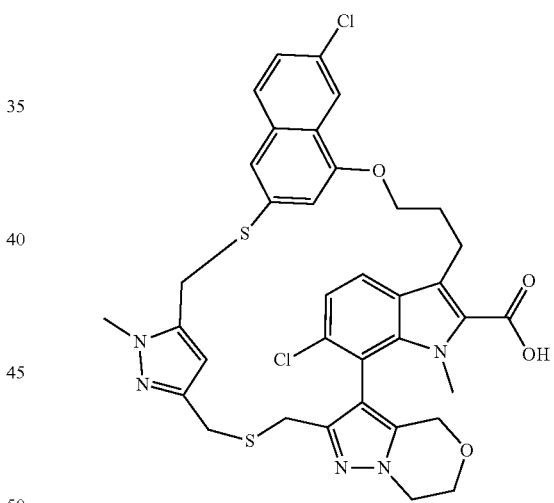

Essentially the same synthetic protocol described in EXAMPLE 1 was used to afford Cpd. No. 18 (18 mg) as a white solid. ¹H NMR (500 MHz, DMSO-d₆) δ 8.03 (s, 1H), 7.87 (d, J=8.6 Hz, 1H), 7.78 (d, J=8.8 Hz, 1H), 7.51 (d, J=8.8 Hz, 1H), 7.41 (s, 1 H), 7.16 (d, J=8.6 Hz, 1H), 6.72 (s, 1H), 4.76 (s, 1H), 4.52 (d, J=15.1 Hz, 1H), 4.42 (d, J=15.0 Hz, 1H), 4.27 (s, 2H), 4.15-4.07 (m, 5H), 3.86 (d, J=4.8 Hz, 1H), 3.70 (s, 3H), 3.53 (s, 3H), 3.45-3.42 (m, 2H), 3.20 (d, J=12.8 Hz, 1H), 3.12-3.04 (m, 2H), 2.92 (d, J=14.1 Hz, 1H), 2.40-2.34 (m, 1H), 2.26-2.18 (m, 1H). MS: 734.2 (M+H⁺).

Example 17

Synthesis of (Z)-1⁶,9⁶-dichloro-1¹,6¹-dimethyl-2⁶,2⁷-dihydro-1¹H,2⁴H,6¹H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-1²-carboxylic acid (Cpd. No. 19)

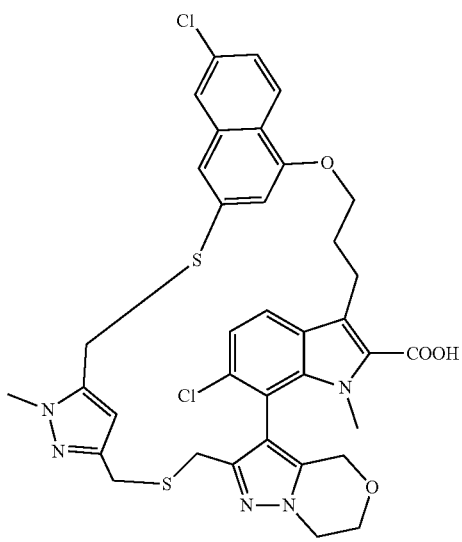 [SMILES: Cn1nc2cc1CSc1cc(c3ccc(Cl)cc3c1)OCCCc1c(C(=O)O)n(C)c3c(c(Cl)ccc13)-c1c(nn3c1COCC3)CSC2]

Essentially the synthetic protocol described in EXAMPLE 1 was used to afford Cpd. No. 19 (3.1 mg) as a white solid. $^1$H NMR (500 MHz, DMSO-$d_6$) δ 8.09 (d, J=9.0 Hz, 1H), 7.90-7.80 (m, 2H), 7.49-7.40 (m, 1H), 7.37 (s, 1H), 7.14 (d, J=8.6 Hz, 1H), 6.69 (s, 1H), 4.78 (s, 1H), 4.55-4.36 (m, 2H), 4.28 (s, 2H), 4.18-4.02 (m, 5H), 3.70 (s, 3H), 3.53 (s, 3H), 3.49-3.40 (m, 2H), 3.30-3.27 (m, 2H), 3.22 (d, J=12.7 Hz, 1H), 3.10 (d, J=14.0 Hz, 1H), 2.92 (d, J=14.1 Hz, 1H), 2.66-2.54 (m, 1H), 2.42-2.15 (m, 1H). MS: 735.9 (M+H⁺).

Example 18

Synthesis of (Z)-1⁶-chloro-9⁷-fluoro-1¹,6¹-dimethyl-2⁶,2⁷-dihydro-1¹H,2⁴H,6¹H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-1²-carboxylic acid (Cpd. No. 16)

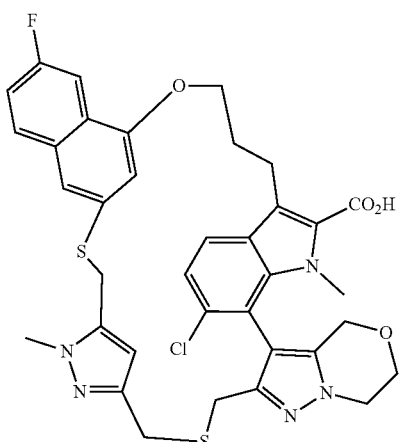

Essentially the same synthetic protocol described in EXAMPLE 1 was used to afford Cpd. No. 16 (31 mg) as a white solid. $^1$H NMR (500 MHz, DMSO-$d_6$): δ 7.87-7.82 (m, 2H), 7.73-7.70 (m, 1H), 7.44-7.39 (m, 2H), 7.14 (d, J=9.0 Hz, 1H), 6.69 (s, 1H), 4.75 (s, 1H), 4.52 (d, J=15 Hz, 1H), 4.42 (d, J=15 Hz, 1H), 4.25 (s, 2H), 4.14-4.08 (m, 5H), 3.86-3.82 (m, 1H), 3.69 (s, 3H), 3.54 (s, 3H), 3.45-3.42 (m, 2H), 3.21 (d, J=12.5 Hz, 1H), 3.08 (d, J=14 Hz, 1H), 3.09-3.05 (m, 1H), 2.89 (d, J=14.0 Hz, 1H), 2.35 (brs, 1H), 2.21 (brs, 1H). MS: 719.9 (M+H⁺).

Example 19

Synthesis of (Z)-1⁶-chloro-9⁶-fluoro-1¹,6¹-dimethyl-2⁵,2⁶-dihydro-1¹H,2⁴H,6¹H-10-oxa-4,8-dithia-1(7,3)-indola-2(3,2)-pyrrolo[1,2-b]pyrazola-6(3,5)-pyrazola-9(3,1)-naphthalenacyclotridecaphane-1²-carboxylic acid (Cpd. No. 27)

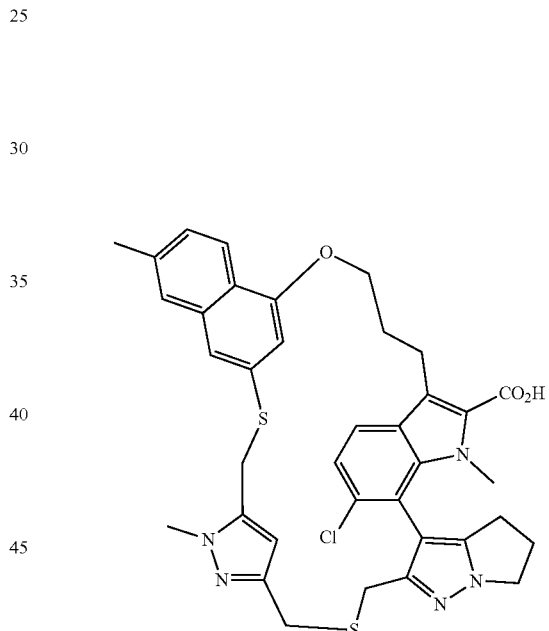

Essentially the same synthetic protocol described in EXAMPLE 1 was used to afford t Cpd. No. 27 (30 mg) as a white solid. $^1$H NMR (500 MHz, DMSO-$d_6$): δ 8.15 (dd, J=9.1, 5.9 Hz, 1H), 7.84 (d, J=9.0 Hz, 1H), 7.52-7.50 (m, 1H), 7.36-7.31 (m, 2H), 7.12 (d, J=9.0 Hz, 1H), 6.66 (s, 1H), 4.79 (s, 1H), 4.28 (s, 2H), 4.16-4.07 (m, 3H), 3.88-3.84 (m, 1H), 3.71 (s, 3H), 3.54 (s, 3H), 3.50-3.42 (m, 2H), 3.24 (d, J=12.5 Hz, 1H), 3.12-3.05 (m, 2H), 2.91 (d, J=14.5 Hz, 1H), 2.70-2.53 (m, 4H), 2.39-2.32 (m, 1H), 2.24-2.17 (m, 1H). MS: 702.2, 704.0 (M+H⁺).

Example 20

Synthesis of 1⁶-chloro-9⁶-fluoro-1¹,6²-dimethyl-2⁵,2⁶-dihydro-1¹H,2⁴H-10-oxa-4,8-dithia-1(7,3)-indola-2(3,2)-pyrrolo[1,2-b]pyrazola-9(3,1)-naphthalena-6(1,4)-benzenacyclotridecaphane-1²-carboxylic acid (Cpd. No. 29)

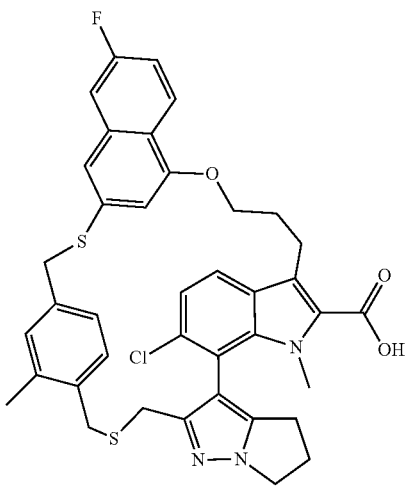 [SMILES: Cc1cc2ccc1CSCc1nn3c(c1-c1c(Cl)ccc4c(c(C(=O)O)n(C)c14)CCCOc1cc(cc4cc(F)ccc14)SC2)CCC3]

Essentially the same synthetic protocol described in Example 1 was used to afford Cpd. No. 29 (3 mg) as a white solid. $^1$H NMR (500 MHz, DMSO-d$_6$) δ 13.31 (s, 1H), 8.28-8.21 (m, 1H), 7.56 (d, J=8.9 Hz, 2H), 7.42 (s, 1H), 7.36 (dd, J=8.8, 2.4 Hz, 1H), 7.01 (s, 1H), 6.95 (d, J=8.6 Hz, 1H), 6.69 (s, 1H), 6.39 (d, J=7.8 Hz, 1H), 5.55 (d, J=7.9 Hz, 1H), 4.18-4.12 (m, 4H), 4.07 (dd, J=11.8, 4.8 Hz, 1H), 3.98-3.94 (m, 1H), 3.56 (s, 3H), 3.41 (dd, J=13.5, 6.9 Hz, 1H), 3.34 (d, J=13.4 Hz, 1H), 3.21 (dd, J=29.1, 14.8 Hz, 3H), 3.13-3.08 (m, 1H), 2.72-2.54 (m, 4H), 2.32-2.15 (m, 2H), 1.98 (s, 3H); MS: 712.2 (M+H⁺).

Example 21

Synthesis of 1⁶-chloro-9⁶-fluoro-1¹,6³-dimethyl-2⁵,2⁶-dihydro-1¹H,2⁴H-10-oxa-4,8-dithia-1(7,3)-indola-2(3,2)-pyrrolo[1,2-b]pyrazola-9(3,1)-naphthalena-6(1,4)-benzenacyclotridecaphane-1²-carboxylic acid (Cpd. No. 30)

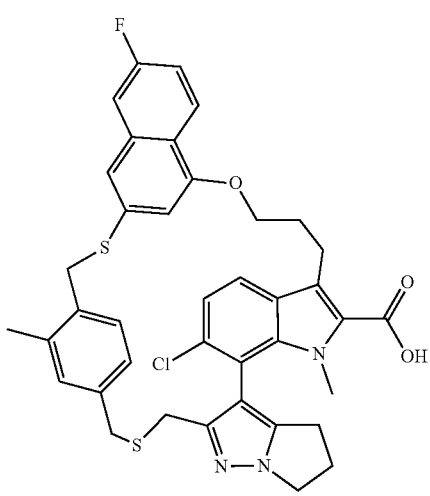 [SMILES: Cc1cc2ccc1CSc1cc(c3ccc(F)cc3c1)OCCCc1c(C(=O)O)n(C)c3c(c(Cl)ccc13)-c1c(nn3c1CCC3)CSC2]

Essentially the same synthetic protocol described in EXAMPLE 1 was used to afford Cpd. No. 30 (2.9 mg) as a white solid. $^1$H NMR (500 MHz, DMSO-d$_6$) δ 13.33 (s, 1H), 8.25 (dd, J=9.2, 5.8 Hz, 1H), 7.65-7.55 (m, 2H), 7.51 (s, 1H), 7.38 (dd, J=8.8, 2.5 Hz, 1H), 7.00 (d, J=8.6 Hz, 1H), 6.64 (s, 1H), 6.47-6.41 (m, 2H), 5.54 (d, J=7.2 Hz, 1H), 4.18-4.10 (m, 4H), 3.88 (dd, J=12.4, 6.2 Hz, 2H), 3.61 (s, 3H), 3.40 (dd, J=11.9, 6.0 Hz, 2H), 3.21-3.11 (m, 3H), 2.99 (d, J=13.8 Hz, 1H), 2.75-2.63 (m, 2H), 2.59-2.54 (m, 2H), 2.30-2.23 (m, 1H), 2.20-2.14 (m, 4H). MS. 713.3 (M+H⁺).

Example 22

Synthesis of 1⁶-chloro-9⁶-fluoro-1¹-methyl-2⁵,2⁶-dihydro-1¹H,2⁴H-10-oxa-4,8-dithia-1(7,3)-indola-2(3,2)-pyrrolo[1,2-b]pyrazola-6(5,2)-pyridina-9(3,1)-naphthalenacyclotridecaphane-1²-carboxylic acid (Cpd. No. 32)

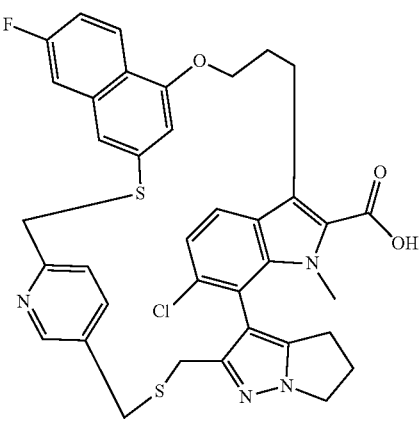 [SMILES: Cn1c(C(=O)O)c2c3ccc(Cl)c(c31)-c1c(nn3c1CCC3)CSCc1ccc(nc1)CSc1cc(c3ccc(F)cc3c1)OCCCC2]

Essentially the same synthetic protocol described in EXAMPLE 1 was used to afford Cpd. No. 32 (48 mg) as a white solid. $^1$H NMR (500 MHz, DMSO-d$_6$) δ 8.27-8.18 (m, 1H), 7.58 (d, J=8.6 Hz, 1H), 7.54 (d, J=10.1 Hz, 1H), 7.47 (s, 1H), 7.40 (s, 1H), 7.35 (t, J=8.5 Hz, 1H), 7.00 (d, J=8.0 Hz, 1H), 6.96 (s, 1H), 6.94 (d, J=8.6 Hz, 1H), 6.87 (d, J=7.6 Hz, 1H), 4.32 (s, 2H), 4.14 (d, J=5.9 Hz, 2H), 4.07 (d, J=6.0 Hz, 2H), 3.55 (s, 3H), 3.46-3.20 (m, 6H), 2.73-2.62 (m, 2H), 2.59-2.53 (m, 2H), 2.40-2.15 (m, 2H). MS: 700.6 (M+H⁺).

Example 23

Synthesis of $1^6$-chloro-$9^6$-fluoro-$1^1$-methyl-$2^5$,$2^6$-dihydro-$1^1$H,$2^4$H-10-oxa-4,8-dithia-1(7,3)-indola-2(3,2)-pyrrolo[1,2-b]pyrazola-6(2,5)-pyridina-9(3,1)-naphthalenacyclotridecaphane-$1^2$-carboxylic acid (Cpd. No. 31)

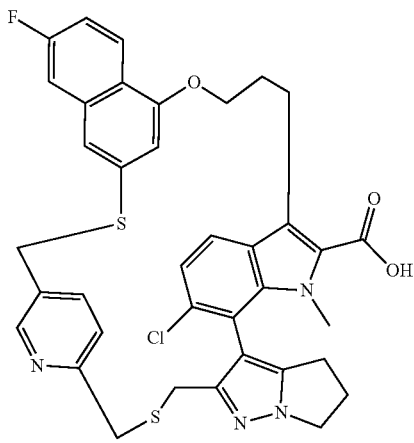 [SMILES: Cn1c(C(=O)O)c2c3ccc(Cl)c(c31)-c1c(nn3c1CCC3)CSCc1ccc(cn1)CSc1cc(c3ccc(F)cc3c1)OCCCC2]

Essentially the same synthetic protocol described in EXAMPLE 1 was used to afford Cpd. No. 31 (8 mg) as a white solid. H NMR (500 MHz, DMSO-$d_6$) δ 8.25 (dd, J=9.2, 5.9 Hz, 1H), 8.05 (s, 1H), 7.60-7.54 (m, 2H), 7.44 (s, 1H), 7.39 (dd, J=8.9, 2.6 Hz, 1H), 7.23 (dd, J=8.0, 2.1 Hz, 1H), 6.91 (d, J=8.6 Hz, 1H), 6.82 (s, 1H), 6.30 (d, J=8.0 Hz, 1H), 4.30 (q, J=15.0 Hz, 2H), 4.22-4.04 (m, 4H), 3.55 (s, 3H), 3.53-3.27 (m, 6H), 2.74-2.50 (m, 4H), 2.35-2.15 (m, 2H). MS: 700.6 (M+H$^+$).

Example 24

Synthesis of (Z)-$1^6$-chloro-$9^6$-fluoro-$1^1$,$6^1$-dimethyl-24,25,26,27-tetrahydro-1H,6H-10-oxa-4,8-dithia-2(3,2)-pyrazolo[1,5-a]pyridina-1(7,3)-indola-6(3,5)-pyrazola-9(3,1)-naphthalenacyclotridecaphane-$1^2$-carboxylic acid (Cpd. No. 26)

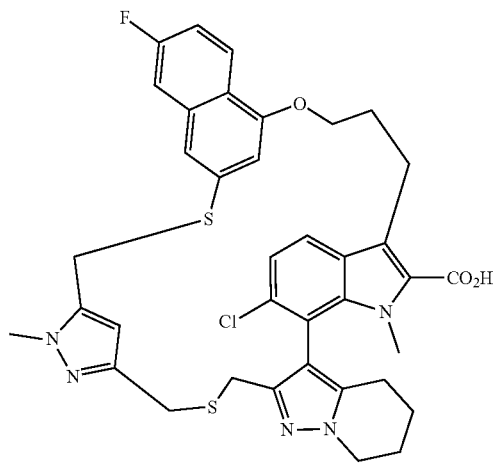 [SMILES: Cn1nc2cc1CSc1cc(c3ccc(F)cc3c1)OCCCc1c(C(=O)O)n(C)c3c(c(Cl)ccc13)-c1c(nn3c1CCCC3)CSC2]

Essentially the same synthetic protocol described in EXAMPLE 1 was used to afford Cpd. No. 26 (11.6 mg) as a white solid. H NMR (500 MHz, DMSO-$d_6$) δ 8.14 (dd, J=9.2, 5.9 Hz, 1H), 7.87 (d, J=8.6 Hz, 1H), 7.51 (dd, J=10.3, 2.4 Hz, 1H), 7.39-7.30 (m, 2H), 7.15 (d, J=8.6 Hz, 1H), 6.67 (s, 1H), 4.75 (s, 1H), 4.29 (s, 2H), 4.20-4.01 (m, 3H), 3.90-3.80 (m, 1H), 3.72 (s, 3H), 3.47-3.39 (m, 5H), 3.26-3.11 (m, 2H), 3.11-3.03 (m, 1H), 2.93 (d, J=14.2 Hz, 1H), 2.44-2.17 (m, 4H), 2.05-1.90 (m, 2H), 1.83-1.66 (m, 2H). MS: 717.6 (M+H$^+$).

Example 25

Synthesis of (Z)-$1^6$-chloro-$9^6$-fluoro-$1^1$,$6^1$-dimethyl-$2^6$,$2^7$-dihydro-$1^1$H,$2^4$H,$6^1$H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-$1^2$-carboxylic acid (Cpd. No. 17)

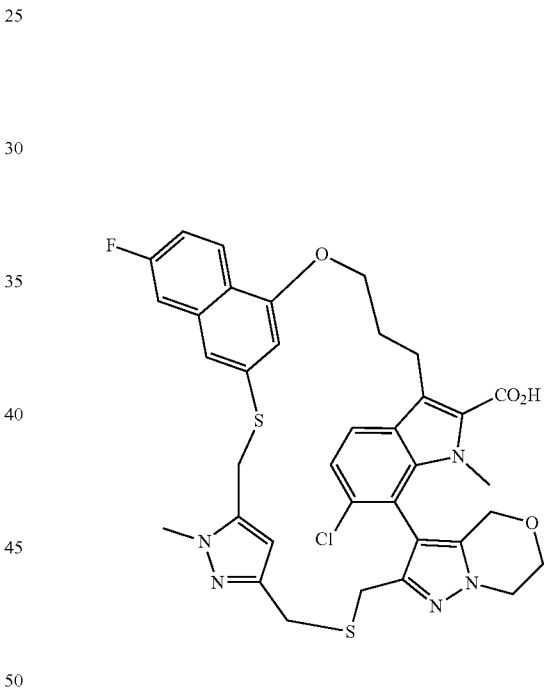

Essentially the synthetic protocol described in EXAMPLE 1 was used to afford Cpd. No. 17 (44 mg) as a white solid. $^1$H NMR (500 MHz, DMSO-$d_6$): δ 8.14 (dd, J=9.1, 5.9 Hz, 1H), 7.86 (d, J=8.5 Hz, 1H), 7.51 (dd, J=10.3, 2.3 Hz, 1H), 7.36-7.31 (m, 2H), 7.14 (d, J=8.5 Hz, 1H), 6.64 (s, 1H), 4.79 (s, 1H), 4.51 (d, J=15 Hz, 1H), 4.42 (d, J=15 Hz, 1H), 4.27 (s, 2H), 4.14-4.08 (m, 5H), 3.88-3.83 (m, 1H), 3.70 (s, 3H), 3.53 (s, 3H), 3.47-3.43 (m, 2H), 3.25-3.22 (m, 1H), 3.12-3.05 (m, 2H), 2.92 (d, J=14 Hz, 1H), 2.39-2.31 (m, 1H), 2.35-2.17 (m, 1H). MS: 718.3 (M+H$^+$).

Example 26

Synthesis of (R)-(Z)-1⁶-chloro-9⁶-fluoro-1¹,6¹-dimethyl-26,27-dihydro-1¹H,2⁴H,6¹H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-1²-carboxylic acid (Cpd. No. 40)

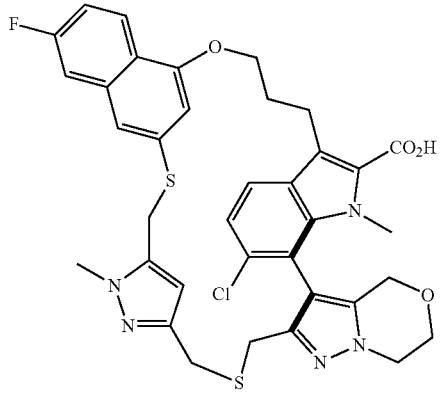

Cpd. No. 17 (429 mg) was subjected to chiral SFC resolution with CHIRALPAK® IA column to provide Cpd. No. 40 (162 mg, 99% ee) as a white solid. MS: 718.2 (M+H⁺).

Example 27

Synthesis of (S)-(Z)-1⁶-chloro-9⁶-fluoro-1¹,6¹-dimethyl-26,27-dihydro-1¹H,2⁴H,6¹H-10-oxa-4,8-dithia-2(3,2)-pyrazolo[5,1-c][1,4]oxazina-1(7,3)-indola-6(3,5)-pyrazola-9(3,1)-naphthalenacyclotridecaphane-1²-carboxylic acid (Cpd. No. 39)

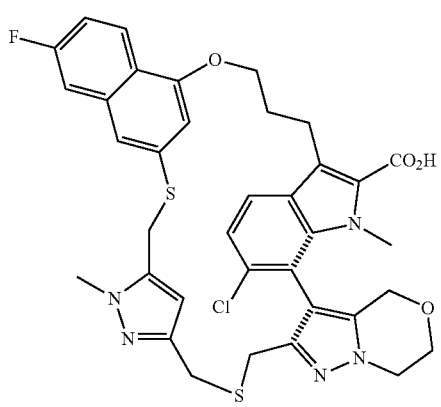

Cpd. No. 17 (429 mg) was subjected to chiral SFC resolution with CHIRALPAK® IA column to provide Cpd. No. 39 (165 mg, 99% ee) as a white solid. MS: 718.2 (M+H⁺).

Example 28

Synthesis of (Z)-1⁶-chloro-9⁶-fluoro-1¹,6¹-dimethyl-2⁵,2⁶,2⁷,2⁸-tetrahydro-1¹H,2⁴H,6¹H-10-oxa-4,8-dithia-2(3,2)-pyrazolo[1,5-a]azepina-1(7,3)-indola-6(3,5)-pyrazola-9(3,1)-naphthalenacyclotridecaphane-1²-carboxylic acid (Cpd. No. 28)

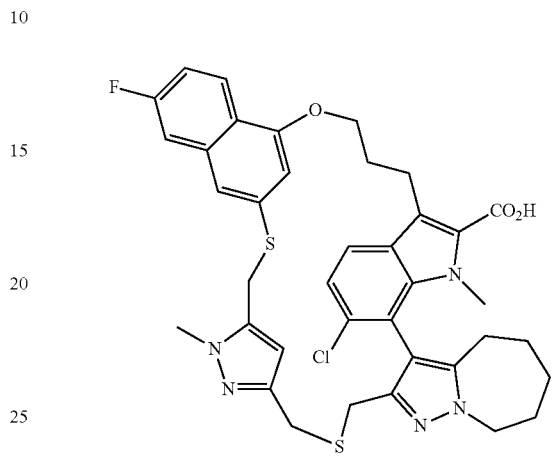

Essentially the same protocol of preparation of EXAMPLE 1 was used to afford the example (32 mg) as a white solid. ¹H NMR (500 MHz, DMSO-d₆): δ 8.14 (dd, J=9.1, 5.9 Hz, 1H), 7.85 (d, J=8.5 Hz, 1H), 7.51 (dd, J=10.2, 2.0 Hz, 1H), 7.36-7.31 (m, 2H), 7.14 (d, J=9 Hz, 1H), 6.64 (s, 1H), 4.77 (s, 1H), 4.27 (s, 2H), 4.25-4.22 (m, 2H), 4.13-4.08 (m, 1H), 3.88-3.84 (m, 1H), 3.71 (s, 3H), 3.53 (s, 3H), 3.42-3.39 (m, 2H), 3.16-3.06 (m, 3H), 2.91 (d, J=14.5 Hz, 1H), 2.43-2.21 (m, 4H), 1.77-1.41 (m, 6H). MS: 730.3, 732.0 (M+H⁺), 752.2 (M+Na⁺).

Example 29

Synthesis of (Z)-1⁶-chloro-1'-methyl-2⁵,2⁶-dihydro-1¹H,2⁴H-10-oxa-4,8-dithia-6(3,5)-isoxazola-1(7,3)-indola-2(3,2)-pyrrolo[1,2-b]pyrazola-9(3,1)-naphthalenacyclotridecaphane-1²-carboxylic acid (Cpd. No. 8)

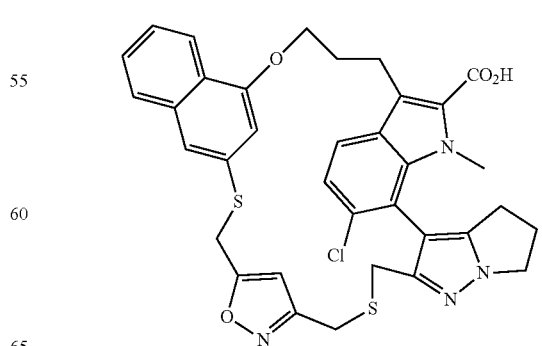

Step A: Ethyl 6-chloro-3-(3-((3-((4-methoxybenzyl)thio)naphthalen-1-yl)oxy)propyl)-1-methyl-7-(2-(((((5-(((tetrahydro-2H-pyran-2-yl)oxy)methyl)isoxazol-3-yl)methyl)thio)methyl)-5,6-dihydro-4H-pyrrolo[1,2-b]pyrazol-3-yl)-1H-indole-2-carboxylate

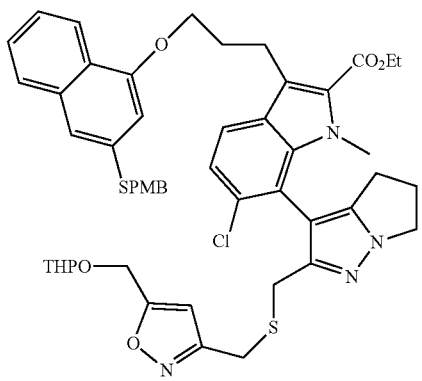

Under Ar, the mixture of ethyl 7-(2-(bromomethyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate (Step A of EXAMPLE 1, 200 mg, 0.259 mmol) and KSAc (59.1 mg, 0.517 mmol) in THF (10 mL) was stirred at 50° C. for 1 h. After cooling down to room temperature, the mixture was filtered off and the filtrate was concentrated under reduced pressure to dryness. The residue was re-dissolved in MeOH (10 mL), and the resulting solution was treated with $K_2CO_3$ (179 mg, 1.29 mmol) and 3-(bromomethyl)-5-(((tetrahydro-2H-pyran-2-yl)oxy)methyl)isoxazole (Intermediate D7, 107 mg, 0.39 mmol), the reaction mixture was stirred at room temperature for overnight. After removal of volatiles under reduced pressure, the residue was purified by silica gel column (DCM:EA, 1:0→1:1) to afford the title compound (200 mg, 84%) as a yellow oil. MS: 922.4 (M+H$^+$).

Step B: Ethyl 6-chloro-7-(2-(((((5-(hydroxymethyl)isoxazol-3-yl)methyl)thio)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate

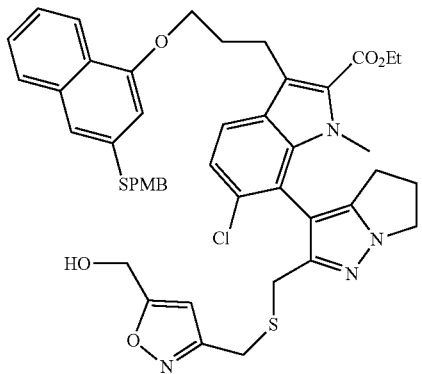

Under Ar, a mixture of ethyl 6-chloro-3-(3-((3-((4-methoxybenzyl)thio)naphthalen-1-yl)oxy)propyl)-1-methyl-7-(2-(((((5-(((tetrahydro-2H-pyran-2-yl)oxy)methyl)isoxazol-3-yl)methyl)thio)methyl)-5,6-dihydro-4H-pyrrolo[1,2-b]pyrazol-3-yl)-1H-indole-2-carboxylate (Step A, 200 mg, 0.217 mmol) and 4-methylbenzenesulfonic acid hydrate (41.3 mg, 0.217 mmol, 1) in dry MeOH (10 mL) was stirred at room temperature for 18 h. After removal of volatiles under reduced pressure, the residue was purified by silica gel column (DCM:MeOH, 20:1) to give the title compound (155 mg, 85%) as a colorless oil. MS: 838.1 (M+H$^+$).

Step C: Ethyl 7-(2-(((((5-(bromomethyl)isoxazol-3-yl)methyl)thio)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate

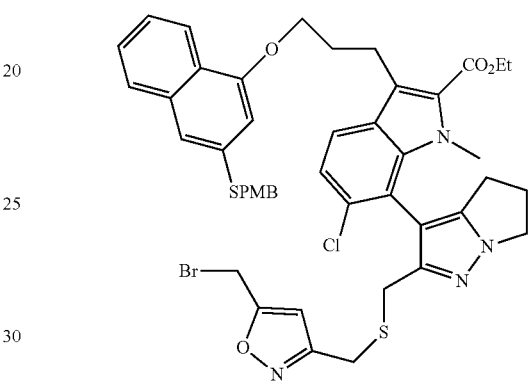

Under Ar, to a solution of ethyl 6-chloro-7-(2-(((((5-(hydroxymethyl)isoxazol-3-yl)methyl)thio)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate (Step B, 155 mg, 0.185 mmol) in dry THF (10 mL) was added $Ph_3P$ (97 mg, 0.370 mmol) and $CBr_4$ (123 mg, 0.370 mmol) at 0° C., the mixture was stirred at 0° C. for 1 h. After removal of volatiles under reduced pressure, the residue was purified by silica gel column (hexane:EA, 1:1) to afford the title compound (120 mg, 72%) as a yellow oil. MS: 899.2 (M+H$^+$), 923.0 (M+Na$^+$).

Step D: Ethyl (Z)-1$^6$-chloro-1$^1$-methyl-2$^5$,2$^6$-dihydro-1$^1$H,2$^4$H-10-oxa-4,8-dithia-6(3,5)-isoxazola-1(7,3)-indola-2(3,2)-pyrrolo[1,2-b]pyrazola-9(3,1)-naphthalenacyclotridecaphane-1$^2$-carboxylate

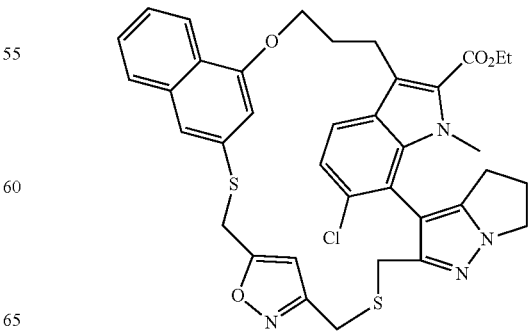

Under Ar, a mixture of ethyl 7-(2-(((((5-(bromomethyl)isoxazol-3-yl)methyl)thio)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate (Step C, 120 mg, 0.133 mmol) in DCM (2 mL), TFA (6 mL), and TES (2 mL) was stirred at 30° C. for overnight. After removal of volatiles under reduced pressure, the residue was re-dissolved into acetonitrile (10 mL) and K$_2$CO$_3$ (184 mg, 1.333 mmol) was added. The reaction mixture stirred at room temperature for 2 h. After filtration and removal of volatiles under reduced pressure, the crude title compound was directly used without purification. MS: 699.3, 701.1 (M+H$^+$).

Step E: (Z)-1$^6$-chloro-1$^1$-methyl-2$^5$,2$^6$-dihydro-1$^1$H,2$^4$H-10-oxa-4,8-dithia-6(3,5)-isoxazola-1(7,3)-indola-2(3,2)-pyrrolo[1,2-b]pyrazola-9(3,1)-naphthalenacyclotridecaphane-1$^2$-carboxylic acid To a solution of the crude ethyl (Z)-1$^6$-chloro-1$^1$-methyl-2$^5$,2$^6$-dihydro-1$^1$H,2$^4$H-10-oxa-4,8-dithia-6(3,5)-isoxazola-1(7,3)-indola-2(3,2)-pyrrolo[1,2-b]pyrazola-9(3,1)-naphthalenacyclotridecaphane-1$^2$-carboxylate (Step D) in a mixed solvent of THF (6 mL) and MeOH (6 mL) was added 2N NaOH (6 mL), the reaction mixture was stirred at room temperature for overnight. After removal of volatiles under reduced pressure, the residue was retaken into water and adjusted to pH=2 with 1N HCl, the resulting mixture was extracted with DCM twice, the combined DCM layer was washed with brine, and concentrated under reduced pressure to give a dark oil, which was purified by C18 pre-HPLC column to afford the title compound (14 mg, 12% over 2 steps) as a white solid. $^1$H NMR (500 MHz, DMSO-d$_6$): δ 13.26 (brs, 1H), 8.09 (d, J=8.0 Hz, 1H), 7.90 (d, J=9.0 Hz, 1H), 7.71 (d, J=8.5 Hz, 1H), 7.50-7.43 (m, 2H), 7.35 (s, 1H), 7.08 (d, J=9.0 Hz, 1H), 6.92 (s, 1H), 5.02 (s, 1H), 4.52 (d, J=15.5 Hz, 1H), 4.39 (d, J=15.0 Hz, 1H), 4.32-4.26 (m, 1H), 4.16-4.08 (m, 2H), 4.00-3.95 (m, 1H), 3.49-3.38 (m, 2H), 3.47 (s, 3H), 3.28-3.22 (m, 2H), 3.06-3.00 (m, 2H), 2.69-2.53 (m, 4H), 2.38-2.33 (m, 1H), 2.25-2.18 (m, 1H). MS: 671.1 (M+H$^+$).

Example 30

Synthesis of 1$^6$-chloro-1$^1$,6$^4$-dimethyl-2$^5$,2$^6$-dihydro-1$^1$H,2$^4$H-10-oxa-4,8-dithia-6(2,5)-thiazola-1(7,3)-indola-2(3,2)-pyrrolo[1,2-b]pyrazola-9(3,1)-naphthalenacyclotridecaphane-12-carboxylic acid (Cpd. No. 5)

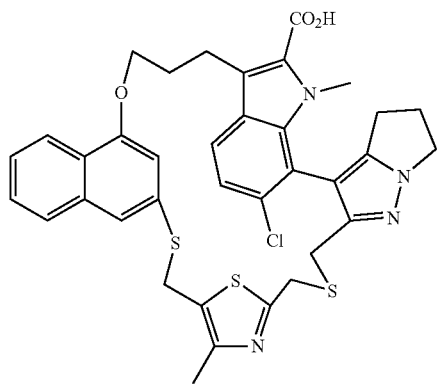 [SMILES: CC1=C2CSc3cc(c4ccccc4c3)OCCCc3c(C(=O)O)n(C)c4c(c(Cl)ccc34)-c3c(nn4c3CCC4)CSCC(=N1)S2]

Step A: Ethyl 6-chloro-7-(2-(((((5-(hydroxymethyl)-4-methylthiazol-2-yl)methyl)thio)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate

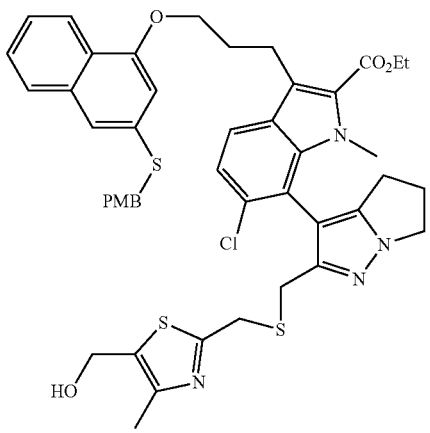

Under Ar, to a solution of ethyl 7-(2-(bromomethyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate (Step A of EXAMPLE 1, 300 mg, 0.388 mmol) in dry THF (10 mL) was added KSAc (89 mg, 0.776 mmol) and the reaction mixture was heated to reflux for 2 h. After filtration, the filtrate was concentrated under reduced pressure to dryness. Under Ar, the residue was re-taken into dry MeOH (10 mL), and the resulting solution was treated with K$_2$CO$_3$ (536 mg, 3.88 mmol) and 2-(bromomethyl)-5-(((tert-butyldimethylsilyl)oxy)methyl)-4-methylthiazole (Intermediate D10, 196 mg, 0.582 mmol); the reaction mixture was stirred at room temperature for overnight at room temperature. The resulting mixture was filtered off and concentrated under reduced pressure to give a brown oil. Under Ar the brown oil was re-dissolved into dry THF (10 mL) and then TBAF (0.8 mL, 0.8 mmol, 1.0 M in THF) was added, the reaction was stirred at room temperature for 1 h. After removal of volatiles under reduced pressure, the residue was purified by silica gel column (DCM:EA, 1:0→1:3) to afford the crude title compound (220 mg, 65% over 3 steps) as a yellow oil. MS: 868.7 (M+H$^+$).

Step B: Ethyl 7-(2-((((5-(bromomethyl)-4-methyl-thiazol-2-yl)methyl)thio)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate

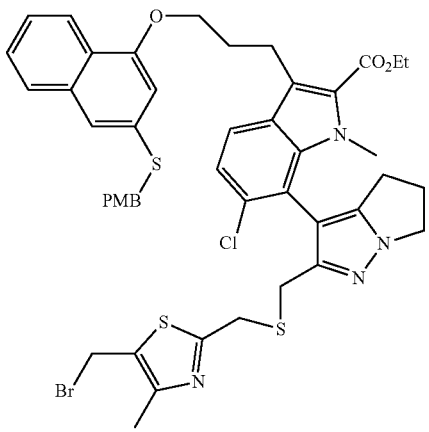

Under Ar, to a solution of the crude ethyl 6-chloro-7-(2-((((5-(hydroxymethyl)-4-methylthiazol-2-yl)methyl)thio)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate (Step A, 220 mg) in dry DCM (20 mL) was added Ph$_3$P (133 mg, 0.507 mmol), followed by CBr$_4$ (168 mg, 0.507 mmol), the reaction mixture was stirred at 0° C. for 1 h. After removal of volatiles under reduced pressure, the residue was purified by silica gel column (DCM:MeOH, 20:1) to give the crude title compound (170 mg) as a yellow solid, which was used for the next step without further purification. MS: 931.3 (M+H$^+$).

Step C: Ethyl 1$^6$-chloro-1$^1$,6$^4$-dimethyl-2$^5$,2$^6$-dihydro-1$^1$H,2$^4$H-10-oxa-4,8-dithia-6(2,5)-thiazola-1(7,3)-indola-2(3,2)-pyrrolo[1,2-b]pyrazola-9(3,1)-naphthalenacyclotridecaphane-1$^2$-carboxylate

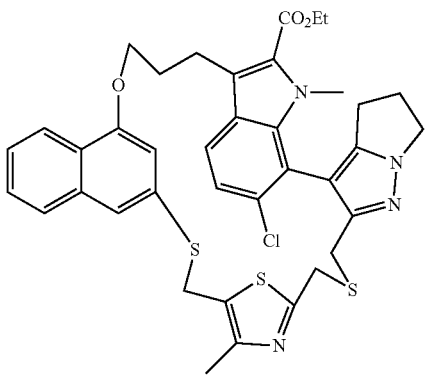 [SMILES: CCOC(=O)c1c2c3ccc(Cl)c(c3n1C)-c1c(nn3c1CCC3)CSCC1=NC(C)=C(CSc3cc(c4ccccc4c3)OCCC2)S1]

Under Ar, to a solution of the crude ethyl 7-(2-((((5-(bromomethyl)-4-methylthiazol-2-yl)methyl)thio)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate (Step B, 170 mg) in DCM (2 mL) was added TFA (6 mL) and TES (2 mL), the reaction mixture was stirred at room temperature for overnight. After removal of volatiles under reduced pressure, under Ar the residue was retaken into dry acetonitrile (10 mL) and K$_2$CO$_3$ (25.3 mg, 0.183 mmol) was added; the reaction mixture was stirred at room temperature for 2 h. After filtration and removal of volatiles under reduced pressure, the residue (130 mg) was directly used without purification. MS: 730.6 (M+H$^+$).

Step D: 1$^6$-chloro-1$^1$,6$^4$-dimethyl-2$^5$,2$^6$-dihydro-1$^1$H,2$^4$H-10-oxa-4,8-dithia-6(2,5)-thiazola-1(7,3)-indola-2(3,2)-pyrrolo[1,2-b]pyrazola-9(3,1)-naphthalenacyclotridecaphane-12-carboxylic acid To a solution of the above residue (Step C, 130 mg) in a mixed solvent of THF (3 mL) and MeOH (3 mL) was added 2N NaOH (6 mL), the reaction mixture was stirred at room temperature for 2 h. After removal of volatiles under reduced pressure, the residue was adjusted to pH=3 with 1N HCl. The resulting mixture was extracted with DCM twice, the DCM layer was combined, washed with brine, and concentrated under reduced pressure to give a brown oil, which was purified by C$_{18}$ pre-HPLC column to afford the title compound (5.1 mg, 4% over 4 steps) as a white solid. $^1$H NMR (500 MHz, DMSO-d$_6$): δ 8.07 (d, J=8.0 Hz, 1H), 7.92 (d, J=9.0 Hz, 1H), 7.70 (d, J=8.5 Hz, 1H), 7.49-7.42 (m, 2H), 7.34 (s, 1H), 7.05 (d, J=8.5 Hz, 1H), 6.92 (s, 1H), 4.52 (d, J=16 Hz, 1H), 4.39 (d, J=16 Hz, 1H), 4.36-4.32 (m, 1H), 4.15-4.08 (m, 2H), 3.96-3.91 (m, 1H), 3.61-3.38 (m, 9H), 3.00-2.97 (m, 1H), 2.62-2.53 (m, 3H), 2.39-2.33 (m, 1H), 2.25-2.18 (m, 1H), 2.21 (s, 3H). MS: 701.3 (M+H$^+$).

Example 31

Synthesis of 1$^6$-chloro-1$^1$-methyl-2$^5$,2$^6$-dihydro-1$^1$H,2$^4$H-10-oxa-4,8-dithia-6(2,5)-thiazola-1(7,3)-indola-2(3,2)-pyrrolo[1,2-b]pyrazola-9(3,1)-naphthalenacyclotridecaphane-1$^2$-carboxylic acid (Cpd, No. 4)

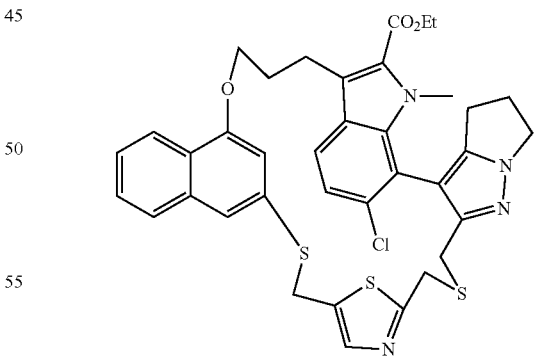

Essentially the same synthetic protocol described in Example 30 was used to afford Cpd, No. 4 (2.8 mg) as a white solid. $^1$H NMR (500 MHz, DMSO-d$_6$): δ 8.09 (d, J=8.1 Hz, 1H), 7.85 (d, J=8.3 Hz, 1H), 7.71 (d, J=8.2 Hz, 1H), 7.48-7.44 (m, 2H), 7.36 (d, J=5.7 Hz, 2H), 6.98 (d, J=7.9 Hz, 2H), 4.61 (d, J=16 Hz, 1H), 4.53 (d, J=15.5 Hz, 1H), 4.39-4.34 (m, 1H), 4.15-4.08 (m, 2H), 4.01-3.95 (m, 1H), 3.68-3.60 (m, 4H), 3.48 (s, 3H), 3.40-3.35 (m, 2H), 3.00-2.95 (m, 1H), 2.63-2.54 (m, 2H), 2.39-2.33 (m, 1H), 2.23-2.17 (m, 1H), 2.01-1.96 (m, 1H). MS: 687.1 (M+H$^+$).

Example 32

Synthesis of (Z)-1$^6$-chloro-1$^1$,6$^5$-dimethyl-2$^5$,2$^6$-dihydro-1$^1$H,2$^4$H-10-oxa-4,8-dithia-6(2,4)-oxazola-1(7,3)-indola-2(3,2)-pyrrolo[1,2-b]pyrazola-9(3,1)-naphthalenacyclotridecaphane-12-carboxylic acid (Cpd. No. 11)

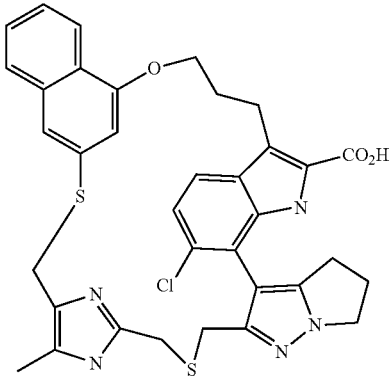 [SMILES: Cc1[nH]c2nc1CSc1cc(c3ccccc3c1)OCCCc1c(C(=O)O)[nH]c3c(c(Cl)ccc13)-c1c(nn3c1CCC3)CSC2]

Essentially the same synthetic protocol described in Example 30 was used to Cpd. No. 11 (11.8 mg) as a white solid. $^1$H NMR (500 MHz, DMSO-d$_6$): δ 13.32 (brs, 1H), 8.26 (d, J=9.5 Hz, 1H), 7.81 (d, J=7.0 Hz, 1H), 7.58-7.52 (m, 4H), 6.81 (d, J=9.0 Hz, 1H), 6.34 (s, 1H), 4.18-4.09 (m, 2H), 3.93-3.85 (m, 3H), 3.63-3.53 (m, 3H), 3.53 (s, 3 H), 3.41-3.36 (m, 1H), 3.22 (d, J=14.5 Hz, 1H), 3.20-3.15 (m, 1H), 2.98 (d, J=14.5 Hz, 1H), 2.66-2.50 (m, 4H), 2.36-2.28 (m, 1H), 2.22-2.16 (m, 1H), 1.76 (s, 3H). MS: 686.2 (M+H$^+$).

Example 33

Synthesis of (Z)-1$^6$-chloro-1$^1$,6$^1$-dimethyl-2$^5$,2$^6$-dihydro-1$^1$H,2$^4$H,6$^1$H-10-oxa-4,8-dithia-1(7,3)-indola-2(3,2)-pyrrolo[1,2-b]pyrazola-6(3,5)-pyrazola-9(3,1)-naphthalenacyclotridecaphane-1$^2$-carboxylic acid 4,4-dioxide (Cpd. No. 9)

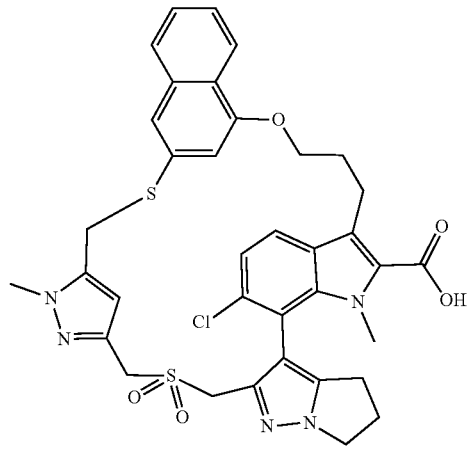 [SMILES: Cn1nc2cc1CSc1cc(c3ccccc3c1)OCCCc1c(C(=O)O)n(C)c3c(c(Cl)ccc13)-c1c(nn3c1CCC3)CS(=O)(=O)C2]

Step A: Ethyl 7-(2-(((((5-(((tert-butyldimethylsilyl)oxy)methyl)-1-methyl-1H-pyrazol-3-yl)methyl)sulfonyl)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate

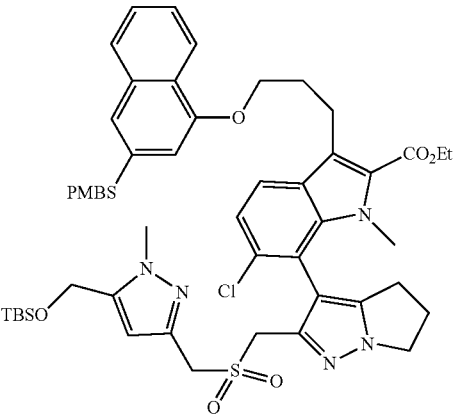

Under Ar, to a stirred solution of sodium (5-(((tert-butyldimethylsilyl)oxy)methyl)-1-methyl-1H-pyrazol-3-yl)methanesulfinate (Intermediate D16, 0.11 mmol) in dry DMF (2.0 mL) was added ethyl 7-(2-(bromomethyl)-5,6-dihydro-4H-pyrrolo[1,2-b]pyrazol-3-yl)-6-chloro-3-(3-((4-methoxybenzyl)thio)naphthalen-1-yl)oxy)propyl)-1-methyl-1H-indole-2-carboxylate (Step A of EXAMPLE 1, 85 mg, 0.11 mmol) at room temperature. The reaction was stirred at room temperature for 1 h and then heated to 50° C. for another 1 h. The reaction was quenched by NaHCO$_3$ aq. and extracted by EA twice, the combined organic layer was washed by H$_2$O, dried over by Na$_2$SO$_4$, and concentrated under reduced pressure, the residue was purified by silica gel column (EtOAc:Hexane, 1:2) to afford the title compound (45 mg, 41%) as a white solid. MS: 996.2 (M+H$^+$).

Step B: Ethyl 6-chloro-7-(2-(((((5-(hydroxymethyl)-1-methyl-1H-pyrazol-3-yl)methyl)sulfonyl)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate

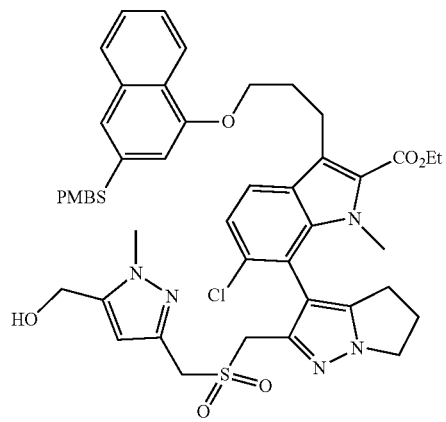

Under Ar, to a stirred solution of ethyl 7-(2-(((((5-(((tert-butyldimethylsilyl)oxy)methyl)-1-methyl-1H-pyrazol-3-yl)methyl)sulfonyl)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate (Step A, 42 mg, 0.042 mmol) in dry THF (2.0 mL) was added AcOH (5 mg, 0.084 mmol) and TBAF (0.13 mL, 1.0 M in THF, 0.13 mmol). The reaction was stirred for overnight at 22° C. After removal of volatiles under reduced pressure, the residue was purified by silica gel column (MeOH:CH$_2$Cl$_2$, 1:20→1:10) to afford the crude title compound (50 mg) as a yellow oil, which was used in the next step without further purification. MS: 882.2 (M+H$^+$).

Step C: Ethyl 7-(2-(((((5-(bromomethyl)-1-methyl-1H-pyrazol-3-yl)methyl)sulfonyl)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate

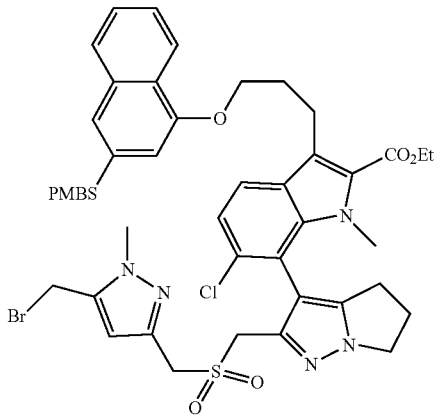

Under Ar, to a stirred solution of the crude ethyl 6-chloro-7-(2-(((((5-(hydroxymethyl)-1-methyl-1H-pyrazol-3-yl)methyl)sulfonyl)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate (Step B, 37 mg) in dry CH$_2$Cl$_2$ (2.0 mL) was added PPh$_3$ (17 mg, 0.063 mmol) and CBr$_4$ (21 mg, 0.063 mmol). The reaction was stirred at room temperature for 1 h. After removal of volatiles under reduced pressure, the residue was purified by silica gel column (MeOH:CH$_2$Cl$_2$, 1:20) to afford the title compound (33 mg, 83% over 2 steps) as a light yellow foam. MS: 946.0 (M+H$^+$).

Step D: (Z)-1$^6$-chloro-1$^1$,6$^1$-dimethyl-2$^5$,2$^6$-dihydro-1$^1$H,2$^4$H,6$^1$H-10-oxa-4,8-dithia-1(7,3)-indola-2(3,2)-pyrrolo[1,2-b]pyrazola-6(3,5)-pyrazola-9(3,1)-naphthalenacyclo-tridecaphane-1$^2$-carboxylic acid 4,4-dioxide To a stirred solution of ethyl 7-(2-(((((5-(bromomethyl)-1-methyl-1H-pyrazol-3-yl)methyl)sulfonyl)methyl)-5,6-dihydro-4H-pyrrolo[1,2-b]pyrazol-3-yl)-6-chloro-3-(3-((3-((4-methoxybenzyl)thio)naphthalen-1-yl)oxy)propyl)-1-methyl-1H-indole-2-carboxylate (Step C, 40 mg, 0.042 mmol) in CH$_2$Cl$_2$ (0.5 mL) was added triethylsilane (488 mg, 4.20 mmol) and TFA (1.5 mL). The reaction was heated to 36° C. and stirred at this temperature for 24 h. After removal of volatiles under reduced pressure, the resulting yellow oil was directly used in the next step without further purification. MS: 826.0 (M+H$^+$).

Under Ar, to a stirred solution of the above yellow oil in dry acetonitrile (15 mL) was added K$_2$CO$_3$ (58 mg, 0.42 mmol) at room temperature, the reaction mixture was heated to 36° C. and stirred further for 2 h. After removal of volatiles under reduced pressure, the resulting brown oil was used directly in the next step without purification. MS: 745.4 (M+H$^+$).

To a stirred solution of the above brown oil in the mixed solvent of THF (2.0 mL), MeOH (2.0 mL) and H$_2$O (1.0 mL) was added 2N NaOH (1.0 mL, 2.1 mmol) at room temperature. The mixture was heated to 40° C. and stirred for overnight. The resulting mixture was acidified by 1N HCl to pH=2 and extracted by CH$_2$Cl$_2$ 4 times, the combined organic layer was dried over Na$_2$SO$_4$, and concentrated under reduced pressure. The residue was purified by C$_{18}$ pre-HPLC column to afford the title compound (5.8 mg, 19% for 3 steps) as a white solid. $^1$H NMR (500 MHz, DMSO-d$_6$) δ 8.10 (d, J=8.0 Hz, 1H), 7.87 (d, J=8.6 Hz, 1H), 7.74 (d, J=7.8 Hz, 1H), 7.48 (t, J=8.4 Hz, 2H), 7.44 (s, 1H), 7.12 (d, J=8.6 Hz, 1H), 6.60 (s, 1H), 5.10 (s, 1H), 4.33 (d, J=15.6 Hz, 1H), 4.25 (d, J=15.6 Hz, 1H), 4.25-4.18 (m, 2H), 4.18-4.05 (m, 4H), 3.94 (d, J=14.6 Hz, 1H), 3.70 (s, 3H), 3.74-3.67 (m, 1H), 3.65 (d, J=14.8 Hz, 1H), 3.54 (s, 3H), 3.03 (t, J=10.6 Hz, 1H), 2.77-2.68 (m, 1H), 2.67-2.53 (m, 4H), 2.42-2.15 (m, 1H). MS: 717.9 (M+H$^+$).

Example 34

Synthesis of (Z)-1$^6$-chloro-9$^6$-fluoro-1$^1$,6$^1$-dimethyl-4-(methylsulfonyl)-2$^5$,2$^6$-dihydro-1$^1$H,2$^4$H,6$^1$H-10-oxa-8-thia-4-aza-1(7,3)-indola-2(3,2)-pyrrolo[1,2-b]pyrazola-6(3,5)-pyrazola-9(3,1)-naphthalenacyclotridecaphane-1$^2$-carboxylic acid (Cpd. No. 44)

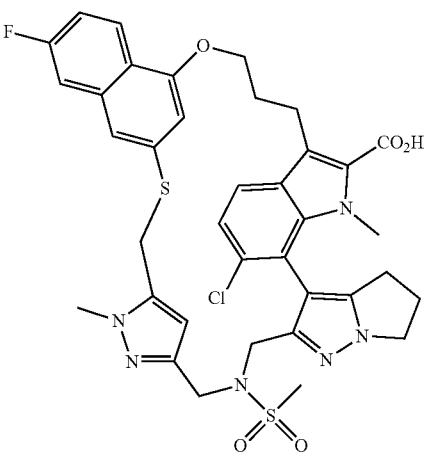 [SMILES: Cn1nc2cc1CSc1cc(c3ccc(F)cc3c1)OCCCc1c(C(=O)O)n(C)c3c(c(Cl)ccc13)-c1c(nn3c1CCC3)CN(S(C)(=O)=O)C2]

Step A: Ethyl 6-chloro-3-(3-((6-fluoro-3-((4-methoxybenzyl)thio)naphthalen-1-yl)oxy)propyl)-7-(2-formyl-5,6-dihydro-4H-pyrrolo[1,2-b]pyrazol-3-yl)-1-methyl-1H-indole-2-carboxylate

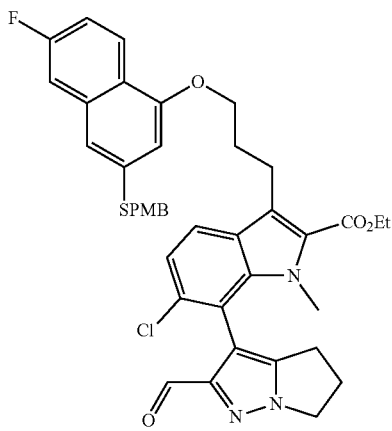

Under Ar, to a solution of ethyl 6-chloro-3-(3-((6-fluoro-3-((4-methoxybenzyl)thio)naphthalen-1-yl)oxy)propyl)-7-(2-(hydroxymethyl)-5,6-dihydro-4H-pyrrolo[1,2-b]pyrazol-3-yl)-1-methyl-1H-indole-2-carboxylate (Intermediate E9, 1.4 g, 1.92 mmol) in dry THF (25 mL) was added manganese(IV) oxide (5.0 g, 57.7 mmol), and the reaction mixture was stirred at 80° C. for 2 h. After cooling down to room temperature, the resulting mixture was filtered off, and concentrated under reduced pressure to give a yellow oil, which was purified by silica gel column (DCM:EA, 1:0→2:3) to afford the title compound (1 g, 72%) as a light yellow oil. MS: 726.5 (M+H$^+$); 748.6, 750.4 (M+Na$^+$).

Step B: Ethyl 7-(2-(((tert-butoxycarbonyl)amino)methyl)-5,6-dihydro-4H-pyrrolo[1,2-b]pyrazol-3-yl)-6-chloro-3-(3-((6-fluoro-3-((4-methoxybenzyl)thio)naphthalen-1-yl)oxy)propyl)-1-methyl-1H-indole-2-carboxylate

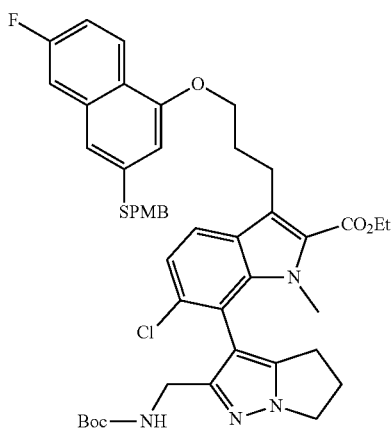

Under Ar, to a solution of ethyl 6-chloro-3-(3-((6-fluoro-3-((4-methoxybenzyl)thio)naphthalen-1-yl)oxy)propyl)-7-(2-formyl-5,6-dihydro-4H-pyrrolo[1,2-b]pyrazol-3-yl)-1-methyl-1H-indole-2-carboxylate (Step A, 1 g, 1.38 mmol), tert-butyl carbamate (0.81 g, 6.9 mmol) and triethylsilane (1.60 g, 13.8 mmol) in dry DCM (40 mL) was dropwise added TFA (0.94 g, 8.3 mmol) at 0° C., and the reaction mixture was allowed to warm up to room temperature slowly and stirred for overnight. The resulting mixture was diluted with DCM, washed with aq. NaHCO$_3$, brine, dried over Na$_2$SO$_4$, and concentrated under reduced pressure to give a yellow oil, which was purified by silica gel column (DCM:MeOH, 20:1) to afford the title compound (1.14 g, quantitatively) as a white foam. MS: 829.0 (M+H$^+$); 849.8 (M+Na$^+$).

Step C: Ethyl 7-(2-(aminomethyl)-5,6-dihydro-4H-pyrrolo[1,2-b]pyrazol-3-yl)-6-chloro-3-(3-((6-fluoro-3-((4-methoxybenzyl)thio)naphthalen-1-yl)oxy)propyl)-1-methyl-1H-indole-2-carboxylate

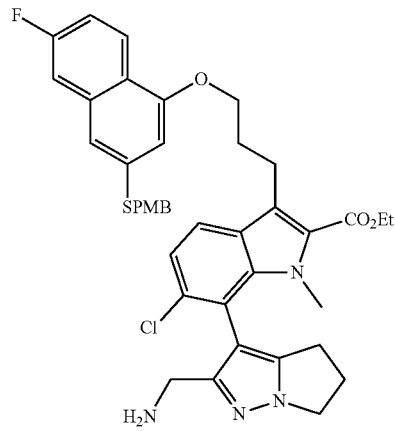

Under Ar, the mixture of ethyl 7-(2-(((tert-butoxycarbonyl)amino)methyl)-5,6-dihydro-4H-pyrrolo[1,2-b]pyrazol-3-yl)-6-chloro-3-(3-((6-fluoro-3-((4-methoxybenzyl)thio)naphthalen-1-yl)oxy)propyl)-1-methyl-1H-indole-2-carboxylate (Step B, 1.14 g, 1.40 mmol) in a mixed solvent of TFA (2 mL) and DCM (10 mL) was stirred at room temperature for overnight. After dilution with DCM, the resulting mixture was washed with aq. NaHCO$_3$, brine, dried over Na$_2$SO$_4$, and concentrated under reduced pressure to give a brown oil, which was purified by silica gel column (DCM:MeOH, 10:1) to afford the title compound (868 mg, 85%) as a white foam. MS: 728.4 (M+H$^+$); 749.6 (M+Na$^+$).

Step D: Ethyl 7-(2-(((((5-(((tert-butyldimethylsilyl)oxy)methyl)-1-methyl-1H-pyrazol-3-yl)methyl)amino)methyl)-5,6-dihydro-4H-pyrrolo[1,2-b]pyrazol-3-yl)-6-chloro-3-(3-((6-fluoro-3-((4-methoxybenzyl)thio)naphthalen-1-yl)oxy)propyl)-1-methyl-1H-indole-2-carboxylate

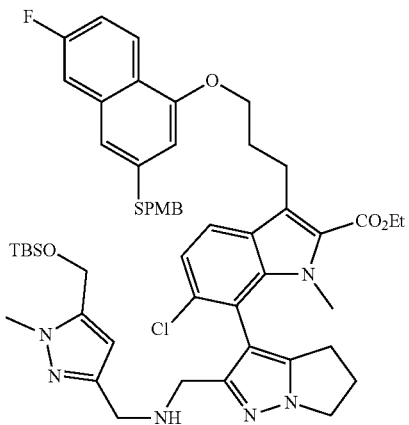

Under Ar, to solution of ethyl 7-(2-(aminomethyl)-5,6-dihydro-4H-pyrrolo[1,2-b]pyrazol-3-yl)-6-chloro-3-(3-((6-fluoro-3-((4-methoxybenzyl)thio)naphthalen-1-yl)oxy)propyl)-1-methyl-1H-indole-2-carboxylate (Step C, 858 mg, 1.18 mmol) and 5-(((tert-butyldimethylsilyl)oxy)methyl)-1-methyl-1H-pyrazole-3-carbaldehyde (Step A of Intermediate C9, 250 mg, 0.98 mmol) in dry DCM (10 mL) was added sodium triacetoxyborohyride (625 mg, 2.95 mmol), and the reaction mixture was stirred at room temperature for overnight. After dilution with DCM, the resulting mixture was washed with aq. NaHCO$_3$ and brine, dried over Na$_2$SO$_4$, and concentrated under reduced pressure to give a yellow oil, which was purified by silica gel column (DCM:MeOH, 10:1) to afford the title compound (854 mg, 90%) as a white foam. MS: 965.7, 967.9 (M+H$^+$).

Step E: Ethyl 6-chloro-3-(3-((6-fluoro-3-((4-methoxybenzyl)thio)naphthalen-1-yl)oxy)propyl)-7-(2-((N-((5-(hydroxymethyl)-1-methyl-1H-pyrazol-3-yl)methyl)methylsulfonamido)methyl)-5,6-dihydro-4H-pyrrolo[1,2-b]pyrazol-3-yl)-1-methyl-1H-indole-2-carboxylate

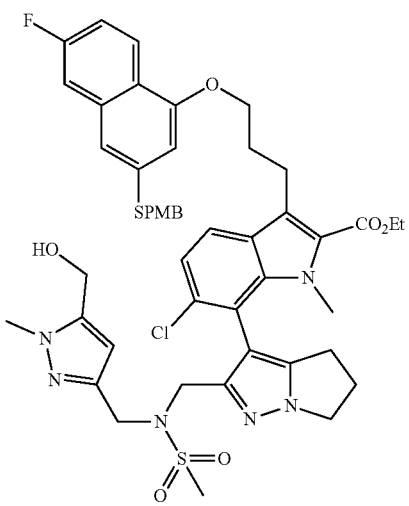

Under Ar, to a solution of ethyl 7-(2-((N-((5-(((tert-butyldimethylsilyl)oxy)methyl)-1-methyl-1H-pyrazol-3-yl)methyl)methylsulfonamido)methyl)-5,6-dihydro-4H-pyrrolo[1,2-b]pyrazol-3-yl)-6-chloro-3-(3-((6-fluoro-3-((4-methoxybenzyl)thio)naphthalen-1-yl)oxy)propyl)-1-methyl-1H-indole-2-carboxylate (Step D, 164 mg, 0.16 mmol) in dry THF (10 mL) was added TBAF-3H$_2$O (125 mg, 0.48 mmol) and acetic acid (18.87 mg, 0.31 mmol), and the reaction mixture was stirred at room temperature for overnight. After dilution with EA, the resulting mixture was washed with aq. NaHCO$_3$ and brine, dried over Na$_2$SO$_4$, and concentrated under reduced pressure to give a yellow oil, which was purified by silica gel column (DCM:MeOH, 20:1) to afford the title compound as a white solid (124 mg, 85%). MS: 929.6, 931.6 (M+H$^+$).

Step F: Ethyl 7-(2-((N-((5-(bromomethyl)-1-methyl-1H-pyrazol-3-yl)methyl)methylsulfonamido)methyl)-5,6-dihydro-4H-pyrrolo[1,2-b]pyrazol-3-yl)-6-chloro-3-(3-((6-fluoro-3-((4-methoxybenzyl)thio)naphthalen-1-yl)oxy)propyl)-1-methyl-1H-indole-2-carboxylate

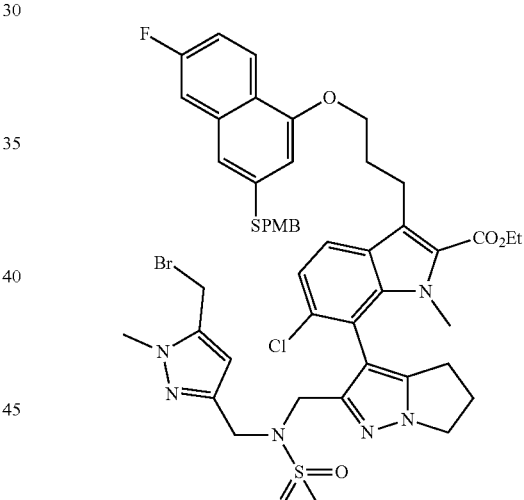

Under Ar, to a solution of ethyl 6-chloro-3-(3-((6-fluoro-3-((4-methoxybenzyl)thio)naphthalen-1-yl)oxy)propyl)-7-(2-((N-((5-(hydroxymethyl)-1-methyl-1H-pyrazol-3-yl)methyl)methylsulfonamido)methyl)-5,6-dihydro-4H-pyrrolo[1,2-b]pyrazol-3-yl)-1-methyl-1H-indole-2-carboxylate (Step E, 120 mg, 0.13 mmol) in dry DCM (20 mL) was added PPh$_3$ (67.7 mg, 0.26 mmol) and CBr$_4$ (86 mg, 0.26 mmol) at 0° C., then the reaction mixture was stirred at room temperature for 3 h. After removal of volatiles under reduced pressure, the residue was purified by silica gel column (DCM MeOH, 20:1) to afford the crude title compound as a yellow foam, which was used for the next step without further purification. MS: 991.5, 993.7 (M+H$^+$).

203

Step G: Ethyl (Z)-1⁶-chloro-9⁶-fluoro-1¹,6¹-dimethyl-4-(methylsulfonyl)-2⁵,2⁶-dihydro-1¹H,2⁴H,6¹H-10-oxa-8-thia-4-aza-1(7,3)-indola-2(3,2)-pyrrolo[1,2-b]pyrazola-6(3,5)-pyrazola-9(3,1)-naphthalenacyclotridecaphane-1²-carboxylate

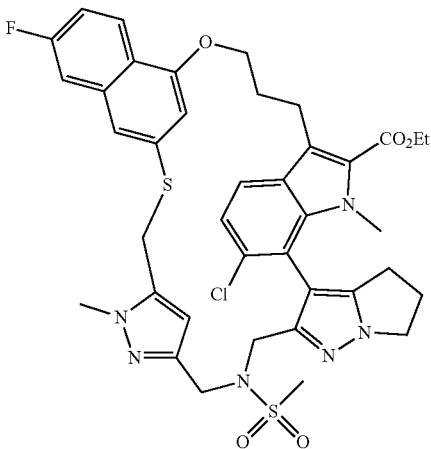 [SMILES: CCOC(=O)c1c2c3ccc(Cl)c(c3n1C)-c1c(nn3c1CCC3)CN(S(C)(=O)=O)Cc1cc(n(C)n1)CSc1cc(c3ccc(F)cc3c1)OCCC2]

Under Ar, to a solution of the crude ethyl 7-(2-((N-((5-(bromomethyl)-1-methyl-1H-pyrazol-3-yl)methyl)methylsulfonamido)methyl)-5,6-dihydro-4H-pyrrolo[1,2-b]pyrazol-3-yl)-6-chloro-3-(3-((6-fluoro-3-((4-methoxybenzyl)thio)naphthalen-1-yl)oxy)propyl)-1-methyl-1H-indole-2-carboxylate (Step F, 200 mg) in DCM (1 mL) was added TFA (5 mL) and anisole (0.5 mL), and the reaction mixture was stirred at 50° C. for overnight. After removal of volatiles under reduced pressure, under Ar the residue was re-dissolved into dry acetonitrile (10 mL), and K₂CO₃ (285 mg, 2.1 mmol) was added; the reaction mixture was stirred at room temperature for 2 h. The resulting mixture was filtered off, and concentrated under reduced pressure to give the crude title compound (300 mg) as a brown oil, which was directly used without purification. MS: 791.7, 793.5 (M+H⁺); 813.4 (M+Na⁺).

Step H: (Z)-1⁶-chloro-9⁶-fluoro-1¹,6¹-dimethyl-4-(methylsulfonyl)-25,26-dihydro-1¹H,2⁴H,6¹H-10-oxa-8-thia-4-aza-1(7,3)-indola-2(3,2)-pyrrolo[1,2-b]pyrazola-6(3,5)-pyrazola-9(3,1)-naphthalenacyclotridecaphane-1²-carboxylic acid To a solution of the crude ethyl (Z)-1⁶-chloro-9⁶-fluoro-1¹,6¹-dimethyl-4-(methylsulfonyl)-2⁵,2⁶-dihydro-1¹H,2⁴H,6¹H-10-oxa-8-thia-4-aza-1(7,3)-indola-2(3,2)-pyrrolo[1,2-b]pyrazola-6(3,5)-pyrazola-9(3,1)-naphthalenacyclotridecaphane-1²-carboxylate (Step G, 300 mg) in a mixed solvent of THF (9 mL) and MeOH (9 mL) was added 2N NaOH (6 mL), the reaction mixture was stirred at room temperature for 2 h. After removal of volatiles under reduced pressure, the residue was adjusted to pH=1-2 with 1N HCl, and the resulting mixture was extracted with DCM twice. The combined DCM layer was washed with brine, and concentrated under reduced pressure

204 to give a brown oil, which was purified by C18 pre-HPLC column to afford the title compound (32 mg, 11% over 3 steps) as a white solid. ¹H NMR (500 MHz, DMSO-d₆): δ 13.35 (brs, 1H), 8.18 (dd, J=9.1, 5.9 Hz, 1H), 7.64 (d, J=8.5 Hz, 1H), 7.52 (dd, J=10.2, 2.3 Hz, 1H), 7.38-7.33 (m, 2H), 6.88 (d, J=8.5 Hz, 1H), 6.49 (s, 1H), 4.76 (s, 1H), 4.27 (d, J=15.5 Hz, 1H), 4.18 (d, J=15 Hz, 1H), 4.19-4.14 (m, 2H), 3.91-3.77 (m, 5H), 3.68 (s, 3H), 3.50 (s, 3H), 3.44-3.41 (m, 2H), 3.17-3.11 (m, 1H), 2.76 (s, 3H), 2.71-2.54 (m, 4H), 2.39-2.34 (m, 1H), 2.25-2.18 (m, 1H). MS: 763.6, 765.4 (M+H⁺).

Example 35

Synthesis of (Z)-4-(benzylsulfonyl)-1⁶-chloro-9⁶-fluoro-1¹,6¹-dimethyl-2⁵,2⁶-dihydro-1¹H,2⁴H,6¹H-10-oxa-8-thia-4-aza-1(7,3)-indola-2(3,2)-pyrrolo[1,2-b]pyrazola-6(3,5)-pyrazola-9(3,1)-naphthalenacyclotridecaphane-1²-carboxylic acid
(Cpd. No. 41)

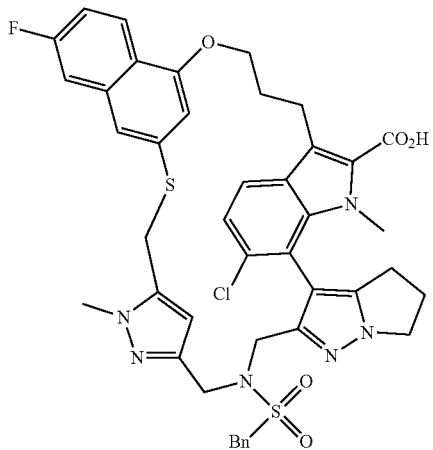 [SMILES: Cn1nc2cc1CSc1cc(c3ccc(F)cc3c1)OCCCc1c(C(=O)O)n(C)c3c(c(Cl)ccc13)-c1c(nn3c1CCC3)CN(S(=O)(=O)Cc1ccccc1)C2]

Essentially the same protocol of preparation of Example 34 was used to afford the example (33 mg) as a white solid. ¹H NMR (500 MHz, DMSO-d₆): δ 8.22-8.19 (m, 1H), 7.61 (d, J=8.6 Hz, 1H), 7.51 (d, J=9.2 Hz, 1H), 7.39 (s, 1H), 7.37-7.34 (t, J=7.8 Hz, 1H), 7.25 (s, 3H), 7.13 (s, 2H), 6.85 (d, J=8.5 Hz, 1H), 6.50 (s, 1H), 4.83 (s, 1H), 4.34-4.29 (m, 3H), 4.21-4.15 (m, 3H), 3.89-3.78 (m, 5H), 3.69 (s, 3H), 3.50-3.47 (m, 4H), 3.17-3.11 (m, 1H), 2.72-2.62 (m, 2H), 2.60-2.54 (m, 3H), 2.37 (brs, 1H), 2.21 (brs, 1H). MS: 839.8, 841.6 (M+H⁺).

Example 36

Synthesis of (Z)-1⁶-chloro-9⁶-fluoro-1¹,6¹-dimethyl-4-(methylsulfonyl)-2⁶,2⁷-dihydro-1¹H,2⁴H,6¹H-10-oxa-8-thia-4-aza-2(3,2)-pyrazolo[5,1-c][1,4]oxazina-1(7,3)-indola-6(3,5)- pyrazola-9(3,1)-naphthalenacyclotridecaphane-1²-carboxylic acid (Cpd. No. 42)

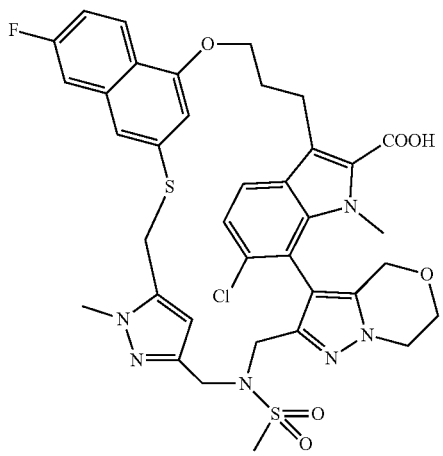 [SMILES: Cn1nc2cc1CSc1cc(c3ccc(F)cc3c1)OCCCc1c(C(=O)O)n(C)c3c(c(Cl)ccc13)-c1c(nn3c1COCC3)CN(S(C)(=O)=O)C2]

Essentially the same synthetic protocol described in Example 34 was used to afford Cpd. No. 42 (9.3 mg) as a white solid. $^1$H NMR (500 MHz, DMSO-d$_6$) δ 13.37 (s, 1H), 8.18 (dd, J=9.1, 5.8 Hz, 1H), 7.67 (d, J=8.7 Hz, 1H), 7.53 (dd, J=10.2, 2.0 Hz, 1H), 7.39 (s, 1H), 7.35 (dd, J=9.4, 2.1 Hz, 1H), 6.90 (d, J=8.5 Hz, 1H), 6.48 (s, 1H), 4.77 (s, 1H), 4.53 (d, J=15.2 Hz, 1H), 4.43 (d, J=15.1 Hz, 1H), 4.27 (d, J=15.6 Hz, 1H), 4.18 (d, J=16.0 Hz, 3H), 4.10 (s, 2H), 3.88-3.81 (m, 4H), 3.76 (d, J=15.5 Hz, 1H), 3.68 (s, 3H), 3.48 (s, 3H), 3.42 (d, J=12.2 Hz, 2H), 3.13 (dd, J=18.7, 8.7 Hz, 1H), 2.77 (s, 3H), 2.36 (s, 1H), 2.23 (t, J=18.3 Hz, 1H); MS: 779.7 (M+H⁺).

Example 37

Synthesis of (Z)-1⁶-chloro-4-(cyclopropylsulfonyl)-9⁶-fluoro-1¹,6¹-dimethyl-2⁶,2⁷-dihydro-1¹H,2⁴H,6¹H-10-oxa-8-thia-4-aza-2(3,2)-pyrazolo[5,1-c][1,4]oxazina-1(7,3)-indola-6(3,5)- pyrazola-9(3,1)-naphthalenacyclotridecaphane-1²-carboxylic acid (Cpd. No. 43)

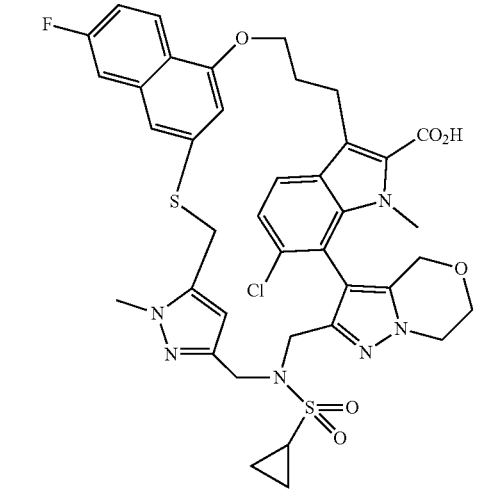 [SMILES: Cn1nc2cc1CSc1cc(c3ccc(F)cc3c1)OCCCc1c(C(=O)O)n(C)c3c(c(Cl)ccc13)-c1c(nn3c1COCC3)CN(S(=O)(=O)C1CC1)C2]

Essentially the same synthetic protocol described in Example 34 was used to afford Cpd. No. 43 (6 mg) as a white solid. $^1$H NMR (500 MHz, DMSO-d$_6$) δ 13.37 (s, 1H), 8.15 (dd, J=9.0, 6.0 Hz, 1H), 7.76 (d, J=8.7 Hz, 1H), 7.51 (dd, J=10.2, 1.8 Hz, 1H), 7.38 (s, 1H), 7.33 (dd, J=9.0, 2.2 Hz, 1H), 7.00 (d, J=8.5 Hz, 1H), 6.53 (s, 1H), 4.72 (s, 1H), 4.53 (d, J=15.1 Hz, 1H), 4.45 (d, J=15.2 Hz, 1H), 4.27 (s, 2H), 4.19 (d, J=5.0 Hz, 2H), 4.14-4.06 (m, 2H), 4.00 (dd, J=14.3, 5.8 Hz, 1H), 3.95 (s, 1H), 3.88 (d, J=15.7 Hz, 1H), 3.83 (d, J=15.3 Hz, 1H), 3.77-3.71 (m, 1H), 3.69 (s, 3H), 3.49 (s, 3H), 3.48-3.41 (m, 2H), 3.14-3.07 (m, 1H), 2.39 (dd, J=13.4, 7.6 Hz, 1H), 2.25 (dd, J=12.6, 7.7 Hz, 2H), 0.78-0.70 (m, 2H), 0.51 (dd, J=19.3, 9.0 Hz, 2H). MS: 805.6 (M+H⁺).

Example 38

Synthesis of (Z)-1⁶-chloro-9⁶-fluoro-1¹,2¹,2⁵,6¹-tetramethyl-4-(methylsulfonyl)-11H,2H,6¹H-10-oxa-8-thia-4-aza-1(7,3)-indola-2(4,3),6(3,5)-dipyrazola-9(3,1)-naphthalenacyclotridecaphane-1²-carboxylic acid (Cpd. No. 45)

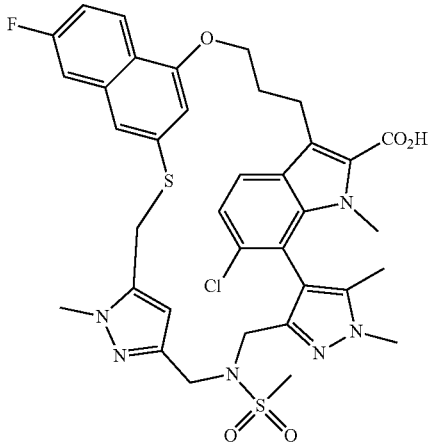 [SMILES: Cc1c2c(nn1C)CN(S(C)(=O)=O)Cc1cc(n(C)n1)CSc1cc(c3ccc(F)cc3c1)OCCCc1c(C(=O)O)n(C)c3c-2c(Cl)ccc13]

Step A: Ethyl 6-chloro-3-(3-((6-fluoro-3-((4-methoxybenzyl)thio)naphthalen-1-yl)oxy)propyl)-7-(3-formyl-1,5-dimethyl-1H-pyrazol-4-yl)-1-methyl-1H-indole-2-carboxylate

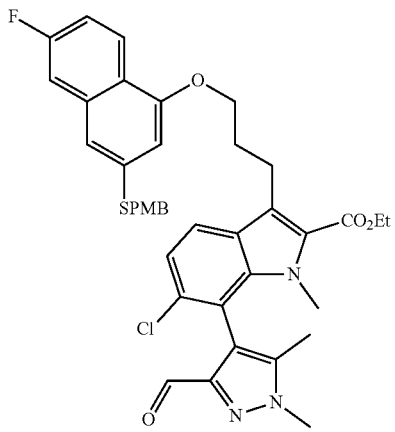

Under Ar, the reaction mixture of ethyl 6-chloro-3-(3-((6-fluoro-3-((4-methoxybenzyl)thio)naphthalen-1-yl)oxy)propyl)-7-(3-(hydroxymethyl)-1,5-dimethyl-1H-pyrazol-4-yl)-1-methyl-1H-indole-2-carboxylate (Intermediate E19, 10.1 g, 14.1 mmol) and MnO₂ (12.26 g, 141 mmol) in dry THF (80 mL) was stirred at 50° C. for overnight, and then the 2″ batch MnO₂ (49 g, 564 mmol) was followed; the reaction mixture was further stirred at 80° C. for 3 h. After cooling down to room temperature, the resulting mixture was filtered off, and concentrated under reduced pressure to give a dark oil, which was purified by silica gel column (DCM:EA, 1:0→4:1) to afford the title compound (7.2 g, 72%) as a white foam. MS: 714.8, 716.5 (M+H⁺); 736.8, 738.5 (M+Na⁺).

Step B: Ethyl 7-(3-(((tert-butoxycarbonyl)amino)methyl)-1,5-dimethyl-1H-pyrazol-4-yl)-6-chloro-3-(3-((6-fluoro-3-((4-methoxybenzyl)thio)naphthalen-1-yl)oxy)propyl)-1-methyl-1H-indole-2-carboxylate

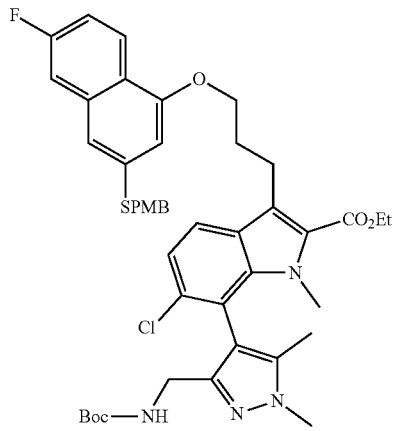

Under Ar, to a solution of ethyl 6-chloro-3-(3-((6-fluoro-3-((4-methoxybenzyl)thio)naphthalen-1-yl)oxy)propyl)-7-(3-formyl-1,5-dimethyl-1H-pyrazol-4-yl)-1-methyl-1H-indole-2-carboxylate (Step A, 7.2 g, 10.1 mmol), tert-butyl carbamate (5.90 g, 50.4 mmol) and triethylsilane (11.72 g, 101 mmol) in dry DCM (30 mL) was added TFA (6.90 g, 60.5 mmol) at 0° C., then the reaction mixture was stirred at room temperature for overnight. After dilution with DCM and cold water, the resulting organic layer was washed with aq. NaHCO₃, brine, dried over Na₂SO₄, and concentrated under reduced pressure to give a yellow oil, which was purified by silica gel column (DCM:EA, 1:0→1:4) to afford the title compound (6.8 g, 83%) as a white foam. MS: 815.9, 817.8 (M+H⁺).

Step C: Ethyl 7-(3-(aminomethyl)-1,5-dimethyl-1H-pyrazol-4-yl)-6-chloro-3-(3-((6-fluoro-3-((4-methoxybenzyl)thio)naphthalen-1-yl)oxy)propyl)-1-methyl-1H-indole-2-carboxylate

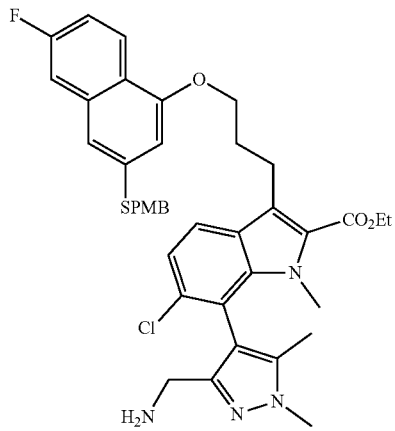

Under Ar, to a solution of ethyl 7-(3-(((tert-butoxycarbonyl)amino)methyl)-1,5-dimethyl-1H-pyrazol-4-yl)-6-chloro-3-(3-((6-fluoro-3-((4-methoxybenzyl)thio)naphthalen-1-yl)oxy)propyl)-1-methyl-1H-indole-2-carboxylate (Step B, 6.8 g, 8.34 mmol) in dry DCM (70 mL) was added TFA (14 mL) slowly at 0° C., followed by drops of water. Then the reaction mixture was stirred at room temperature for overnight. After dilution with DCM and cold water, the resulting organic layer was washed with aq. NaHCO$_3$, brine, dried over Na$_2$SO$_4$, and concentrated under reduced pressure to give a yellow oil, which was purified by silica gel column (DCM:MeOH, 20:1) to afford the title compound (4.64 g, 78%) as a white foam. MS: 716.4, 718.6 (M+H$^+$); 737.5, 739.4 (M+Na$^+$).

Step D: Ethyl 7-(3-((((5-(((tert-butyldimethylsilyl)oxy)methyl)-1-methyl-1H-pyrazol-3-yl)methyl)amino)methyl)-1,5-dimethyl-1H-pyrazol-4-yl)-6-chloro-3-(3-((6-fluoro-3-((4-methoxybenzyl)thio)naphthalen-1-yl)oxy)propyl)-1-methyl-1H-indole-2-carboxylate

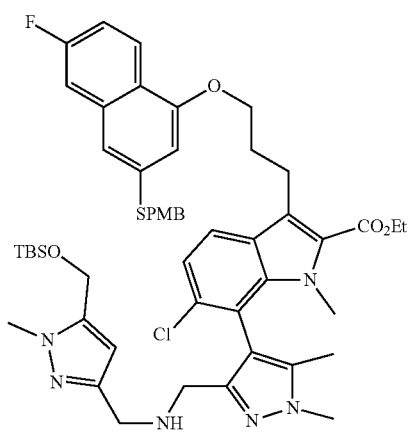

Under Ar, to a solution of ethyl 7-(3-(aminomethyl)-1,5-dimethyl-1H-pyrazol-4-yl)-6-chloro-3-(3-((6-fluoro-3-((4-methoxybenzyl)thio)naphthalen-1-yl)oxy)propyl)-1-methyl-1H-indole-2-carboxylate (Step C, 4.66 g, 6.51 mmol) and 5-(((tert-butyldimethylsilyl)oxy)methyl)-1-methyl-1H-pyrazole-3-carbaldehyde (Step A of Intermediate C9, 1.38 g, 5.42 mmol) in dry DCM (50 mL) was added NaBH(OAc)$_3$ (3.45 g, 16.27 mmol) at 0° C.; then the reaction mixture was allowed to warm up to room temperature and stirred for overnight. After dilution with DCM and cold water, the resulting organic layer was washed with aq. NaHCO$_3$, brine, dried over Na$_2$SO$_4$, and concentrated under reduced pressure to give a brown oil, which was purified by silica gel column (DCM:MeOH, 1:0→10:1) to afford the title compound (4.3 g, 83%) as a white foam. MS: 954.9 (M+H$^+$).

Step E: Ethyl 7-(3-((N-((5-((((tert-butyldimethylsilyl)oxy)methyl)-1-methyl-1H-pyrazol-3-yl)methyl)methylsulfonamido)methyl)-1,5-dimethyl-1H-pyrazol-4-yl)-6-chloro-3-(3-((6-fluoro-3-((4-methoxybenzyl)thio)naphthalen-1-yl)oxy)propyl)-1-methyl-1H-indole-2-carboxylate

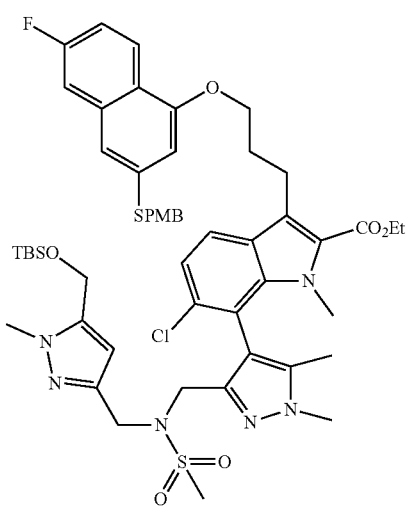

Under Ar, to a solution of ethyl 7-(3-((((5-(((tert-butyldimethylsilyl)oxy)methyl)-1-methyl-1H-pyrazol-3-yl)methyl)amino)methyl)-1,5-dimethyl-1H-pyrazol-4-yl)-6-chloro-3-(3-((6-fluoro-3-((4-methoxybenzyl)thio)naphthalen-1-yl)oxy)propyl)-1-methyl-1H-indole-2-carboxylate (Step D, 4.3 g, 4.51 mmol) in dry DCM (50 mL) was added Et$_3$N (1.37 g, 13.5 mmol) at 0° C., followed by MsCl (568 mg, 4.96 mmol), the reaction mixture was stirred at 0° C. for 1 h. After dilution with DCM, the resulting mixture was washed with aq. NaHCO$_3$, brine, dried over Na$_2$SO$_4$, and concentrated under reduced pressure to give a yellow oil, which was purified by silica gel column (DCM:MeOH, 30:1) to afford the title compound (3.8 g, 82%) as a white foam. MS: 1031.9, 1033.9 (M+H$^+$).

Step F: Ethyl 6-chloro-3-(3-((6-fluoro-3-((4-methoxybenzyl)thio)naphthalen-1-yl)oxy)propyl)-7-(3-((N-((5-(hydroxymethyl)-1-methyl-1H-pyrazol-3-yl)methyl)methylsulfonamido)methyl)-1,5-dimethyl-1H-pyrazol-4-yl)-1-methyl-1H-indole-2-carboxylate

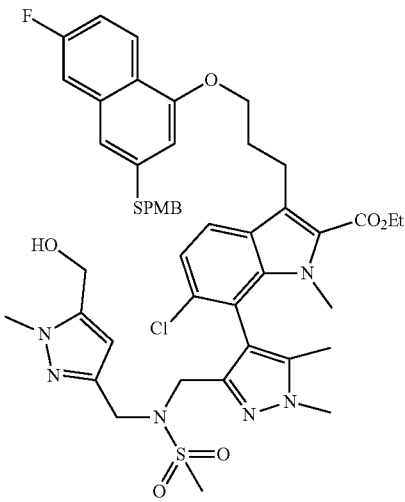

Under Ar, to a solution of ethyl 7-(3-((N-((5-(((tert-butyldimethylsilyl)oxy)methyl)-1-methyl-1H-pyrazol-3-yl)methyl)methylsulfonamido)methyl)-1,5-dimethyl-1H-pyrazol-4-yl)-6-chloro-3-(3-((6-fluoro-3-((4-methoxybenzyl)thio)naphthalen-1-yl)oxy)propyl)-1-methyl-1H-indole-2-carboxylate (Step E, 3.8 g, 3.68 mmol) in dry THF (30 mL) was added acetic acid (0.44 g, 7.37 mmol), followed by TBAF·3H$_2$O (2.93 g, 11.21 mmol); the reaction mixture was stirred at room temperature for overnight. After dilution with DCM, the resulting mixture was washed with aq. NaHCO$_3$, brine, dried over Na$_2$SO$_4$, and concentrated under reduced pressure to give a brown oil, which was purified by silica gel column (DCM:MeOH, 20:1) to afford the title compound as a white foam (3.3 g, 98%). MS: 917.6, 919.7 (M+H$^+$).

Step G: Ethyl 7-(3-((N-((5-(bromomethyl)-1-methyl-1H-pyrazol-3-yl)methyl)methylsulfonamido)methyl)-1,5-dimethyl-1H-pyrazol-4-yl)-6-chloro-3-(3-((6-fluoro-3-((4-methoxybenzyl)thio)naphthalen-1-yl)oxy)propyl)-1-methyl-1H-indole-2-carboxylate

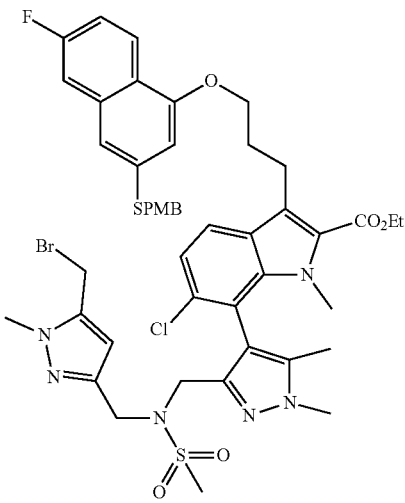

Under Ar, to a solution of ethyl 6-chloro-3-(3-((6-fluoro-3-((4-methoxybenzyl)thio)naphthalen-1-yl)oxy)propyl)-7-(3-((N-((5-(hydroxymethyl)-1-methyl-1H-pyrazol-3-yl)methyl)methylsulfonamido)methyl)-1,5-dimethyl-1H-pyrazol-4-yl)-1-methyl-1H-indole-2-carboxylate (Step F, 3.3 g, 3.60 mmol) in dry DCM (30 mL) was added Ph$_3$P (1.42 g, 5.40 mmol) at 0° C., followed by CBr$_4$ (1.79 g, 5.40 mmol); the reaction mixture was stirred at 0° C. for 1 h. After removal of volatiles under reduced pressure, the residue was purified by silica gel column (DMC:MeOH, 10:1) to afford the crude title compound (4.6 g) as a white foam, which was used for the next step without further purification. MS: 979.6, 982.0 (M+H$^+$).

Step H: Ethyl (Z)-1$^6$-chloro-9$^6$-fluoro-1$^1$,2$^1$,2$^5$,6$^1$-tetramethyl-4-(methylsulfonyl)-1$^1$H,2$^1$H,6$^1$H-10-oxa-8-thia-4-aza-1(7,3)-indola-2(4,3),6(3,5)-dipyrazola-9(3,1)-naphthalenacyclotridecaphane-1$^2$-carboxylate

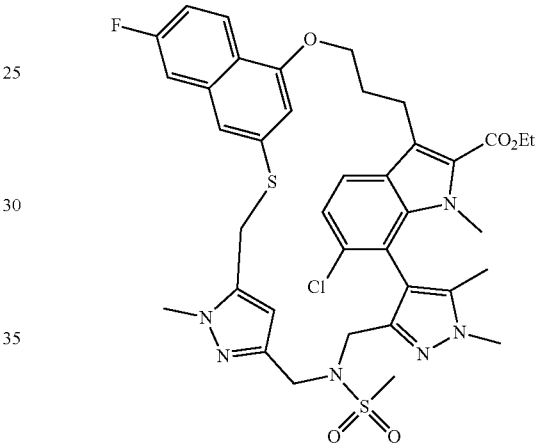

Under Ar, to a solution of the crude ethyl 7-(3-((N-((5-(bromomethyl)-1-methyl-1H-pyrazol-3-yl)methyl)methylsulfonamido)methyl)-1,5-dimethyl-1H-pyrazol-4-yl)-6-chloro-3-(3-((6-fluoro-3-((4-methoxybenzyl)thio)naphthalen-1-yl)oxy)propyl)-1-methyl-1H-indole-2-carboxylate (Step G, 4.6 g) in DCM (10 mL) was added anisole (5 mL) and TFA (50 mL), the reaction mixture was stirred at 50° C. for overnight. After removal of volatiles under reduced pressure, under Ar the residue was re-dissolved in dry acetonitrile (50 mL) and K$_2$CO$_3$ (6.48 g, 46.9 mmol) was added; the reaction mixture was stirred at room temperature for 1 h. The resulting mixture was filtered off, and the filtrate was concentrated under reduced pressure to give a brown oil, which was purified by silica gel column (DCM:MeOH, 20:1) to afford the crude title compound (3 g) as a white foam. MS: 779.6, 781.5 (M+H$^+$).

Step I: (Z)-1$^6$-chloro-9$^6$-fluoro-1$^1$,2$^1$,2$^5$,6$^1$-tetramethyl-4-(methylsulfonyl)-1$^1$H,2$^1$H,6$^1$H-10-oxa-8-thia-4-aza-1(7,3)-indola-2(4,3),6(3,5)-dipyrazola-9(3,1)-naphthalenacyclotridecaphane-1$^2$-carboxylic acid To a solution of the crude ethyl (Z)-1$^6$-chloro-9$^6$-fluoro-1$^1$,2$^1$,2$^5$,6$^1$-tetramethyl-4-(methylsulfonyl)-1$^1$H,2$^1$H,6$^1$H-10-oxa-8-thia-4-aza-1(7,3)-indola-2(4,3),6(3,5)-dipyrazola-9(3,1)-naphthalenacyclotridecaphane-1$^2$-carboxylate (Step H, 3 g) in a mixed solvent of THF (12 mL) and MeOH (12 mL) was added 2N NaOH (12 mL), the reaction mixture was stirred at room temperature for 2 h. After removal of volatiles under reduced pressure, the residue was adjusted to pH=2 with 1N HCl, and the resulting mixture was extracted with DCM twice, the combined DCM layer was washed with brine, dried over $Na_2SO_4$, and concentrated under reduced pressure to give a brown oil, which was purified by C18 pre-HPLC column to afford the title compound (210 mg, 7% over 3 steps) as a white solid. $^1$H NMR (500 MHz, DMSO-$d_6$) δ 8.18 (dd, J=9.1, 5.9 Hz, 1H), 7.66 (d, J=8.6 Hz, 1H), 7.52 (dd, J=10.2, 2.2 Hz, 1H), 7.40-7.30 (m, 2H), 6.90 (d, J=8.6 Hz, 1H), 6.48 (s, 1H), 4.73 (s, 1H), 4.26 (d, J=15.5 Hz, 1H), 4.18 (d, J=16 Hz, 1H), 3.92-3.73 (m, 8H), 3.68 (s, 3H), 3.45 (s, 3H), 3.36-3.33 (m, 2H), 3.18-3.12 (m, 1H), 2.77 (s, 3H), 2.36 (m, 1H), 2.23 (m, 1H), 1.97 (s, 3H). MS: 751.8, 753.6 (M+H$^+$).

Example 39

Synthesis of (R)-(Z)-1$^6$-chloro-9$^6$-fluoro-1$^1$,2$^1$,2$^5$, 6$^1$-tetramethyl-4-(methylsulfonyl)-1$^1$H,2$^1$H,6$^1$H-10-oxa-8-thia-4-aza-1(7,3)-indola-2(4,3),6(3,5)-dipyrazola-9(3,1)- naphthalenacyclotridecaphane-1$^2$-carboxylic acid (Cpd. No. 48)

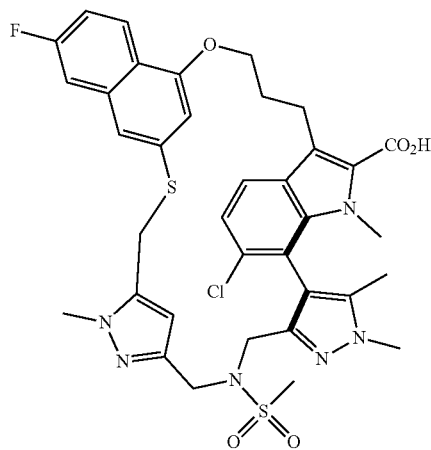

Cpd. No. 45 (351 mg) was subjected to chiral SFC resolution with (R,R)-WHELK-O1-Kromasil column to provide Cpd. No. 48 (143 mg, 98% ee) as a white solid. MS: 751.2 (M+H$^+$).

Example 40

Synthesis of (S)-(Z)-1$^6$-chloro-9$^6$-fluoro-1$^1$,2$^1$,2$^5$,6$^1$-tetramethyl-4-(methylsulfonyl)-1$^1$H,2$^1$H,6$^1$H-10-oxa-8-thia-4-aza-1(7,3)-indola-2(4,3),6(3,5)-dipyrazola-9(3,1)- naphthalenacyclotridecaphane-1$^2$-carboxylic acid (Cpd. No. 47)

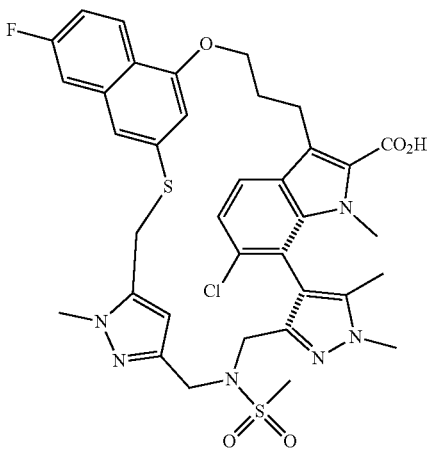

Cpd. No. 45 (351 mg) was subjected to chiral SFC resolution with (R,R)-WHELK-O1-Kromasil column to provide Cpd. No. 47 (141 mg, 98% ee) as a white solid. MS: 751.2 (M+H$^+$).

Example 41

Synthesis of (Z)-1$^6$-chloro-9$^6$-fluoro-1$^1$,2$^1$,2$^5$,6$^1$-tetramethyl-4-((trifluoromethyl)sulfonyl)-1$^1$H,2$^1$H, 6$^1$H-10-oxa-8-thia-4-aza-1(7,3)-indola-2(4,3),6(3,5)-dipyrazola-9(3,1)- naphthalenacyclotridecaphane-1$^2$-carboxylic acid (Cpd. No. 46)

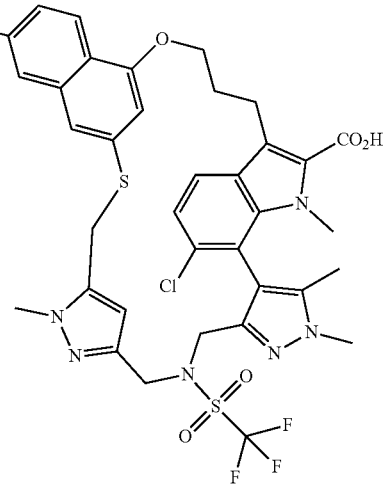

Essentially the same synthetic protocol described in Example 38 was used to afford Cpd. No. 46 (48 mg) as a white solid. $^1$H NMR (500 MHz, DMSO-$d_6$) δ 8.12 (dd, J=9.1, 5.9 Hz, 1H), 7.74 (d, J=7.2 Hz, 1H), 7.49 (d, J=10.2

Hz, 1H), 7.38 (s, 1H), 7.34-7.29 (m, 1H), 6.99 (d, J=8.5 Hz, 1H), 6.47 (s, 1H), 4.96-4.78 (m, 1H), 4.31 (s, 2H), 4.10-3.91 (m, 5H), 3.84-3.72 (m, 5H), 3.66 (s, 3H), 3.44 (s, 3H), 3.15-3.10 (m, 1H), 2.39-2.33 (m, 1H), 2.27-2.21 (m, 1H), 1.99 (s, 3H). MS: 805.8, 807.6 (M+H$^+$).

Example 42

Synthesis of (Z)-1$^6$-chloro-1$^1$,2$^1$,2$^5$,6$^1$-tetramethyl-4-(methylsulfonyl)-1$^1$H,2$^1$H,6$^1$H-10-oxa-8-thia-4-aza-1(7,3)-indola-2(4,3),6(3,5)-dipyrazola-9(3,1)-naphthalenacyclotridecaphane-1$^2$-carboxylic acid (Cpd. No. 36)

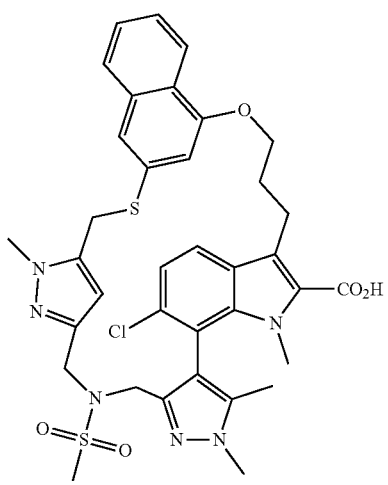 [SMILES: Cc1c2c(nn1C)CN(S(C)(=O)=O)Cc1cc(n(C)n1)CSc1cc(c3ccccc3c1)OCCCc1c(C(=O)O)n(C)c3c-2c(Cl)ccc13]

Essentially the same synthetic protocol described in Example 38 was used to afford Cpd. No. 36 (6.8 mg) as a white solid. $^1$H NMR (500 MHz, DMSO-d$_6$) δ 8.13 (d, J=7.9 Hz, 1H), 7.74 (d, J=7.3 Hz, 1H), 7.67 (d, J=8.7 Hz, 1H), 7.54-7.45 (m, 2H), 7.39 (s, 1H), 6.87 (d, J=8.6 Hz, 1H), 6.50 (s, 1H), 4.68 (s, 1H), 4.24 (d, J=15.5 Hz, 1H), 4.14 (d, J=15.6 Hz, 1H), 3.91-3.85 (m, 1H), 3.84-3.78 (m, 7H), 3.68 (s, 3H), 3.45 (s, 3 H), 3.31 (d, J=15.6 Hz, 2H), 3.19-3.11 (m, 1H), 2.75 (s, 3H), 2.42-2.34 (m, 1H), 2.28-2.18 (m, 1H), 1.97 (s, 3H). MS: 733.3 (M+H$^+$); 755.3 (M+Na$^+$).

Example 43

Synthesis of (Z)-4-acetyl-1$^6$-chloro-1$^1$,2$^1$,2$^5$,6$^1$-tetramethyl-1$^1$H,2$^1$H,6$^1$H-10-oxa-8-thia-4-aza-1(7,3)-indola-2(4,3),6(3,5)-dipyrazola-9(3,1)-naphthalenacyclotridecaphane-1$^2$-carboxylic acid (Cpd. No. 35)

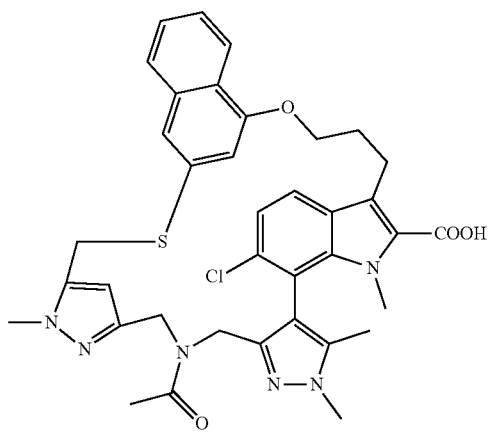 [SMILES: CC(=O)N1Cc2cc(n(C)n2)CCSc2cc(c3ccccc3c2)OCCCc2c(C(=O)O)n(C)c3c(c(Cl)ccc23)-c2c(nn(C)c2C)C1]

Essentially the same synthetic protocol described in Example 38 was used to afford Cpd. No. 35 (15 mg) as a white solid. Due to the sterical veto of N-inversion, two sets peaks in $^1$H NMR was observed with the molar ratio=1:0.65. $^1$H NMR (500 MHz, DMSO-d$_6$) δ 8.18 (d, J=8.7 Hz, 0.65H), 8.15 (d, J=8.1 Hz, 1H), 7.75 (d, J=7.7 Hz, 1H), 7.70 (d, J=7.8 Hz, 0.65H), 7.66 (d, J=8.7 Hz, 1H), 7.63 (d, J=8.7 Hz, 0.65H), 7.56-7.45 (m, 4H), 7.41 (s, 1H), 7.33 (s, 0.65H), 6.86 (d, J=8.6 Hz, 1H), 6.75 (d, J=8.6 Hz, 0.65H), 6.56 (s, 0.65H), 6.44 (s, 1H), 4.84 (s, 1H), 4.77 (s, 0.65H), 4.28 (d, J=15.8 Hz, 0.65H), 4.24 (d, J=15.6 Hz, 1H), 4.11 (d, J=5.6 Hz, 1H), 4.08 (d, J=5.5 Hz, 0.65H), 4.00-3.95 (m, 1H), 3.94-3.89 (m, 1H), 3.89-3.82 (m, 2H), 3.80 (s, 3H), 3.82-3.75 (m, 5H), 3.70 (s, 3H), 3.65 (s, 3H), 3.67-3.63 (m, 1H), 3.41 (s, 6H), 2.40-2.33 (m, 2H), 2.29-2.20 (m, 2H), 2.16 (s, 3H), 2.00 (s, 3H), 1.97 (s, 2H), 1.96 (s, 2H). MS: 698.8 (M+H$^+$).

Example 44

Synthesis of (Z)-1⁶-chloro-2³-(difluoromethyl)-9⁶-fluoro-1¹,2¹,6¹-trimethyl-4-(methylsulfonyl)-1¹H,2¹H,6¹H-10-oxa-8-thia-4-aza-1(7,3)-indola-2(4,5),6(3,5)-dipyrazola-9(3,1)-naphthalenacyclotridecaphane-1²-carboxylic acid (Cpd. No. 51)

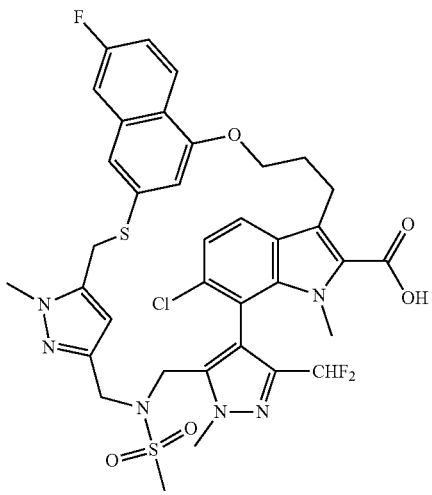 [SMILES: Cn1nc2cc1CSc1cc(c3ccc(F)cc3c1)OCCCc1c(C(=O)O)n(C)c3c(c(Cl)ccc13)-c1c(C(F)F)nn(C)c1CN(S(C)(=O)=O)C2]

Essentially the same synthetic protocol described in Example 38 was used to afford Cpd. No. 51 (4.3 mg) as a white solid. $^1$H NMR (500 MHz, DMSO-$d_6$) δ 13.47 (s, 1H), 8.32 (dd, J=9.0, 5.9 Hz, 1H), 7.65 (d, J=8.2 Hz, 2H), 7.54 (s, 1H), 7.45 (dd, J=8.9, 2.1 Hz, 1H), 6.98-6.72 (m, 2H), 6.42 (s, 1H), 4.71 (s, 1H), 4.27 (t, J=15.5 Hz, 1H), 4.16 (t, J=12.5 Hz, 1H), 4.02 (s, 3H), 3.89 (dd, J=18.2, 7.9 Hz, 2H), 3.83-3.72 (m, 5H), 3.55 (s, 3H), 3.25-3.19 (m, 2H), 2.80 (s, 3H), 2.45-2.36 (m, 2H), 2.25-2.11 (m, 2H). MS: 787.5 (M+H$^+$).

Example 45

Synthesis of (Z)-1⁶-chloro-4-cyclopropyl-1¹,2¹,2⁵,6¹-tetramethyl-1¹H,2¹H,6¹H-10-oxa-8-thia-4-aza-1(7,3)-indola-2(4,3),6(3,5)-dipyrazola-9(3,1)-naphthalenacyclotridecaphane-1²-carboxylic acid (Cpd. No. 49)

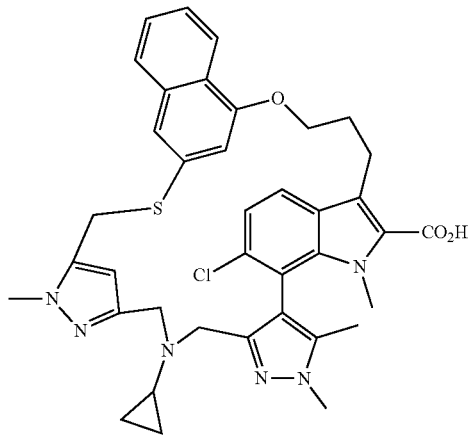 [SMILES: Cc1c2c(nn1C)CN(C1CC1)Cc1cc(n(C)n1)CSc1cc(c3ccccc3c1)OCCCc1c(C(=O)O)n(C)c3c-2c(Cl)ccc13]

Step A: Ethyl 6-chloro-7-(3-formyl-1,5-dimethyl-1H-pyrazol-4-yl)-3-(3-((3-((4-methoxybenzyl)thio)naphthalen-1-yl)oxy)propyl)-1-methyl-1H-indole-2-carboxylate

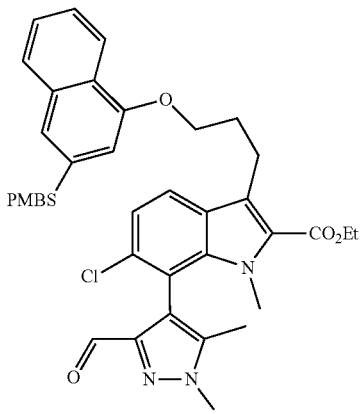

Under Ar, to a stirred solution of ethyl 6-chloro-7-(3-(hydroxymethyl)-1,5-dimethyl-1H-pyrazol-4-yl)-3-(3-((3-((4-methoxybenzyl)thio)naphthalen-1-yl)oxy)propyl)-1-methyl-1H-indole-2-carboxylate (Intermediate E18, 0.95 g, 1.36 mmol) in dry CH$_2$Cl$_2$ (30 mL) was added manganese (IV) oxide (1.18 g, 13.6 mmol) at room temperature. The mixture was stirred at room temperature for 24 h. The resulting mixture was filtered off and the filtrate was concentrated under reduced pressure to give the crude compound (0.9 g) as a yellow oil, which was used directly in the next step without purification. MS: 696.3 (M+H$^+$).

Step B: Ethyl 6-chloro-7-(3-((cyclopropylamino)methyl)-1,5-dimethyl-1H-pyrazol-4-yl)-3-(3-((3-((4-methoxybenzyl)thio)naphthalen-1-yl)oxy)propyl)-1-methyl-1H-indole-2-carboxylate

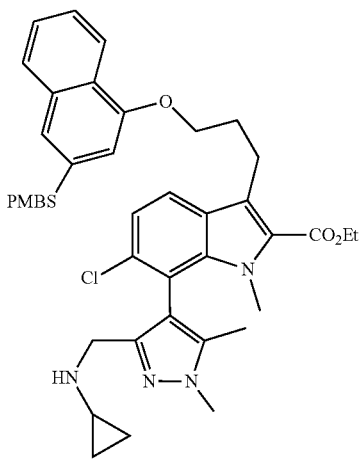

Under Ar, to a stirred solution of the crude ethyl 6-chloro-7-(3-formyl-1,5-dimethyl-1H-pyrazol-4-yl)-3-(3-((3-((4-methoxybenzyl)thio)naphthalen-1-yl)oxy)propyl)-1-methyl-1H-indole-2-carboxylate (Step A, 300 mg) and cyclopropanamine (73.8 mg, 1.29 mmol) in dry CH$_2$Cl$_2$ (5.0 mL) was added NaBH(OAc)₃ (274 mg, 1.29 mmol); the reaction was stirred at room temperature for overnight. After removal of volatiles under reduced pressure, the crude title compound was used in the next step without purification. MS: 736.4 (M+H⁺).

Step C: Ethyl 7-(3-(((((5-(((tert-butyldimethylsilyl)oxy)methyl)-1-methyl-1H-pyrazol-3-yl)methyl)(cyclopropyl)amino)methyl)-1,5-dimethyl-1H-pyrazol-4-yl)-6-chloro-3-(3-((3-((4-methoxybenzyl)thio)naphthalen-1-yl)oxy)propyl)-1-methyl-1H-indole-2-carboxylate

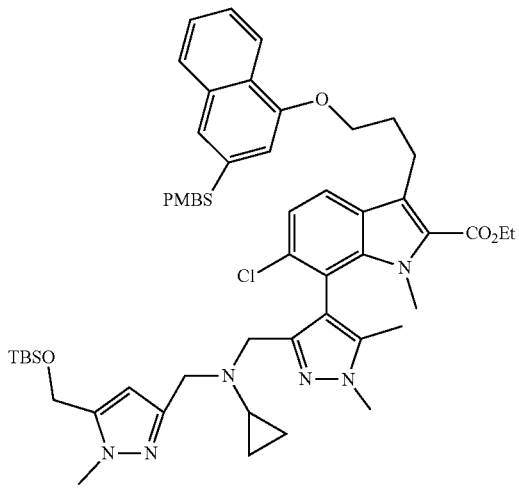

Under Ar, to a stirred solution of the crude ethyl 6-chloro-7-(3-((cyclopropylamino)methyl)-1,5-dimethyl-1H-pyrazol-4-yl)-3-(3-((3-((4-methoxybenzyl)thio)naphthalen-1-yl)oxy)propyl)-1-methyl-1H-indole-2-carboxylate (Step B, 317 mg) in dry CH₂Cl₂ (5.0 mL) was added 5-(((tert-butyldimethylsilyl)-oxy)methyl)-1-methyl-1H-pyrazole-3-carbaldehyde (Step A of Intermediate C9, 107 mg, 0.86 mmol), NaBH(OAc)₃ (182 mg, 0.86 mmol) and AcOH (26 mg, 0.43 mmol); the reaction mixture was stirred at room temperature for overnight. The resulting mixture was treated with sat. NaHCO₃ (20 mL) and was extracted with dichloromethane 3 times. The combined organic layer was dried over Na₂SO₄, and concentrated under reduced pressure to give the crude product, which was added to a silica gel column and was eluted with MeOH:CH₂Cl₂ (1:30) to afford the title compound (0.32 g, 76% over 3 steps) as a white solid. MS: 976.9 (M+H⁺).

Step D: Ethyl 6-chloro-7-(3-((cyclopropyl((5-(hydroxymethyl)-1-methyl-1H-pyrazol-3-yl)methyl)amino)methyl)-1,5-dimethyl-1H-pyrazol-4-yl)-3-(3-((3-((4-methoxybenzyl)thio)naphthalen-1-yl)oxy)propyl)-1-methyl-1H-indole-2-carboxylate

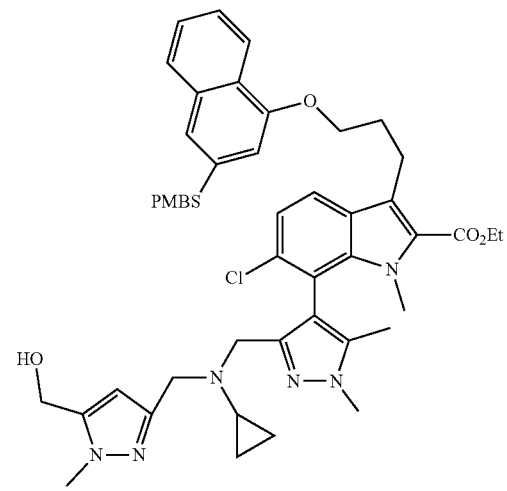

In a argon flushed 25 mL round-bottomed flask, ethyl 7-(3-(((((5-(((tert-butyldimethylsilyl)oxy)methyl)-1-methyl-1H-pyrazol-3-yl)methyl)(cyclopropyl)-amino)methyl)-1,5-dimethyl-1H-pyrazol-4-yl)-6-chloro-3-(3-((3-((4-methoxybenzyl)thio)naphthalen-1-yl)oxy)propyl)-1-methyl-1H-indole-2-carboxylate (Step C, 0.2 g, 0.205 mmol), acetic acid (0.037 g, 0.615 mmol), and TBAF·3H₂O (0.21 g, 0.803 mmol) were dissolved in dry THF (5.0 mL) to give a yellow solution; the reaction was stirred at 22° C. for overnight. Sat. NaHCO₃ (10 mL) was added to the reaction mixture followed by extraction with dichloromethane 3 times. The combined organic layer was dried over Na₂SO₄, and concentrated under reduced pressure to give the crude product, which was added to a silica gel column and was eluted with MeOH:CH₂C₂(1:15) to afford the title compound (100 mg, 57%) as a light yellow oil. MS: 862.9 (M+H⁺).

Step E: Ethyl 7-(3-(((((5-(bromomethyl)-1-methyl-1H-pyrazol-3-yl)methyl)(cyclo-propyl)amino)methyl)-1,5-dimethyl-1H-pyrazol-4-yl)-6-chloro-3-(3-((3-((4-methoxybenzyl)thio)naphthalen-1-yl)oxy)propyl)-1-methyl-1H-indole-2-carboxylate

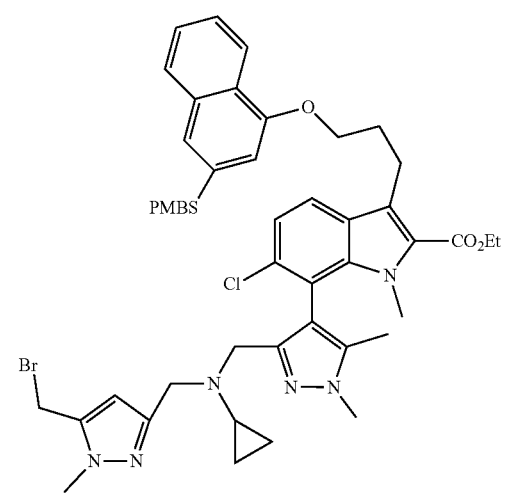

In a argon flushed 25 mL round-bottomed flask, ethyl 6-chloro-7-(3-((cyclopropyl((5-(hydroxymethyl)-1-methyl-1H-pyrazol-3-yl)methyl)amino)methyl)-1,5-dimethyl-1H-pyrazol-4-yl)-3-(3-((3-((4-methoxybenzyl)thio)naphthalen-1-yl)oxy)propyl)-1-methyl-1H-indole-2-carboxylate (Step D, 100 mg, 0.116 mmol) and PPh$_3$ (91 mg, 0.348 mmol) were dissolved in dry CH$_2$Cl$_2$ (3 mL). CBr$_4$ (57.7 mg, 0.174 mmol) was added to the reaction under argon to give a yellow solution; the reaction was stirred at room temperature for 1 h. After removal of volatiles under reduced pressure, the crude product was added to a silica gel column and was eluted with MeOH:CH$_2$Cl$_2$ (1:25) to afford the title compound (100 mg, 93%) a light yellow oil. MS: 925.5 (M+H$^+$).

Step F: (Z)-1$^6$-chloro-4-cyclopropyl-1$^1$,2$^1$,2$^5$,6$^1$-tetramethyl-1$^1$H,2$^1$H,6$^1$H-10-oxa-8-thia-4-aza-1(7,3)-indola-2(4,3),6(3,5)-dipyrazola-9(3,1)-naphthalenacyclotridecaphane-1$^2$-carboxylic acid In an argon flushed 25 mL round-bottomed flask, ethyl 7-(3-((((5-(bromomethyl)-1-methyl-1H-pyrazol-3-yl)methyl)(cyclopropyl)amino)methyl)-1,5-dimethyl-1H-pyrazol-4-yl)-6-chloro-3-(3-((3-((4-methoxybenzyl)thio)naphthalen-1-yl)oxy)propyl)-1-methyl-1H-indole-2-carboxylate (Step E, 110 mg, 0.119 mmol) and triethylsilane (692 mg, 5.95 mmol) were dissolved in TFA (3.0 mL) and CH$_2$Cl$_2$ (1.0 mL) under argon to give a yellow solution; the reaction mixture was heated to 40° C. for overnight. After removal of volatiles under reduced pressure, the resulting yellow oil was directly used in the next step without purification. MS: 805.5 (M+H$^+$).

In an argon flushed 50 mL round-bottomed flask, the above yellow oil and K$_2$CO$_3$ (68.7 mg, 0.497 mmol) were treated with dry acetonitrile (30 mL); the reaction was stirred at room temperature for 5 h, the reaction color turn to green. After removal of volatiles under reduced pressure, the resulting brown oil was directly used in the next step without purification. MS: 724.8 (M+H$^+$).

In an argon flushed 25 mL round-bottomed flask, the above brown oil and sodium hydroxide (43.1 mg, 1.078 mmol) were dissolved in THF (1.0 mL), MeOH (3.0 mL) and H$_2$O (3.0 mL) to give a yellow solution; the reaction was stirred at room temperature for 16 h. The resulting mixture was acidified with 1N HCl (1.0 mL) and extracted with dichloromethane 3 times. The combined organic layer was dried over Na$_2$SO$_4$, and concentrated under reduced pressure to give the crude product, which was purified by C18 prep-HPLC column to afford the title compound (6 mg, 8% over 3 steps) as a white solid. H NMR (500 MHz, MeOD-d$_4$) δ 8.06 (s, 1H), 7.78 (s, 1H), 7.61 (s, 1H), 7.45 (s, 2H), 7.30 (s, 1H), 7.08 (d, J=6.7 Hz, 1H), 6.52 (s, 1H), 4.15 (d, J=15.0 Hz, 1H), 4.06-3.94 (m, 2H), 3.89 (s, 3H), 3.80 (s, 3H), 3.85-3.75 (m, 1H), 3.72-3.56 (m, 4H), 3.51 (s, 3H), 3.68-3.22 (m, 4H), 2.40-2.33 (m, 2H), 2.12 (s, 3H), 1.38-1.25 (m, 4H). MS: 696.9 (M+H$^+$).

Example 46

Synthesis of (Z)-1$^6$-chloro-4-(2-hydroxyethyl)-1$^1$,2$^1$,2$^5$,6$^1$-tetramethyl-1$^1$H,2$^1$H,6$^1$H-10-oxa-8-thia-4-aza-1(7,3)-indola-2(4,3),6(3,5)-dipyrazola-9(3,1)-naphthalenacyclotridecaphane-1$^2$-carboxylic acid (Cpd. No. 50)

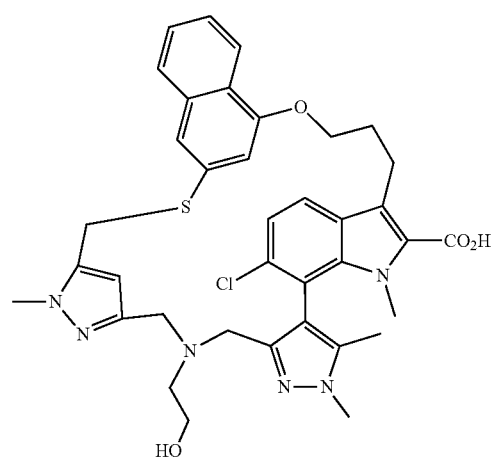 [SMILES: Cc1c2c(nn1C)CN(CCO)Cc1cc(n(C)n1)CSc1cc(c3ccccc3c1)OCCCc1c(C(=O)O)n(C)c3c-2c(Cl)ccc13]

Step A: ethyl 6-chloro-7-(3-(((2-hydroxyethyl)amino)methyl)-1,5-dimethyl-1H-pyrazol-4-yl)-3-(3-((3-((4-methoxybenzyl)thio)naphthalen-1-yl)oxy)propyl)-1-methyl-1H-indole-2-carboxylate

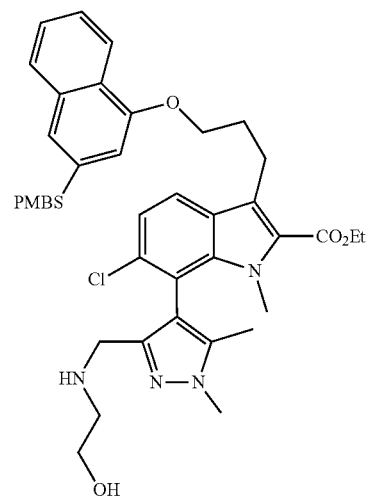

Under Ar, to a stirred solution of ethyl 6-chloro-7-(3-formyl-1,5-dimethyl-1H-pyrazol-4-yl)-3-(3-((4- methoxybenzyl)thio)naphthalen-1-yl)oxy)propyl)-1-methyl-1H-indole-2-carboxylate (Step A of Example 45, 0.42 g, 0.603 mmol), 2-aminoethan-1-ol (0.111 g, 1.810 mmol) in dry CH$_2$Cl$_2$ (20 mL) was added NaBH(OAc)$_3$ (0.384 g, 1.810 mmol); the reaction was stirred at room temperature for overnight. After removal of volatiles under reduced pressure, the residue was added to a silica gel column and was eluted with MeOH:CH$_2$Cl$_2$ (1:20→1:10) to afford the title compound (0.40 g, 89%) as a white solid. MS: 742.9 (M+H$^+$).

Step B: Ethyl 7-(3-(((((5-(((tert-butyldimethylsilyl)oxy)methyl)-1-methyl-1H-pyrazol-3-yl)methyl)(2-hydroxyethyl)amino)methyl)-1,5-dimethyl-1H-pyrazol-4-yl)-6-chloro-3-(3-((3-((4-methoxybenzyl)thio)naphthalen-1-yl)oxy)propyl)-1-methyl-1H-indole-2-carboxylate Step C: Ethyl 7-(3-(((2-((4-bromobenzoyl)oxy)ethyl)((5-(((tert-butyldimethylsilyl)oxy)methyl)-1-methyl-1H-pyrazol-3-yl)methyl)amino)methyl)-1,5-dimethyl-1H-pyrazol-4-yl)-6-chloro-3-(3-((3-((4-methoxybenzyl)thio)naphthalen-1-yl)oxy)propyl)-1-methyl-1H-indole-2-carboxylate

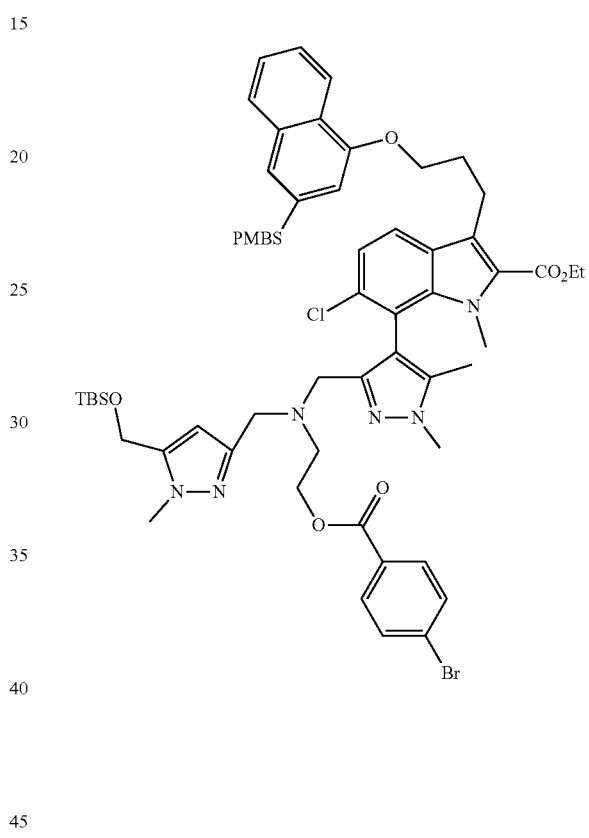

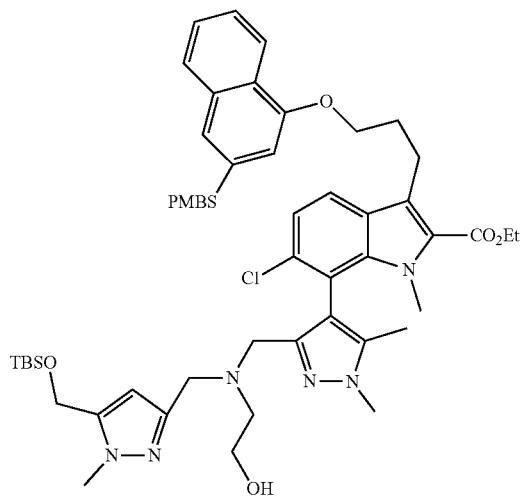

Under Ar, to a stirred solution of ethyl 6-chloro-7-(3-(((2-hydroxyethyl)amino)methyl)-1,5-dimethyl-1H-pyrazol-4-yl)-3-(3-((3-((4-methoxybenzyl)thio)naphthalen-1-yl)oxy)propyl)-1-methyl-1H-indole-2-carboxylate (Step A, 0.4 g, 0.540 mmol), 5-(((tert-butyldimethylsilyl)-oxy)methyl)-1-methyl-1H-pyrazole-3-carbaldehyde (Step A of Intermediate C9, 0.206 g, 0.809 mmol) in dry CH$_2$Cl$_2$ (20 mL) was added NaBH(OAc)$_3$ (0.343 g, 1.619 mmol); the reaction was stirred at room temperature for overnight. After removal of volatiles under reduced pressure, the residue was added to a silica gel column and was eluted with MeOH:CH$_2$Cl$_2$ (1:20) to afford the title compound (0.42 g, 79%) as a white solid. MS: 981.1 (M+H$^+$).

In an argon flushed 100 mL round-bottomed flask, ethyl 7-(3-(((((5-(((tert-butyldimethylsilyl)oxy)methyl)-1-methyl-1H-pyrazol-3-yl)methyl)(2-hydroxyethyl)amino)methyl)-1,5-dimethyl-1H-pyrazol-4-yl)-6-chloro-3-(3-((3-((4-methoxybenzyl)thio)naphthalen-1-yl)oxy)propyl)-1-methyl-1H-indole-2-carboxylate (Step B, 0.42 g, 0.429 mmol), 4-bromobenzoyl chloride (0.141 g, 0.643 mmol), and triethylamine (0.130 g, 1.286 mmol) were dissolved in dry CH$_2$Cl$_2$ (5 mL) to give a yellow solution; the reaction was stirred at room temperature for 3 h. Sat. NaHCO$_3$ (10 mL) was added to the reaction mixture followed by extraction with dichloromethane 3 times. The combined organic layer was dried over Na$_2$SO$_4$, and concentrated under reduced pressure to give the crude product, which was added to a silica gel column and was eluted with MeOH:CH$_2$Cl$_2$ (1:20) to afford the title compound (0.43 g, 86%) as a light yellow oil. MS: 1163.7 (M+H$^+$).

225

Step D: Ethyl 7-(3-(((2-((4-bromobenzoyl)oxy)ethyl)((5-(hydroxymethyl)-1-methyl-1H-pyrazol-3-yl)methyl)amino)methyl)-1,5-dimethyl-1H-pyrazol-4-yl)-6-chloro-3-(3-((3-((4-methoxybenzyl)thio)naphthalen-1-yl)oxy)propyl)-1-methyl-1H-indole-2-carboxylate

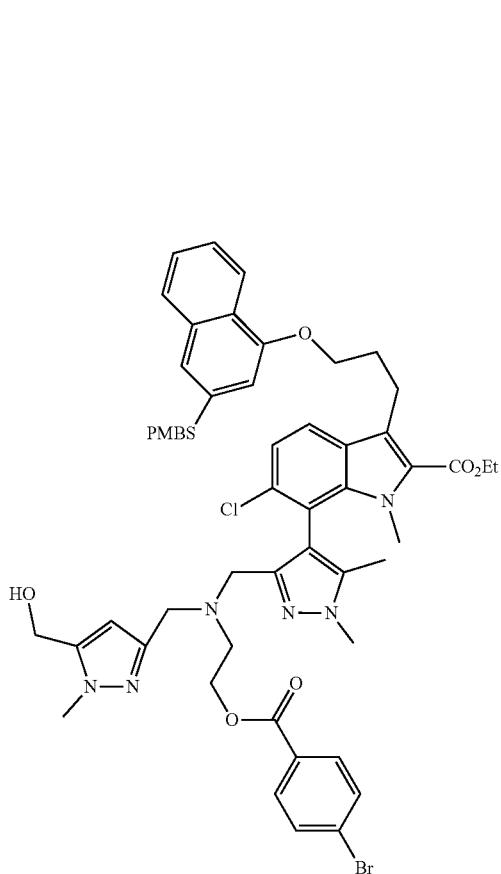

In an argon flushed 50 mL round-bottomed flask, ethyl 7-(3-(((2-((4-bromobenzoyl)oxy)ethyl)((5-(((tert-butyldimethylsilyl)oxy)methyl)-1-methyl-1H-pyrazol-3-yl)methyl)amino)methyl)-1,5-dimethyl-1H-pyrazol-4-yl)-6-chloro-3-(3-((3-((4-methoxybenzyl)thio)naphthalen-1-yl)oxy)propyl)-1-methyl-1H-indole-2-carboxylate (Step C, 0.47 g, 0.404 mmol), acetic acid (0.049 g, 0.808 mmol), and TBAF-H$_2$O (0.317 g, 1.212 mmol) were dissolved in dry THF (10 mL) to give a yellow solution; the reaction was stirred at room temperature for overnight. After removal of volatiles under reduced pressure, the residue was added to a silica gel column, eluted with MeOH:CH$_2$C$_2$(1:20) to afford the title compound (0.39 g, 92%) as a light yellow oil. MS: 1049.5 (M+H$^+$).

226

Step E: Ethyl 7-(3-(((2-((4-bromobenzoyl)oxy)ethyl)((5-(bromomethyl)-1-methyl-1H-pyrazol-3-yl)methyl)amino)methyl)-1,5-dimethyl-1H-pyrazol-4-yl)-6-chloro-3-(3-((3-((4-methoxy-benzyl)thio)naphthalen-1-yl)oxy)propyl)-1-methyl-1H-indole-2-carboxylate

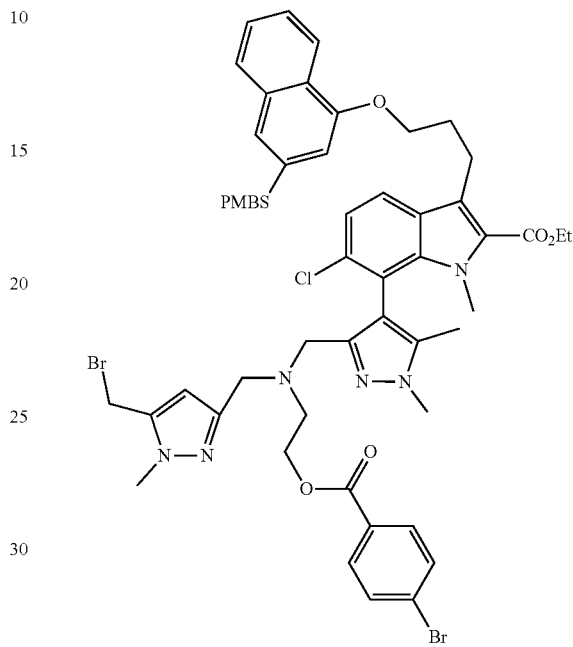

In an argon flushed 100 mL round-bottomed flask, ethyl 7-(3-(((2-((4-bromobenzoyl)oxy)ethyl)((5-(hydroxymethyl)-1-methyl-1H-pyrazol-3-yl)methyl)amino)methyl)-1,5-dimethyl-1H-pyrazol-4-yl)-6-chloro-3-(3-((3-((4-methoxybenzyl)thio)naphthalen-1-yl)oxy)propyl)-1-methyl-1H-indole-2-carboxylate (Step D, 0.39 g, 0.372 mmol), PPh$_3$ (0.146 g, 0.558 mmol), and CBr$_4$ (0.148 g, 0.446 mmol) were dissolved in dry CH$_2$Cl$_2$ (10 mL) to give a light yellow solution; the reaction was stirred at room temperature for 3 h. After removal of volatiles under reduced pressure, the residue was added to a silica gel column, eluted with MeOH:CH$_2$Cl$_2$ (1:20→1:10) to afford the title compound (0.33 g, 80%) as a yellow oil. MS: 1113.0 (M+H$^+$).

Step F: (Z)-1$^6$-chloro-4-(2-hydroxyethyl)-1$^1$,2$^1$,2$^5$,6$^1$-tetramethyl-1$^1$H,2$^1$H,6$^1$H-10-oxa-8-thia-4-aza-1(7,3)-indola-2(4,3),6(3,5)-dipyrazola-9(3,1)-naphthalenacyclotridecaphane-1$^2$-carboxylic acid In an argon flushed 100 mL round-bottomed flask, ethyl 7-(3-(((2-((4-bromobenzoyl)oxy)ethyl)((5-(bromomethyl)-1-methyl-1H-pyrazol-3-yl)methyl)amino)methyl)-1,5-dimethyl-1H-pyrazol-4-yl)-6-chloro-3-(3-((3-((4-methoxy-benzyl)thio)naphthalen-1-yl)oxy)propyl)-1-methyl-1H-indole-2-carboxylate (Step E, 0.4 g, 0.36 mmol) and triethylsilane (0.209 g, 1.8 mmol) were dissolved in CH$_2$Cl$_2$ (1.0 mL) and TFA (3.0 mL) to give a yellow solution; the reaction was stirred at 36° C. for overnight. After removal of volatiles under reduced pressure, the resulting yellow oil was used directly in the next step without purification. MS: 992.1 (M+H$^+$).

In an argon flushed 100 mL round-bottomed flask, the above yellow oil was dissolved in dry MeCN (10 mL) to give a color solution, $K_2CO_3$ (2.59 g, 18.75 mmol) was added and the reaction mixture was stirred at room temperature for 3 h. Sat. $NaHCO_3$ (20 mL) was added to the reaction mixture followed by extraction with DCM 3 times. The combined organic layer was dried over $Na_2SO_4$, and concentrated under reduced pressure to give a brown oil, which was directly used without purification. MS: 911.7 $(M+H^+)$.

In an argon flushed 100 mL round-bottomed flask the above brown oil and NaOH (0.097 g, 2.42 mmol) were dissolved in THF (5.0 mL), MeOH (5.0 mL) and $H_2O$ (5.0 mL) to give a yellow solution; the reaction mixture was heated to 40° C. and stirred for 2 h. The resulting mixture was adjusted to pH=5 with 1N HCl and extracted with $CH_2Cl_2$ 3 times. The combined organic layer was concentrated under reduced pressure to give a brown oil, which was purified by C18 prep-HPLC column to afford the title compound (46 mg, 27% over 3 steps) as a white solid. Due to the sterical veto of N-inversion, two sets peaks in $^1$H-NMR was observed with the molar ratio=1:0.6. $^1$H NMR (500 MHz, DMSO-$d_6$) δ 9.20 (s, 0.6H), 8.10 (s, 1H), 7.91 (d, J=8.6 Hz, 1H), 7.72 (d, J=7.9 Hz, 1H), 7.53-7.43 (m, 3H), 7.40 (s, 1H), 7.10 (s, 2H), 6.79 (s, 0.6H), 5.20 (s, 1H), 4.35 (s, 2H), 4.21-4.05 (m, 2H), 3.86 (s, 3H), 3.95-3.82 (m, 3H), 3.77 (s, 3H), 3.81-3.69 (m, 3H), 3.75-3.55 (m, 2H), 3.52-3.45 (m, 2H), 3.42 (s, 3H), 3.18-3.05 (m, 2H), 3.12-2.90 (m, 1H), 2.48-2.39 (m, 1H), 2.30-2.15 (m, 1H), 2.08 (s, 3H). MS: 700.8 $(M+H^+)$.

Example 47

Synthesis of (Z)-1$^6$-chloro-1$^1$,6$^1$-dimethyl-9$^5$-(trifluoromethyl)-2$^6$,2$^7$-dihydro-11H,2$^4$H,6$^1$H-10-oxa-4,8-dithia-2(3,2)-pyrazolo[5,1-c][1,4]oxazina-1(7,3)-indola-6(3,5)-pyrazola-9(1,3)-benzenacyclotridecaphane-1$^2$-carboxylic acid (Cpd. No. 33)

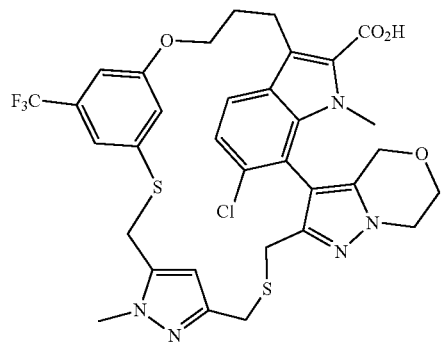 [SMILES: Cn1nc2cc1CSc1cc(cc(C(F)(F)F)c1)OCCCc1c(C(=O)O)n(C)c3c(c(Cl)ccc13)-c1c(nn3c1COCC3)CSC2]

Essentially the same synthetic protocol described in EXAMPLE 1 was used to afford Cpd. No. 33 (92 mg) as a white solid. $^1$H NMR (500 MHz, DMSO-$d_6$) δ 7.85 (d, J=8.6 Hz, 1H), 7.18 (d, J=8.6 Hz, 1H), 7.12 (s, 1H), 7.07 (s, 1H), 6.90 (s, 1H), 4.81 (s, 1H), 4.50 (dd, J=44.6, 15.1 Hz, 2H), 4.34-4.23 (m, 2H), 4.15 (brs, 2H), 4.13-4.11 (m, 3H), 3.94-3.89 (m, 1H), 3.83-3.78 (m, 1H), 3.68 (s, 3H), 3.58 (s, 3H), 3.54 (s, 3H), 3.29 (d, J=13.1 Hz, 1H), 3.12 (d, J=13.8 Hz, 1H), 3.05-2.99 (m, 1H), 2.95 (d, J=13.9 Hz, 1H), 2.23-2.16 (m, 1H), 2.12-2.03 (m, 1H). MS: 719.3 $(M+H^+)$.

Example 48

Synthesis of (Z)-1$^6$,9$^5$-dichloro-1$^1$,6$^1$,9$^6$-trimethyl-2$^4$,2$^5$,2$^6$ 2$^7$-tetrahydro-1$^1$H,6$^1$-10-oxa-4,8-dithia-2(3,2)-pyrazolo[1,5-a]pyridina-1(7,3)-indola-6(3,5)-pyrazola-9(1,3)-benzenacyclotridecaphane-1$^2$-carboxylic acid (Cpd. No. 37)

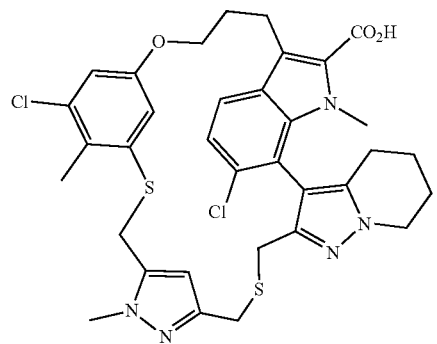 [SMILES: Cc1c(Cl)cc2cc1SCc1cc(nn1C)CSCc1nn3c(c1-c1c(Cl)ccc4c(c(C(=O)O)n(C)c14)CCCO2)CCCC3]

Essentially the same synthetic protocol described in EXAMPLE 1 was used to afford Cpd. No. 37 (1.8 mg) as a white solid. $^1$H NMR (500 MHz, DMSO-$d_6$) δ 7.85 (d, J=8.5 Hz, 1H), 7.24 (d, J=8.5 Hz, 1H), 6.84 (s, 1H), 6.63 (s, 1H), 4.81 (s, 1H), 4.24 (q, J=15.7 Hz, 2H), 4.12-4.03 (m, 2H), 3.88-3.84 (m, 1H), 3.69 (s, 3H), 3.52 (s, 3H), 3.51-3.47 (m, 4H), 3.24 (d, J=12.8 Hz, 1H), 3.14 (d, J=14.0 Hz, 1H), 3.03-2.96 (m, 1H), 2.64 (brs, 2H), 2.38-2.34 (m, 2H), 2.00-1.95 (m, 2H), 1.79-1.70 (m, 2H), 1.23 (s, 3H). MS: 696.2, 698.3 $(M+H^+)$.

Example 49

Synthesis of Intermediate A1:
3-((4-Methoxybenzyl)thio)naphthalen-1-ol

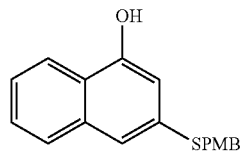

Step A:
4-((tert-Butyldimethylsilyl)oxy)naphthalen-2-ol

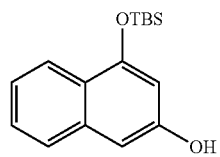 [SMILES: CC(C)(C)[Si](C)(C)Oc1cc(O)cc2ccccc12]

Under Ar, to a solution of naphthalene-1,3-diol (40 g, 250 mmol) in dry DCM (200 mL) was added imidazole (25.5 g, 375 mmol) at 0° C., followed by TBSCl (35.8 g, 237 mmol). The reaction mixture was allowed to warm up to room temperature and stirred for 3 h. Water was added to quench the reaction, and the resulting mixture was extracted with DCM twice. The combined DCM layer was washed with brine, dried over $Na_2SO_4$, and concentrated under reduced pressure to give a yellow oil, which was purified by silica gel column (hexane:EA, 1:0→10:1) to afford the title compound (37 g, 54%) as a yellow oil. $^1$H NMR (500 MHz, DMSO-$d_6$) δ 9.63 (s, 1H), 7.91 (d, J=8.3 Hz, 1H), 7.61 (d, J=8.2 Hz, 1H), 7.36 (t, J=7.5 Hz, 1H), 7.23 (t, J=7.5 Hz, 1H), 6.75 (d, J=1.7 Hz, 1H), 6.55 (d, J=2.1 Hz, 1H), 1.04 (s, 9H), 0.26 (s, 6H).

Step B: 4-((tert-Butyldimethylsilyl)oxy)naphthalen-2-yl trifluoromethanesulfonate

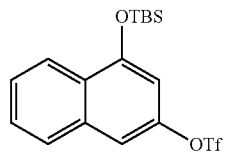 [SMILES: CC(C)(C)[Si](C)(C)Oc1cc(OS(=O)(=O)C(F)(F)F)cc2ccccc12]

Under Ar, to a solution of 4-((tert-butyldimethylsilyl)oxy)naphthalen-2-ol (Step A, 37.1 g, 135 mmol) in dry DCM (200 mL) was added DIEPA (26.2 g, 203 mmol) at 0° C., followed by $Tf_2O$ (49.6 g, 176 mmol), the reaction mixture was stirred at 0° C. for 1 h. Water was added to quench the reaction, and the resulting mixture was extracted with DCM twice. The combined DCM layer was dried over $Na_2SO_4$, and concentrated under reduced pressure to give a brown oil, which was purified by silica gel column (hexane:DCM, 10:1) to afford the title compound (47.4 g, 86%) as a colorless oil. $^1$H NMR (500 MHz, DMSO-$d_6$) δ 8.13 (m, 1H), 8.04 (m, 1H), 7.75 (d, J=2.5 Hz, 1H), 7.67-7.63 (m, 2H), 6.94 (d, J=2.5 Hz, 1H), 1.04 (s, 9H), 0.31 (s, 6H). MS: 407.1 (M+H$^+$).

Step C: tert-Butyl((3-((4-methoxybenzyl)thio)naphthalen-1-yl)oxy)dimethylsilane

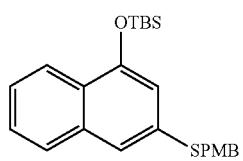

Under Ar, to a solution of 4-((tert-butyldimethylsilyl)oxy)naphthalen-2-yl trifluoromethanesulfonate (Step B, 47.4 g, 117 mmol) and (4-methoxyphenyl)methanethiol (23.38 g, 152 mmol) in dry dioxane (150 mL) was added $Pd_2(dba)_3$ (5.34 g, 5.83 mmol), Xantphos (6.75 g, 11.66 mmol) and DIEPA (45.2 g, 350 mmol), the reaction mixture was heated to reflux for overnight. After removal of volatiles under reduced pressure, the residue was purified by silica gel column (hexane:EA, 10:1) to afford the title compound (42.3 g, 88%) as a white solid. $^1$H NMR (500 MHz, DMSO-$d_6$) δ 7.99 (d, J=8.5 Hz, 1H), 7.78 (d, J=8.0 Hz, 1H), 7.51-7.44 (m, 3H), 7.30 (d, J=8.5 Hz, 2H), 6.85 (d, J=8.0 Hz, 2H), 6.75 (s, 1H), 4.26 (s, 2H), 3.71 (s, 3H), 1.03 (s, 9H), 0.23 (s, 6H). MS: 411.5 (M+H$^+$).

Step D: 3-((4-Methoxybenzyl)thio)naphthalen-1-ol (Intermediate A1)

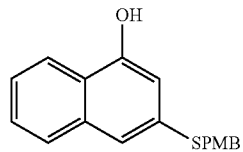

Under Ar, to a solution of tert-butyl((3-((4-methoxybenzyl)thio)naphthalen-1-yl)oxy)dimethylsilane (Step C, 64.9 g, 158 mmol) in dry THE (200 mL) was added TBAF·$3H_2O$ (20.7 g, 79 mmol), the reaction mixture was stirred at room temperature for 1 h. The formed precipitate was collected by filtration to afford the title compound (45 g, 96%) as a white solid. $^1$H NMR (500 MHz, DMSO-$d_6$) δ 10.25 (s, 1H), 8.03 (d, J=8.3 Hz, 1H), 7.70 (d, J=8.2 Hz, 1H), 7.45 (t, J=7.5 Hz, 1H), 7.36 (t, J=7.6 Hz, 1H), 7.33-7.27 (m, 3H), 6.86 (d, J=8.4 Hz, 2H), 6.79 (s, 1H), 4.24 (s, 2H), 3.71 (s, 3H). MS: 297.2 (M+H$^+$).

Example 50

Synthesis of Intermediate A2: 6-Fluoro-3-((4-methoxybenzyl)thio)naphthalen-1-ol

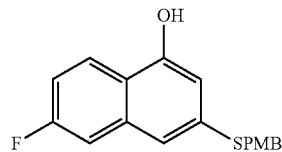

Step A: 2-(3-Fluorophenyl)acetyl chloride

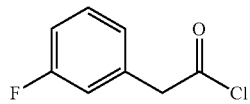 [SMILES: O=C(Cl)Cc1cccc(F)c1]

To a solution of 2-(3-fluorophenyl)acetic acid (150 g, 973 mmol) in DCM was added sulfurous dichloride (579 g, 4866 mmol) slowly, the reaction mixture was heated to 50° C. for 4 h. After cooling down to room temperature and removal of volatiles under reduced pressure, the residue was directly used without purification.

Step B: Ethyl 4-(3-fluorophenyl)-3-oxobutanoate

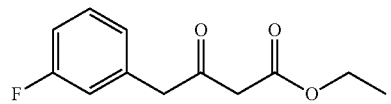 [SMILES: CCOC(=O)CC(=O)Cc1cccc(F)c1]

To a solution of 2,2-dimethyl-1,3-dioxane-4,6-dione (140 g, 973 mmol) in DCM was added DIEPA (151 g, 1168 mmol), then a solution of 2-(3-fluorophenyl)acetyl chloride (Step A, 168 g, 973 mmol) in DCM was added dropwise to the mixture at 0° C.

After addition, the reaction mixture was allowed to warm up to room temperature and stirred for overnight. The reaction was quenched with water and the resulting mixture was partitioned with DCM and water, the aqueous layer was extracted with DCM twice, the organic layer was combined, washed with 1N HCl and brine, dried over Na$_2$SO$_4$, and concentrated under reduced pressure to afford a yellow solid, which was re-taken into EtOH. The resulting mixture was then heated to 90° C. for overnight. After removal of volatiles under reduced pressure, the mixture was purified by silica gel column (hexane:EA, 19:1→9:1) to afford the title compound (190 g, 90% over 2 steps) as a white solid. MS: 225.2 (M+H$^+$).

Step C: 6-Fluoronaphthalene-1,3-diol

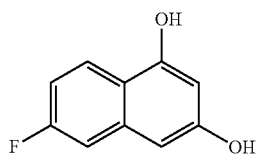 [SMILES: Oc1cc(O)c2ccc(F)cc2c1]

Ethyl 4-(3-fluorophenyl)-3-oxobutanoate (Step B, 34 g, 152 mmol) was added into concentrated sulfuric acid (112 g, 1137 mmol) with small portions at 0° C. After addition, the mixture was stirred for overnight at room temperature. The mixture was poured onto ice, and the resulting mixture was extracted with DCM twice, the organic layer was combined, washed with brine, dried over Na$_2$SO$_4$, and concentrated under reduce pressure to afford a yellow oil, which was purified by silica gel column (hexane:EA, 1:1→1:4) to afford the title compound (15 g, 56%) as an white solid. MS: 179.0 (M+H$^+$).

Step D: 4-((tert-Butyldimethylsilyl)oxy)-7-fluoronaphthalen-2-ol

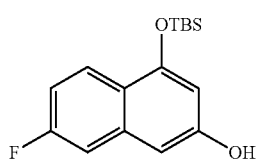 [SMILES: CC(C)(C)[Si](C)(C)Oc1cc(O)cc2cc(F)ccc12]

Under Ar, to a solution of 6-fluoronaphthalene-1,3-diol (Step C, 58 g, 326 mmol), imidazole (26.6 g, 391 mmol) in dry DCM (150 mL) was slowly added TBSCl (46.6 g, 309 mmol) at −5° C., then the reaction mixture was stirred 2 h at −5° C., and quenched with water. The mixture was extracted with DCM 3 times, the organic layer was combined, washed with brine, dried over Na$_2$SO$_4$, and concentrated under reduce pressure to afford a yellow oil, which was purified by silica gel column (DCM:MeOH, 19:1) to afford the title compound (69.5 g, 73%) as a yellow solid. MS: 293.2 (M+H$^+$).

Step E: 4-((tert-Butyldimethylsilyl)oxy)-7-fluoronaphthalen-2-yl trifluoromethanesulfonate

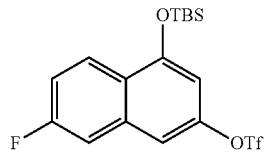 [SMILES: CC(C)(C)[Si](C)(C)Oc1cc(OS(=O)(=O)C(F)(F)F)cc2cc(F)ccc12]

Under Ar, to a solution of 4-((tert-butyldimethylsilyl)oxy)-7-fluoronaphthalen-2-ol (Step D, 40.3 g, 138 mmol) in dry DCM (200 mL) was added DIEPA (21.4 g, 165 mmol) and Tf$_2$O (42.7 g, 151 mmol) slowly at 0° C., then the reaction mixture was stirred for 30 min. Water was added to quench the reaction and the resulting mixture was extracted with DCM twice, the organic layer was combined, washed with brine, dried over Na$_2$SO$_4$, and concentrated under reduce pressure to afford a yellow oil, which was purified by silica gel column (hexane:EA, 10:1) to afford the title compound (40.5 g, 69%) as a yellow oil. MS: 370.2 (M−TBS+H$^+$).

Step F: tert-Butyl((6-fluoro-3-((4-methoxybenzyl)thio)naphthalen-1-yl)oxy)dimethylsilane

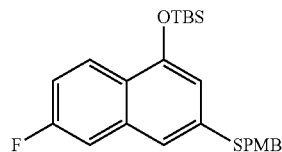

Under Ar, to a mixture of 4-((tert-butyldimethylsilyl)oxy)-7-fluoronaphthalen-2-yl trifluoromethane sulfonate (Step E, 40.5 g, 96 mmol), Xantphos (5.53 g, 9.55 mmol), and Pd$_2$(dba)$_3$ (4.37 g, 4.78 mmol) was added dry dioxane and DIEPA (37.0 g, 287 mmol), (4-methoxyphenyl)methanethiol (19.2 g, 124 mmol) were followed, then the reaction mixture was degassed for 10 min, and heated to 110° C. for overnight. After cooling down to room temperature, the mixture was filtrated off and the filtrate was concentrated to give a dark oil, which was purified by silica gel column (hexane:EA, 50:1) to afford the title compound (41.0 g, quantitatively) as a light yellow solid. MS: 429.3 (M+H$^+$).

Step G: 6-Fluoro-3-((4-methoxybenzyl)thio)naphthalen-1-ol (Intermediate A2)

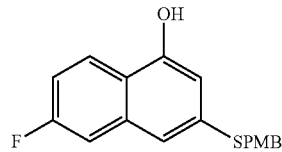

Under Ar, to a solution of tert-butyl((6-fluoro-3-((4-methoxybenzyl)thio)naphthalen-1-yl)oxy)dimethylsilane (Step F, 41.0 g, 96 mmol) in dry THF (150 mL) was added TBAF·3H$_2$O (10.0 g, 38.3 mmol) with small portions, then the reaction mixture was stirred for 3 h at room temperature.

Water was added to quench the reaction and the resulting mixture was extracted with EA twice, the organic layer was combined, washed with brine, dried over Na$_2$SO$_4$, and concentrated under reduce pressure to afford a yellow oil, which was purified by silica gel column (hexane:DCM, 1:4) to afford the title compound (25.0 g, 83%) as a white solid. $^1$H NMR (500 MHz, DMSO-d$_6$) δ 10.43 (s, 1H), 8.06 (dd, J=9.2, 6.0 Hz, 1H), 7.48 (dd, J=10.5, 2.5 Hz, 1H), 7.33 (d, J=8.6 Hz, 2H), 7.28 (s, 1H), 7.23 (dd, J=8.9, 2.5 Hz, 1H), 6.86 (d, J=8.6 Hz, 2H), 6.74 (d, J=1.4 Hz, 1H), 4.24 (s, 2H), 3.71 (s, 3H); MS: 315.1 (M+H$^+$).

Example 51

Synthesis of Intermediate A3:
7-Fluoro-3-((4-methoxybenzyl)oxy)naphthalen-1-ol

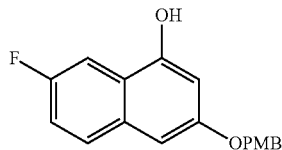

Step A: Ethyl 4-(4-fluorophenyl)-3-oxobutanoate

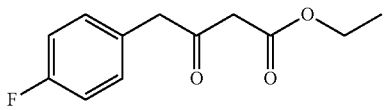 [SMILES: CCOC(=O)CC(=O)Cc1ccc(F)cc1]

Under N$_2$, in a dried 250 mL three-necked round-bottomed flask 2,2-dimethyl-1,3-dioxane-4,6-dione (13.2 g, 91 mmol) and DIEPA (22.7 g, 174 mmol) were dissolved into dry DCM (100 mL), and then the mixture was cooled to 0° C., 2-(4-fluorophenyl) acetyl chloride (15.0 g, 87 mmol) was dropwise added into the mixture over 1 h; the reaction was stirred for 1 h at 0° C., then allowed to warm up to room temperature for overnight. The reaction was quenched with water and acidified with 0.1N HCl to adjust pH=3. The organic layer was separated, and the aqueous layer was extracted with DCM twice. The combined DCM layer was dried over Na$_2$SO$_4$, concentrated under reduced pressure to afford a yellow solid, which was re-taken into EtOH. The resulting mixture was then heated to 90° C. for overnight. After removal of volatiles under reduced pressure, the mixture was purified by silica gel column (hexane:EA, 9:1) to afford the title compound (8.5 g, 44% over 2 steps) as a white solid. MS: 224.0 (M+H$^+$).

Step B: 7-Fluoronaphthalene-1,3-diol

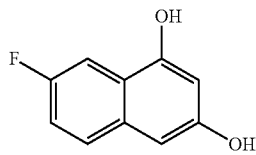 [SMILES: Oc1cc(O)c2cc(F)ccc2c1]

Ethyl 4-(4-fluorophenyl)-3-oxobutanoate (Step A, 8.5 g, 37.9 mmol) was added into concentrated sulfuric acid (34 g, 346.9 mmol) with small portions at 0° C. After addition, the mixture was stirred for overnight at room temperature. The mixture was poured onto ice, and the resulting mixture was extracted with DCM twice, the organic layer was combined, washed with brine, dried over Na$_2$SO$_4$, and concentrated under reduce pressure to afford a yellow oil, which was purified by silica gel column (hexane:EA, 2:1→1:4) to afford the title compound (2.3 g, 34%) as an off-white solid. $^1$H NMR (400 MHz, CD$_3$OD) δ 7.63 (dd, J=10.7, 2.6 Hz, 1H), 7.56 (dd, J=9.0, 5.5 Hz, 1H), 7.15 (dd, J=8.8, 2.7 Hz, 1H), 6.66 (d, J=2.0 Hz, 1H), 6.53 (d, J=2.0 Hz, 1H). MS: 179.1 (M+H$^+$).

Step C: 4-((tert-Butyldimethylsilyl)oxy)-6-fluoronaphthalen-2-ol

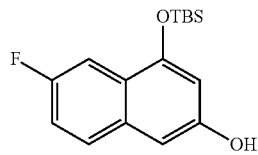 [SMILES: CC(C)(C)[Si](C)(C)Oc1cc(O)cc2ccc(F)cc12]

Under Ar, to a solution of 7-fluoronaphthalene-1,3-diol (Step B, 1.9 g, 10.7 mmol) in dry DCM (30 mL) was added imidazole (1.09 g, 16.0 mmol) at 0° C., followed by TBSCl (1.61 g, 10.7 mmol), the reaction mixture was stirred at room temperature for 3 h. Water was added to quench the reaction, and the resulting mixture was extracted with DCM twice. The combined DCM layer was washed with brine, dried over Na$_2$SO$_4$, and concentrated under reduced pressure to give a yellow oil, which was purified by silica gel column (hexane:EA, 10:1) to afford the title compound (1.15 g, 37%) as a yellow oil. $^1$H NMR (500 MHz, DMSO-d$_6$) δ 9.69 (s, 1H), 7.73-7.70 (m, 1H), 7.51-7.48 (m, 1H), 7.32-7.27 (m, 1H), 6.81 (d, J=2.0 Hz, 1H), 6.60 (d, J=2.5 Hz, 1H), 1.03 (s, 9H), 0.27 (s, 6H).

Step D: 4-((tert-Butyldimethylsilyl)oxy)-6-fluoronaphthalen-2-yl trifluoromethanesulfonate

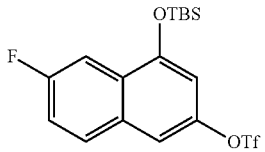 [SMILES: CC(C)(C)[Si](C)(C)Oc1cc(OS(=O)(=O)C(F)(F)F)cc2ccc(F)cc12]

Under Ar, to a solution of 4-((tert-butyldimethylsilyl)oxy)-6-fluoronaphthalen-2-ol (Step C, 1.15 g, 3.93 mmol) in dry DCM (20 mL) was added DIEPA (0.762 g, 5.90 mmol) at 0° C., followed by Tf$_2$O (1.44 g, 5.11 mmol); the reaction mixture was stirred at 0° C. for 1 h. Water was added to quench the reaction, and the resulting mixture was extracted with DCM twice. The combined DCM layer was dried over Na$_2$SO$_4$, and concentrated under reduced pressure to give a brown oil, which was purified by silica gel column (hexane) to afford the title compound (1.14 g, 68%) as a colorless oil. $^1$H NMR (500 MHz, DMSO-d$_6$) δ 8.17-8.15 (m, 1H), 7.83

(d, J=2.0 Hz, 1H), 7.71-7.68 (m, 1H), 7.63-7.59 (m, 1H), 7.04 (d, J=3.0 Hz, 1H), 1.03 (s, 9H), 0.31 (s, 6H).

Step E: tert-Butyl((7-fluoro-3-((4-methoxybenzyl) thio)naphthalen-1-yl)oxy)dimethylsilane

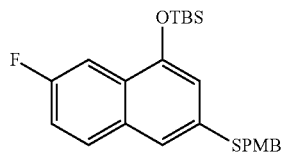

Under Ar, to a solution mixture of 4-((tert-butyldimethylsilyl)oxy)-6-fluoronaphthalen-2-yl trifluoromethanesulfonate (Step D, 1.14 g, 2.69 mmol) in dry dioxane (10 mL) was added (4-methoxyphenyl)methanethiol (538 mg, 3.49 mmol), Pd$_2$(dba)$_3$ (123 mg, 0.134 mmol), Xantphos (155 mg, 0.269 mmol) and DIEPA (1.041 g, 8.06 mmol), then the reaction mixture was heated to reflux for overnight. After cooling down to room temperature and removal of volatiles under reduced pressure, the residue was purified by silica gel column (hexane:EA, 10:1) to afford the title compound (880 mg, 76%) as a white solid. MS: 429.0 (M+H$^+$).

Step F: 7-Fluoro-3-((4-methoxybenzyl)thio)naphthalen-1-ol (Intermediate A3)

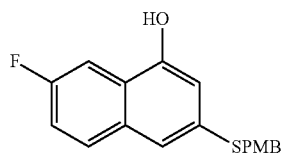

Under Ar, to a solution of tert-butyl((7-fluoro-3-((4-methoxybenzyl)thio)naphthalen-1-yl)oxy)dimethylsilane (Step E, 1.25 g, 2.92 mmol) in dry THF (20 mL) was added TBAF·3H$_2$O (760 mg, 2.91 mmol), the reaction mixture was stirred at room temperature for 30 min. After removal of volatiles under reduced pressure, the residue was treated with water and the resulting mixture was extracted with DCM twice. The combined DCM layer was washed with brine, dried over Na$_2$SO$_4$, and concentrated under reduced pressure to give a yellow oil, which was purified by silica gel column (DCM) to afford the title compound (870 mg, 95%) as a yellow solid. MS: 315(M+H$^+$).

Example 52

Synthesis of Intermediate A4: 6-Chloro-3-((4-methoxybenzyl)thio)naphthalen-1-ol

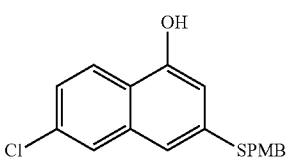

Step A: 2-(3-Chlorophenyl)acetyl chloride

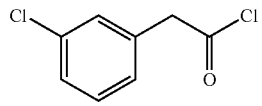 [SMILES: O=C(Cl)Cc1cccc(Cl)c1]

In a 250 mL round flask, 2-(3-chlorophenyl)acetic acid (25.0 g, 147.0 mmol) was dissolved in DCM (100 mL), SOCl$_2$ (34.75 g, 293.0 mmol) was slowly added to the reaction mixture and then the mixture was refluxed for 2 h. After cooling down to room temperature and removal of volatiles under reduced pressure, the residue was directly used for the next step without purification.

Step B: Ethyl 4-(3-chlorophenyl)-3-oxobutanoate

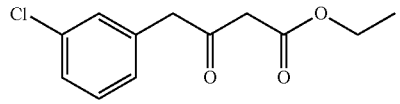 [SMILES: CCOC(=O)CC(=O)Cc1cccc(Cl)c1]

In a dried 250 mL three-necked round-bottomed flask, 2,2-dimethyl-1,3-dioxane-4,6-dione (22.1 g, 153 mmol) and DIEPA (37.7 g, 292 mmol) were dissolved into DCM (150 mL), then the mixture was cooled down to 0° C., 2-(4-chlorophenyl) acetyl chloride (Step A, 27.6 g, 146.8 mmol) was dropwise added into the mixture over 1.5 h. The reaction mixture was stirred for 1 h at 0° C., then allowed to warm up to room temperature for overnight. The reaction was quenched with water and acidified with 0.1N HCl to adjust pH=3, the organic layer was separated, and the aqueous layer was extracted with DCM twice. The combined DCM layer was dried Na$_2$SO$_4$, and concentrated to give a yellow solid, which was re-taken into EtOH. The resulting mixture was then heated to 90° C. for overnight. After removal of volatiles under reduced pressure, the residue was purified by silica gel column (hexane:EA, 9:1) to afford the title compound (13.5 g, 38% over 2 steps) as a white solid. MS: 241.3 (M+H$^+$).

Step C: 6-Chloronaphthalene-1,3-diol

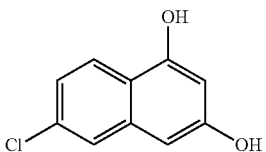 [SMILES: Oc1cc(O)c2ccc(Cl)cc2c1]

Ethyl 4-(3-chlorophenyl)-3-oxobutanoate (Step B, 18.0 g, 74.8 mmol) was added into concentrated sulfuric acid (72.0 g, 734.6 mmol) with small portions at 0° C. After addition, the mixture was stirred for overnight at room temperature. The mixture was poured onto ice, and the resulting mixture was extracted with DCM twice, the organic layer was combined, washed with brine, dried over Na$_2$SO$_4$, and concentrated under reduce pressure to afford a yellow oil, which was purified by silica gel column (hexane:EA, 1:1→1:9) to afford the title compound (10.0 g, 69%) as an off-white solid. $^1$H NMR (400 MHz, CD$_3$OD) δ 8.01 (d, J=8.9 Hz, 1H), 7.53 (d, J=2.0 Hz, 1H), 7.12 (dd, J=8.9, 2.1 Hz, 1H), 6.57 (d, J=2.1 Hz, 1H), 6.48 (d, J=2.1 Hz, 1H). MS: 195.0 (M+H$^+$).

Step D: 4-((tert-Butyldimethylsilyl)oxy)-7-chloronaphthalen-2-ol

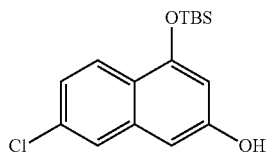 [SMILES: CC(C)(C)[Si](C)(C)Oc1cc(O)cc2cc(Cl)ccc12]

Under Ar, to a solution of 6-chloronaphthalene-1,3-diol (Step C, 2 g, 10.3 mmol) and imidazole (0.84 g, 12.3 mmol) in dry DCM (20 mL) was added TBSCl (1.55 g, 10.3 mmol) at 0° C., then the reaction mixture was stirred for 1 h at 0° C. The resulting mixture was diluted with DCM (20 mL), washed with brine, dried over Na$_2$SO$_4$ and concentrated under reduced pressure to give a yellow oil, which was purified by silica gel column (hexane:EA, 20:1) to afford the title compound (0.65 g, 21%) as a yellow oil. MS: 309.15 (M+H$^+$).

Step E: 4-((tert-Butyldimethylsilyl)oxy)-7-chloronaphthalen-2-yl trifluoromethanesulfonate

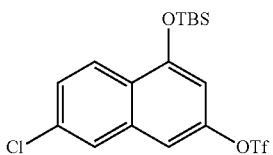 [SMILES: CC(C)(C)[Si](C)(C)Oc1cc(OS(=O)(=O)C(F)(F)F)cc2cc(Cl)ccc12]

Under Ar, to a solution of 4-((tert-butyldimethylsilyl)oxy)-7-chloronaphthalen-2-ol (Step D, 650 mg, 2.1 mmol) and Et$_3$N (319 mg, 3.16 mmol) in dry DCM (10 mL) was added Tf$_2$O (712 mg, 2.53 mmol) at 0° C., then the reaction mixture was stirred for 1 h at 0° C. the mixture was diluted with DCM, washed with brine, dried over Na$_2$SO$_4$ and concentrated under reduced pressure to give a yellow oil, which was purified by silica gel column (hexane) to afford the title compound (650 mg, 70%) as a yellow oil. MS: 439.1 (M−H$^-$).

Step F: tert-Butyl((6-chloro-3-((4-methoxybenzyl)thio)naphthalen-1-yl)oxy)dimethylsilane

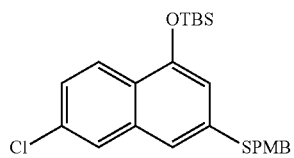

Under Ar, to a mixture of 4-((tert-butyldimethylsilyl)oxy)-7-chloronaphthalen-2-yl trifluoromethanesulfonate (Step E, 650 mg, 1.47 mmol), 4-methoxybenzenethiol (248 mg, 1.77 mmol), Pd$_2$dba$_3$ (67.5 mg, 0.074 mmol) and Xantphos (85 mg, 0.15 mmol) was added dry dioxane (5 mL) and DIEPA (572 mg, 4.42 mmol), then the reaction mixture was stirred at 100° C. for 16 h. After cooling down to room temperature and removal of volatiles under reduced pressure, the residue was diluted with DCM, washed with brine, dried over Na$_2$SO$_4$ and concentrated under reduced pressure to give a yellow oil, which was purified by silica gel column (hexane:EA, 20:1) to afford the title compound (550 mg, 84%) as a light yellow solid. MS: 445.2 (M+H$^+$).

Step G: 6-Chloro-3-((4-methoxybenzyl)thio)naphthalen-1-ol (Intermediate A4)

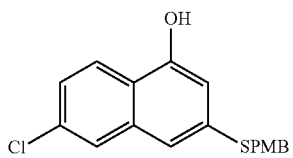

Under Ar, to a solution of tert-butyl((6-chloro-3-((4-methoxybenzyl)thio)naphthalen-1-yl)oxy)dimethylsilane (Step F, 550 mg, 1.24 mmol) in dry THF (10 mL) was added TBAF (5 mL, 5 mmol, 1.0 M in THF), then the reaction mixture was stirred at room temperature for 16 h. Water was added to quench the reaction and the resulting mixture was extracted with EA twice, the organic layer was combined, washed with brine, dried over Na$_2$SO$_4$, and concentrated under reduce pressure to give the crude title compound (440 mg) as a brown solid. MS: 331.0 (M+H$^+$).

Example 53

Synthesis of Intermediate A5: 7-Chloro-3-((4-methoxybenzyl)thio)naphthalen-1-ol

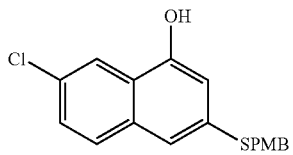

Step A: 2-(4-Chlorophenyl)acetyl chloride

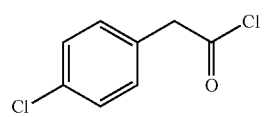 [SMILES: O=C(Cl)Cc1ccc(Cl)cc1]

In a 250 mL round flask, 2-(4-chlorophenyl)acetic acid (25.0 g, 147.0 mmol) was dissolved in DCM (100 mL), SOCl$_2$ (139.0 g, 1172 mmol) was dropwise added into the mixture and the reaction was heated to reflux for 2 h. After cooling down to room temperature and removal of volatiles under reduced pressure, the residue was directly used for the next step without purification.

Step B: Ethyl 4-(4-chlorophenyl)-3-oxobutanoate

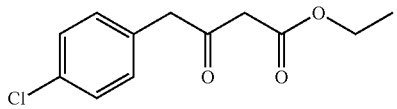 [SMILES: CCOC(=O)CC(=O)Cc1ccc(Cl)cc1]

In a dried 250 mL three-necked round-bottomed flask, 2,2-dimethyl-1,3-dioxane-4,6-dione (12.0 g, 83 mmol) and DIEPA (20.5 g, 159 mmol) were dissolved in DCM (100 mL), then the mixture was cooled down to 0° C., 2-(4-chloro-phenyl) acetyl chloride (Step A, 15.0 g, 79 mmol) was dropwise added into the reaction mixture over 1 h. The reaction mixture was stirred for 1 h at 0° C., then allowed to warm up to room temperature for overnight. The reaction was quenched with water and acidified with 0.1N HCl to adjust pH=3. The organic layer was separated, the aqueous layer was extracted with DCM twice. The combined DCM layer was dried over $Na_2SO_4$, and concentrated under reduced pressure to afford a yellow solid, which was re-taken into EtOH. The resulting mixture was then heated to 90° C. for overnight. After removal of volatiles under reduced pressure, the mixture was purified by silica gel column (hexane:EA, 9:1) to afford the title compound (8.5 g, 44% over 2 steps) as a white solid. $^1$H NMR (400 MHz, $CDCl_3$) δ 7.34 (d, 2H), 7.16 (d, J=8.3 Hz, 2H), 4.20 (q, J=7.1, 3.0 Hz, 2H), 3.84 (s, 2H), 3.48 (s, 2H), 1.29 (t, J=7.1 Hz, 3H). MS: 241.3 (M+H$^+$).

Step C: 7-Chloronaphthalene-1,3-diol

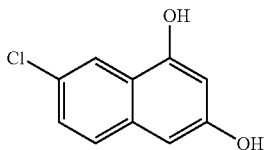 [SMILES: Oc1cc(O)c2cc(Cl)ccc2c1]

Ethyl 4-(4-chlorophenyl)-3-oxobutanoate (Step B, 10.0 g, 41.5 mmol) was added into concentrated sulfuric acid (32.6 g, 332 mmol) with small portions at 0° C. After addition, the mixture was stirred for overnight at room temperature. The mixture was poured onto ice, and the resulting mixture was extracted with DCM twice, the organic layer was combined, washed with brine, dried over $Na_2SO_4$, and concentrated under reduce pressure to afford a yellow oil, which was purified by silica gel column (hexane:EA, 1:1→1:9) to afford the title compound (1.8 g, 22%) as an off-white solid. $^1$H NMR (400 MHz, $CD_3OD$) δ 7.99 (s, 1H), 7.53 (d, J=8.8 Hz, 1H), 7.28 (d, J=8.8, 1.6 Hz, 1H), 6.64 (s, 1H), 6.52 (s, 1H). MS: 195.0 (M+H$^+$).

Step D: 4-((tert-Butyldimethylsilyl)oxy)-6-chloronaphthalen-2-ol

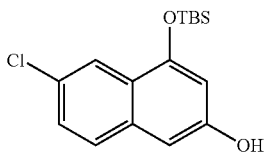 [SMILES: CC(C)(C)[Si](C)(C)Oc1cc(O)cc2ccc(Cl)cc12]

Under Ar, to a solution of 7-chloronaphthalene-1,3-diol (Step C, 480 mg, 2.47 mmol) in dry DCM (10 mL) was added imidazole (403 mg, 5.92 mmol) at 0° C., followed by TBSCl (353 mg, 2.34 mmol). The reaction mixture was allowed to warm up to room temperature and stirred for 3 h. Water was added to quench the reaction, and the resulting mixture was extracted with DCM twice. The combined DCM layer was washed with brine, dried over $Na_2SO_4$, and concentrated under reduced pressure to give a yellow oil, which was purified by silica gel column (hexane:EtOAc, 10:1) to afford the title compound (300 mg, 40%) as a yellow oil. MS: 309.1 (M+H$^+$).

Step E: 4-((tert-Butyldimethylsilyl)oxy)-6-chloronaphthalen-2-yl trifluoromethanesulfonate

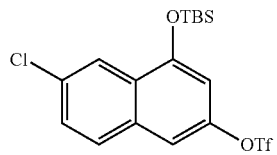 [SMILES: CC(C)(C)[Si](C)(C)Oc1cc(OS(=O)(=O)C(F)(F)F)cc2ccc(Cl)cc12]

Under Ar, to a solution of 4-((tert-butyldimethylsilyl)oxy) naphthalen-2-ol (Step D, 300 mg, 0.97 mmol) in dry DCM (10 mL) was added DIEPA (188 mg, 1.46 mmol) at 0° C., followed by Tf$_2$O (274 mg, 0.97 mmol), the reaction mixture was stirred at 0° C. for 0.5 h. Water was added to quench the reaction, and the resulting mixture was extracted with DCM twice. The combined DCM layer was dried over $Na_2SO_4$, and concentrated under reduced pressure to give a brown oil, which was purified by silica gel column (hexane:EtOAc, 10:1) to afford the title compound (428 mg, quantitatively) as a colorless oil. MS: 439.1 (M−H$^-$).

Step F: tert-Butyl((7-chloro-3-((4-methoxybenzyl)thio)naphthalen-1-yl)oxy)dimethylsilane

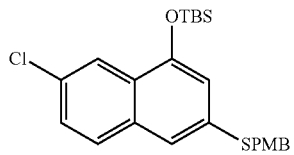

Under Ar, to a solution of 4-((tert-butyldimethylsilyl)oxy) naphthalen-2-yl trifluoromethanesulfonate (Step E, 428 mg, 0.97 mmol) and (4-methoxyphenyl)methanethiol (195 mg, 1.26 mmol) in dry dioxane (12 mL) was added Pd$_2$(dba)$_3$ (89 mg, 0.10 mmol), Xantphos (112 mg, 0.20 mmol) and DIEPA (376 mg, 2.91 mmol), the reaction mixture was heated to reflux for 17 h. After removal of volatiles under reduced pressure, the residue was purified by silica gel column (hexane:EtOAc, 10:1) to afford the title compound (390 mg, 90%) as a white solid. MS: 445.2 (M+H$^+$).

Step G: 7-Chloro-3-((4-methoxybenzyl)thio)naphthalen-1-ol (Intermediate A5)

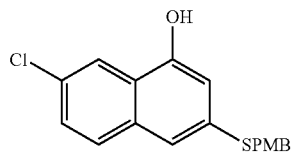

Under Ar, to a solution of tert-butyl((3-((4-methoxybenzyl)thio)naphthalen-1-yl)oxy)dimethylsilane (Step F, 390 mg, 0.88 mmol) in dry THF (10 mL) was added TBAF·3H$_2$O (229 mg, 0.88 mmol), the reaction mixture was stirred at room temperature for 1 h. After removal of volatiles under reduced pressure, the residue was purified by silica gel column (DCM:MeOH, 20:1) to afford the title compound (250 mg, 86%) as a white solid. MS: 331.1 (M+H$^+$).

Example 54

Synthesis of Intermediate A6: 3-((4-Methoxybenzyl)thio)-5-(trifluoromethyl)phenol

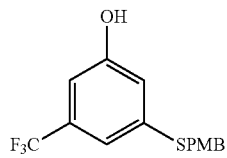

Step A: (3-Bromo-5-(trifluoromethyl)phenoxy)(tert-butyl)dimethylsilane

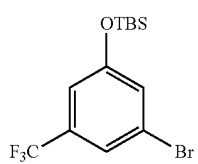

Under Ar, to a solution of 3-bromo-5-(trifluoromethyl)phenol (4.0 g, 16.6 mmol) and Et$_3$N (2.52 g, 24.9 mmol) in dry DCM (20 mL) was added TBSCl (3.00 g, 19.92 mmol), and then the reaction was stirred at room temperature for 5 h. Water (30 mL) was added to the reaction mixture followed by extraction with DCM 3 times. The combined organic layer was dried over Na$_2$SO$_4$, and concentrated under reduced pressure to give a yellow oil, which was purified by silica gel column (hexane) to afford the title compound (5.5 g, 93%) as a colorless oil. $^1$H NMR (500 MHz, CDCl$_3$) δ 7.36 (s, 1H), 7.15 (s, 1H), 6.99 (s, 1H), 0.99 (s, 9H), 0.23 (s, 6H).

Step B: tert-Butyl(3-((4-methoxybenzyl)thio)-5-(trifluoromethyl)phenoxy) dimethylsilane

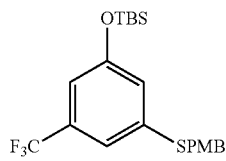

Under Ar, to a mixture of (3-bromo-5-(trifluoromethyl)phenoxy)(tert-butyl)dimethylsilane (Step A, 0.5 g, 1.41 mmol), (4-methoxyphenyl)methanethiol (0.26 g, 1.69 mmol), Pd$_2$dba$_3$ (0.064 g, 0.070 mmol) and Xantphos (0.081 g, 0.14 mmol) was added dry dioxane (6 mL) and DIEPA (0.546 g, 4.22 mmol), then the reaction mixture was stirred at 110° C. for 16 h After cooling down to room temperature and removal of volatiles under reduced pressure, the residue was purified by silica gel column (hexane) to afford the title compound (500 mg, 83%) as a white solid. $^1$H NMR (500 MHz, CDCl$_3$) δ 7.22 (d, J=8.6 Hz, 2H), 7.12 (s, 1H), 6.84 (t, J=11.6 Hz, 4H), 4.09 (s, 2H), 3.79 (s, 3H), 0.96 (s, 9H), 0.22-0.07 (m, 6H).

Step C: 3-((4-Methoxybenzyl)thio)-5-(trifluoromethyl)phenol (Intermediate A6)

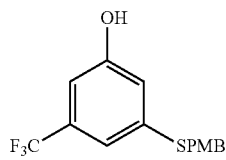

Under Ar, to a solution of tert-butyl(3-((4-methoxybenzyl)thio)-5-(trifluoromethyl)phenoxy)dimethylsilane (Step B, 500 mg, 1.17 mmol) in dry THF (6 mL) was added TBAF·3H$_2$O (0.31 g, 1.17 mmol) at room temperature, then the reaction was stirred at room temperature for 30 min. After removal of volatiles under reduced pressure, the residue was diluted with DCM, washed with brine, dried over Na$_2$SO$_4$ and concentrated under reduced pressure to give a yellow oil, which was purified by silica gel column (hexane:EA, 2:1) to afford the title compound (360 mg, 98%) as a white solid. MS: 314.3 (M+H$^+$).

Example 55

Synthesis of Intermediate A7: 3-Chloro-5-((4-methoxybenzyl)thio)-4-methylphenol

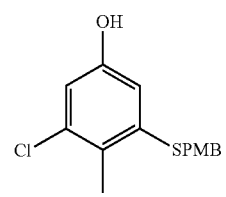

Step A: (3-Bromo-5-chloro-4-methylphenoxy) tert-butyl)dimethylsilane

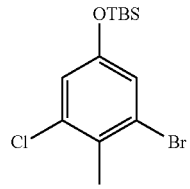 [SMILES: Cc1c(Cl)cc(O[Si](C)(C)C(C)(C)C)cc1Br]

Under Ar, to a solution of 3-bromo-5-chloro-2-methylphenol (1.6 g, 7.22 mmol) in dry DCM (15 mL) was added Et₃N (1.1 g, 10.84 mmol) at 0° C., followed by TBSCl (1.31 g, 8.67 mmol). The reaction mixture was allowed to warm up to room temperature and stirred for 5 h. Water was added to quench the reaction, and the resulting mixture was extracted with DCM twice. The combined DCM layer was washed with brine, dried over Na₂SO₄, and concentrated under reduced pressure to give a yellow oil, which was purified by silica gel column (hexane) to afford the title compound (2.0 g, 82%) as a colorless oil.

Step B: tert-Butyl(3-chloro-5-((4-methoxybenzyl)thio)-4-methylphenoxy) dimethylsilane

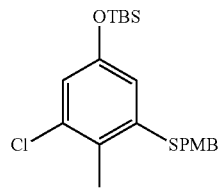

Under Ar, to a solution of (3-bromo-5-chloro-4-methylphenoxy)(tert-butyl)dimethylsilane (Step A, 1.0 g, 2.99 mmol) and (4-methoxyphenyl)methanethiol (553 mg, 3.59 mmol) in dry dioxane (15 mL) was added Pd₂(dba)₃ (137 mg, 0.15 mmol), Xantphos (173 mg, 0.3 mmol) and DIPEA (1.16 g, 9.0 mmol), the reaction mixture was heated to reflux for overnight. After cooling down to room temperature and removal of volatiles under reduced pressure, the residue was purified by silica gel column (hexane) to afford the title compound (1.2 g, 98%) as a white solid. MS: 407.2 (M−H⁻).

Step C: 3-Chloro-5-((4-methoxybenzyl)thio)-4-methylphenol (Intermediate A7)

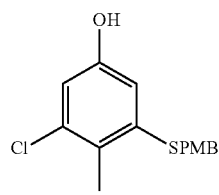

Under Ar, to a solution of tert-butyl(3-chloro-5-((4-methoxybenzyl)thio)-4-methylphenoxy)dimethylsilane (Step B, 1.2 g, 2.93 mmol) in dry THF (10 mL) was added TBAF (2.93 mL, 2.93 mmol, 1.0 M in THF), the reaction mixture was stirred at room temperature for 0.5 h. Brine was added to quench the reaction, and the resulting mixture was extracted with ethyl acetate twice. The combined organic layer was dried over Na₂SO₄, and concentrated under reduced pressure to give a colorless oil, which was purified by silica gel column (DCM) to afford the title compound (700 mg, 81%) as a colorless oil.

Example 56

Synthesis of Intermediate B: Ethyl 7-bromo-3-(3-bromopropyl)-6-chloro-1H-indole-2-carboxylate

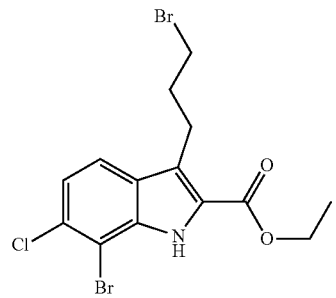 [SMILES: CCOC(=O)c1[nH]c2c(Br)c(Cl)ccc2c1CCCBr]

Step A: (E)-5-((2-bromo-3-chlorophenyl)diazenyl)-6-methoxy-6-oxohexanoic acid

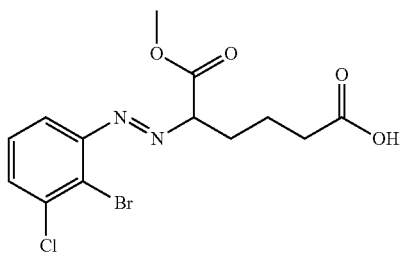 [SMILES: COC(=O)C(CCCC(=O)O)/N=N/c1cccc(Cl)c1Br]

To a solution of 2-bromo-3-chloroaniline (25 g, 121 mmol) in AcOH (80 mL) was added into a mixed solution of conc. HCl/H₂O (30 mL/900 mL), a solution of sodium nitrite (8.35 g, 121 mmol) in H₂O (150 mL) was added slowly at 0° C., the resulting mixture was stirred for 20 min at 0° C., then a solution of sodium acetate (55.6 g, 678 mmol) in H₂O (150 mL) was added to the reaction, followed by methyl 2-oxocyclopentane-1-carboxylate (17.21 g, 121 mmol). The reaction mixture was stirred for 30 min at 0° C., and filtrated off to generate a yellow solid, which was collected and retaken with DCM; the organic solution was washed with brine, dried over Na₂SO₄, and concentrated under reduced pressure to afford a yellow solid, which was directly used without purification.

Step B: Ethyl 7-bromo-6-chloro-3-(3-ethoxy-3-oxopropyl)-1H-indole-2-carboxylate

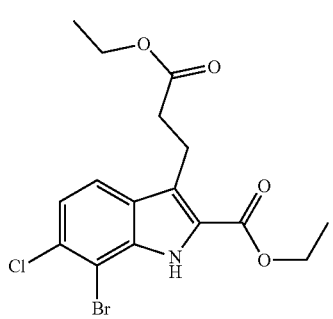 [SMILES: CCOC(=O)CCc1c(C(=O)OCC)[nH]c2c(Br)c(Cl)ccc12]

To a solution of crude (E)-5-((2-bromo-3-chlorophenyl)diazenyl)-6-methoxy-6-oxohexanoic acid (Step A, 15.84 g, 41.9 mmol) in EtOH was added concentrated sulfuric acid (32.9 g, 336 mmol) slowly. The reaction mixture was heated to 100° C. for overnight. After cooling down to room temperature, the mixture was poured onto ice and extracted with DCM 3 times. The organic layer was combined, washed with brine, dried over Na$_2$SO$_4$. and concentrated under reduced pressure to give a dark yellow solid, which was purified by silica gel column (hexane:EA, 1:2) to afford the title compound (12.3 g, 73% over 2 steps) as a yellow solid. MS: 404.6 (M+H$^+$).

Step C: Ethyl 7-bromo-6-chloro-3-(3-hydroxypropyl)-1H-indole-2-carboxylate

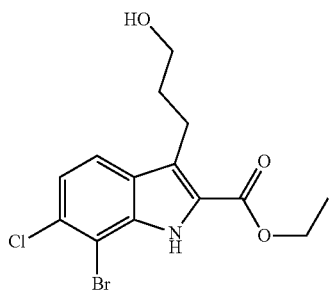 [SMILES: CCOC(=O)c1[nH]c2c(Br)c(Cl)ccc2c1CCCBr]

Under Ar, to a solution of ethyl 7-bromo-6-chloro-3-(3-ethoxy-3-oxopropyl)-1H-indole-2-carboxylate (Step B, 17.4 g, 43.1 mmol) in dry THF was added BH$_3$·THF (5.56 g, 64.7 mmol) slowly at 0° C. The reaction mixture was allowed to warm up to room temperature and stirred for overnight. MeOH (20 mL) was slowly added to quench the reaction and the resulting mixture was stirred for 0.5 h. Water was added to the mixture, and the resulting mixture was extracted with EA 3 times, the organic layer was combined, washed with brine, dried over Na$_2$SO$_4$, and concentrated under reduced pressure to give a light yellow oil, which was retaken into a mixed solution of hexane and EA (v/v, 1:1, 150 mL), the formed solid was collected by filtration to afford the title compound (14.2 g, 91%) as white solid. $^1$H NMR (500 MHz, DMSO-d$_6$) δ 11.46 (s, 1H), 7.73 (d, J=8.5 Hz, 1H), 7.29 (d, J=8.5 Hz, 1H), 4.47 (t, J=5.2 Hz, 1H), 4.35 (q, J=7.1 Hz, 2H), 3.41 (dd, J=11.8, 6.4 Hz, 2H), 3.06-2.98 (m, 2H), 1.76-1.68 (m, 2H), 1.36 (t, J=7.1 Hz, 3H). MS: 362.0 (M+H$^+$).

Step D: Ethyl 7-bromo-3-(3-bromopropyl)-6-chloro-1H-indole-2-carboxylate (Intermediate B)

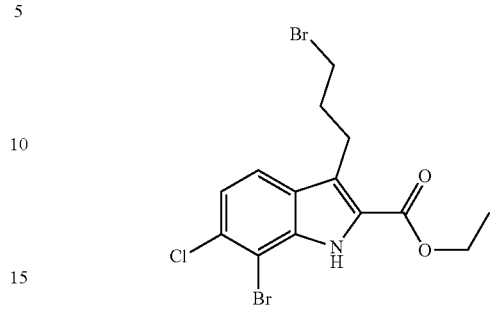

Under Ar, to a solution of ethyl 7-bromo-6-chloro-3-(3-hydroxypropyl)-1H-indole-2-carboxylate (Step C, 10.0 g, 27.7 mmol) in dry DCM was added Ph$_3$P (8.73 g, 33.3 mmol), dropwise followed by a solution of CBr$_4$ (11.0 g, 33.3 mmol) in dry DCM (30 mL) at 0° C.; the reaction mixture was stirred for overnight at room temperature and quenched with water, the resulting mixture was extracted with DCM three times, the organic layer was combined, washed with brine, dried over Na$_2$SO$_4$, and concentrated under reduced pressure to give a yellow oil, which was purified by silica gel column (hexane:EA, 1:2) to afford the title compound (10.1 g, 86%) as a white solid. $^1$H NMR (500 MHz, DMSO-d$_6$) δ 11.52 (s, 1H), 7.76 (d, J=8.5 Hz, 1H), 7.30 (d, J=8.5 Hz, 1H), 4.37 (q, J=7.1 Hz, 2H), 3.53 (t, J=6.6 Hz, 2H), 3.14 (t, J=7.4 Hz, 2H), 2.24-2.02 (m, 2H), 1.37 (t, J=7.1 Hz, 3H).

Example 57

Synthesis of Intermediate C1: 2-(((Tetrahydro-2H-pyran-2-yl)oxy)methyl)-3-(4,4,5,5-tetramethyl-1,3,2-dioxaborolan-2-yl)-5,6-dihydro-4H-pyrrolo[1,2-b]pyrazole

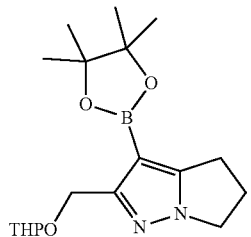

Step A: Nitrosoproline

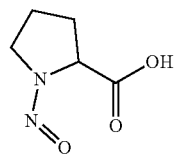

To a solution of L-proline (50 g, 434 mmol) in water (50 mL) was added conc. HCl (40 mL), a solution of sodium nitrite (47.9 g, 695 mmol) in water (50 mL) was slowly added at 0° C. The reaction mixture was stirred for 1 h and extracted with DCM 10 times, the organic layer was combined, dried over $Na_2SO_4$, and concentrated under reduced pressure to give the crude title compound as a white solid (57.7 g, 92%), which was directly use without purification. MS: 144.9 (M+H$^+$).

Step B: 3-Oxo-5,6-dihydro-3H-pyrrolo[1,2-c][1,2,3]oxadiazol-7(4H)-ium-3a-ide

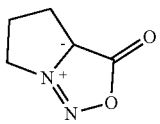

To a solution of nitroso-L-proline (Step A, 57.7 g, 401 mmol) in DCM was added TFAA (84 g, 401 mmol) slowly at 5° C., and the reaction mixture was stirred for 0.5 h. After removal of volatiles under reduced pressure, the crude title compound as a brown solid was collected and directly used without purification (50.5 g, quantitatively). $^1$H NMR (500 MHz, CDCl$_3$) δ 4.47 (t, J=7.7 Hz, 2H), 2.99-2.92 (m, 2H), 2.85-2.76 (m, 2H). MS: 127.0 (M+H$^+$).

Step C: Methyl 5,6-dihydro-4H-pyrrolo[1,2-b]pyrazole-2-carboxylate

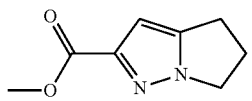

3-oxo-5,6-dihydro-3H-pyrrolo[1,2-c][1,2,3]oxadiazol-7(4H)-ium-3a-ide (Step B, 21 g, 167 mmol) was added into 1,2-diethoxyethylene, and methyl propiolate (42.0 g, 500 mmol) was followed. The reaction mixture was heated to 130° C. for overnight. After cooling down to room temperature and removal of volatiles under reduced pressure, the residue was purified by silica gel column (hexane:EA, 5:1) to afford the title compound (6.6 g, 24%) as a white solid. $^1$H NMR (500 MHz, DMSO-d$_6$) δ 6.48 (s, 1H), 4.12 (t, J=7.3 Hz, 2H), 3.76 (s, 3H), 2.85 (t, J=7.4 Hz, 2H), 2.18-2.09 (m, 2H). MS: 166.9 (M+H$^+$).

Step D: (5,6-Dihydro-4H-pyrrolo[1,2-b]pyrazol-2-yl)methanol

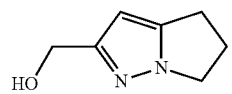

Under Ar, to a mixture of methyl 5,6-dihydro-4H-pyrrolo[1,2-b]pyrazole-2-carboxylate (Step C, 4.5 g, 27.1 mmol) in dry THF (100 mL) was added LiAlH$_4$ (1.23 g, 32.5 mmol) with small portions at 0° C. The reaction mixture was stirred at 0° C. for 2 h and quenched with cold water (4.5 mL), followed by aq. NaOH (15%, 4.5 mL) and water (13.5 mL). The resulting mixture was further stirred for 40 min at room temperature. After filtration through celite, the filtrate was concentrated under reduced pressure to afford the crude title compound as a colorless oil, which was directly used for without purification. MS: 139.0 (M+H$^+$).

Step E: (3-Iodo-5,6-dihydro-4H-pyrrolo[1,2-b]pyrazol-2-yl)methanol

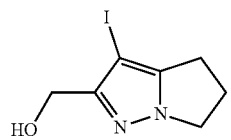 [SMILES: OCc1nn2c(c1I)CCC2]

Under Ar, to a mixture of (5,6-dihydro-4H-pyrrolo[1,2-b]pyrazol-2-yl)methanol (Step D, 3.0 g, 21.71 mmol) in dry acetonitrile (80 mL) was added NIS (5.37 g, 23.88 mmol) slowly at 0° C., then the reaction mixture was stirred for 1 h at room temperature. Water was added into the mixture, and the resulting mixture was extracted with EA 3 times, the organic layer was combined, washed with brine, dried over $Na_2SO_4$, concentrated under reduced pressure to afford the crude title compound (4.1 g, 63% over 2 steps) as a white solid, which was directly used without purification. $^1$H NMR (500 MHz, DMSO-d$_6$) δ 4.84 (t, J=5.4 Hz, 1H), 4.21 (d, J=5.5 Hz, 2H), 4.04 (t, J=7.2 Hz, 2H), 2.67 (t, J=7.3 Hz, 2H), 2.49-2.40 (m, 2H). MS: 265.1 (M+H$^+$).

Step F: 3-Iodo-2-(((tetrahydro-2H-pyran-2-yl)oxy)methyl)-5,6-dihydro-4H-pyrrolo[1,2-b]pyrazole

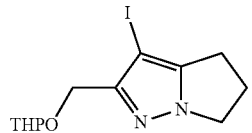

Under Ar, to a solution of (3-iodo-5,6-dihydro-4H-pyrrolo[1,2-b]pyrazol-2-yl)methanol (Step E, 4.1 g, 15.5 mmol) in dry THF (20 mL) was added DHP (1.96 g, 23.29 mmol) and TsOH·H$_2$O (0.30 g, 1.55 mmol), and the reaction mixture was stirred at 40° C. for 4 h. After concentrated under reduced pressure, the residue was purified by silica gel column (hexane:EA, 2:1→1:2) to afford the title compound (4.3 g, 80%) as a colorless oil. MS: 349.1 (M+H$^+$).

Step G: 2-(((Tetrahydro-2H-pyran-2-yl)oxy)methyl)-3-(4,4,5,5-tetramethyl-1,3,2-dioxaborolan-2-yl)-5,6-dihydro-4H-pyrrolo[1,2-b]pyrazole (Intermediate C1)

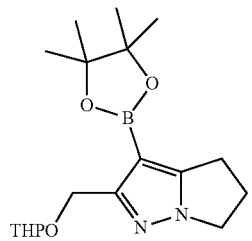

Under Ar, to a mixture of 3-iodo-2-(((tetrahydro-2H-pyran-2-yl)oxy)methyl)-5,6-dihydro-4H-pyrrolo[1,2-b]pyrazole (Step F, 2.0 g, 5.74 mmol) in dry THF (20 mL) was added i-PrMgBr (1.69 g, 11.47 mmol) at 0° C., then the reaction mixture was stirred at 0° C. for 30 min, 2-isopropoxy-4,4,5,5-tetramethyl-1,3,2-dioxaborolane (3.21 g, 17.23 mmol) was followed, and the reaction mixture was further stirred for 2 h at room temperature. The reaction was quenched with aqueous NH$_4$Cl, extracted with EA 3 times. The organic layer was combined, washed with brine, dried over Na$_2$SO$_4$, and concentrated under reduced pressure to give a yellow oil, which was purified by silica gel column (hexane:EA, 4:1→1:2) to afford the title compound (2.3 g, 98%) as a colorless oil. MS: 349.4 (M+H$^+$).

Example 58

Synthesis of Intermediate C2: 6-(((Tetrahydro-2H-pyran-2-yl)oxy)methyl)-7-(4,4,5,5-tetramethyl-1,3,2-dioxaborolan-2-yl)-2,3-dihydropyrazolo[5,1-b]oxazole

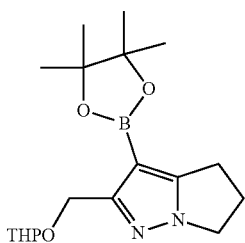

Step A: Methyl 2,3-dihydropyrazolo[5,1-b]oxazole-6-carboxylate

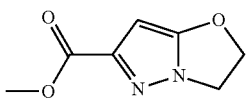

Under Ar, methyl 5-hydroxy-1H-pyrazole-3-carboxylate (9.5 g, 66.8 mmol), potassium carbonate (37.0 g, 267 mmol), and 1,2-dibromoethane (15.1 g, 80 mmol) were dissolved into dry acetonitrile (500 mL). The reaction mixture was heated to reflux for 36 h. After cooling down to room temperature and removal of volatiles under reduced pressure, the residue was purified by silica gel column (DCM:MeOH, 60:1) to afford the title compound (6.2 g, 55%) as a light yellow solid. $^1$H NMR (500 MHz, CDCl$_3$) δ 5.92 (d, J=2.0 Hz, 1H), 5.15-5.04 (m, 2H), 4.41-4.32 (m, 2H), 3.90 (d, J=1.9 Hz, 3H). MS: 169.0 (M+H$^+$).

Step B: (2,3-Dihydropyrazolo[5,1-b]oxazol-6-yl)methanol

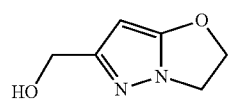

Under Ar, to a solution of methyl 2,3-dihydropyrazolo[5,1-b]oxazole-6-carboxylate (Step A, 6.2 g, 36.9 mmol) in dry THF (80 mL) was added LiAlH$_4$ (2.1 g, 55.3 mmol) at 0° C., and the reaction mixture was stirred for 1 h. The reaction was quenched with water (2 mL) and then 15% NaOH solution (2 mL). After filtration through celite, the filtrate was concentrated under reduced pressure to give the crude title compound (3.8 g, 74%) as a light yellow oil, which was directly used without purification. $^1$H NMR (500 MHz, CDCl$_3$) δ 5.39 (s, 1H), 5.02 (t, J=7.9 Hz, 2H), 4.57 (s, 2H), 4.26 (t, J=7.9 Hz, 2H). MS: 141.1 (M+H$^+$).

Step C: (7-Iodo-2,3-dihydropyrazolo[5,1-b]oxazol-6-yl)methanol

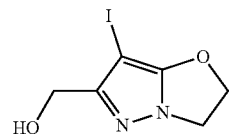 [SMILES: OCc1nn2c(c1I)OCC2]

Under Ar, to a solution of (2,3-dihydropyrazolo[5,1-b]oxazol-6-yl)methanol (Step B, 3.8 g, 27.1 mmol) in dry acetonitrile (50 mL) was added NIS (6.71 g, 29.8 mmol) at 0° C., and the resulting mixture was stirred for 30 min. Brine was added to quench the reaction mixture, and the mixture was extracted with EA 3 times, the organic layer was combined, dried Na$_2$SO$_4$, and concentrated under reduced pressure to give a yellow solid, which was purified by silica gel column (hexane:EA, 1:1) to afford the title compound (4.3 g, 60%) as a light yellow solid. $^1$H NMR (500 MHz, CDCl$_3$) δ 5.09 (t, J=8.0 Hz, 2H), 4.55 (d, J=4.5 Hz, 2H), 4.35 (t, J=8.0 Hz, 2H). MS: 267.3 (M+H$^+$).

Step D: 7-Iodo-6-(((tetrahydro-2H-pyran-2-yl)oxy)methyl)-2,3-dihydropyrazolo[5,1-b]oxazole

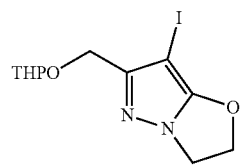

Under Ar, a mixture of (7-iodo-2,3-dihydropyrazolo[5,1-b]oxazol-6-yl)methanol (Step C, 4.3 g, 16.16 mmol), 3,4-dihydro-2H-pyran (2.039 g, 24.24 mmol), and 4-methylbenzenesulfonic acid hydrate (0.307 g, 1.616 mmol) in dry THF (80 mL) was stirred at 45° C. for 3 h. The mixture was concentrated to dryness and the resulting residue was purified by silica gel column (hexane:EA, 5:1) to afford the title compound (2.9 g, 51%) as a yellow oil. MS: 350.9 (M+H$^+$); 373.1 (M+Na$^+$).

Step E: 6-(((Tetrahydro-2H-pyran-2-yl)oxy)methyl)-7-(4,4,5-trimethyl-1,3,2-dioxaborolan-2-yl)-2,3-dihydropyrazolo[5,1-b]oxazole (Intermediate C2)

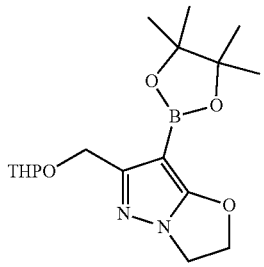

Under Ar, to a solution of 7-iodo-6-(((tetrahydro-2H-pyran-2-yl)oxy)methyl)-2,3-dihydropyrazolo[5,1-b]oxazole (Step D, 1.5 g, 4.28 mmol) in dry THF (50 mL) was added i-PrMgBr (1.89 g, 12.85 mmol) dropwise at 0° C., then the reaction mixture was stirred at 0° C. for 1 h, 2-isopropoxy-4,4,5,5-tetramethyl-1,3,2-dioxaborolane (2.39 g, 12.85 mmol) was added slowly. The reaction mixture was stirred at room temperature for 2 h, and then quenched with aq. NH₄Cl. The resulting mixture was extracted with EA twice, the organic layer was combined, washed with brine, dried over Na₂SO₄, and concentrated under reduced pressure to give a light yellow oil, which was purified by silica gel column (hexane:EA, 10:1→1:9) to afford the title compound as a colorless oil (1.08 g, 72%). MS: 351.1 (M+H$^+$); 373.07 (M+Na$^+$).

Example 59

Synthesis of Intermediate C3: 2-(((Tetrahydro-2H-pyran-2-yl)oxy)methyl)-3-(4,4,5,5-tetramethyl-1,3,2-dioxaborolan-2-yl)-4,5,6,7-tetrahydropyrazolo[1,5-a]pyridine

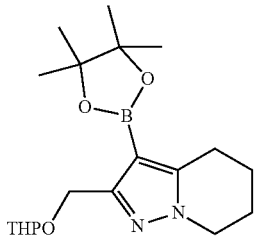

Step A: 1-Nitrosopiperidine-2-carboxylic acid

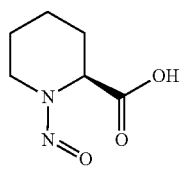 [SMILES: O=NN1CCCC[C@H]1C(=O)O]

To a solution of (S)-piperidine-2-carboxylic acid (10 g, 77 mmol) in water (50 mL) was added conc. HCl (7 mL), and a solution of sodium nitrite (5.34 g, 77 mmol) in water (10 mL) at 0° C. The reaction mixture was stirred for 1 h and then extracted with DCM 10 times, the organic layer was combined, dried over Na₂SO₄, and concentrated under reduced pressure to give the title compound (8.65 g, 71%) as a white solid, which was directly used without purification. MS: 159.0 (M+H$^+$).

Step B: 3-Oxo-4,5,6,7-tetrahydro-[1,2,3]oxadiazolo[3,4-a]pyridin-8(3H)-ium-3a-ide

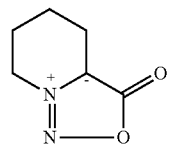

To a solution of (S)-1-nitrosopiperidine-2-carboxylic acid (Step A, 8.65 g, 54.7 mmol) in DCM was added TFAA (11.49 g, 54.7 mmol) slowly at 5° C., the reaction mixture was stirred for 30 min. After removal of volatiles under reduced pressure, the crude title compound as a brown solid was collected and directly used without purification. MS: 141.1 (M+H$^+$).

Step C: Methyl 4,5,6,7-tetrahydropyrazolo[1,5-a]pyridine-2-carboxylate

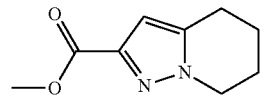

To a solution of 3-oxo-4,5,6,7-tetrahydro-[1,2,3]oxadiazolo[3,4-a]pyridin-8(3H)-ium-3a-ide (Step B, 8.7 g, 62.1 mmol) in xylene (200 mL) was added methyl propiolate (7.83 g, 93 mmol). The reaction mixture was heated to 125° C. for 3 h, then the second portion of methyl propiolate (13 mL) was added and the reaction mixture was heated to 125° C. for 7 h. After cooling down to room temperature and removal of volatiles under reduced pressure, the residue was purified by silica gel column to afford the title compound (11.0 g, 98% over 2 steps) as a white solid. MS: 181.0 (M+H$^+$) Step D: (4,5,6,7-Tetrahydropyrazolo[1,5-a]pyridin-2-yl)methanol

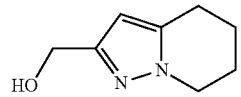

Under Ar, to a mixture of methyl 4,5,6,7-tetrahydropyrazolo[1,5-a]pyridine-2-carboxylate (Step C, 11.0 g, 61.0 mmol) in dry THF (100 mL) was added LiAlH₄ (3.48 g, 92 mmol) with small portions at 0° C. The reaction mixture was stirred at 0° C. for 2 h and quenched with cold water (4.5 mL), followed by aq.NaOH (15%, 4.5 mL) and water (13.5 mL). The resulting mixture was further stirred for 40 min at room temperature. After filtration through celite, the filtrate was concentrated under reduced pressure to afford the crude title compound as a colorless oil, which was directly used without purification. MS: 153.1 (M+H⁺).

Step E: (3-Iodo-4,5,6,7-tetrahydropyrazolo[1,5-a]pyridin-2-yl)methanol

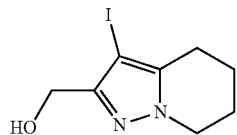 [SMILES: OCc1nn2c(c1I)CCCC2]

Under Ar, to a solution of (4,5,6,7-tetrahydropyrazolo[1,5-a]pyridin-2-yl)methanol (Step D, 8.53 g, 56.0 mmol) in dry acetonitrile (150 mL) was added NIS (12.6 g, 56.0 mmol) slowly at 0° C., then the reaction mixture was stirred at room temperature for 30 min. Water was added and the resulting mixture was extracted with EA 3 times, the organic layer was combined, washed with brine, dried over Na₂SO₄, and concentrated under reduced pressure to give the crude title compound as a brown solid, which was directly used without purification. MS: 279.21 (M+H⁺).

Step F: 3-Iodo-2-(((tetrahydro-2H-pyran-2-yl)oxy)methyl)-4,5,6,7-tetrahydropyrazolo[1,5-a]pyridine

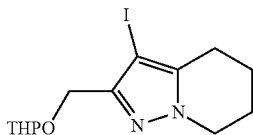

Under Ar, to a solution of the crude (3-iodo-4,5,6,7-tetrahydropyrazolo[1,5-a]pyridin-2-yl)methanol (Step E, 5.6 g) in dry THF (100 mL) was added DHP (3.39 g, 40.3 mmol), and TsOH·H₂O (0.192 g, 1.0 mmol). The reaction mixture was stirred at 40° C. for overnight. After cooling down to room temperature and removal of volatiles under reduced pressure, the residue was purified by silica gel column to afford the title compound (6.3 g, 28% over 3 steps) as a colorless oil. MS: 279.21 (M−THP+H⁺).

Step G: 2-(((Tetrahydro-2H-pyran-2-yl)oxy)methyl)-3-(4,4,5,5-tetramethyl-1,3,2-dioxaborolan-2-yl)-4,5,6,7-tetrahydropyrazolo[1,5-a]pyridine (Intermediate C3)

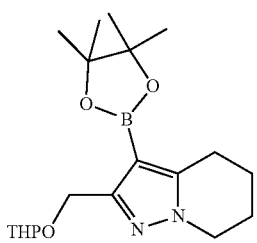

Under Ar, to a solution of 3-iodo-2-(((tetrahydro-2H-pyran-2-yl)oxy)methyl)-4,5,6,7-tetrahydropyrazolo[1,5-a]pyridine (Step F, 3.0 g, 8.28 mmol) in dry THF (30 mL) was added i-PrMgBr (2.44 g, 16.56 mmol) at 0° C., then the reaction mixture was stirred at 0° C. for 30 min, 2-isopropoxy-4,4,5,5-tetramethyl-1,3,2-dioxaborolane (3.08 g, 16.56 mmol) was added. The reaction mixture was further stirred at room temperature for 2 h, quenched with aq. NH₄Cl, and extracted with EA twice. The combined EA layer was washed with brine, dried over Na₂SO₄, and concentrated under reduced pressure to give a light brown oil, which was purified by silica gel column (hexane:EA, 3:1) to afford the title compound (1.8 g, 60%) as a colorless oil. MS: 363.4 (M+H⁺).

Example 60

Synthesis of Intermediate C4: 2-(((Tetrahydro-2H-pyran-2-yl)oxy)methyl)-3-(4,4,5,5-tetramethyl-1,3,2-dioxaborolan-2-yl)-6,7-dihydro-5H-pyrazolo[5,1-b][1,3]oxazine

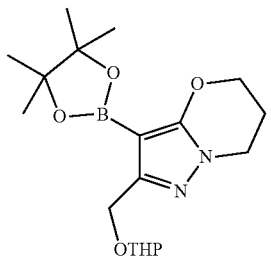

Step A: Ethyl 6,7-dihydro-5H-pyrazolo[5,1-b][1,3]oxazine-2-carboxylate

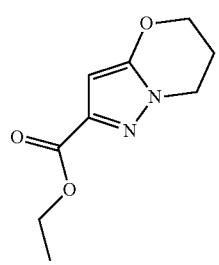

Under Ar, ethyl 3-hydroxy-1H-pyrazole-5-carboxylate (8.7 g, 55.7 mmol) and 1,3-dibromopropane (12.37 g, 61.3 mmol) was dissolved into dry acetonitrile (600 mL) at room temperature and K₂CO₃ (30.8 g, 223 mmol) was followed; the reaction mixture was stirred at 70° C. for 16 h. After cooling down to room temperature and removal of volatiles under reduced pressure, the residue was purified by silica gel column (hexane:EA, 2:3) to afford the title compound (8.52 g, 78%) as a white solid. MS: 197.5 (M+H⁺).

Step B: (6,7-Dihydro-5H-pyrazolo[5,1-b][1,3]oxazin-2-yl)methanol

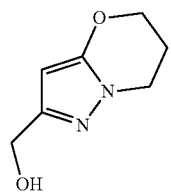 [SMILES: OCc1cc2n(n1)CCCO2]

Under Ar, to a solution of ethyl 6,7-dihydro-5H-pyrazolo[5,1-b][1,3]oxazine-2-carboxylate (Step A, 2.0 g, 10.19 mmol) in dry THF (30 mL) was added LiAlH$_4$ (0.580 g, 15.29 mmol) in portions at 0° C., and the reaction mixture was stirred at 0° C. for 2 h. Water and 15% NaOH were added to quench the reaction. After filtration through celite, the filtrate was concentrated under reduced pressure to give the crude title compound as a white solid, which was directly used without purification.

Step C: (3-Iodo-6,7-dihydro-5H-pyrazolo[5,1-b][1,3]oxazin-2-yl)methanol

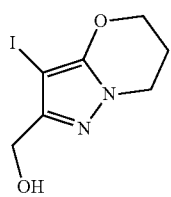 [SMILES: OCc1nn2c(c1I)OCCC2]

Under Ar, to a solution of the crude (6,7-dihydro-5H-pyrazolo[5,1-b][1,3]oxazin-2-yl)methanol (Step B, 1.26 g) in dry acetonitrile (20 mL) was added NIS (1.84 g, 8.17 mmol) in portions over 30 min, and the reaction mixture was stirred at room temperature for 1 h. After removal of volatiles under reduced pressure, the residue was partitioned with water (30 mL) and EA, the aqueous layer was extracted with EA twice. The combined organic layer was dried over Na$_2$SO$_4$, and concentrated under reduced pressure to give the crude title compound as a yellow solid. MS: 281.3 (M+H$^+$).

Step D: 3-Iodo-2-(((tetrahydro-2H-pyran-2-yl)oxy)methyl)-6,7-dihydro-5H-pyrazolo[5,1-b][1,3]oxazine

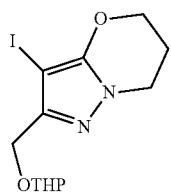

Under Ar, to a solution of the crude (3-iodo-6,7-dihydro-5H-pyrazolo[5,1-b][1,3]oxazin-2-yl)methanol (Step C, 4 g) in dry THF (20 mL) was added DHP (2.403 g, 28.6 mmol) and TsOH·H$_2$O (0.136 g, 0.714 mmol) at room temperature, and the reaction mixture was stirred at 25° C. for 3 h. After removal of volatiles under reduced pressure, the residue was purified by silica gel column (hexane:EA, 7:3) to afford the title compound (5 g, 61% over 3 steps) as a yellow solid. MS: 365.1 (M+H$^+$).

Step E: 2-(((Tetrahydro-2H-pyran-2-yl)oxy)methyl)-3-(4,4,5,5-tetramethyl-1,3,2-dioxaborolan-2-yl)-6,7-dihydro-5H-pyrazolo[5,1-b][1,3]oxazine (Intermediate C4)

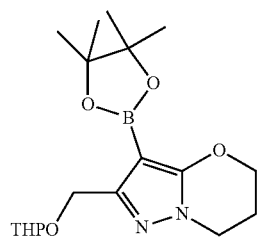

Under Ar, to a solution of 3-iodo-2-(((tetrahydro-2H-pyran-2-yl)oxy)methyl)-6,7-dihydro-5H-pyrazolo[5,1-b][1,3]oxazine (Step D, 1.5 g, 4.12 mmol) in dry THF (20 mL) was added i-PrMgBr (1.22 g, 8.28 mmol) at 0° C., then the reaction mixture was stirred at 0° C. for 30 min; 2-isopropoxy-4,4,5,5-tetramethyl-1,3,2-dioxaborolane (1.53 g, 8.24 mmol) was added, and the reaction mixture was stirred at room temperature for 2 h. The reaction was quenched with aq. NH$_4$Cl and the resulting mixture was extracted with EA twice. The combined EA layer was washed with brine, dried over Na$_2$SO$_4$, and concentrated under reduced pressure to a yellow oil, which was purified by silica gel column (hexane:EA, 3:1) to afford the title compounds (1.3 g, 87%) as a colorless oil. MS: 365.4 (M+H$^+$).

Example 61

Synthesis of Intermediate C5: 2-(((Tetrahydro-2H-pyran-2-yl)oxy)methyl)-3-(4,4,5,5-tetramethyl-1,3,2-dioxaborolan-2-yl)-6,7-dihydro-4H-pyrazolo[5,1-c][1,4]oxazine

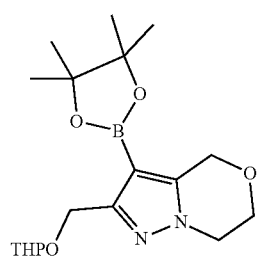

Step A: 4-Nitrosomorpholine-3-carboxylic acid

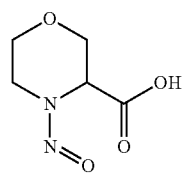 [SMILES: O=NN1CCOCC1C(=O)O]

To a solution of morpholine-3-carboxylic acid (62.6 g, 477 mmol) in H$_2$O (50 mL) was added conc. HCl (70 mL), and a solution of sodium nitrite (52.7 g, 764 mmol) in H$_2$O (80 mL) was followed slowly at 0° C. The reaction mixture was stirred for 1 h, and then extracted with DCM 10 times. The organic layer was combined, dried over Na$_2$SO$_4$, and concentrated under reduced pressure to give the title compound (73.6 g, 96%) as a white solid, which was directly used without purification. MS: 161.1 (M+H$^+$).

Step B: 3-Oxo-6,7-dihydro-3H-[1,2,3]oxadiazolo[4,3-c][1,4]oxazin-8(4H)-ium-3a-ide

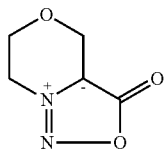

To a solution of 4-nitrosomorpholine-3-carboxylic acid (Step A, 73.6 g, 460 mmol) in DCM was added TFAA (97 g, 460 mmol) slowly at 5° C., and the reaction mixture was stirred for 30 min. After removal of volatiles under reduced pressure, the brown residue was passed through a short silica gel column to afford the title compound (55.0 g, 84%) as a white solid. MS: 163.0 (M+H$^+$)

Step C: Methyl 6,7-dihydro-4H-pyrazolo[5,1-c][1,4]oxazine-2-carboxylate

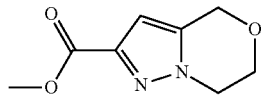

To a solution of 3-oxo-6,7-dihydro-3H-[1,2,3]oxadiazolo[4,3-c][1,4]oxazin-8(4H)-ium-3a-ide (Step B, 16.0 g, 113 mmol) in xylene (200 mL) was added methyl propiolate (25.1 g, 298 mmol), the reaction mixture was heated to 125° C. for 3 h. After cooling down to room temperature, the second portion of methyl propiolate (13 mL)) was added and the reaction was heated to 125° C. for another 7 h. After cooling down to room temperature and removal of volatiles under reduced pressure, the residue was recrystallized from hexane and ethyl acetate (v/v, 10/1) to afford the title compound (20 g, 98%) as a white solid. MS: 183.0 (M+H$^+$).

Step D: (6,7-Dihydro-4H-pyrazolo[5,1-c][1,4]oxazin-2-yl)methanol

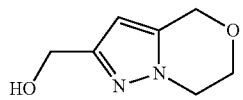

Under Ar, to a mixture of methyl 6,7-dihydro-4H-pyrazolo[5,1-c][1,4]oxazine-2-carboxylate (Step C, 20.5 g, 113 mmol) in dry THF (100 mL) was added LiAlH$_4$ (4.27 g, 113 mmol) at 0° C., then the reaction mixture was stirred at 0° C. for 2 h. Water (4.3 mL) was dropwise added to quench the reaction at 0° C., 15% NaOH (4.3 mL) was followed, and water (13 mL) was added finally. The resulting mixture was stirred for 40 min at room temperature. After filtration through celite, the filtrate was concentrated under reduced pressure to give the crude title compound as a colorless oil, which was directly used without purification. MS: 155.1 (M+H$^+$).

Step E: (3-Iodo-6,7-dihydro-4H-pyrazolo[5,1-c][1,4]oxazin-2-yl)methanol

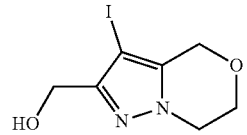

Under Ar, to a mixture of the crude (6,7-dihydro-4H-pyrazolo[5,1-c][1,4]oxazin-2-yl)methanol (Step D, 17.7 g, 115 mmol) in dry acetonitrile (150 mL) was added NIS (38.8 g, 172 mmol) slowly at 0° C., then the reaction mixture was stirred at room temperature for 3 h. Water was added to the reaction, and the resulting mixture was extracted with EA 3 times, the organic layer was combined, washed with brine, dried over Na$_2$SO$_4$, and concentrated under reduced pressure to give the crude title compound as a brown solid, which was directly used without purification. MS: 281.3 (M+H$^+$).

Step F: 3-Iodo-2-(((tetrahydro-2H-pyran-2-yl)oxy)methyl)-6,7-dihydro-4H-pyrazolo[5,1-c][1,4]oxazine

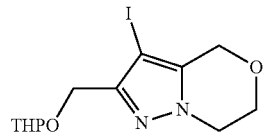

Under Ar, to a solution of the crude (3-iodo-6,7-dihydro-4H-pyrazolo[5,1-c][1,4]oxazin-2-yl)methanol (Step E, 25.0 g) in dry THF (200 mL) was added DHP (7.51 g, 89 mmol) and TsOH·H$_2$O (0.424 g, 2.232 mmol), and the reaction mixture was heated to 40° C. for 4 h. After cooling down to room temperature and removal of volatiles under reduced pressure, the residue was purified by silica gel column (hexane:EA, 1:4) to afford the title compound (25.0 g, 77% over 3 steps) as a colorless oil. MS: 281.3 (M−THP+H$^+$).

Step G: 2-(((Tetrahydro-2H-pyran-2-yl)oxy)methyl)-3-(4,4,5,5-tetramethyl-1,3,2-dioxaborolan-2-yl)-6,7-dihydro-4H-pyrazolo[5,1-c][1,4]oxazine (Intermediate C5)

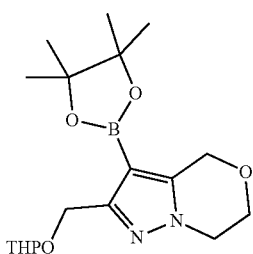

Under Ar, to a solution of 3-iodo-2-(((tetrahydro-2H-pyran-2-yl)oxy)methyl)-6,7-dihydro-4H-pyrazolo[5,1-c][1,4]oxazine (Step G, 5.0 g, 13.73 mmol) in dry THF (10 mL) was added i-PrMgBr (4.0 g, 27.4 mmol) at 0° C., then the mixture was stirred at 0° C. for 30 min. 2-isopropoxy-4,4,5,5-tetramethyl-1,3,2-dioxaborolane (5.11 g, 27.5 mmol) was followed, the reaction mixture was stirred at room temperature for another 2 h, and quenched with aq. NH$_4$Cl. The resulting mixture was extracted with EA 3 times, the organic layer was combined, washed with brine, dried over Na$_2$SO$_4$, and concentrated under reduced pressure to give a light yellow oil, which was purified by silica gel column (hexane:EA, 3:1) to afford the title compound (3.36 g, 67%) as a colorless oil. MS: 365.2 (M+H$^+$).

Example 62

Synthesis of Intermediate C6: 2-(((Tetrahydro-2H-pyran-2-yl)oxy)methyl)-3-(4,4,5,5-tetramethyl-1,3,2-dioxaborolan-2-yl)-6,7-dihydro-4H-pyrazolo[5,1-c][1,4]thiazine

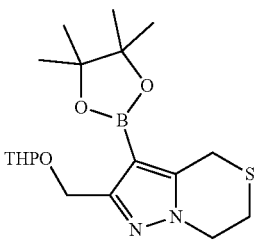

Step A: S-(2-Hydroxyethyl)-L-cysteine

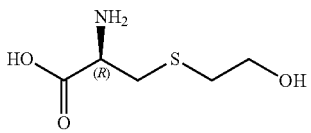

A solution of L-cysteine (22 g, 182 mmol) and 2-bromoethan-1-ol (22.7 g, 182 mmol) in aq. NaOH (73 mL, 5.0 M) and MeOH (80 mL) was stirred at room temperature for overnight. Aq. HCl was added and the resulting mixture was concentrated under reduced pressure. The residue was triturated with EtOH at room temperature for 1 h. After filtration, the filtrate was treated with Et$_3$N to adjusted pH=6-7. The formed solid was collected and crystalized from EtOH/H$_2$O (240 mL/40 mL) to afford the title compound (25 g, 83%) as a white solid. $^1$H NMR (500 MHz, D$_2$O) δ 3.87-3.84 (m, 1H), 3.73-3.65 (m, 2H), 3.11-3.03 (m, 1H), 3.00-2.96 (m, 1H), 2.74-2.66 (m, 2H).

Step B: (R)-1-carboxy-2-((2-chloroethyl)thio)ethan-1-aminium chloride

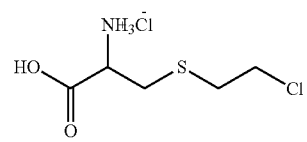

A solution of S-(2-hydroxyethyl)-L-cysteine (Step A, 8.2 g, 49.6 mmol) in conc. HCl (80 mL) was stirred at 95° C. for overnight. After cooling down to 0° C., the formed solid was collected by filtration, and then triturated with i-PrOH (100 mL) at 0° C. to afford the title compound (5.8 g, 53%) as a white solid.

Step C: (R)-thiomorpholine-3-carboxylic acid

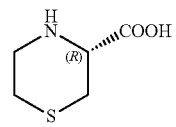

A mixture of (R)-1-carboxy-2-((2-chloroethyl)thio)ethan-1-aminium chloride (Step B, 5.8 g, 26.4 mmol), Et$_3$N (8.0 g, 79 mmol) and EtOH (60 mL) was stirred at 80° C. for 4 h. After cooling down to 0° C., the resulting mixture was further stirred for 30 min. The formed solid was collected and dried in vacuo to afford the title compound (3.88 g, quantitatively) as a white solid.

Step D: 3a,4,6,7-Tetrahydro-3H-[1,2,3]oxadiazolo[4,3-c][1,4]thiazin-8-ium-3-olate

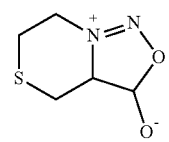

To a solution of (R)-thiomorpholine-3-carboxylic acid (Step C, 3.9 g, 26.4 mmol) in 3N HCl (10 mL) was added sodium nitrite (2.7 g, 39.7 mmol) in portions at 0° C. The reaction mixture was stirred at 0° C. for 1 h and then extracted with DCM 10 times. The organic layer was combined, dried over Na$_2$SO$_4$ and concentrated under reduced pressure to give a brown solid. which was directly used without purification. Under Ar, the above solid was re-taken into dry DCM (30 mL) and TFAA (5.64 g, 26.8 mmol) was added in portions at 0° C. The reaction mixture was stirred at 0° C. for 1 h. After removal of volatiles under reduced pressure, the residue was purified by silica gel column (hexane:EA, 2:1→1:1) to afford the title compound (2.24 g, 57%) as a yellow solid. MS: 159.0 (M+H⁺).

Step E: Ethyl 6,7-dihydro-4H-pyrazolo[5,1-c][1,4]thiazine-2-carboxylate

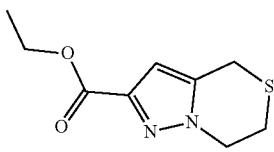

A mixture of ethyl propiolate (1.37 g, 13.98 mmol) and 3a,4,6,7-tetrahydro-3H-[1,2,3]oxadiazolo[4,3-c][1,4]thiazin-8-ium-3-olate (Step D, 2.24 g, 13.98 mmol) in 1,2-diethoxyethane (30 mL) was stirred at 120° C. for 10 h. After removal of volatiles under reduced pressure, the residue was purified by silica gel column (hexane:EA, 5:1→1:1) to afford the title compound (2.3 g, 77%) as a yellow oil. MS: 213.5 (M+H⁺).

Step F: (6,7-Dihydro-4H-pyrazolo[5,1-c][1,4]thiazin-2-yl)methanol

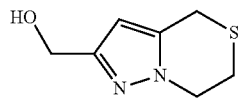

Under Ar, to a solution of ethyl 6,7-dihydro-4H-pyrazolo[5,1-c][1,4]thiazine-2-carboxylate (Step E, 800 mg, 3.77 mmol) in dry THF (20 mL) was added LiAlH₄ (186 mg, 4.90 mmol) in portions at 0° C. The reaction mixture was stirred at 0° C. for 30 min, and then subsequently quenched with water, 15% NaOH, and water (0.2 mL/0.2 mL/0.6 mL). The resulting mixture was stirred at room temperature for 30 min. After filtration through celite, the filtrate was concentrated under reduced pressure to give the crude title compound as a light yellow, which was directly used without purification. MS: 171.1 (M+H⁺).

Step G: 2-(((Tetrahydro-2H-pyran-2-yl)oxy)methyl)-6,7-dihydro-4H-pyrazolo[5,1-c][1,4]thiazine

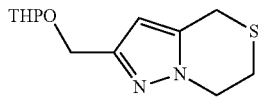

Under Ar, to a solution of (6,7-dihydro-4H-pyrazolo[5,1-c][1,4]thiazin-2-yl)methanol (Step F, 570 mg, 3.35 mmol) in dry THF (10 mL) was added TsOH·H₂O (32 mg, 0.167 mmol) and DHP (704 mg, 8.37 mmol), the reaction mixture was stirred at room temperature for overnight. After removal of volatiles under reduced pressure, the residue was purified by silica gel column (hexane:EA, 3:1→1:1) to afford the title compound (770 mg, 90%) as a yellow oil. MS: 255.1 (M+H⁺).

Step H: 3-Iodo-2-(((tetrahydro-2H-pyran-2-yl)oxy)methyl)-6,7-dihydro-4H-pyrazolo[5,1-c][1,4]thiazine

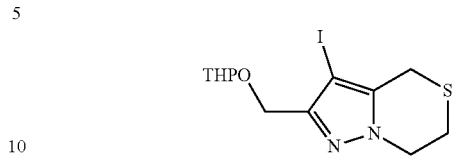

Under Ar, to a solution of (6,7-dihydro-4H-pyrazolo[5,1-c][1,4]thiazin-2-yl)methanol (Step G, 770 mg, 3.03 mmol) in dry acetonitrile (8 mL) was added NIS (681 mg, 3.03 mmol) in portions at 0° C., and the reaction mixture was stirred for 30 min at 0° C. Water was added and the resulting mixture was extracted with EA twice. The combined organic layer was washed with brine, dried over Na₂SO₄ and concentrated under pressure to give a yellow oil, which was purified by silica gel column (hexane:EA, 3:1→1:1) to afford the title compound (1.1 g, 96%) as a colorless oil. MS: 380.9 (M+H⁺).

Step I: 2-(((Tetrahydro-2H-pyran-2-yl)oxy)methyl)-3-(4,4,5,5-tetramethyl-1,3,2-dioxaborolan-2-yl)-6,7-dihydro-4H-pyrazolo[5,1-c][1,4]thiazine (Intermediate C6)

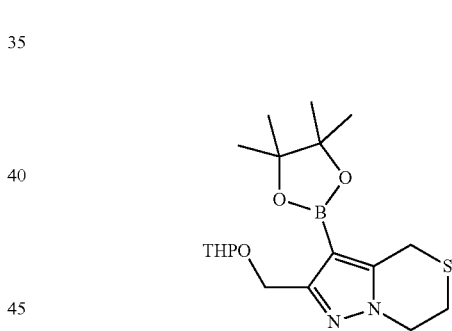

Under Ar, to a solution of 3-iodo-2-(((tetrahydro-2H-pyran-2-yl)oxy)methyl)-6,7-dihydro-4H-pyrazolo[5,1-c][1,4]thiazine (Step H, 500 mg, 1.32 mmol) in dry THF (10 mL) was added i-PrMgBr (2.3 mL, 2.3 mmol, 1.0 M in THF) at 0° C. The reaction mixture was stirred at 0° C. for 1 h. 2-isopropoxy-4,4,5,5-tetramethyl-1,3,2-dioxaborolane (558 mg, 3.0 mmol) was added, and the reaction mixture was further stirred at room temperature for 16 h. The reaction was quenched with sat. NH₄Cl and the resulting mixture was extracted with EA twice. The combined EA layer was washed with brine, dried over Na₂SO₄ and concentrated under reduced pressure to give a light yellow oil, which was purified by silica gel column (hexane:EA, 5:1→2:1) to afford the title compound (450 mg, 90%) as a colorless oil. MS: 381.4 (M+H⁺).

Example 63

Synthesis of Intermediate C7: 5-(Methylsulfonyl)-2-(((tetrahydro-2H-pyran-2-yl)oxy)methyl)-3-(4,4,5,5-tetramethyl-1,3,2-dioxaborolan-2-yl)-4,5,6,7-tetrahydropyrazolo[1,5-a]pyrazine

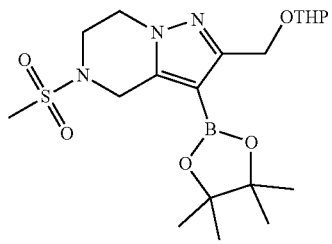

Step A: 4-Nitrobenzyl 2-(hydroxymethyl)-6,7-dihydropyrazolo[1,5-a]pyrazine-5(4H)-carboxylate

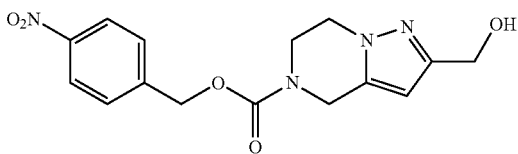 [SMILES: O=C(OCc1ccc([N+](=O)[O-])cc1)N1CCn2nc(CO)cc2C1]

Under Ar, to a solution of 4-nitrobenzyl 2-(((tert-butyldimethylsilyl)oxy)methyl)-6,7-dihydropyrazolo[1,5-a] pyrazine-5(4H)-carboxylate (2.0 g, 4.48 mmol) in dry THF (20 mL) was added TBAF (4.5 mL, 1.0 M in THF). The reaction was stirred at room temperature for 1 h. Water was added and the resulting mixture was extracted with EA 3 times. The combined EA layer was washed with brine, dried over $Na_2SO_4$, and concentrated under reduced pressure to give a yellow oil, which was purified by silica gel column (DCM:MeOH, 20:1) to afford the title compound (1.0 g, 67%) as a yellow solid. MS: 333.4 (M+H$^+$).

Step B: 4-Nitrobenzyl 2-(((tetrahydro-2H-pyran-2-yl)oxy)methyl)-6,7-dihydropyrazolo[1,5-a]pyrazine-5(4H)-carboxylate

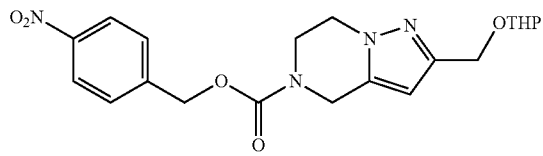

Under Ar, to a solution of 4-nitrobenzyl 2-(hydroxymethyl)-6,7-dihydropyrazolo[1,5-a] pyrazine-5(4H)-carboxylate (Step A, 1.0 g, 3.01 mmol) in dry THF (30 mL) was added DHP (633 mg, 7.52 mmol) and 4-methylbenzenesulfonic acid hydrate (29 mg, 0.15 mmol); the reaction mixture was stirred at room temperature for 16 h. After removal of volatiles under reduced pressure, the residue was purified by silica gel column (hexane:EA, 1:1) to afford the title compound (1.0 g, 80%) as a yellow oil.

Step C: 2-(((Tetrahydro-2H-pyran-2-yl)oxy)methyl)-4,5,6,7-tetrahydropyrazolo[1,5-a]pyrazine

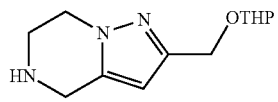

Under Ar, to a solution of 4-nitrobenzyl 2-(((tetrahydro-2H-pyran-2-yl)oxy)methyl)-6,7-dihydropyrazolo[1,5-a] pyrazine-5(4H)-carboxylate (Step B, 1.0 g, 2.4 mmol) in MeOH (20 mL) was 10% Pd/C (0.5 g). $H_2$ was introduced and the reaction mixture was stirred at room temperature for 3 h. After filtration through celite, the filtrate was concentrated under reduced pressure to give the crude title compound as a light yellow oil, which was directly used without purification.

Step D: 5-(Methylsulfonyl)-2-(((tetrahydro-2H-pyran-2-yl)oxy)methyl)-4,5,6,7-tetrahydropyrazolo[1,5-a]pyrazine

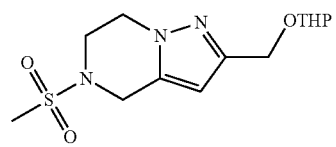

Under Ar, to a solution of 2-(((tetrahydro-2H-pyran-2-yl)oxy)methyl)-4,5,6,7-tetrahydropyrazolo[1,5-a]pyrazine (Step C, 570 mg, 2.4 mmol) and triethylamine (486 mg, 4.8 mmol) in dry DCM (20 mL) was added MsCl (413 mg, 3.6 mmol) at 0° C. The reaction mixture was stirred at 0° C. for 1 h. Water was added and the resulting mixture was extracted with DCM twice, the organic layer was combined, dried over $Na_2SO_4$ and concentrated under reduced pressure to give a yellow oil, which was purified by silica gel column (hexane:EA, 1:3) to afford the title compound (630 mg, 83% over 2 steps) as a colorless oil. MS: 316.2 (M+H$^+$).

Step E: 3-Iodo-5-(methylsulfonyl)-2-(((tetrahydro-2H-pyran-2-yl)oxy)methyl)-4,5,6,7-tetrahydropyrazolo[1,5-a]pyrazine

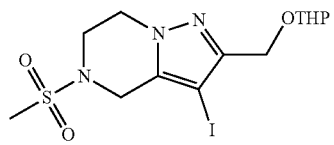

Under Ar, to a solution of 5-(methylsulfonyl)-2-(((tetrahydro-2H-pyran-2-yl)oxy)methyl)-4,5,6,7-tetrahydropyrazolo[1,5-a]pyrazine (Step D, 630 mg, 2.00 mmol) in dry acetonitrile (20 mL) was added NIS (719 mg, 3.20 mmol) in portions at 0° C. The reaction mixture was stirred at 35° C. for 16 h. Water was added, and the resulting mixture was extracted with EA twice, the organic layer was combined, dried over $Na_2SO_4$, and concentrated under reduced pressure to give a yellow oil, which was purified by silica gel column (DCM:MeOH, 100:1→50:1) to afford the title compound (880 mg, 99%) as a colorless oil. MS: 442.0 (M+H⁺).

Step F: 5-(Methylsulfonyl)-2-(((tetrahydro-2H-pyran-2-yl)oxy)methyl)-3-(4,4,5,5-tetramethyl-1,3,2-dioxaborolan-2-yl)-4,5,6,7-tetrahydropyrazolo[1,5-a]pyrazine (Intermediate C7)

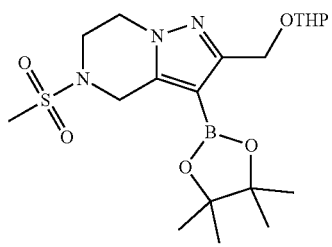

Under Ar, to a solution of 3-iodo-5-(methylsulfonyl)-2-(((tetrahydro-2H-pyran-2-yl)oxy)methyl)-4,5,6,7-tetrahydropyrazolo[1,5-a]pyrazine (Step E, 880 mg, 1.99 mmol) in dry THF (5 mL) was added i-PrMgBr (4 mL, 4 mmol, 1.0 M in THF) at 0° C., followed by 2-isopropyl-4,4,5,5-tetramethyl-1,3,2-dioxaborolane (678 mg, 1.99 mmol). The reaction mixture was stirred at room temperature for 2 h, and then quenched with sat. NH₄Cl. The resulting mixture was extracted with EA twice. The combined EA layer was dried over Na₂SO₄ and concentrated under reduced pressure to give a light yellow oil, which was purified by silica gel column (hexane:EA, 3:1→1:1) to afford the title compound (550 mg, 63%) as a colorless oil. MS: 442.4 (M+H⁺).

Example 64

Synthesis of Intermediate C8: 2-(((Tetrahydro-2H-pyran-2-yl)oxy)methyl)-3-(4,4,5,5-tetramethyl-1,3,2-dioxaborolan-2-yl)-5,6,7,8-tetrahydro-4H-pyrazolo[1,5-a]azepine

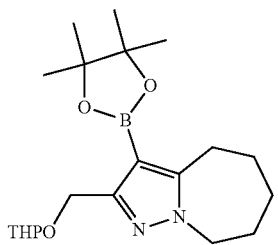

Step A: Diethyl 1-(5-ethoxy-5-oxopentyl)-1H-pyrazole-3,5-dicarboxylate

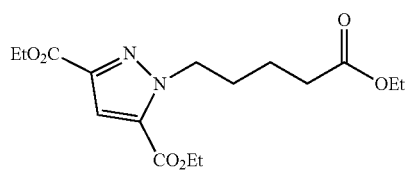 [SMILES: CCOC(=O)CCCCn1nc(C(=O)OCC)cc1C(=O)OCC]

Under Ar, to a solution of diethyl 1H-pyrazole-3,5-dicarboxylate (1.06 g, 5.00 mmol) in dry acetonitrile (10 mL) was added K₂CO₃ (0.69 g, 5.00 mmol) and ethyl 5-bromopentanoate (1.04 g, 5.00 mmol) at room temperature. The reaction mixture was stirred at 90° C. for 2 h. After cooling down to room temperature and removal of volatiles under reduced pressure, the residue was partitioned with EA and water, the aqueous layer was extracted with EA twice, the organic layer was combined, dried over Na₂SO₄, and concentrated under reduced pressure to give the crude title compound as a light yellow oil, which was directly used without purification. MS: 363.6 (M+Na⁺).

Step B: Diethyl 4-oxo-5,6,7,8-tetrahydro-4H-pyrazolo[1,5-a]azepine-2,5-dicarboxylate

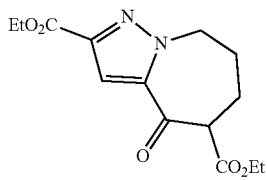 [SMILES: CCOC(=O)c1cc2n(n1)CCCC(C(=O)OCC)C2=O]

Under Ar, to a solution of the crude diethyl 1-(5-ethoxy-5-oxopentyl)-1H-pyrazole-3,5-dicarboxylate (Step A, 18.76 g) in dry toluene (150 mL) was added t-BuOK (6.80 g, 60.6 mmol) at room temperature. The reaction mixture was stirred at room temperature for 15 min and then heated to reflux for 4 h. After cooling down to room temperature, the reaction mixture was adjusted to pH=5~6 with aq. HCl (5%), and the resulting mixture was partitioned with EA and water. The aqueous layer was extracted with EA twice, the organic solution was combined, dried over Na₂SO₄ and concentrated under reduced pressure to give a yellow oil, which was purified by silica gel column (hexane:EA, 1:1) to give the title compound (9.96 g, 61% over 2 steps) as a white solid. MS: 295.6 (M+H⁺).

Step C: 4-Oxo-5,6,7,8-tetrahydro-4H-pyrazolo[1,5-a]azepine-2-carboxylic acid

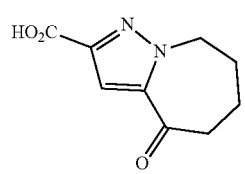

A mixture of diethyl 4-oxo-5,6,7,8-tetrahydro-4H-pyrazolo[1,5-a]azepine-2,5-dicarboxylate (Step B, 9.456 g, 32.1 mmol) in 4N HCl (95 mL) was heated to reflux for 5 h. After cooling down to room temperature, the reaction mixture was concentrated under reduced pressure to dryness and titrated with toluene and ethanol to afford the title compound (6.12 g, 98%) as a white solid, which was directly used without further purification. MS: 195.1 (M+H⁺).

Step D: Ethyl 4-oxo-5,6,7,8-tetrahydro-4H-pyrazolo[1,5-a]azepine-2-carboxylate

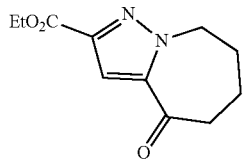 [SMILES: O=C(O)c1cc2n(n1)CCCCC2=O]

Concentrated sulfuric acid (6.48 g, 66.1 mmol) was added to a solution of 4-oxo-5,6,7,8-tetrahydro-4H-pyrazolo[1,5-a]azepine-2-carboxylic acid (Step C, 6.58 g, 33.9 mmol) in ethanol (100 mL) at room temperature, and the reaction mixture was heated to reflux for 2 h. After cooling down to room temperature and removal of volatiles under reduced pressure, the residue was poured onto ice and neutralised with sat. NaHCO$_3$. The resulting mixture was extracted with DCM 5 times, the organic layer was combined, washed with brine, dried over Na$_2$SO$_4$, and concentrated under reduced pressure to give the crude title compound as a yellow oil, which was directly used without purification. MS: 223.5 (M+H$^+$).

Step E: Ethyl 4-hydroxy-5,6,7,8-tetrahydro-4H-pyrazolo[1,5-a]azepine-2-carboxylate

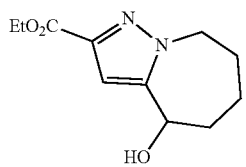 [SMILES: CCOC(=O)c1cc2n(n1)CCCCC2O]

NaBH$_4$ (1.34 g, 35.4 mmol) was added to a solution of the crude ethyl 4-oxo-5,6,7,8-tetrahydro-4H-pyrazolo[1,5-a]azepine-2-carboxylate (Step D, 7.15 g) in ethanol (150 mL) at 0° C., and the reaction mixture was stirred for 2 h at room temperature. Aq. NH$_4$Cl was added to quench reaction. After removal of volatiles under reduced pressure, the residue was partitioned with cold water and DCM, and the aqueous phase was extracted with DCM twice, the organic layer was combined, washed with water and brine, dried over Na$_2$SO$_4$, and concentrated under reduced pressure to give the crude title compound as a yellow oil, which was directly used without purification. MS: 225.6 (M+H$^+$).

Step F: Ethyl 7,8-dihydro-6H-pyrazolo[1,5-a]azepine-2-carboxylate

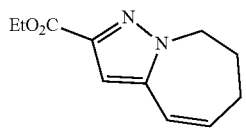 [SMILES: CCOC(=O)c1cc2n(n1)CCCC=C2]

Under Ar, TsOH·H$_2$O (1.0 g, 5.25 mmol) was added to a solution of ethyl 4-hydroxy-5,6,7,8-tetrahydro-4H-pyrazolo[1,5-a]azepine-2-carboxylate (Step E, 7.36 g) in dry toluene (100 mL) at room temperature and the reaction mixture was heated to reflux for 4 h. After cooling down to room temperature, the reaction mixture was neutralised with sat. NaHCO$_3$, and extracted with EA twice. The organic layer was combined, washed with brine, dried over Na$_2$SO$_4$, and concentrated under reduced pressure to give the crude title compound as a yellow oil, which was directly used without purification. MS: 207.5 (M+H$^+$).

Step G: Ethyl 5,6,7,8-tetrahydro-4H-pyrazolo[1,5-a]azepine-2-carboxylate

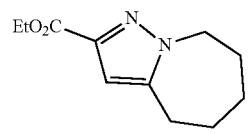 [SMILES: CCOC(=O)c1cc2n(n1)CCCCC2]

Under Ar, 10% Pd/C (0.285 g, 2.68 mmol, 0.5) was added into a solution of the crude ethyl 7,8-dihydro-6H-pyrazolo[1,5-a]azepine-2-carboxylate (Step F, 1.1 g) in ethanol (25 mL) at room temperature. H$_2$ was introduced and the reaction mixture was stirred at 40-50° C. for 16 h. The mixture was filtered off through silica gel/celite, the filtrate was concentrated under reduced pressure to afford the crude title compound as a yellow oil, which was directly used without purification. MS: 209.5 (M+H$^+$).

Step H: (5,6,7,8-Tetrahydro-4H-pyrazolo[1,5-a]azepin-2-yl)methanol

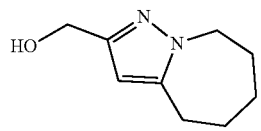 [SMILES: OCc1cc2n(n1)CCCCC2]

Under Ar, to a solution of the crude ethyl 5,6,7,8-tetrahydro-4H-pyrazolo[1,5-a]azepine-2-carboxylate (Step G, 907 mg) in dry THF was added LiAlH$_4$ (248 mg, 6.53 mmol) in portions at 0° C. The reaction mixture was stirred at 0° C. for 30 min. The mixture was quenched with water, 15% aq. NaOH and water (0.5 mL, 0.5 mL, 1.5 mL) and the resulting mixture was stirred at room temperature for 30 min. After filtration, the filtrate was concentrated under reduced pressure to give the crude title compound as a light yellow oil, which was directly used without purification. MS: 167.1 (M+H$^+$).

Step I: 2-(((Tetrahydro-2H-pyran-2-yl)oxy)methyl)-5,6,7,8-tetrahydro-4H-pyrazolo[1,5-a]azepine

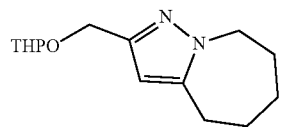

Under Ar, to a solution of the crude (5,6,7,8-tetrahydro-4H-pyrazolo[1,5-a]azepin-2-yl)methanol (Step H, 724 mg) in dry THF was added TsOH·H$_2$O (166 mg, 0.871 mmol) and DHP (916 mg, 10.89 mmol). The reaction mixture was stirred at room temperature for overnight. Sat. NaHCO₃ was added and the resulting mixture was extracted with EA twice, the organic layer was combined, washed with water and brine, dried over Na₂SO₄ and concentrated under reduced pressure to give the crude title compound as a light yellow oil, which was directly used without purification. MS: 167.4 (M-THP+H⁺).

Step J: 3-Iodo-2-(((tetrahydro-2H-pyran-2-yl)oxy) methyl)-5,6,7,8-tetrahydro-4H-pyrazolo[1,5-a] azepine

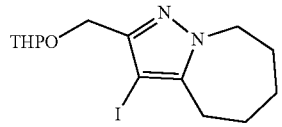

Under Ar, at 0° C. to a solution of the crude 2-(((tetrahydro-2H-pyran-2-yl)oxy)methyl)-5,6,7,8-tetrahydro-4H-pyrazolo[1,5-a]azepine (Step I, 1.1 g) in dry acetonitrile (20 mL) was added NIS (1.8 g, 7.84 mmol) in portions and the reaction mixture was stirred for 30 min. Water was added and the resulting mixture was extracted with EA twice, the organic layer was combined, washed with brine, dried over Na₂SO₄ and concentrated under reduced pressure to give a yellow oil, which was purified by silica gel column (hexane: EA, 3:1→1:1) to give the title compound (1.5 g, 46% over 6 steps) as a colorless oil. MS: 293.5 (M-THP+H⁺).

Step K: 2-(((Tetrahydro-2H-pyran-2-yl)oxy) methyl)-3-(4,4,5,5-tetramethyl-1,3,2-dioxaborolan-2-yl)-5,6,7,8-tetrahydro-4H-pyrazolo[1,5-a]azepine (Intermediate C8)

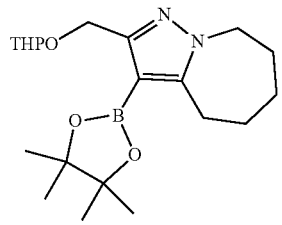

Under Ar, to a solution of 3-iodo-2-(((tetrahydro-2H-pyran-2-yl)oxy)methyl)-5,6,7,8-tetrahydro-4H-pyrazolo[1,5-a]azepine (Step J, 1.5 g, 3.87 mmol) in dry THF (30 mL) was added i-PrMgBr (1.71 g, 11.60 mmol) at 0° C. The mixture was stirred at 0° C. for 30 min, and then 2-isopropoxy-4,4,5,5-tetramethyl-1,3,2-dioxaborolane (2.16 g, 11.60 mmol) was followed; the reaction mixture was stirred at room temperature for 2 h and then quenched with aq. NH₄Cl. The resulting mixture was extracted with EA twice, the organic layer was combined, washed with brine, dried over Na₂SO₄, and concentrated under reduced pressure to give a yellow oil, which was purified by silica gel column (hexane:EA, 3:1) to afford the title compound (1.25 g, 86%) as a colorless oil. ¹H NMR (500 MHz, CDCl₃) δ 4.89 (s, 1H), 4.80 (d, J=10.9 Hz, 1H), 4.46 (d, J=10.9 Hz, 1H), 4.22-4.20 (m, 2H), 4.04 (dd, J=10.9, 2.4 Hz, 1H), 3.59-3.49 (m, 1H), 3.02-2.93 (m, 2H), 1.81 (s, 2H), 1.74-1.63 (m, 8H), 1.50 (d, J=17.9 Hz, 2H), 1.26 (s, 12H). MS: 377.2 (M+H⁺).

Example 65

Synthesis of Intermediate C9: 5-(Difluoromethyl)-1-methyl-3-(((tetrahydro-2H-pyran-2-yl)oxy) methyl)-4-(4,4,5,5-tetramethyl-1,3,2-dioxaborolan-2-yl)-1H-pyrazole

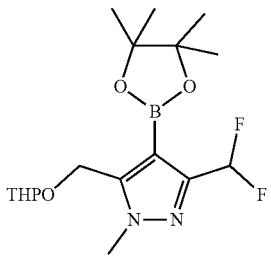

Step A: 5-(((tert-Butyldimethylsilyl)oxy)methyl)-1-methyl-1H-pyrazole-3-carbaldehyde

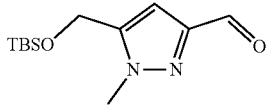 [SMILES: Cn1nc(C=O)cc1CO[Si](C)(C)C(C)(C)C]

Under Ar, to a solution of (5-(((tert-butyldimethylsilyl) oxy)methyl)-1-methyl-1H-pyrazol-3-yl)methanol (2.00 g, 7.80 mmol) in dry DCM (20 mL) was added DMP (6.62 g, 15.60 mmol) at 0° C. The reaction mixture was stirred at room temperature for 2 h. A mixed solvent of EA and hexane (v/v, 1:1) was added, and the formed precipitate was filtered off. The filtrate was concentrated under reduced pressure to give a yellow oil, which was purified by silica gel column (hexane:EA, 10:1→5:1) to afford the title compound (1.70 g, 86%) as a white foam. MS: 255.7 (M+H⁺).

Step B: 5-(((tert-Butyldimethylsilyl)oxy)methyl)-3-(difluoromethyl)-1-methyl-1H-pyrazole

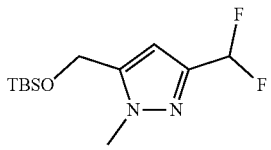 [SMILES: Cn1nc(C(F)F)cc1CO[Si](C)(C)C(C)(C)C]

Under Ar, to a solution of 5-(((tert-butyldimethylsilyl) oxy)methyl)-1-methyl-1H-pyrazole-3-carbaldehyde (Step A, 500 mg, 1.97 mmol) in dry DCM (15 mL) was added DAST (950 mg, 5.90 mmol) at 0° C. The reaction was stirred at room temperature for 4 h and then quenched with sat. NaHCO₃. The resulting mixture was extracted with DCM 3 times, the combined organic layer was dried over Na₂SO₄ and concentrated under reduced pressure to give a yellow oil, which was purified by silica gel column (hexane:EA, 20:1→10:1) to afford the title compound (160 mg, 30%) as a colorless oil. MS: 277.3 (M+H⁺).

Step C: (3-(Difluoromethyl)-1-methyl-1H-pyrazol-5-yl)methanol

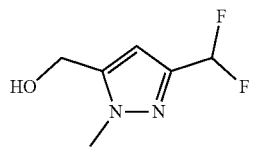

Under Ar, to a solution of 5-(((tert-butyldimethylsilyl)oxy)methyl)-3-(difluoromethyl)-1-methyl-1H-pyrazole (Step B, 250 mg, 0.904 mmol) in dry THF (5 mL) was added TBAF (890 µL, 0.89 mmol, 1.0 M in THF), the reaction solution was stirred at room temperature for 1 h. After removal of volatiles under reduced pressure, the crude title compound (147 mg) as a yellow oil was directly used for the next step without purification. MS: 163.2 (M+H$^+$).

Step D: (3-(Difluoromethyl)-1-methyl-1H-pyrazol-5-yl)methyl benzoate

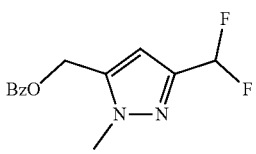

Under Ar, to a solution of the crude (3-(difluoromethyl)-1-methyl-1H-pyrazol-5-yl)methanol (Step C, 147 mg) in dry DCM (5 mL) was added Et$_3$N (274 mg, 2.71 mmol) and BzCl (254 mg, 1.81 mmol), the reaction was stirred at room temperature for 1 h. Water was added to quench the reaction and the resulting mixture was extracted with DCM twice. The combined organic layer was washed with brine, dried over Na$_2$SO$_4$, and concentrated under reduced pressure to give a yellow oil, which was purified by silica gel column (hexane:EA, 20:1→5:1) to afford the title compound (215 mg, 89% over 2 steps) as a colorless oil. MS: 267.6 (M+H$^+$).

Step E: (3-(Difluoromethyl)-4-iodo-1-methyl-1H-pyrazol-5-yl)methyl benzoate

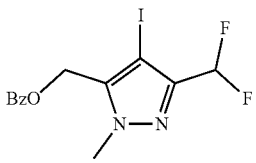

Under Ar, to a solution of (3-(difluoromethyl)-1-methyl-1H-pyrazol-5-yl)methyl benzoate (Step D, 215 mg, 0.81 mmol) in AcOH (2 mL) was added a solution of NIS (218 mg, 0.969 mmol) in TFA (1 mL). The reaction solution was stirred at 75° C. for 1 h. After cooling down to room temperature, the resulting mixture was treated with aq. NaHCO$_3$ and Na$_2$S$_2$O$_3$, and extracted with EA twice. The combined EA layer was washed with brine, dried over Na$_2$SO$_4$, and concentrated under reduced pressure to give a light yellow oil, which was purified by silica gel column (hexane:EA, 5:1) to afford the title compound (265 mg, 84%) as a colorless oil. MS: 393.2 (M+H$^+$).

Step F: (3-(Difluoromethyl)-4-iodo-1-methyl-1H-pyrazol-5-yl)methanol

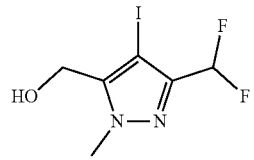

Under Ar, a mixture of (3-(difluoromethyl)-4-iodo-1-methyl-1H-pyrazol-5-yl)methyl benzoate (Step E, 265 mg, 0.676 mmol) and K$_2$CO$_3$ (280 mg, 2.027 mmol) in MeOH (5 mL) was stirred at room temperature for 1 h. The mixture was diluted with EA, washed with brine, dried over Na$_2$SO$_4$, and concentrated under reduced pressure to give the crude title compound (195 mg) as a white solid, which was directly used without purification. MS: 289.3 (M+H$^+$).

Step G: 3-(Difluoromethyl)-4-iodo-1-methyl-5-(((tetrahydro-2H-pyran-2-yl)oxy)methyl)-1H-pyrazole

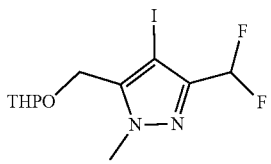

Under Ar, a mixture of (3-(difluoromethyl)-4-iodo-1-methyl-1H-pyrazol-5-yl)methanol (Step F, 195 mg, 0.676 mmol), DHP (171 mg, 2.031 mmol) and TsOH·H$_2$O (12.88 mg, 0.068 mmol) in dry THF (5 mL) was stirred at room temperature for overnight. After removal of volatiles under reduced pressure, the residue was purified by silica gel column (hexane:EA, 10:1→4:1) to afford the title compound (240 mg, 95% over 2 steps) as a colorless oil. MS: 373.7 (M+H$^+$).

Step H: 3-(Difluoromethyl)-1-methyl-5-(((tetrahydro-2H-pyran-2-yl)oxy)methyl)-4-(4,4,5,5-tetramethyl-1,3,2-dioxaborolan-2-yl)-1H-pyrazole (Intermediate C9)

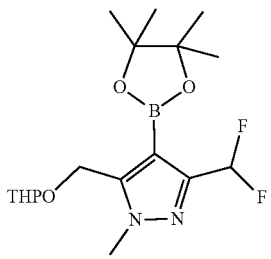

Under Ar, to a solution of 3-(difluoromethyl)-4-iodo-1-methyl-5-(((tetrahydro-2H-pyran-2-yl)oxy)methyl)-1H-pyrazole (Step G, 240 mg, 0.645 mmol) in dry THF (5 mL) was added i-PrMgBr (0.691 mL, 1.935 mmol, 2.8 M in THF) at 0° C. and the mixture was stirred for 20 min, 2-isopropoxy-4,4,5,5-tetramethyl-1,3,2-dioxaborolane (360 mg, 1.935 mmol) was added and the reaction mixture was stirred at room temperature for 1 h. Sat. NH$_4$Cl was added to quench the reaction and the resulting mixture was extracted with EA twice. The combined organic layer was dried over Na$_2$SO$_4$ and concentrated under reduced pressure to give a yellow oil, which was purified by silica gel column (hexane:EA, 10:1) to afford the title compound (140 mg, 58%) as a colorless oil. MS: 373.5 (M+H$^+$).

Example 66

Synthesis of Intermediate D1: S-((5-(((tert-butyldimethylsilyl)oxy)methyl)-1-methyl-1H-pyrazol-3-yl)methyl) ethanethioate

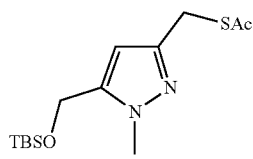

Step A: 3-(Bromomethyl)-5-(((tert-butyldimethylsilyl)oxy)methyl)-1-methyl-1H-pyrazole

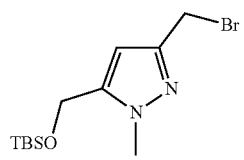 [SMILES: Cn1nc(CBr)cc1CO[Si](C)(C)C(C)(C)C]

Under Ar, PPh$_3$ (511 mg, 1.95 mmol) and CBr$_4$ (647 mg, 1.95 mmol) were added subsequently to a solution of (5-(((tert-butyldimethylsilyl)oxy)methyl)-1-methyl-1H-pyrazol-3-yl)methanol (250 mg, 0.98 mmol) in dry DCM (10 mL). The reaction mixture was stirred for 3 h. After removal of volatiles under reduced pressure, the residue was purified by silica gel column (hexane:DCM, 1:4) to afford the title compound (300 mg, 96%) as a yellow oil. MS: 320.6 (M+H$^+$).

Step B: S-((5-(((tert-butyldimethylsilyl)oxy)methyl)-1-methyl-1H-pyrazol-3-yl)methyl) ethanethioate (Intermediate D1)

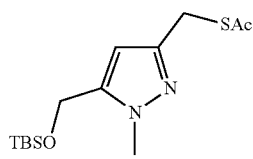

Under Ar, to a solution of 3-(bromomethyl)-5-(((tert-butyldimethylsilyl)oxy)methyl)-1-methyl-1H-pyrazole (Step A, 380 mg, 1.19 mmol) in dry THE (15 mL) was added KSAc (272 mg, 2.38 mmol), then the reaction mixture was heated to reflux for 1 h. After cooling down to room temperature and removal of volatiles under reduced pressure, the residue was purified by silica gel column (hexane:EA, 3:2) to afford the title compound (110 mg, 29%) as a yellow oil. MS: 316.1 (M+H$^+$); 337.2 (M+Na$^+$).

Example 67

Synthesis of Intermediate D2: (5-((Acetylthio)methyl)-1-methyl-1H-pyrazol-3-yl)methyl benzoate

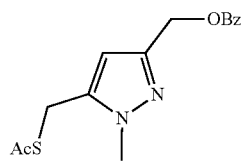

Step A: (5-(((tert-butyldimethylsilyl)oxy)methyl)-1-methyl-1H-pyrazol-3-yl)methyl benzoate

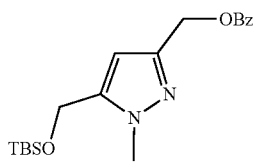

Under Ar, to a solution of (5-(((tert-butyldimethylsilyl)oxy)methyl)-1-methyl-1H-pyrazol-3-yl)methanol (15 g, 58.5 mmol), DMAP (0.715 g, 5.85 mmol) and DIEPA (22.68 g, 175 mmol) in dry CH$_2$Cl$_2$ (150 mL) was added benzoic anhydride (14.56 g, 64.3 mmol) at 0° C., then the resulting mixture was stirred at room temperature for overnight. After removal of volatiles under reduced pressure, the residue was purified by silica gel column (hexane:EtOAc, 1:1) to afford the title compound (21 g, quantitatively) as a yellow oil. MS: 362.02 (M+H$^+$); 384.37 (M+Na$^+$).

Step B: (5-(hydroxymethyl)-1-methyl-1H-pyrazol-3-yl)methyl benzoate

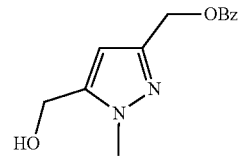

Under Ar, to a solution of (5-(((tert-butyldimethylsilyl)oxy)methyl)-1-methyl-1H-pyrazol-3-yl)methyl benzoate (Step A, 21 g, 58.2 mmol) in dry THF (150 mL) was added AcOH (5.25 g, 87 mmol) and TBAF·3H$_2$O (30.5 g, 116 mmol), then the reaction mixture was stirred at room temperature for overnight. The resulting mixture was diluted with EtOAc, washed with aq. NaHCO₃, brine, dried over Na₂SO₄, and concentrated under reduced pressure to give a yellow oil, which was purified by silica gel column (hexane: EtOAc, 1:0→0:1) to afford the title compound (10.32 g, 72%) as a white solid. MS: 247.21 (M+H⁺); 269.19 (M+Na⁺).

Step C: (5-(Bromomethyl)-1-methyl-1H-pyrazol-3-yl)methyl benzoate

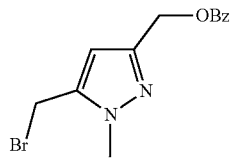

Under Ar, to a solution of (5-(hydroxymethyl)-1-methyl-1H-pyrazol-3-yl)methyl benzoate (Step B, 10.32 g, 41.9 mmol) in dry CH₂Cl₂ (100 mL) was added Ph₃P (16.49 g, 62.9 mmol) at 0° C., followed by CBr₄ (20.85 g, 62.9 mmol), the reaction mixture was stirred at 0° C. for 1 h. After removal of volatiles under reduced pressure, the residue was purified by silica gel column (hexane:EtOAc, 3:1) to afford the title compound (10.1 g, 78%) as a colorless oil. MS: 309.04 (M+H⁺).

Step D: (5-((acetylthio)methyl)-1-methyl-1H-pyrazol-3-yl)methyl benzoate (Intermediate D2)

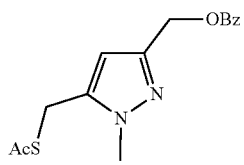

Under Ar, to a solution of (5-(bromomethyl)-1-methyl-1H-pyrazol-3-yl)methyl benzoate (Step C, 55 mg, 0.18 mmol) in dry THF (10 mL) was added KSAc (41 mg, 0.36 mmol), the reaction was heated to 70° C. with oil bath and stirred for 1 h. After cooling down to room temperature and filtration, the filtrate was concentrated under reduced pressure to give the crude title compound (54 mg) as a yellow oil, which was used directly for the next step without purification. MS: 305.43 (M+H⁺); 327.24 (M+Na⁺).

Example 68

Synthesis of Intermediate D3: (3-((Acetylthio)methyl)-4-chloro-1-methyl-1H-pyrazol-5-yl)methyl benzoate

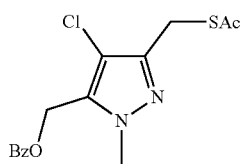

Step A: (3-(Bromomethyl)-4-chloro-1-methyl-1H-pyrazol-5-yl)methyl benzoate

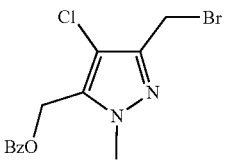

Under Ar, to a solution of (4-chloro-3-(hydroxymethyl)-1-methyl-1H-pyrazol-5-yl)methyl benzoate (80 mg, 0.29 mmol) in dry DCM (10 mL) was added triphenylphosphine (150 mg, 0.57 mmol) and CBr₄ (189 mg, 0.57 mmol) subsequently, then the reaction solution was stirred at room temperature for 1 h. After removal of volatiles under reduced pressure, the residue was purified by silica gel column (hexane:DCM, 1:0→0:1) to afford the title compound (91 mg, 93%) as a colorless oil. MS: 344.4 (M+H⁺).

Step B: (3-((Acetylthio)methyl)-4-chloro-1-methyl-1H-pyrazol-5-yl)methyl benzoate (Intermediate D3)

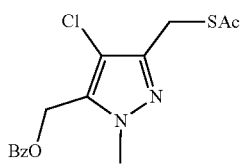

Under Ar, to a solution of (3-(bromomethyl)-4-chloro-1-methyl-1H-pyrazol-5-yl)methyl benzoate (Step A, 96 mg, 0.28 mmol) in dry THF was added KSAc (63.8 mg, 0.56 mmol), then the reaction mixture was heated to reflux for 1 h. After cooling down to room temperature and filtration, the filtrate was concentrated under reduced pressure to give the crude title compound (98 mg), which was used directly for the next step without purification. MS: 340.3 (M+H⁺).

Example 69

Synthesis of Intermediate D4: S-((2-(((tert-butyldimethylsilyl)oxy)methyl)oxazol-4-yl)methyl) ethanethioate

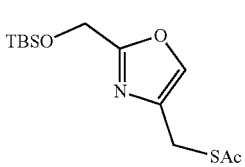

Step A: Methyl 2-(dichloromethyl)-4,5-dihydrooxazole-4-carboxylate

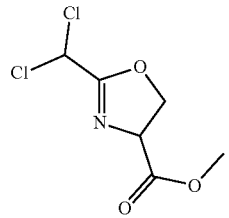

Under Ar, to a solution of sodium methanolate (25% w/w, 2.52 g, 11.68 mmol) in methanol (100 mL) was added 2,2-dichloroacetonitrile (12.8 g, 116 mmol) at −10° C. over 30 min; the mixture was stirred for 30 min, and then 3-hydroxy-1-methoxy-1-oxopropan-2-aminium (18.1 g, 151 mmol) was added in portions at −10° C. The reaction mixture was allowed to warm up to room temperature and stirred for overnight. DCM and water were added into the reaction mixture and the DCM layer was separated. The aqueous layer was extracted with DCM twice, the combined organic layer was dried over Na$_2$SO$_4$, and concentrated under reduced pressure to give the crude title compound as a brown oil, which was directly used without purification.

Step B: Methyl 2-(chloromethyl)-4-methoxy-4,5-dihydrooxazole-4-carboxylate

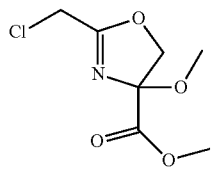

Under Ar, to a solution of the crude methyl 2-(dichloromethyl)-4,5-dihydrooxazole-4-carboxylate (Step A, 7.0 g) in MeOH (45 mL) was added sodium methanolate (7.13 g, 33.0 mmol) in portions at 0° C., then the reaction was allowed to warm up to room temperature and stirred for overnight. DCM and water were added into the reaction mixture and the DCM layer was separated, the aqueous layer was extracted with DCM twice. The combined DCM layer was washed with brine, dried over Na$_2$SO$_4$, and concentrated reduced pressure to give the crude title compound as a yellow oil, which was directly used without purification. MS: 230.1 (M+Na$^+$).

Step C: Methyl 2-(chloromethyl)oxazole-4-carboxylate

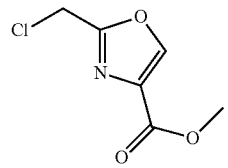

Under Ar, to a solution of the crude methyl 2-(chloromethyl)-4-methoxy-4,5-dihydrooxazole-4-carboxylate (Step B, 5.3 g) in dry toluene (45 mL) was added CSA (920 mg, 3.96 mmol); the reaction mixture was stirred at 70° C. for 2 h. After cooling down to room temperature, the resulting mixture was washed with aq. K$_2$CO$_3$ (10%) and water. The aqueous layer was extracted with toluene twice, the combined organic layers was rinsed with brine, dried over Na$_2$SO$_4$, and concentrated under reduced pressure to give a yellow oil, which was purified by silica gel column (hexane:EA, 6:1) to afford the title compound (850 mg, 19% yield over 3 steps) as a light yellow solid. $^1$H NMR (500 MHz, CDCl$_3$) δ 8.25 (s, 1H), 4.64 (s, 2H), 3.93 (s, 3H). MS: 230.1 (M+Na$^+$).

Step D: Methyl 2-(acetoxymethyl)oxazole-4-carboxylate

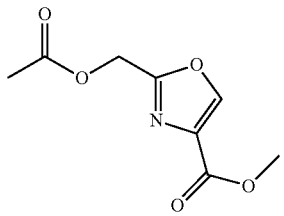

Under Ar, to a solution of methyl 2-(chloromethyl)oxazole-4-carboxylate (Step C, 280 mg, 1.6 mmol) in AcOH (6 mL) was added Ac$_2$O (163 mg, 1.6 mmol) and sodium acetate (1.0 g, 12.36 mmol), then the reaction solution was heated at 130° C. for overnight. After cooling down to room temperature, the resulting mixture was neutralized with sat. Na$_2$CO$_3$ to adjust pH to 7~8. The mixture was extracted with EA twice, the combined EA layer was washed with brine, dried over Na$_2$SO$_4$, and concentrated under reduced pressure to give the crude title compound as a brown oil, which was directly used without purification. MS: 200.1 (M+H$^+$); 222.10 (M+Na$^+$).

Step E: Methyl 2-(hydroxymethyl)oxazole-4-carboxylate

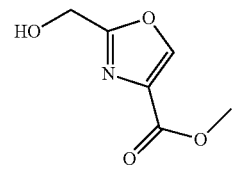

Under Ar, to a solution of the crude methyl 2-(acetoxymethyl)oxazole-4-carboxylate (Step D, 390 mg) in MeOH (5 mL) was added NaOMe (52.9 mg, 1.0 mmol) in portions at 0° C.; the reaction mixture was stirred for 40 min. Sat. NH$_4$Cl was added to quench the reaction, the resulting mixture was extracted with EA twice. The combined organic layer was dried over Na$_2$SO$_4$, and concentrated under reduced pressure to give a yellow oil, which was purified by silica gel column (hexane:EA, 1:9) to afford the title compound (165 mg, 54% over 2 steps) as a yellow solid. $^1$H NMR (500 MHz, CDCl$_3$) δ 8.22 (s, 1H), 4.80 (s, 2H), 3.92 (s, 3H). MS: 158.1 (M+H$^+$); 180.1 (M+Na$^+$).

Step F: Methyl 2-(((tert-butyldimethylsilyl)oxy)methyl)oxazole-4-carboxylate

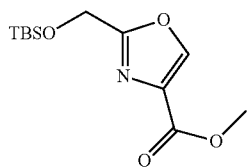 [SMILES: COC(=O)c1coc(CO[Si](C)(C)C(C)(C)C)n1]

Under Ar, TBSCl (1535 mg, 10.18 mmol) was added in portions to a stirred solution of methyl 2-(hydroxymethyl)oxazole-4-carboxylate (Step E, 800 mg, 5.09 mmol) and imidazole (763 mg, 11.20 mmol) in dry DCM (20 mL) at 0° C.; the reaction solution was stirred for overnight at room temperature. The resulting mixture was treated with DCM and water, and the organic layer was separated. The aqueous layer was extracted with DCM twice, the combined DCM layers was washed with brine, dried over $Na_2SO_4$, and concentrated under reduced pressure to give the crude title compound as a colorless oil, which was used directly without purification. MS: 272.6 (M+H$^+$).

Step G: (2-(((tert-Butyldimethylsilyl)oxy)methyl)oxazol-4-yl)methanol

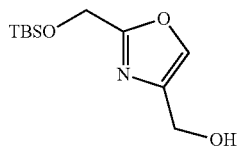 [SMILES: CC(C)(C)[Si](C)(C)OCc1nc(CO)co1]

Under Ar, to a stirred solution of the crude methyl 2-(((tert-butyldimethylsilyl)oxy)methyl)oxazole-4-carboxylate (Step F, 170 mg) in dry THF (6 mL) was added LiAlH$_4$ (23.77 mg, 0.63 mmol) at 0° C.; the reaction was stirred for 1 h, and then quenched with water and 2N NaOH solution. After filtration, the residue was concentrated under reduced pressure to give a light yellow oil, which was purified by silica gel column (silica gel column, hexane:EA, 4:1) to afford the title compound (95 mg, 62% over 2 steps) as a colorless oil. $^1$H NMR (500 MHz, CDCl$_3$) δ 7.57 (s, 1H), 4.74 (s, 2H), 4.59 (s, 2H), 0.91 (d, J=2.5 Hz, 9H), 0.11 (d, J=2.8 Hz, 6H). MS: 244.5 (M+H$^+$).

Step H: 2-(((tert-Butyldimethylsilyl)oxy)methyl)-4-(chloromethyl)oxazole

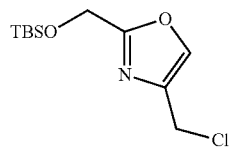 [SMILES: CC(C)(C)[Si](C)(C)OCc1nc(CCl)co1]

Under Ar, to a stirred solution of (2-(((tert-butyldimethylsilyl)oxy)methyl)oxazol-4-yl)methanol (Step G, 300 mg, 1.23 mmol) in dry DCM (10 mL) was added triethyl amine (312 mg, 3.08 mmol), TsCl (282 mg, 1.48 mmol) and DMAP (15.1 mg, 0.12 mmol) at room temperature; the reaction was stirred for overnight. After removal of volatiles under reduced pressure, the crude title compound as a yellow oil was used directly without purification. MS: 263.1 (M+H$^+$).

Step I: S-((2-(((tert-butyldimethylsilyl)oxy)methyl)oxazol-4-yl)methyl) ethanethioate (Intermediate D4)

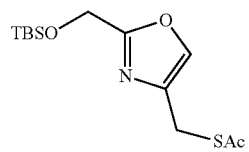

Under Ar, the crude 2-(((tert-butyldimethylsilyl)oxy)methyl)-4-(chloromethyl)oxazole (Step H, 323 mg) and KSAc (342 mg, 3.0 mmol) were charged into a reaction vial, and then dry THF (10 mL) was added via syringe; the reaction mixture was then heated at 75° C. for 1 h. After cooling down to room temperature and removal of volatiles under reduced pressure, the residue was purified by silica gel column (hexane:EA, 9:1) to afford the title compound (200 mg, 54% over 2 steps) as a colorless oil. MS: 303.1 (M+H$^+$).

Example 70

Synthesis of Intermediate D5: S-((5-(((tert-butyldimethylsilyl)oxy)methyl)-4-methyloxazol-2-yl)methyl) ethanethioate

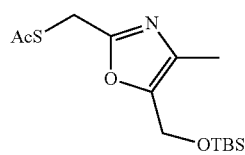

Step A: (4-Methyloxazol-5-yl)methanol

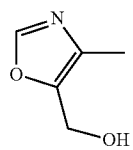

Under Ar, to a solution of methyl 4-methyloxazole-5-carboxylate (3.0 g, 21.26 mmol) in dry THF (20 mL) was added LiAlH$_4$ (0.807 g, 21.26 mmol) slowly at 0° C., the reaction mixture was stirred for 1 h. H$_2$O (0.8 mL) was added slowly, 15% NaOH (0.8 mL) and H$_2$O (0.8 mL) were followed subsequently. The resulting mixture was stirred for 40 min at room temperature, and filtrated off through celite. The filtrate was concentrated under reduced pressure to give the crude title compound (1.9 g) as a colorless oil, which was directly used without purification. MS: 113.9 (M+H$^+$).

Step B: 5-(((tert-Butyldimethylsilyl)oxy)methyl)-4-methyloxazole

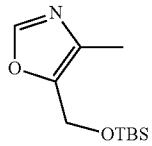

Under Ar, to a solution of the crude (4-methyloxazol-5-yl)methanol (Step A, 3.0 g) in dry DCM (20 mL) was added imidazole (1.81 g, 26.5 mmol) and TBSCl (4.00 g, 26.5 mmol) at 0° C., then the reaction mixture was stirred for overnight at room temperature. Water was added and the resulting mixture was extracted with DCM 3 times, the combined DCM layer was washed with brine, dried over $Na_2SO_4$, and concentrated under reduced pressure to give a yellow oil, which was purified by silica gel column (hexane: EA, 6:1) to afford the title compound (5.3 g, 88% over 2 steps) as a colorless oil. $^1$H NMR (500 MHz, DMSO-$d_6$) δ 8.20 (s, 1H), 4.65 (s, 2H), 2.09 (s, 3H), 0.85 (s, 9H), 0.05 (s, 6H). MS: 228.6 (M+H$^+$).

Step C: 5-(((tert-Butyldimethylsilyl)oxy)methyl)-4-methyloxazole-2-carbaldehyde

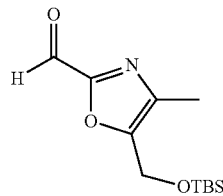 [SMILES: Cc1nc(C=O)oc1CO[Si](C)(C)C(C)(C)C]

Under Ar, to a solution of 5-(((tert-butyldimethylsilyl)oxy)methyl)-4-methyloxazole (Step B, 2.0 g, 8.80 mmol, 1.00) in dry THF (20 mL) was added nBuLi (0.620 g, 9.68 mmol) slowly at −78° C., the mixture was stirred for 1 hr at −78° C., then dry DMF (1.26 g, 17.3 mmol) was added to the mixture, and the reaction mixture was allowed to warm up to room temperature and stirred for overnight. Water was added and the resulting mixture was extracted with EA 3 times, the combined organic layer was washed with brine, dried over $Na_2SO_4$, and concentrated under reduced pressure to give a yellow oil, which was purified by silica gel column (hexane:EA, 4:1) to afford the title compound (1.3 g, 58%) as a colorless oil. $^1$H NMR (500 MHz, DMSO-$d_6$) δ 9.62 (s, 1H), 4.77 (s, 2H), 2.23 (s, 3H), 0.86 (s, 9H), 0.08 (s, 6H). MS: 256.5 (M+H$^+$).

Step D: (5-(((tert-Butyldimethylsilyl)oxy)methyl)-4-methyloxazol-2-yl)methanol

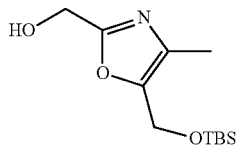 [SMILES: Cc1nc(CO)oc1CO[Si](C)(C)C(C)(C)C]

To a solution of 5-(((tert-butyldimethylsilyl)oxy)methyl)-4-methyloxazole-2-carbaldehyde (Step C, 1.3 g, 5.09 mmol) in THF was added $NaBH_4$ (0.231 g, 6.11 mmol) at 0° C., then the reaction mixture was stirred for 30 min at room temperature. Water was added and the resulting mixture was extracted with EA 3 times, the combined EA layer was washed with brine, dried over $Na_2SO_4$, and concentrated under reduced pressure to give the crude title compound (1.295 g) as a light yellow oil, which was directly used without purification. $^1$H NMR (500 MHz, DMSO-$d_6$) δ 5.60 (t, J=6.2 Hz, 1H), 4.62 (s, 2H), 4.41 (d, J=6.2 Hz, 2H), 2.06 (s, 3H), 0.85 (s, 9H), 0.05 (s, 6H). MS: 258.5 (M+H$^+$).

Step E: 2-(Bromomethyl)-5-(((tert-butyldimethylsilyl)oxy)methyl)-4-methyloxazole

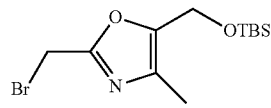

Under Ar, to a solution of the crude (5-(((tert-butyldimethylsilyl)oxy)methyl)-4-methyloxazol-2-yl)methanol (Step D, 250 mg, 0.971 mmol) and $Ph_3P$ (509 mg, 1.942 mmol) in dry DCM (10 mL) was added $CBr_4$ (644 mg, 1.942 mmol) at room temperature, and the reaction mixture was stirred for 2 h. After removal of volatiles under reduced pressure, the residue was purified by silica gel column (hexane:EA, 4:1) to afford the title compound (270 mg, 87% over 2 steps) as a yellow oil. MS: 321.6 (M+H$^+$).

Step F: S-((5-(((tert-butyldimethylsilyl)oxy)methyl)-4-methyloxazol-2-yl)methyl) ethanethioate (Intermediate D5)

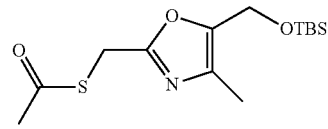 [SMILES: CC(=O)SCc1nc(C)c(CO[Si](C)(C)C(C)(C)C)o1]

Under Ar, a mixture of 2-(bromomethyl)-5-(((tert-butyldimethylsilyl)oxy)methyl)-4-methyloxazole (Step E, 270 mg, 0.843 mmol) and KSAc (193 mg, 1.686 mmol) in dry THF (10 mL) was stirred at 50° C. for 1 h. After cooling down to room temperature, the mixture was filtered off and the filtrate was concentrated under reduced pressure to afford the crude title compound (266 mg) as a brown oil, which was used in next step directly without purification. MS: 316.3 (M+H$^+$).

Example 71

Synthesis of Intermediate D6: 4-(((tert-Butyldimethylsilyl)oxy)methyl)-2-(chloromethyl)-5-methyloxazole

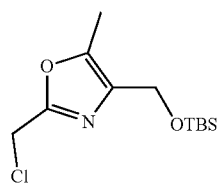 [SMILES: Cc1oc(CCl)nc1CO[Si](C)(C)C(C)(C)C]

Step A: (2-(Chloromethyl)-5-methyloxazol-4-yl)methanol

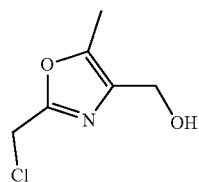

To a solution of methyl 2-(chloromethyl)-5-methyloxazole-4-carboxylate (5.6 g, 29.5 mmol) in THF (30 mL) was added LiBH$_4$ (0.643 g, 29.5 mmol) at −10° C., the resulting mixture was slowly warmed up to room temperature and stirred for overnight. Aq. NaHCO$_3$ was added to quench the reaction and the resulting mixture was extracted with EA twice. The combined EA layer was dried over Na$_2$SO$_4$, and concentrated under reduced pressure to give a yellow oil, which was purified by silica gel column (hexane:EA, 5:1→0:1) to afford the title compound (560 mg, 12%) as a colorless oil. MS: 161.97, 163.99 (M+H$^+$).

Step B: 4-(((tert-Butyldimethylsilyl)oxy)methyl)-2-(chloromethyl)-5-methyloxazole (Intermediate D6)

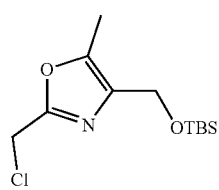 [SMILES: Cc1oc(CCl)nc1CO[Si](C)(C)C(C)(C)C]

Under Ar, to a solution of (2-(chloromethyl)-5-methyloxazol-4-yl)methanol (Step A, 560 mg, 3.47 mmol) in dry DCM (10 mL) was added imidazole (354 mg, 5.20 mmol) at 0° C., followed by TBSCl (627 mg, 4.16 mmol), the reaction mixture was stirred at 0° C. for 30 min. Water was added, and the resulting mixture was extracted with DCM twice. The combined DCM layer was washed with brine, dried over Na$_2$SO$_4$, and concentrated under reduced pressure to give a yellow oil, which was purified by silica gel column (hexane:EA, 5:1) to afford the title compound (492 mg, 52%) as a colorless oil. MS: 276.0 (M+H$^+$).

Example 72

Synthesis of Intermediate D7: 3-(Bromomethyl)-5-(((tetrahydro-2H-pyran-2-yl)oxy)methyl)isoxazole

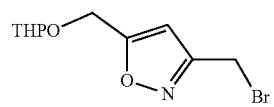

Step A: Ethyl 5-(hydroxymethyl)isoxazole-3-carboxylate

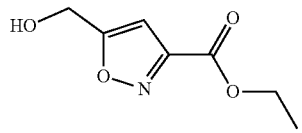

To a solution of prop-2-yn-1-ol (1 g, 17.84 mmol), ethyl 2-nitroacetate (4.75 g, 35.7 mmol) in EtOH (25 mL) in an Ace pressure tube was added DABCO (0.200 g, 1.784 mmol). The reaction was stirred at 80° C. for 20 h. After cooling down to room temperature and removal of volatiles under reduced pressure, the residue was purified by silica gel column (hexane:EA, 1:1) to afford the title compound (3.3 g, quantitatively) as a yellow oil. $^1$H NMR (500 MHz, CDCl$_3$): δ 6.67 (s, 1H), 4.82 (s, 2H), 4.45-4.41 (q, J=7.0 Hz, 2H), 1.41 (t, J=7.0 Hz, 3H).

Step B: Ethyl 5-(((tetrahydro-2H-pyran-2-yl)oxy)methyl)isoxazole-3-carboxylate

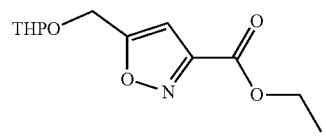

Under Ar, a mixture of ethyl 5-(hydroxymethyl)isoxazole-3-carboxylate (Step A, 1.5 g, 8.76 mmol), TsOH·H$_2$O (0.167 g, 0.876 mmol), and 3,4-dihydro-2H-pyran (1.106 g, 13.15 mmol) in dry THF (25 mL) was stirred at 45° C. for 3 h. After removal of volatiles under reduced pressure, the residue was purified by silica gel column (hexane:EA, 3:1) to afford the crude title compound (2.6 g) as a colorless oil, which was used for the next step without further purification. MS: 256.6 (M+H$^+$).

Step C: (5-(((Tetrahydro-2H-pyran-2-yl)oxy)methyl)isoxazol-3-yl)methanol

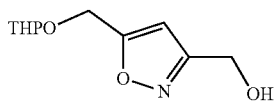

The crude ethyl 5-(((tetrahydro-2H-pyran-2-yl)oxy)methyl)isoxazole-3-carboxylate (Step B, 2.6 g) was dissolved into EtOH, and NaBH₄ (0.385 g, 10.19 mmol) was then added. The mixture was stirred at 50° C. for overnight. After cooling down to room temperature, water was added and the resulting mixture was extracted with EA twice. The combined EA layer was washed with brine, dried over Na₂SO₄, and concentrated under reduced pressure to give a yellow oil, which was purified by silica gel column (DCM:MeOH, 20:1) to afford the title compound (1.5 g, 69% over 2 steps) as a colorless oil. MS: 214.48 (M+H⁺).

Step D: 3-(Bromomethyl)-5-(((tetrahydro-2H-pyran-2-yl)oxy)methyl)isoxazole (Intermediate D7)

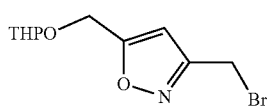

Under Ar, to a solution of (5-(((tetrahydro-2H-pyran-2-yl)oxy)methyl)isoxazol-3-yl)methanol (Step C, 700 mg, 3.28 mmol) in dry DCM (20 mL) was added Ph₃P (1292 mg, 4.92 mmol) at 0° C., followed by CBr₄ (1633 mg, 4.92 mmol). The reaction mixture was stirred at 0° C. for 2 h. After removal of volatiles under reduced pressure, the residue was purified by silica gel column (hexane:EA, 3:2) to afford the title compound (647 mg, 71%) as a colorless oil. MS: 276.1, 277.9 (M+H⁺).

Example 73

Synthesis of Intermediate D8: S-((2-(((tert-butyldimethylsilyl)oxy)methyl)thiazol-4-yl)methyl) ethanethioate

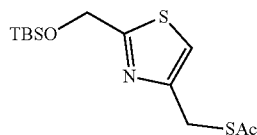

Essentially the same protocol of preparation of Intermediate D4 was used to afford the intermediate (7.3 g) as a light yellow oil. MS: 317.6 (M+H⁺).

Example 74

Synthesis of Intermediate D9: 2-(Bromomethyl)-5-(((tert-butyldimethylsilyl)oxy)methyl)thiazole

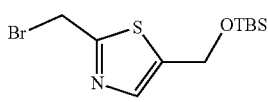 [SMILES: CC(C)(C)[Si](C)(C)OCc1cnc(CBr)s1]

Under Ar, to a solution of (5-(((tert-butyldimethylsilyl)oxy)methyl)thiazol-2-yl)methanol (800 mg, 3.08 mmol) in dry DCM (10 mL) was added triphenylphosphane (1618 mg, 6.17 mmol), followed by CBr₄ (2.05 g, 6.17 mmol), the reaction mixture was stirred at room temperature for 2 h. After removal of volatiles under reduced pressure, the residue was purified by silica gel column (EA) to afford the title compound (406 mg, 41%) as a yellow oil. ¹H NMR (500 MHz, DMSO-d₆) δ 7.64 (s, 1H), 4.98 (s, 2H), 4.89 (s, 2H), 0.87 (s, 9H), 0.08 (s, 6H). MS: 323.5 (M+H⁺).

Example 75

Synthesis of Intermediate D10: 2-(Bromomethyl)-5-(((tert-butyldimethylsilyl)oxy)methyl)-4-methylthiazole

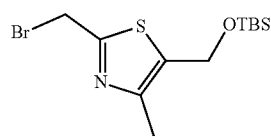

Under Ar, to a solution of (5-(((tert-butyldimethylsilyl)oxy)methyl)-4-methylthiazol-2-yl)methanol (400 mg, 1.463 mmol) in dry DCM (10 mL) was added triphenylphosphane (767 mg, 2.93 mmol), followed by CBr₄ (970 mg, 2.93 mmol), the reaction mixture was stirred at room temperature for 2 h. After removal of volatiles under reduced pressure, the residue was purified by silica gel column (EA) to afford the title compound (330 mg, 67%) as a colorless oil. ¹H NMR (500 MHz, DMSO-d₆): δ 4.92 (s, 2H), 4.81 (s, 2H), 2.26 (s, 3H), 0.88 (s, 9H), 0.08 (s, 6H). MS: 336.08, 338.06 (M+H⁺).

Example 76

Synthesis of Intermediate D11: S-((5-(((tert-butyldimethylsilyl)oxy)methyl)-1-methyl-1H-1,2,4-triazol-3-yl)methyl) ethanethioate

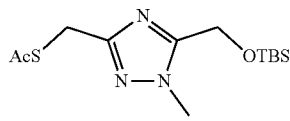

Step A: (4-Amino-4H-1,2,4-triazole-3,5-diyl)dimethanol

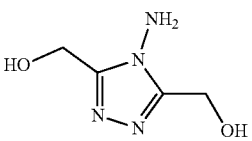

The mixture of 2-hydroxyacetic acid (20 g, 263 mmol) and hydrazine solution in water (8.43 g, 263 mmol) was stirred for 1 h at 160° C. with the microwave assistance. After cooling down to room temperature and removal of volatiles under reduced pressure, EtOH (10 mL) was added to the mixture, and the formed precipitate was collected to give the crude title compound (2.0 g) as a white solid, which was directly used without purification. MS: 144.9 (M+H⁺)

Step B: (4H-1,2,4-triazole-3,5-diyl)dimethanol

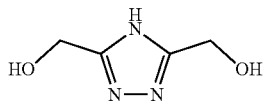

To a solution of the crude (4-amino-4H-1,2,4-triazole-3,5-diyl)dimethanol (Step A, 4 g) in water was added conc. HCl (2 mL) at 0° C., and a solution of sodium nitrite (1.915 g, 27.8 mmol) in water (10 mL) was added. The reaction mixture was warmed up to room temperature and stirred for 1 h. After removal of volatiles under reduced pressure, the crude title compound was directly used without purification. MS: 129.9 (M+H$^+$).

Step C: (1-Methyl-1H-1,2,4-triazole-3,5-diyl)dimethanol

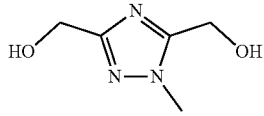

To a solution of the crude (4H-1,2,4-triazole-3,5-diyl)dimethanol (Step B, 3.58 g) in MeOH was added KOH (2.1 g, 36.1 mmol), the mixture was stirred for 1 h at room temperature, then MeI (4.33 g, 30.5 mmol) was added to the mixture. The reaction mixture was stirred at 65° C. for overnight. After removal of volatiles under reduced pressure, the crude title compound was directly used without purification. MS: 144.0 (M+H$^+$).

Step D: 3,5-Bis(((tert-butyldimethylsilyl)oxy)methyl)-1-methyl-1H-1,2,4-triazole

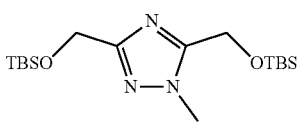 [SMILES: Cn1nc(CO[Si](C)(C)C(C)(C)C)nc1CO[Si](C)(C)C(C)(C)C]

Under Ar, to a solution of the crude (1-methyl-1H-1,2,4-triazole-3,5-diyl)dimethanol (Step C, 3.97 g) in dry DMF was added imidazole (1.89 g, 27.7 mmol) and TBSCl (4.18 g, 27.7 mmol); the reaction mixture was stirred at room temperature for 5 h. Water was added to the mixture, and the resulting mixture was extracted with EA 3 times, the combine EA layer was washed with brine, dried over Na$_2$SO$_4$, and concentrated to give a yellow oil, which was purified by silica gel column (hexane:EA, 3:1) to afford the title compound (3.0 g, 29% over 4 steps). $^1$H NMR (500 MHz, DMSO-d$_6$) δ 4.77 (s, 2H), 4.55 (s, 2H), 3.81 (s, 3H), 0.85 (s, 18H), 0.06 (s, 12H). MS: 372.8 (M+H$^+$).

Step E: (5-(((tert-Butyldimethylsilyl)oxy)methyl)-1-methyl-1H-1,2,4-triazol-3-yl)methanol

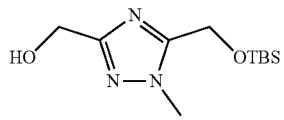 [SMILES: Cn1nc(CO)nc1CO[Si](C)(C)C(C)(C)C]

Under Ar, to a solution of 3,5-bis(((tert-butyldimethylsilyl)oxy)methyl)-1-methyl-1H-1,2,4-triazole (Step D, 1.0 g, 2.69 mmol) in dry THF was added TBAF-3H$_2$O (0.070 g, 0.269 mmol) and the reaction mixture was stirred for 2 h at room temperature. Water was added to the mixture, and the resulting mixture was extracted with EA 3 times, the combine EA layer was washed with brine, dried over Na$_2$SO$_4$, and concentrated under reduced pressure to a yellow oil, which was purified by silica gel column (hexane:EA, 1:1) to afford the title compound (300 mg, 43%) as a white solid. $^1$H NMR (500 MHz, DMSO-d$_6$) δ 5.56 (t, J=5.9 Hz, 1H), 4.55 (d, J=5.9 Hz, 2H), 4.54 (s, 2H), 3.81 (s, 3H), 0.86 (s, 9H), 0.06 (s, 6H). MS: 258.2 (M+H$^+$).

Step F: 3-(Bromomethyl)-5-(((tert-butyldimethylsilyl)oxy)methyl)-1-methyl-1H-1,2,4-triazole

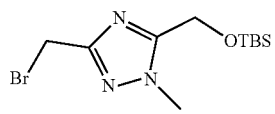 [SMILES: Cn1nc(CBr)nc1CO[Si](C)(C)C(C)(C)C]

Under Ar, to a solution of (5-(((tert-butyldimethylsilyl)oxy)methyl)-1-methyl-1H-1,2,4-triazol-3-yl)methanol (Step E, 200 mg, 0.777 mmol) and Ph$_3$P (408 mg, 1.554 mmol, 2) in dry CH$_2$Cl$_2$ (10 mL) was added CBr$_4$ (515 mg, 1.554 mmol), and the reaction mixture was stirred for 2 h. After removal of volatiles under reduced pressure, the residue was purified by silica gel column (hexane:EA, 4:1) to afford the title compound (240 mg, 96%) as a yellow oil. MS: 321.52 (M+H$^+$).

Step G: S-((5-(((tert-Butyldimethylsilyl)oxy)methyl)-1-methyl-1H-1,2,4-triazol-3-yl)methyl) ethanethioate (Intermediate D11)

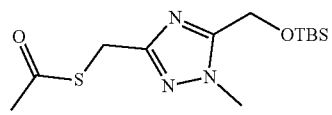 [SMILES: CC(=O)SCc1nc(CO[Si](C)(C)C(C)(C)C)n(C)n1]

Under Ar, the mixture of 3-(bromomethyl)-5-(((tert-butyldimethylsilyl)oxy)methyl)-1-methyl-1H-1,2,4-triazole (Step F, 240 mg, 0.749 mmol) and KSAc (171 mg, 1.499 mmol) in dry THF (10 mL) was stirred at 50° C. for 1 h. The mixture was filtered off and the filtrate was concentrated under reduced pressure to give the crude title compound as a brown oil, which was used in next step directly without purification. MS: 316.3 (M+H$^+$).

Example 77

Synthesis of Intermediates D12 and D13: S-(4-(((tert-butyldimethylsilyl)oxy)methyl)-2-methylbenzyl) ethanethioate and S-(4-(((tert-butyldimethylsilyl)oxy)methyl)-3-methylbenzyl) ethanethioate

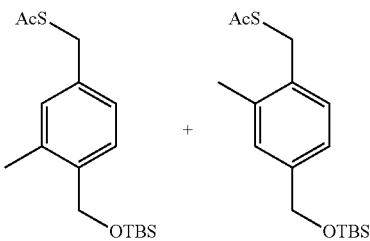

Step A: (((2-Methyl-1,4-phenylene)bis(methylene))bis(oxy))bis(tert-butyldimethylsilane)

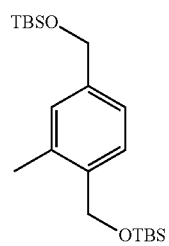 [SMILES: Cc1cc(CO[Si](C)(C)C(C)(C)C)ccc1CO[Si](C)(C)C(C)(C)C]

Under Ar, to a solution of dimethyl 2-methylterephthalate (2.0 g, 9.61 mmol) in dry THF (20 mL) was added LiAlH$_4$ (0.547 g, 14.41 mmol) slowly at 0° C., the reaction mixture was stirred for 2 h. H$_2$O (2 mL) was added slowly to quench the reaction. 15% NaOH (2 mL) and H$_2$O (6 mL) were followed. The mixture was stirred for 40 min at room temperature and then filtrated off through celite, the filtrate was concentrated under reduced pressure to give the crude product (1.11 g) as a colorless oil, which was directly used without purification.

Under Ar, to a solution of the above oil (1.11 g) in dry DCM (20 mL) was added imidazole (2.98 g, 43.8 mmol) and TBSCl (5.50 g, 36.5 mmol) at 0° C., the reaction mixture was stirred for 1 h at room temperature. Water was added and the mixture was extracted with DCM 3 times, the combined DCM layer was washed with brine, dried over Na$_2$SO$_4$, and concentrated under reduced pressure to give a light yellow oil, which was purified by silica gel column (hexane:EA, 10:1) to afford the title compound (2.78 g, 76% over 2 steps) as a colorless oil. MS: 381.9 (M+H$^+$).

Step B: (4-(((tert-Butyldimethylsilyl)oxy)methyl)-3-methylphenyl)methanol and (4-(((tert-butyldimethylsilyl)oxy)methyl)-2-methylphenyl)methanol

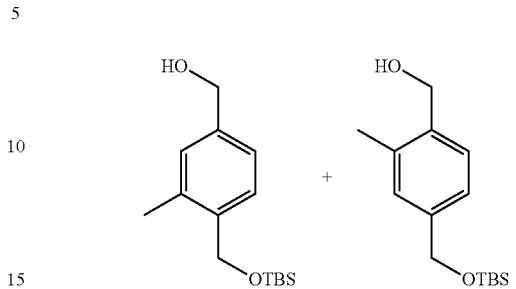

Under Ar, to a solution of (((2-methyl-1,4-phenylene)bis(methylene))bis(oxy))bis(tert-butyldimethylsilane) (1.5 g, 3.94 mmol) in dry THF (15 mL) was added TBAF·3H$_2$O (0.21 g, 0.79 mmol) at 0° C., the reaction mixture was stirred for 30 min. Water was added and the mixture was extracted with EA 3 times, the combined EA layer was washed with brine, dried over Na$_2$SO$_4$, and concentrated under reduced pressure to give a yellow oil, which was purified by silica gel column (hexane:EA, 4:1) to afford the title compounds (410 mg, 39%) as a white solid and an inseparable mixture. MS: 267.3 (M+H$^+$).

Step C: S-(4-(((tert-butyldimethylsilyl)oxy)methyl)-2-methylbenzyl) ethanethioate and S-(4-(((tert-butyldimethylsilyl)oxy)methyl)-3-methylbenzyl) ethanethioate (Intermediates D12 and D13)

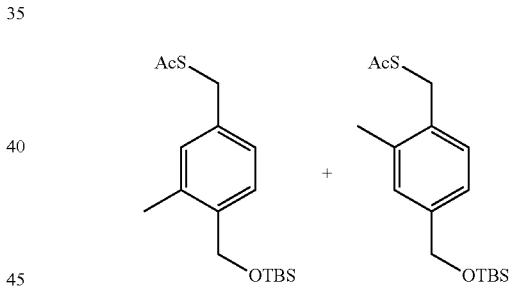

Under Ar, to a solution of the mixture of (4-(((tert-butyldimethylsilyl)oxy)methyl)-3-methylphenyl)methanol and (4-(((tert-butyldimethylsilyl)oxy)methyl)-2-methylphenyl)methanol (408 mg, 1.531 mmol) in dry DCM (15 mL) was added triethylamine (232 mg, 2.297 mmol) and MsCl (263 mg, 2.297 mmol) at 0° C., the reaction mixture was stirred for 30 min. Water was added and the mixture was extracted with DCM 3 times, the combined DCM layer was washed with brine, dried over Na$_2$SO$_4$, und concentrated under reduced pressure to give the crude product (632 mg) as a yellow oil, which was directly used without purification. Under Ar, the mixture of the above yellow oil (528 mg) and KSAc (350 mg, 3.06 mmol) was dissolved into dry THF (10 mL) and the reaction mixture was stirred at 60° C. for 1 h. After cooling down to room temperature, the resulting mixture was filtered off and the filtrate was concentrated under reduced pressure to give a yellow oil, which was purified by silica gel column (hexane:EA, 5:1) to afford the title compounds (409 mg, 82%) as a yellow oil and an inseparable mixture. MS: 347.2 (M+Na$^+$).

Example 78

Synthesis of Intermediates D14 and D15: S-((6-(((tert-butyldimethylsilyl)oxy)methyl)pyridin-3-yl)methyl) ethanethioate and S-((6-(((tert-butyldimethylsilyl)oxy)methyl)pyridin-3-yl)methyl) ethanethioate

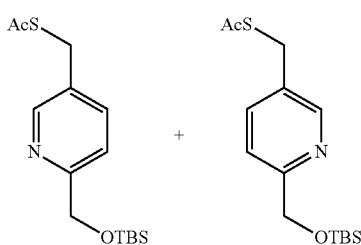

Essentially the same protocol of preparation of Intermediates D12 and D13 was used to afford the intermediate (345 mg) as a colorless oil and an inseparable mixture. MS: 312.6 (M+H$^+$).

Example 79

Synthesis of Intermediate D16: Sodium (5-(((tert-butyldimethylsilyl)oxy)methyl)-1-methyl-1H-pyrazol-3-yl)methanesulfinate

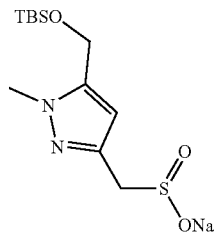

Step A: 2-(((5-(((tert-Butyldimethylsilyl)oxy)methyl)-1-methyl-1H-pyrazol-3-yl)-methyl)thio)pyrimidine

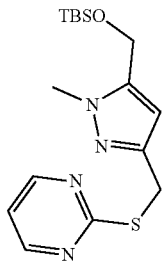 [SMILES: Cn1nc(CSc2ncccn2)cc1CO[Si](C)(C)C(C)(C)C]

Under Ar, to a stirred solution of (5-(((tert-butyldimethylsilyl)oxy)methyl)-1-methyl-1H-pyrazol-3-yl)methanol (200 mg, 0.87 mmol), pyrimidine-2-thiol (117 mg, 1.05 mmol) and PPh$_3$ (458 mg, 1.74 mmol) in dry THF (5.0 mL) was added DIAD (265 mg, 1.31 mmol) dropwise at 0° C.; the reaction mixture was stirred at room temperature for 16 h. The mixture was quenched by aq. NaHCO$_3$ and extracted by EA, the organic phase was washed three times by H$_2$O, dried over by Na$_2$SO$_4$, and concentrated under reduced pressure to give a yellow oil, which was purified by silica gel column (EtOAc:Hexane, 1:5→1:3) to afford title compound (300 mg, 88%) as white solid. MS: 352.3 (M+H$^+$).

Step B: 2-(((5-(((tert-Butyldimethylsilyl)oxy)methyl)-1-methyl-1H-pyrazol-3-yl)methyl)sulfonyl)pyrimidine

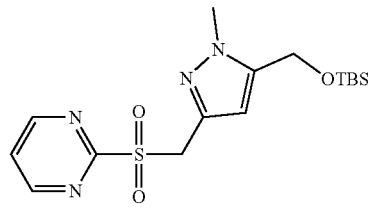 [SMILES: Cn1nc(CS(=O)(=O)c2ncccn2)cc1CO[Si](C)(C)C(C)(C)C]

To a stirred solution of 2-(((5-(((tert-butyldimethylsilyl)oxy)methyl)-1-methyl-1H-pyrazol-3-yl)methyl)thio)pyrimidine (Step A, 250 mg, 0.713 mmol) in a mixed solution of EtOAc, MeOH and H$_2$O (6 mL:3 mL:1 mL) was added Na$_2$WO$_4$ (42 mg, 0.143 mmol) and H$_2$O$_2$(0.4 mL, 30% wt in H$_2$O) at 0° C. The reaction was stirred at 0° C. for 0.5 h, then heated to 50° C. for overnight. After cooling down to room temperature, the reaction mixture was quenched by aq. Na$_2$S$_2$O$_3$ and extracted by EA, the organic phase was washed by brine, dried over by Na$_2$SO$_4$, and concentrated under reduced pressure to give a light yellow oil, which was purified by silica gel column (EtOAc:hexane, 1:4→1:0) to afford the title compound (200 mg, 73% yield) as a white wax. MS: 383.7 (M+H$^+$).

Step C: Sodium (5-(((tert-butyldimethylsilyl)oxy)methyl)-1-methyl-1H-pyrazol-3-yl)methanesulfinate (Intermediate D16)

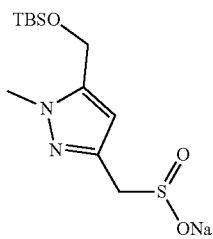

Under Ar, to a stirred solution of 2-(((5-(((tert-butyldimethylsilyl)oxy)methyl)-1-methyl-1H-pyrazol-3-yl)methyl)sulfonyl)pyrimidine (42 mg, 0.11 mmol) in MeOH (2.0 mL) was added MeONa (12 mg, 0.22 mmol) at room temperature; the mixture was stirred further for 0.5 h. After removal of volatiles under reduced pressure, the crude title compound was used for the next step without purification. MS: 327.1 (M+H$^+$).

Example 80

Synthesis of Intermediate E1: Ethyl 6-chloro-7-(2-(hydroxymethyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate

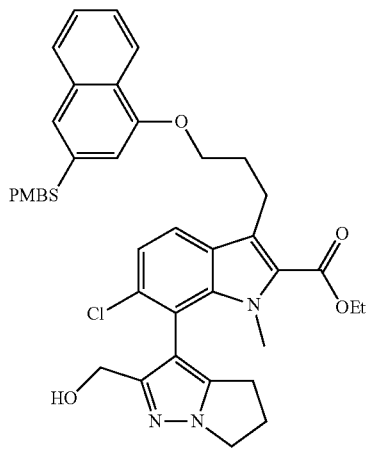

Step A: Ethyl 7-bromo-6-chloro-3-(3-((3-((4-methoxybenzyl)thio)naphthalen-1-yl)oxy)propyl)-1H-indole-2-carboxylate

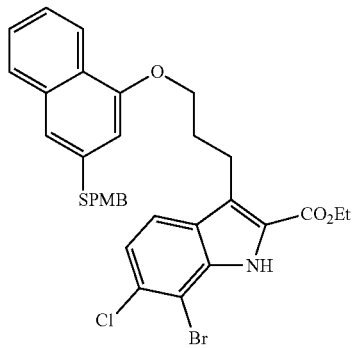

Under Ar, to a solution of 3-((4-methoxybenzyl)thio)naphthalen-1-ol (Intermediate A1, 10 g, 33.7 mmol) in acetone (250 mL) was added ethyl 7-bromo-3-(3-bromopropyl)-6-chloro-1H-indole-2-carboxylate (Intermediate B, 14.29 g, 33.7 mmol) and $K_2CO_3$ (13.99 g, 101 mmol), then the reaction mixture was heated to reflux for overnight. After cooling down to room temperature and removal of volatiles under reduced pressure, the residue was treated with acetone and water, the resulting mixture was stirred at room temperature for 30 min, the formed precipitate was collected by filtration to afford the title compound (18 g, 83%) as a white solid. $^1$H NMR (500 MHz, DMSO-$d_6$) δ 8.04 (d, J=8.3 Hz, 1H), 7.77 (d, J=8.2 Hz, 1H), 7.64 (d, J=8.4 Hz, 1H), 7.52 (t, J=7.5 Hz, 1H), 7.43 (dd, J=14.2, 6.7 Hz, 2H), 7.32 (t, J=11.2 Hz, 2H), 7.05 (d, J=8.4 Hz, 1H), 6.84 (d, J=8.3 Hz, 2H), 6.77 (s, 1H), 4.33-4.22 (m, 4H), 4.15 (t, J=5.9 Hz, 2H), 3.73 (s, 3H), 3.30 (t, J=7.2 Hz, 2H), 2.25-2.14 (m, 2H), 1.37 (t, J=7.5 Hz, 3H).

Step B: Ethyl 6-chloro-3-(3-((3-((4-methoxybenzyl)thio)naphthalen-1-yl)oxy)propyl)-7-(2-(((tetrahydro-2H-pyran-2-yl)oxy)methyl)-5,6-dihydro-4H-pyrrolo[1,2-b]pyrazol-3-yl)-1H-indole-2-carboxylate

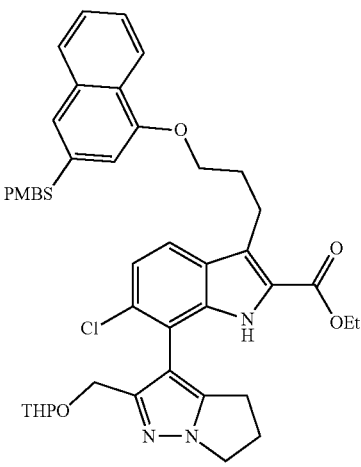

Under Ar, to a solution of ethyl 7-bromo-6-chloro-3-(3-((3-((4-methoxybenzyl)thio)naphthalen-1-yl)oxy)propyl)-1H-indole-2-carboxylate (Step A, 3.0 g, 4.69 mmol) in a mixed solution of dioxane (14 mL) and $H_2O$ (1 mL) was added 2-(((tetrahydro-2H-pyran-2-yl)oxy)methyl)-3-(4,4,5,5-tetramethyl-1,3,2-dioxaborolan-2-yl)-5,6-dihydro-4H-pyrrolo[1,2-b]pyrazole (Intermediate C1, 2.452 g, 7.04 mmol), Pd(PPh$_3$)$_4$ (1.085 g, 0.94 mmol) and $K_2CO_3$ (3.89 g, 28.2 mmol), then the reaction mixture was heated to 110° C. with microwave assistance for 1 h. After cooling down to room temperature and removal of volatiles under reduced pressure, the residue was purified by silica gel column (hexane:EA, 1:1) to afford the title compound (3.8 g, 83%) as a yellow foam. MS: 780.3 (M+H$^+$); 802.3 (M+Na$^+$).

Step C: Ethyl 6-chloro-3-(3-((3-((4-methoxybenzyl)thio)naphthalen-1-yl)oxy)propyl)-1-methyl-7-(2-(((tetrahydro-2H-pyran-2-yl)oxy)methyl)-5,6-dihydro-4H-pyrrolo[1,2-b]pyrazol-3-yl)-1H-indole-2-carboxylate

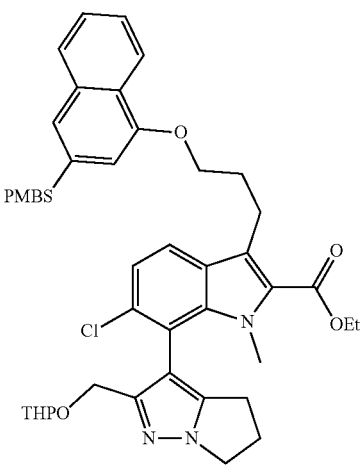

Under Ar, to a solution of ethyl 6-chloro-7-(2-((cyclohexyloxy)methyl)-5,6-dihydro-4H-pyrrolo[1,2-b]pyrazol-3-yl)-3-(3-((3-((4-methoxybenzyl)thio)naphthalen-1-yl)oxy)propyl)-1H-indole-2-carboxylate (Step B, 2 g, 2.56 mmol) in dry DMF (20 mL) was added NaH (92 mg, 3.84 mmol) and MeI (546 mg, 3.84 mmol) at 0° C., then the reaction mixture was stirred for 1 h at 0° C. Water was added to quench the reaction, and the resulting mixture was extracted with DCM twice. The combined DCM layer was washed with brine, dried over $Na_2SO_4$, and concentrated under reduced pressure to give a yellow oil, which was purified by silica gel column (DCM:EA, 3:1) to afford the title compound (1.88 g, 92%) as a yellow oil. MS: 794.3 ($M+H^+$).

Step D: ethyl 6-chloro-7-(2-(hydroxymethyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate (Intermediate E1)

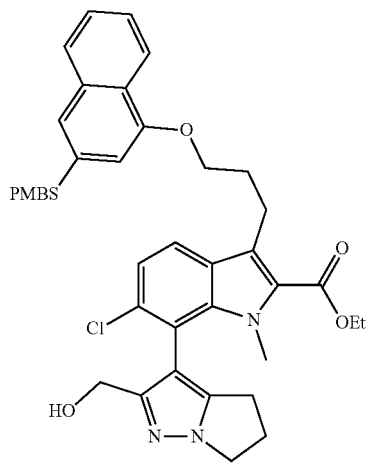

Under Ar, to a solution of ethyl 6-chloro-7-(2-((cyclohexyloxy)methyl)-5,6-dihydro-4H-pyrrolo[1,2-b]pyrazol-3-yl)-3-(3-((3-((4-methoxybenzyl)thio)naphthalen-1-yl)oxy)propyl)-1-methyl-1H-indole-2-carboxylate (Step C, 2.0 g, 2.52 mmol) in dry MeOH (25 mL) and dry DCM (2 mL) was added TsOH·$H_2O$ (48 mg, 0.252 mmol), then the reaction solution was stirred at room temperature for overnight. After removal of volatiles under reduced pressure, the residue was purified by silica gel column (EA) to afford the title compound (840 mg, 47%) as a yellow foam. MS: 710.3 ($M+H^+$).

Example 81

Synthesis of Intermediate E2: Ethyl 6-chloro-7-(6-(hydroxymethyl)-2,3-dihydropyrazolo[5,1-b]oxazol-7-yl)-3-(3-((3-((4-methoxybenzyl)thio)naphthalen-1-yl)oxy)propyl)-1-methyl-1H-indole-2-carboxylate

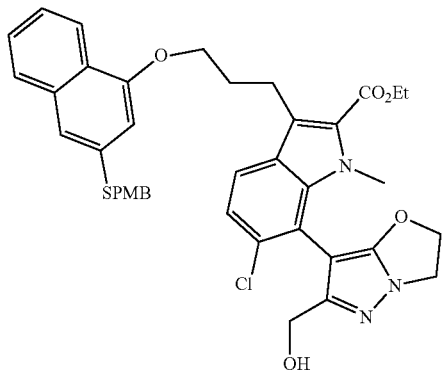

Essentially the same protocol of preparation of Intermediate E1 was used to afford the intermediate (250 mg) as a yellow oil. MS:712.3, 714.1 ($M+H^+$), 734.2 ($M+Na^+$).

Example 82

Synthesis of Intermediate E3: Ethyl 6-chloro-7-(2-(hydroxymethyl)-4,5,6,7-tetrahydropyrazolo[1,5-a]pyridin-3-yl)-3-(3-((3-((4-methoxybenzyl)thio)naphthalen-1-yl)oxy)propyl)-1-methyl-1H-indole-2-carboxylate

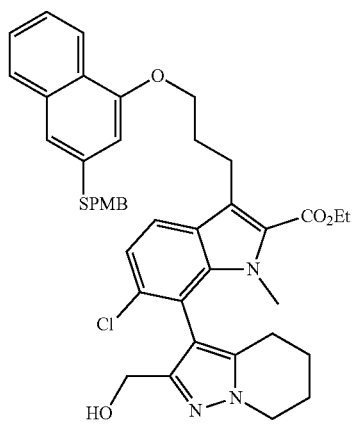

Essentially the same protocol of preparation of Intermediate E1 was used to afford the intermediate (410 mg) as a white foam. MS: 725.6 ($M+H^+$).

Example 83

Synthesis of Intermediate E4: Ethyl 6-chloro-7-(2-(hydroxymethyl)-6,7-dihydro-4H-pyrazolo[5,1-c][1,4]oxazin-3-yl)-3-(3-((3-((4-methoxybenzyl)thio)naphthalen-1-yl)oxy)propyl)-1-methyl-1H-indole-2-carboxylate

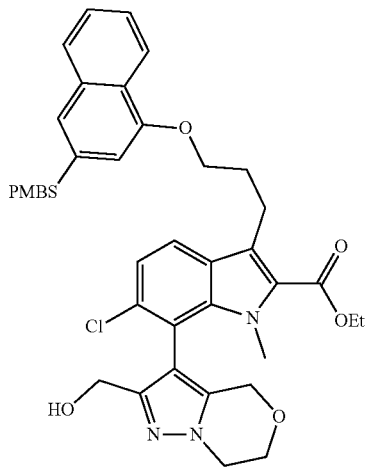

Essentially the same protocol of preparation of Intermediate E1 was used to afford the intermediate (630 mg) as a yellow foam. MS: 726.2 (M+H$^+$).

Example 84

Synthesis of Intermediate E5: Ethyl 6-chloro-7-(2-(hydroxymethyl)-6,7-dihydro-4H-pyrazolo[5,1-c][1,4]thiazin-3-yl)-3-(3-((3-((4-methoxybenzyl)thio)naphthalen-1-yl)oxy)propyl)-1-methyl-1H-indole-2-carboxylate

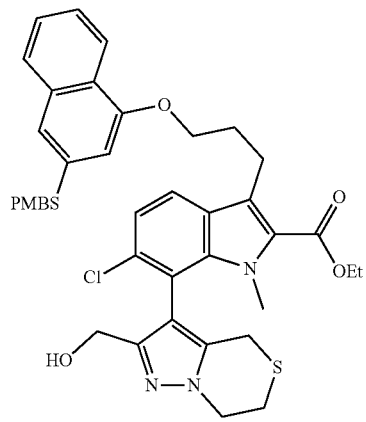

Essentially the same protocol of preparation of Intermediate E1 was used to afford the intermediate (210 mg) as a white solid. MS: 742.3 (M+H$^+$).

Example 85

Synthesis of Intermediate E6: Ethyl 6-chloro-7-(2-(hydroxymethyl)-6,7-dihydro-5H-pyrazolo[5,1-b][1,3]oxazin-3-yl)-3-(3-((3-((4-methoxybenzyl)thio)naphthalen-1-yl)oxy)propyl)-1-methyl-1H-indole-2-carboxylate

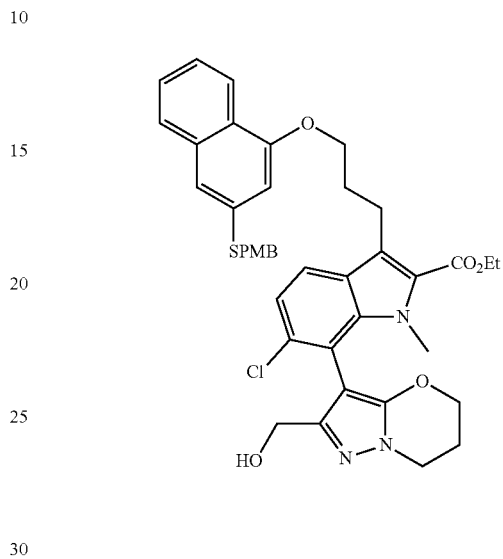

Essentially the same protocol of preparation of Intermediate E1 was used to afford the intermediate (268 mg) as a white foam. MS:726.5, 728.2 (M+H$^+$).

Example 86

Synthesis of Intermediate E7: Ethyl 6-chloro-7-(2-(hydroxymethyl)-5-(methylsulfonyl)-4,5,6,7-tetrahydropyrazolo[1,5-a]pyrazin-3-yl)-3-(3-((3-((4-methoxybenzyl)thio)naphthalen-1-yl)oxy)propyl)-1-methyl-1H-indole-2-carboxylate

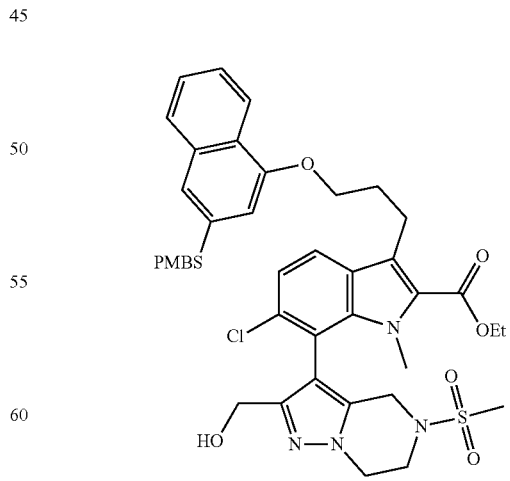

Essentially the same protocol of preparation of Intermediate E1 was used to afford the intermediate (330 mg) as a white solid. MS: 803.4 (M+H$^+$).

Example 87

Synthesis of Intermediate E8: Ethyl 6-chloro-7-(2-(hydroxymethyl)-5,6,7,8-tetrahydro-4H-pyrazolo[1,5-a]azepin-3-yl)-3-(3-((3-((4-methoxybenzyl)thio)naphthalen-1-yl)oxy)propyl)-1-methyl-1H-indole-2-carboxylate

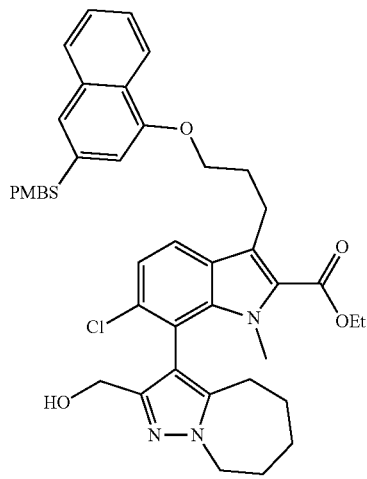

Essentially the same protocol of preparation of Intermediate E1 was used to afford the intermediate (319 mg) as a white solid. MS: 739.5 (M+H$^+$).

Example 88

Synthesis of Intermediate E9: Ethyl 6-chloro-3-(3-((6-fluoro-3-((4-methoxybenzyl)thio)naphthalen-1-yl)oxy)propyl)-7-(2-(hydroxymethyl)-5,6-dihydro-4H-pyrrolo[1,2-b]pyrazol-3-yl)-1-methyl-1H-indole-2-carboxylate

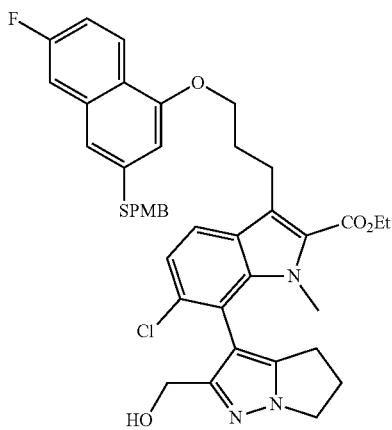

Essentially the same protocol of preparation of Intermediate E1 was used to afford the intermediate (460 mg) as a white foam. MS: 728.4, 730.8 (M+H$^+$).

Example 89

Synthesis of Intermediate E10: Ethyl 6-chloro-3-(3-((6-fluoro-3-((4-methoxybenzyl)thio)naphthalen-1-yl)oxy)propyl)-7-(2-(hydroxymethyl)-4,5,6,7-tetrahydropyrazolo[1,5-a]pyridin-3-yl)-1-methyl-1H-indole-2-carboxylate

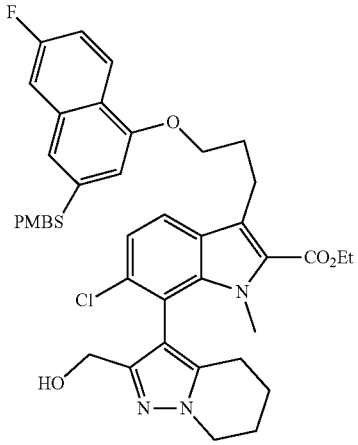

Essentially the same protocol of preparation of Intermediate E1 was used to afford the intermediate (400 mg) as a yellow oil. MS: 742.8 (M+H$^+$).

Example 90

Synthesis of Intermediate E11: ethyl 6-chloro-3-(3-((6-fluoro-3-((4-methoxybenzyl)thio)naphthalen-1-yl)oxy)propyl)-7-(2-(hydroxymethyl)-6,7-dihydro-4H-pyrazolo[5,1-c][1,4]oxazin-3-yl)-1-methyl-1H-indole-2-carboxylate

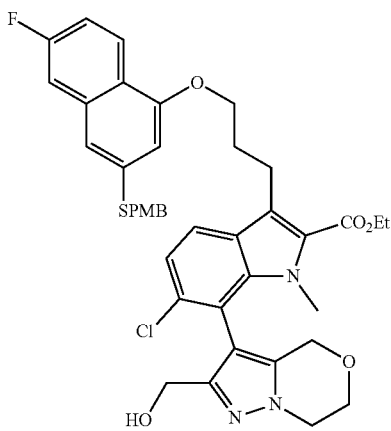

Essentially the same protocol of preparation of Intermediate E1 was used to afford the intermediate (9.4 g) as a white foam. MS: 766.6, 768.3 (M+Na$^+$).

Example 91

Synthesis of Intermediate E12: Ethyl 6-chloro-3-(3-((6-fluoro-3-((4-methoxybenzyl)thio)naphthalen-1-yl)oxy)propyl)-7-(2-(hydroxymethyl)-5,6,7,8-tetrahydro-4H-pyrazolo[1,5-a]azepin-3-yl)-1-methyl-1H-indole-2-carboxylate

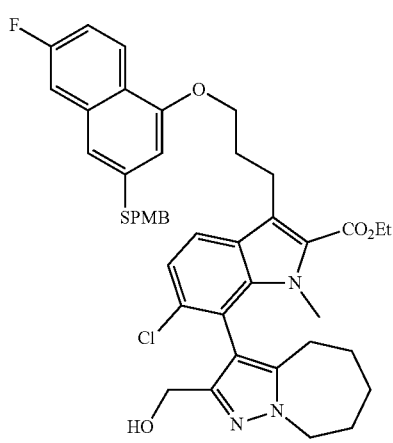

Essentially the same protocol of preparation of Intermediate E1 was used to afford the intermediate (420 mg) as a white foam. MS: 756.3 (M+H$^+$), 778.4 (M+Na$^+$)

Example 92

Synthesis of Intermediate E13: Ethyl 6-chloro-3-(3-((7-fluoro-3-((4-methoxybenzyl)thio)naphthalen-1-yl)oxy)propyl)-7-(2-(hydroxymethyl)-6,7-dihydro-4H-pyrazolo[5,1-c][1,4]oxazin-3-yl)-1-methyl-1H-indole-2-carboxylate

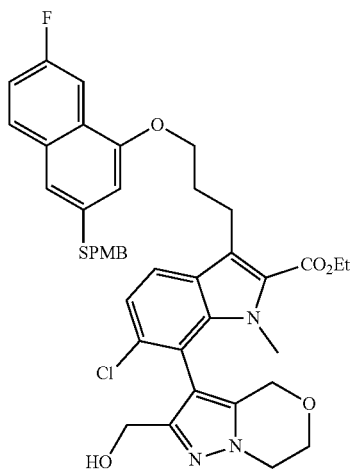

Essentially the same protocol of preparation of Intermediate E1 was used to afford the intermediate (380 mg) as a white foam. MS: 744.1 (M+H$^+$), 766.1 (M+Na$^+$).

Example 93

Synthesis of Intermediate E14: Ethyl 6-chloro-3-(3-((7-chloro-3-((4-methoxybenzyl)thio)naphthalen-1-yl)oxy)propyl)-7-(2-(hydroxymethyl)-6,7-dihydro-4H-pyrazolo[5,1-c][1,4]oxazin-3-yl)-1-methyl-1H-indole-2-carboxylate

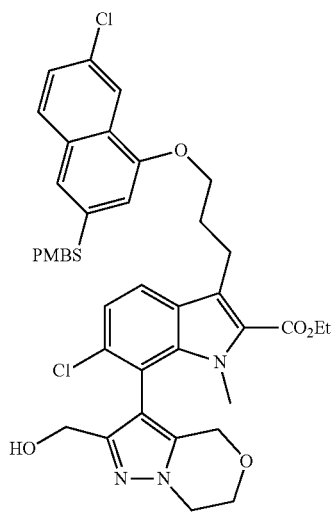

Essentially the same protocol of preparation of Intermediate E1 was used to afford the intermediate (200 mg) as a yellow foam. MS: 760.2 (M+H$^+$); 782.1 (M+Na$^+$).

Example 94

Synthesis of Intermediate E15: Ethyl 6-chloro-3-(3-((6-chloro-3-((4-methoxybenzyl)thio)naphthalen-1-yl)oxy)propyl)-7-(2-(hydroxymethyl)-6,7-dihydro-4H-pyrazolo[5,1-c][1,4]oxazin-3-yl)-1-methyl-1H-indole-2-carboxylate

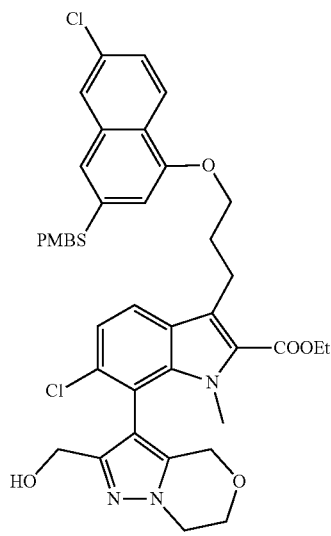

Essentially the same protocol of preparation of Intermediate E1 was used to afford the intermediate (324 mg) as a yellow oil. MS: 762.2 (M+H⁺).

Example 95

Synthesis of Intermediate E16: Ethyl 6-chloro-7-(2-(hydroxymethyl)-6,7-dihydro-4H-pyrazolo[5,1-c][1,4]oxazin-3-yl)-3-(3-(3-((4-methoxybenzyl)thio)-5-(trifluoromethyl)phenoxy)propyl)-1-methyl-1H-indole-2-carboxylate

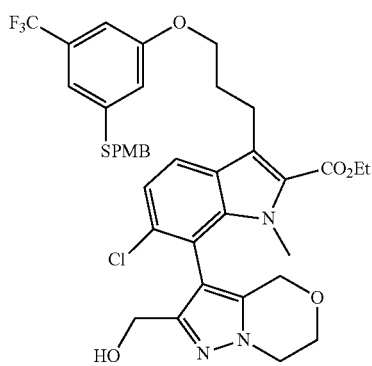

Essentially the same protocol of preparation of Intermediate E1 was used to afford the intermediate (370 mg) as a white foam. MS: 746.0 (M+H⁺).

Example 96

Synthesis of Intermediate E17: Ethyl 6-chloro-3-(3-(3-chloro-5-((4-methoxybenzyl)thio)-4-methylphenoxy)propyl)-7-(2-(hydroxymethyl)-4,5,6,7-tetrahydropyrazolo[1,5-a]pyridin-3-yl)-1-methyl-1H-indole-2-carboxylate

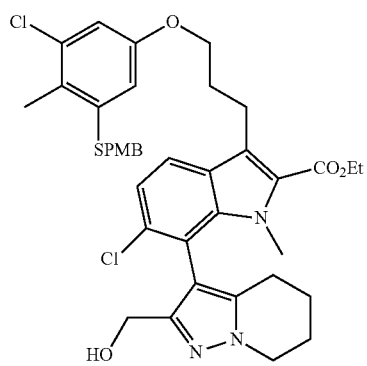

Essentially the same protocol of preparation of Intermediate E1 was used to afford the intermediate (170 mg) as a yellow solid. MS: 722.7, 724.7 (M+H⁺).

Example 97

Synthesis of Intermediate E18: Ethyl 6-chloro-7-(3-(hydroxymethyl)-1,5-dimethyl-1H-pyrazol-4-yl)-3-(3-((3-((4-methoxybenzyl)thio)naphthalen-1-yl)oxy)propyl)-1-methyl-1H-indole-2-carboxylate

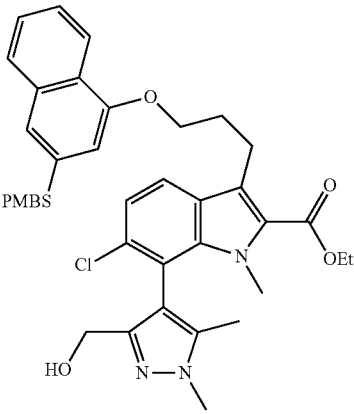

Essentially the same protocol of preparation of Intermediate E1 was used to afford the intermediate (12 g) as a light yellow foam. MS: 699.4 (M+Na⁺).

Example 98

Synthesis of Intermediate E19: Ethyl 6-chloro-3-(3-((6-fluoro-3-((4-methoxybenzyl)thio)naphthalen-1-yl)oxy)propyl)-7-(3-(hydroxymethyl)-1,5-dimethyl-1H-pyrazol-4-yl)-1-methyl-1H-indole-2-carboxylate

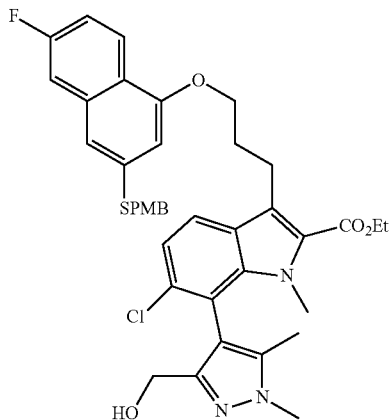

Essentially the same protocol of preparation of Intermediate E1 was used to afford the intermediate (10.1 g) as a light yellow foam. MS: 717.5, 719.6 (M+H⁺).

Example 99

Synthesis of Intermediate E20: Ethyl 6-chloro-7-(3-(difluoromethyl)-5-(hydroxymethyl)-1-methyl-1H-pyrazol-4-yl)-3-(3-((6-fluoro-3-((4-methoxybenzyl)thio)naphthalen-1-yl)oxy)propyl)-1-methyl-1H-indole-2-carboxylate

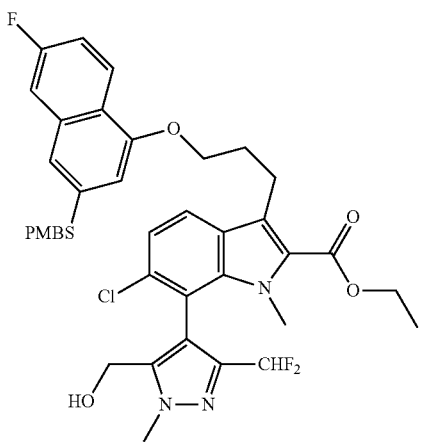

Essentially the same protocol of preparation of Intermediate E1 was used to afford the intermediate (150 mg) as a colorless oil. MS: 774.7 (M+Na$^+$).

Example 100

Synthesis of (R)-(Z)-1$^6$-chloro-1$^1$,6$^1$-dimethyl-2$^5$,2$^6$-dihydro-1$^1$H,2$^4$H,6$^1$H-10-oxa-4,8-dithia-1(7,3)-indola-2(3,2)-pyrrolo[1,2-b]pyrazola-6(3,5)-pyrazola-9(3,1)-naphthalenacyclotridecaphane-1$^2$-carboxylic acid (Cpd. No. 52)

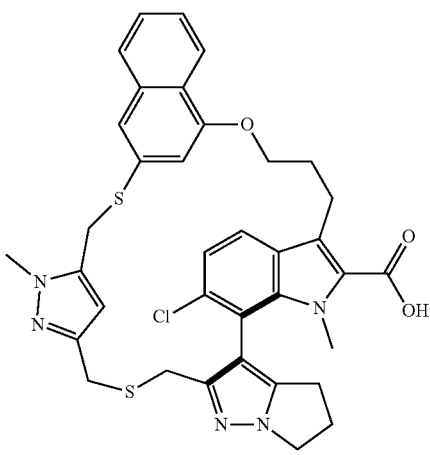

Cpd. No. 1 (850 mg) was subjected to chiral SFC resolution with a CHIRALPAK AD column to provide Cpd. No. 52 (366 mg, 99% ee) as a white solid. MS: 684.2 (M+H$^+$).

Example 101

Synthesis of (S)-(Z)-1$^6$-chloro-1$^1$,6$^1$-dimethyl-2$^5$,2$^6$-dihydro-1$^1$H,2$^4$H,6$^1$H-10-oxa-4,8-dithia-1(7,3)-indola-2(3,2)-pyrrolo[1,2-b]pyrazola-6(3,5)-pyrazola-9(3,1)-naphthalenacyclotridecaphane-1$^2$-carboxylic acid (Cpd. No. 53)

Cpd. No. 1 (850 mg) was subjected to chiral SFC resolution with a CHIRALPAK AD column to provide Cpd. No. 53 (365 mg, 98% ee) as a white solid. MS: 684.3 (M+H$^+$).

Example 102

Mcl-1 Activity

The inhibition of Mcl-1, and cell viability in NCI-H929 and OPM-2 cells of representative Compounds of the Disclosure are provided in Table 5. AZD-5991 ((Z)-1$^6$-chloro-1$^1$,2$^1$,2$^5$,6$^1$-tetramethyl-1H,2$^1$H,6$^1$H-10-oxa-4,8-dithia-1(7,3)-indola-2(4,3),6(3,5)-dipyrazola-9(3,1)-naphthalenacyclotridecaphane-1$^2$-carboxylic acid) is a known Mcl-1 inhibitor. See U.S. Pat. No. 9,840,518.

Inhibition of Mcl-1 by Fluorescence Polarization (FP) Assay.

The relative binding potency of representative Compounds of the Disclosure was determined by a fluorescence polarization (FP) assay (Long et al, *BMC Biotechnology* 13:45 (2013)). The method used a fluorescein labelled peptide (FAM-Bid) which binds to the Mcl-1 protein leading to an increased anisotropy measured in milli-polarization (mP) values using a plate reader. A 21-residue Bid BH3 peptide (residues 79-99) [Swiss-Prot: P55957] was labeled at the N-terminus with 6-carboxyfluorescein succinimidyl ester (FAM) to give FAM-Bid as a tracer in the FP competitive binding assay. Tag-free Mcl-1 protein (residues 171-323) was used in the FP assay (Mady et al, *Scientific Reports* 8: 10210-10210 (2018); Yang et al, *ACS Med. Chem. Lett.* 3:308-312 (2012)). The addition of compounds which binds competitively to the same site as the labelled peptide will result in a greater proportion of unbound peptide in the system indicated by a decreased mP value.

A 10-points serial dilution of each compound was prepared in DMSO and 5 μL solution was transferred into flat bottomed, 96-well back plate (final DMSO concentration 5%). 120 μL of Buffer (PBS, 0.01% BGG (Sigma Cat. #SRE0011), 0.01% Triton X-100), containing the Fluorescein labelled peptide (Final concentration 2 nM) and Mcl-1 protein (final concentration 20 nM) was then added. Assay plates were incubated 30 mins at room temperature with gentle shaking before FP was measured on a Biotek Synergy 1MF reader (Ex. 485 nm, Em. 528 nm, Cut off 510 nm) and mP calculated. The binding of increasing doses of test compounds was expressed as a percentage reduction in mP compared to a window established between 5% DMSO only and 100% inhibition controls (no Mcl-1 protein). 10-points dose response curves were plotted with GraphPad software using Sigmoidal Dose-Response Model and the IC50 values were determined by nonlinear regression fitting of the competition curves.

Cell Viability Assay (NCI-H929 Cells)

NCI-H929 cells were obtained from American Type Culture Collection (ATCC). Cells were maintained in the recommended culture medium (RPMI 1640) with 10% FBS and 0.05 mM BME at 37° C. and an atmosphere of 5% $CO_2$.

The effect of Compounds on cell viability was determined using Cell Counting Kit-8 (CCK-8) assay according to the manufacturer's instructions. 95 μL of NCI-H929 cell suspension (20000 cells/well) in culture medium were seeded into 96-well plates and cultured 4 hrs. Each tested compound was serially diluted in in DMSO, then 5 μL of the compound or DMSO was diluted in 95 μL medium once more. At last, 5 μL of the compound dilution was added to the corresponding well of the cell plate. After the addition of the tested compound, the cells were incubated at 37° C. in an atmosphere of 5% $CO_2$ for 24 hrs. At the end, 10 μL of CCK-8 solution was added to each well of the plate and incubated for 1-4 hours. The plates were read at 450 nm on the microplate reader (BioTek Synergy 1MF). The readings were normalized to the vehicle cells, and the $IC_{50}$ was calculated by nonlinear regression analysis using GraphPad Prism 6 software.

Cell Viability Assay (OPM-2 Cells)

OPM-2 cells were obtained from Deutsche Sammlung von Mikroorganismen und Zellkulturen GmbH (DSMZ). Cells were maintained in the recommended culture medium with 10% FBS at 37° C. and an atmosphere of 5% $CO_2$.

The effect of representative Compounds of the Disclosure on cell viability was determined using Cell Counting Kit-8 (CCK-8) assay (Shanghai Life iLab Bio Technology) according to the manufacturer's instructions. Each tested compound was serially diluted in culture medium, 100 μL of the compound dilution was added into 96-well plates. 100 μL of an OPM-2 cell suspension (20000 cells/well) in culture medium were seeded into the corresponding well of the plate and the cells were incubated at 37° C. in an atmosphere of 5% $CO_2$ for 24 hours. In the next day, 20 μL of CCK-8 solution was added to each well of the plate and incubated for 4 hours.

The plates were read at 450 nm on the microplate spectrophotometer (SpectraMax plus 384, Molecular devices). The readings were normalized to the vehicle cells, and the $IC_{50}$ was calculated by nonlinear regression analysis using GraphPad Prism 6 software.

TABLE 5

| Cpd. No. | FP-Binding (nM) | OPM2 (WST, 5% FBS, nM) | H929 (WST, 5% FBS, nM) |
| --- | --- | --- | --- |
| 1 | 15 | 437 | 123 |
| 2 | 14 | 1141 | 287 |
| 3 | 8.7 | 6581 | 5111 |
| 4 | 19.1 | 5300 | N.A |
| 5 | 11.3 | 973 | 960 |
| 6 | 15 | 1351 | 234 |
| 7 | 150 | 774 | 1130 |
| 8 | 10.2 | >10000 | 2945 |
| 9 | 13 | 1172 | 411 |
| 10 | 10.5 | 8812 | 1971 |
| 11 | 10.6 | >10000 | 3536 |
| 12 | 10.9 | 532 | 81 |
| 13 | 14.6 | >10000 | 4296 |
| 16 | 20.7 | 2399 | 359.7 |
| 17 | 15 | 142 | 43 |
| 18 | 19 | 3488 | 1620 |
| 19 | 16 | 384 | 249.8 |
| 20 | 15.2 | 174 | 49 |
| 21 | 15.8 | 291 | 116 |
| 22 | 15.9 | 1149 | 225 |
| 23 | 10 | 195 | 100 |
| 24 | 14.3 | 4862 | 1640 |
| 25 | 14.9 | 9047 | 4971 |
| 26 | 30.9 | 133 | 44 |
| 27 | 24.9 | 153 | 51 |
| 28 | 15.9 | 184 | 55 |
| 29 | 14.9 | 348 | 157.5 |
| 30 | 14.2 | 255 | 195.9 |
| 31 | 14 | 125 | 63 |
| 32 | 14.3 | 145 | 58 |
| 33 | 12 | 965 | 361 |
| 35 | 16 | 763 | 215 |
| 36 | 19 | 317 | 71 |
| 37 | 38 | 1046 | 535 |
| 38 | 85 | 5875 | 5993 |
| 39 | 1500 | 7773 | 5083 |
| 40 | 5.5 | 48 | 23 |
| 41 | 12 | 327 | 366 |
| 42 | 17 | 357 | 261 |
| 43 | 12 | 451 | 190 |
| 44 | 15 | 506 | 156 |
| 45 | 10 | 44 | 25 |
| 46 | 12 | 49 | 61 |
| 47 | 1800 | 5031 | 4669 |
| 48 | 5.8 | 47 | 23 |
| 49 | 21 | 167 | 55 |
| 50 | 20 | 388 | 66 |
| 51 | 19 | 152 | 110 |
| 52 | n.d. | 353 | 63 |
| 53 | n.d. | 5718 | 4400 |
| AZD5991 | 7 | 148 | 47 |

Example 103

Kinetic Solubility Assay

Representative Compounds of the Disclosure were tested in a solubility assay with pH 6.5 PBS buffer. PBS buffer was prepared by dissolving 4.86 g of potassium dihydrogen phosphate and 5.09 g of disodium hydrogen phosphate dodecahydrate in 1 L of ultrapure water to have final pH value of 6.5. In the solubility assay, 0.5 mg of test sample was dissolved in 1 mL of methanol and the stock solution was transferred into 2 mL EP tube, and evaporated at 50° C. for 3 h. To the tube was added 1 mL of PBS buffer and the mixture was stirred and shaken for 1-2 h. The solution was allowed to stand overnight and then filtered before HPLC analysis. Another 1.5 mg of the sample was dissolved in 3 mL of methanol to prepare a calibration curve with a series of concentration range of 5-500 μM. The solubility of each sample was determined by the measured peak area in HPLC. The results are shown in Table 6.

TABLE 6

| Cpd. No. | Solubility (pH 6.5, µg/mL) |
|---|---|
| 5 | 2 |
| 7 | 1 |
| 11 | <1 |
| 15 | <1 |
| 16 | <1 |
| 18 | <1 |
| 21 | 3 |
| 24 | <1 |
| 26 | 1 |
| 27 | 52 |
| 30 | <1 |
| 36 | 16 |
| 38 | 127 |
| 39 | <1 |
| 40 | 74 |
| 44 | >400 |
| 45 | >400 |
| 47 | <1 |
| 48 | 3 |
| 49 | 28 |
| AZD5991 | <1 |

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof.

All patents, patent applications, and publications cited herein are fully incorporated by reference herein in their entirety.

What is claimed is:

1. A compound of Formula III:

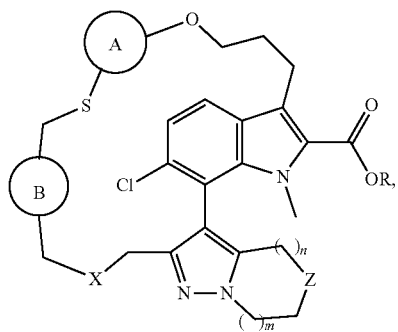

wherein:

R is selected from the group consisting of hydrogen and $C_1$-$C_6$ alkyl;

X is selected from the group consisting of —O—, —S—, —S(═O)—, —S(═O)$_2$—, and —N($R^3$)—;

$R^3$ is selected from the group consisting of hydrogen, $C_1$-$C_4$ alkyl, $C_3$-$C_6$ cycloalkyl, hydroxyalkyl, —C(═O)$R^4$, and —S(═O)$_2R^5$;

$R^4$ is selected from the group consisting of $C_1$-$C_4$ alkyl, $C_1$-$C_4$ haloalkyl, optionally substituted $C_3$-$C_6$ cycloalkyl, optionally substituted 4- to 8-membered heterocyclo, optionally substituted $C_6$-$C_{10}$ aryl, optionally substituted 5- to 10-membered heteroaryl, and ($C_6$-$C_{10}$ aryl)$C_1$-$C_4$ alkyl;

$R^5$ is selected from the group consisting of $C_1$-$C_4$ alkyl, $C_1$-$C_4$ haloalkyl, optionally substituted $C_3$-$C_6$ cycloalkyl, optionally substituted 4- to 8-membered heterocyclo, optionally substituted $C_6$-$C_{10}$ aryl, optionally substituted 5- to 10-membered heteroaryl, and ($C_6$-$C_{10}$ aryl)$C_1$-$C_4$ alkyl;

Ⓐ is selected from the group consisting of:

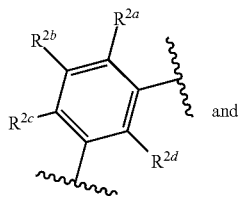

A-1

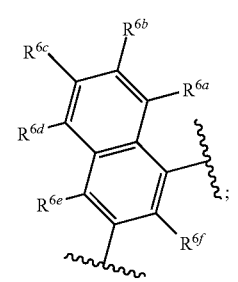

A-2

$R^{2a}$, $R^{2b}$, $R^{2c}$, and $R^{2d}$ are each independently selected from the group consisting of hydrogen, halo, cyano, $C_1$-$C_4$ alkyl, $C_1$-$C_4$ haloalkyl, and $C_1$-$C_4$ alkoxy;

$R^{6a}$, $R^{6b}$, $R^{6c}$, $R^{6d}$, $R^{6e}$, and $R^{6f}$ are each independently selected from the group consisting of hydrogen, halo, cyano, $C_1$-$C_4$ alkyl, $C_1$-$C_4$ haloalkyl, and $C_1$-$C_4$ alkoxy;

Ⓑ is selected from the group consisting of arylenyl and heteroarylenyl;

wherein:

m is 0, 1, or 2;

n is or 1;

with the proviso that when m is 0, Z is —$CR^{13a}R^{13b}$—;

Z is selected from the group consisting of —$CR^{13a}R^{13b}$—, —O—, —S—, S(═O)—, S(═O)$_2$—, and —N($R^{10}$)—;

$R^{10}$ is selected from the group consisting of hydrogen, $C_1$-$C_4$ alkyl, —C(═O)$_2R^{11}$, and —S(═O)$_2R^{12}$;

$R^{11}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl;

$R^{12}$ is selected from the group consisting of $C_1$-$C_4$ alkyl, optionally substituted $C_3$-$C_6$ cycloalkyl, optionally substituted $C_6$-$C_{10}$ aryl, and optionally substituted 5- to 10-membered heteroaryl; and $R^{13a}$ and $R^{13b}$ are independently selected from the group consisting of hydrogen and $C_1$-$C_4$ alkyl, or a pharmaceutically acceptable salt thereof.

2. The compound of claim 1 of Formula III-S or III-R:
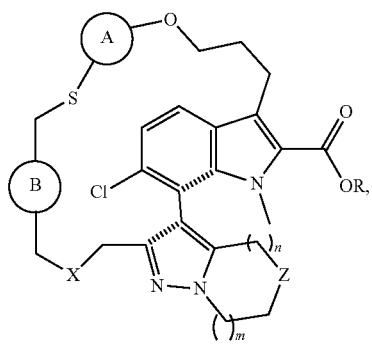
III-S
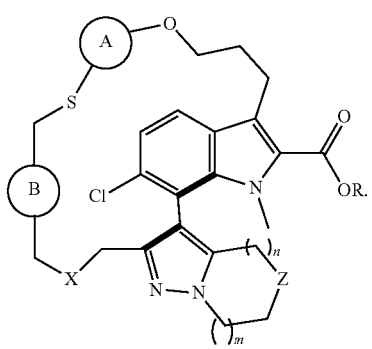
III-R
or a pharmaceutically acceptable salt thereof.
3. The compound of claim 1, wherein Z is —O— or —CH$_2$—, or a pharmaceutically acceptable salt thereof.
4. The compound of claim 1 selected from the group consisting of:
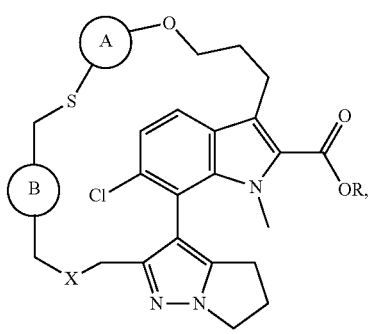
Formula IV
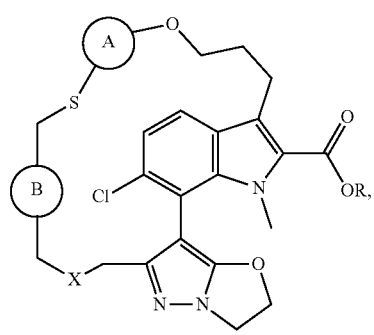
Formula V
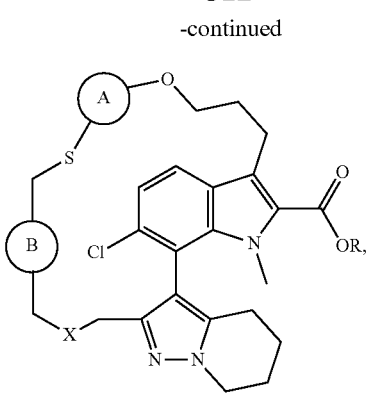
Formula VI
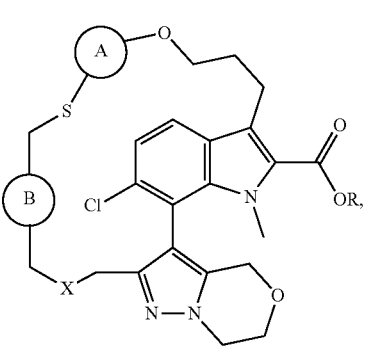
Formula VII
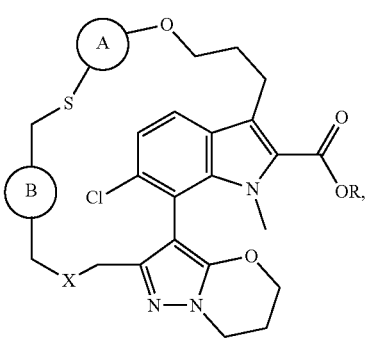
Formula VIII
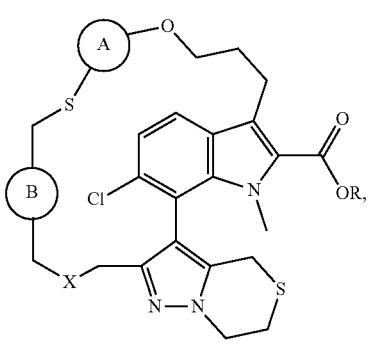
Formula IX Formula X Formula XI or a pharmaceutically acceptable salt thereof.

5. The compound of claim 4 selected from the group consisting of:

Formula IV-S

Formula V-S

Formula VI-S

Formula VII-S

Formula VIII-S

Formula IX-S

Formula X-S
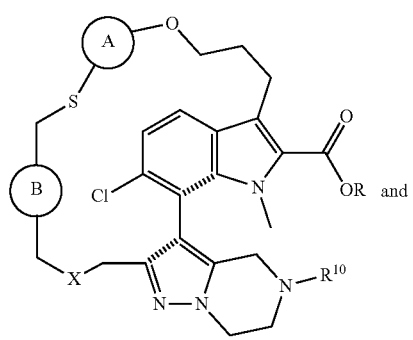
Formula XI-S
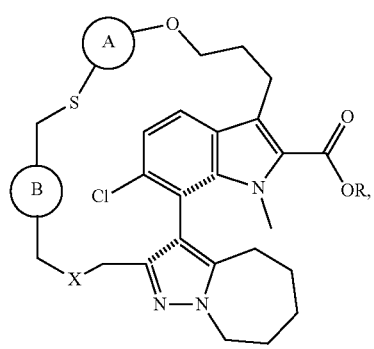
or a pharmaceutically acceptable salt thereof.
6. The compound of claim 4 selected from the group consisting of:
Formula IV-R
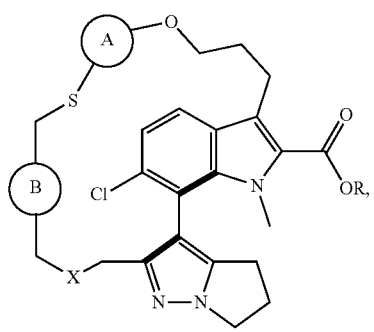
Formula V-R
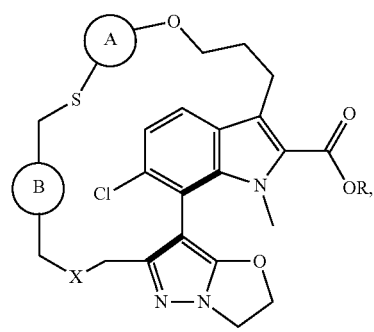
Formula VI-R
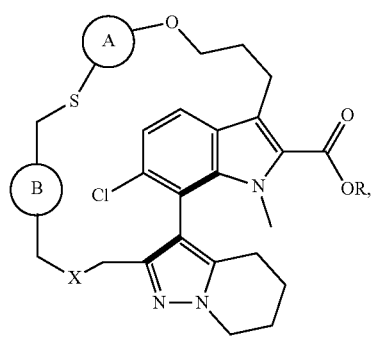
Formula VII-R
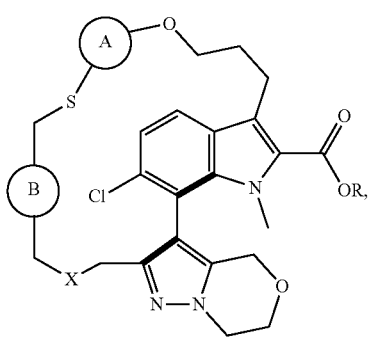
Formula VIII-R
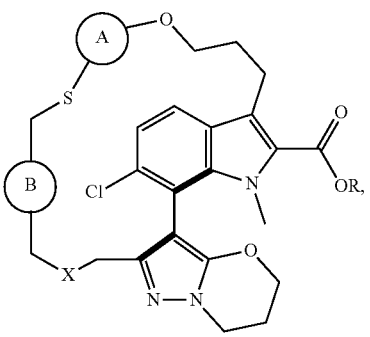
Formula IX-R
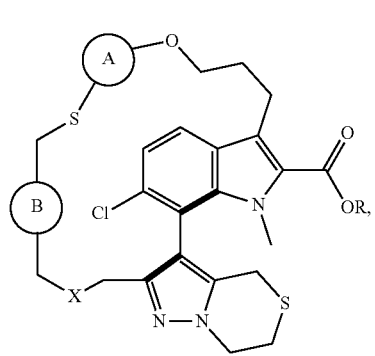

-continued

Formula X-R

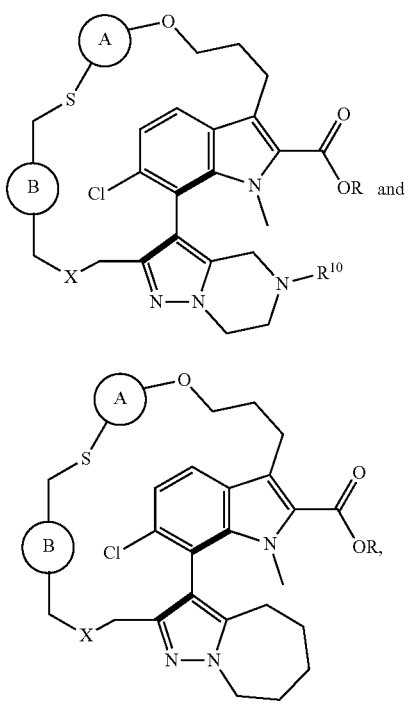

Formula XI-R or a pharmaceutically acceptable salt thereof.

7. The compound of claim 1, wherein Ⓐ is A-1, wherein:

$R^{2a}$, $R^{2b}$, and $R^{2c}$ are each independently selected from the group consisting of hydrogen, halo, and $C_1$-$C_4$ alkyl; and $R^{2d}$ is hydrogen, or a pharmaceutically acceptable salt thereof.

8. The compound of claim 1, wherein Ⓐ is A-2, wherein the 1-position of A-2 is attached to the oxygen atom and the 3-position of A-2 is attached to the sulfur atom, or a pharmaceutically acceptable salt thereof.

9. The compound of claim 8, wherein:

$R^{6a}$, $R^{6b}$, $R^{6c}$, $R^{6d}$ and $R^{6e}$ are each independently selected from the group consisting of hydrogen, halo, and $C_1$-$C_4$ alkyl; and $R^{6f}$ is hydrogen, or a pharmaceutically acceptable salt thereof.

10. The compound of claim 1, wherein:

Ⓑ is selected from the group consisting of:

B-1

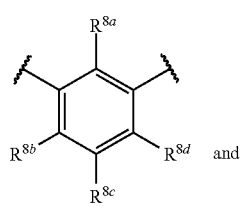

B-2

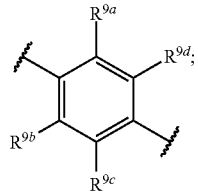

$R^{8a}$, $R^{8b}$, $R^{8c}$, and $R^{8d}$ are each independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl; and $R^{9a}$, $R^{9b}$, $R^{9c}$, and $R^{9d}$ are each independently selected from the group consisting of hydrogen, halo, cyano, $C_1$-$C_4$ alkyl, $C_1$-$C_4$ haloalkyl, $C_1$-$C_4$ alkoxy, and $C_3$-$C_6$ cycloalkyl, or a pharmaceutically acceptable salt thereof.

11. The compound of claim 10, wherein $R^{8a}$, $R^{8b}$, $R^{8c}$, and $R^{8d}$ are each independently selected from the group consisting of hydrogen, halo, and $C_1$-$C_4$ alkyl, or a pharmaceutically acceptable salt thereof.

12. The compound of claim 10, wherein $R^{9a}$, $R^{9b}$, $R^{9c}$, and $R^{9d}$ are each independently selected from the group consisting of hydrogen, halo, and $C_1$-$C_4$ alkyl, or a pharmaceutically acceptable salt thereof.

13. The compound of claim 1, wherein:

Ⓑ is selected from the group consisting of:

B-3

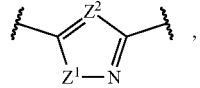

B-4

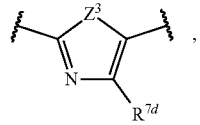

B-5

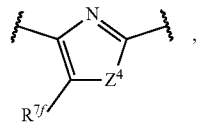

B-6

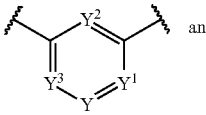

and

B-7

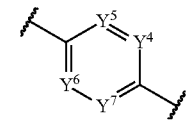

$Z^1$ is selected from the group consisting of —O—, —S—, and —N($R^{7a}$)—;

$R^{7a}$ is selected from the group consisting of hydrogen, $C_1$-$C_4$ alkyl, and $C_3$-$C_6$ cycloalkyl;

$Z^2$ is selected from the group consisting of —C($R^{7b}$)= and —N=;

$R^{7b}$ is selected from the group consisting of hydrogen, halo, $C_1$-$C_4$ alkyl, and $C_3$-$C_6$ cycloalkyl;

$Z^3$ is selected from the group consisting of —O—, —S—, and —N($R^{7c}$)—;

$R^{7c}$ is selected from the group consisting of hydrogen, $C_1$-$C_4$ alkyl, and $C_3$-$C_6$ cycloalkyl;

$R^{7d}$ is selected from the group consisting of hydrogen, halo, $C_1$-$C_4$ alkyl, and $C_3$-$C_6$ cycloalkyl;

$Z^4$ is selected from the group consisting of —O—, —S—, and —N($R^{7e}$)—;

$R^{7e}$ is selected from the group consisting of hydrogen, $C_1$-$C_4$ alkyl, and $C_3$-$C_6$ cycloalkyl;

$R^{7f}$ is selected from the group consisting of hydrogen, halo, $C_1$-$C_4$ alkyl, and $C_3$-$C_6$ cycloalkyl;

Y is selected from the group consisting of —C($R^{10a}$)= and —N=;

$Y^1$ is selected from the group consisting of —C($R^{10b}$)= and —N=;

$Y^2$ is selected from the group consisting of —C($R^{10c}$)= and —N=;

$Y^3$ is selected from the group consisting of —C($R^{10d}$)= and —N=;

with proviso that at least one of Y, $Y^1$, $Y^2$, and $Y^3$ is —N=;

$R^{10a}$, $R^{10b}$, $R^{10c}$, and $R^{10d}$ are each independently selected from the group consisting of hydrogen, halo, cyano, $C_1$-$C_4$ alkyl, $C_1$-$C_4$ haloalkyl, and $C_1$-$C_4$ alkoxy;

$Y^4$ is selected from the group consisting of —C($R^{11a}$)= and —N=;

$Y^5$ is selected from the group consisting of —C($R^{11b}$)= and —N=;

$Y^6$ is selected from the group consisting of —C($R^{11c}$)= and —N=;

$Y^7$ is selected from the group consisting of —C($R^{11d}$)= and —N=;

with proviso that at least one of $Y^4$, $Y^5$, $Y^6$, and $Y^7$ is —N=;

$R^{11a}$, $R^{11b}$, $R^{11c}$, and $R^{11d}$ are each independently selected from the group consisting of hydrogen, halo, cyano, $C_1$-$C_4$ alkyl, $C_1$-$C_4$ haloalkyl, and $C_1$-$C_4$ alkoxy, or a pharmaceutically acceptable salt thereof.

14. The compound of claim 13, wherein Ⓑ is B-3, wherein:

$Z^1$ is selected from the group consisting of —O—, —S—, —N(H)—, and —N($CH_3$)—; and $Z^2$ is selected from the group consisting of —C(H)=, —C($CH_3$)=, and —N=, or a pharmaceutically acceptable salt thereof.

15. The compound of claim 1, wherein Ⓑ is selected from the group consisting of:

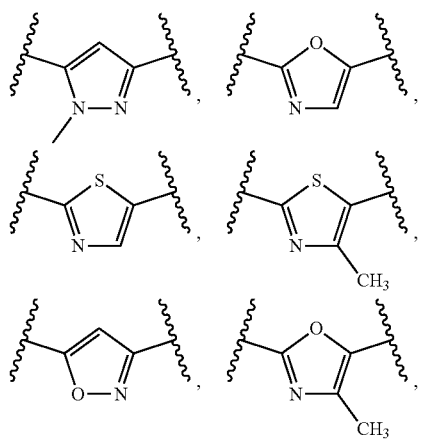

-continued

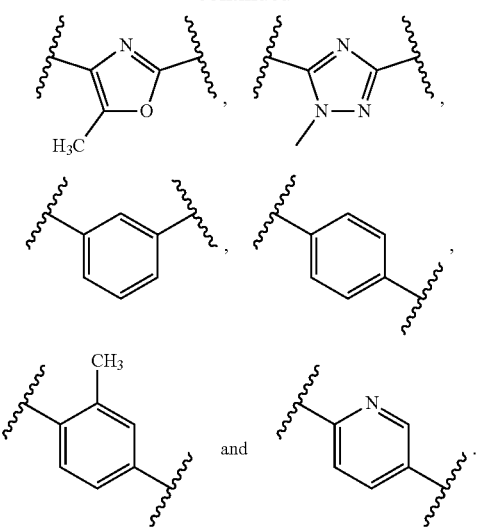

or a pharmaceutically acceptable salt thereof.

16. The compound of claim 1, wherein X is —N($R^3$)—, wherein $R^3$ is selected from the group consisting of —C(=O)$R^4$ and —S(=O)$_2R^5$, or a pharmaceutically acceptable salt thereof.

17. The compound of claim 1, wherein R is hydrogen, or a pharmaceutically acceptable salt thereof.

18. A compound selected from the group consisting of

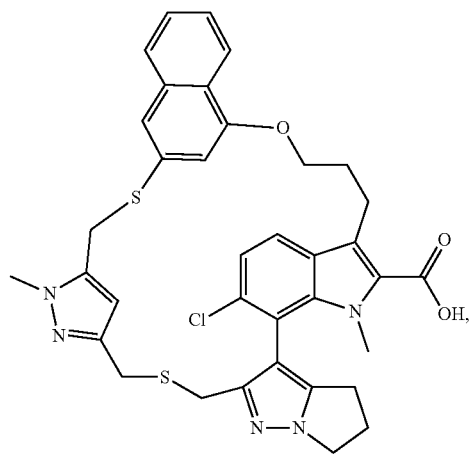

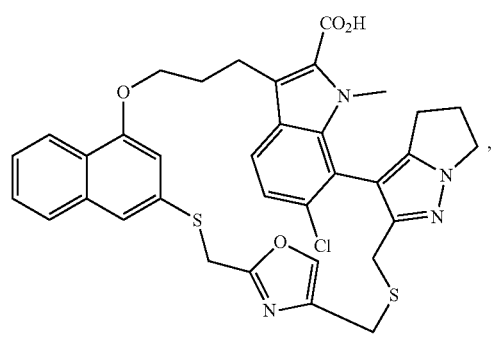

321
-continued
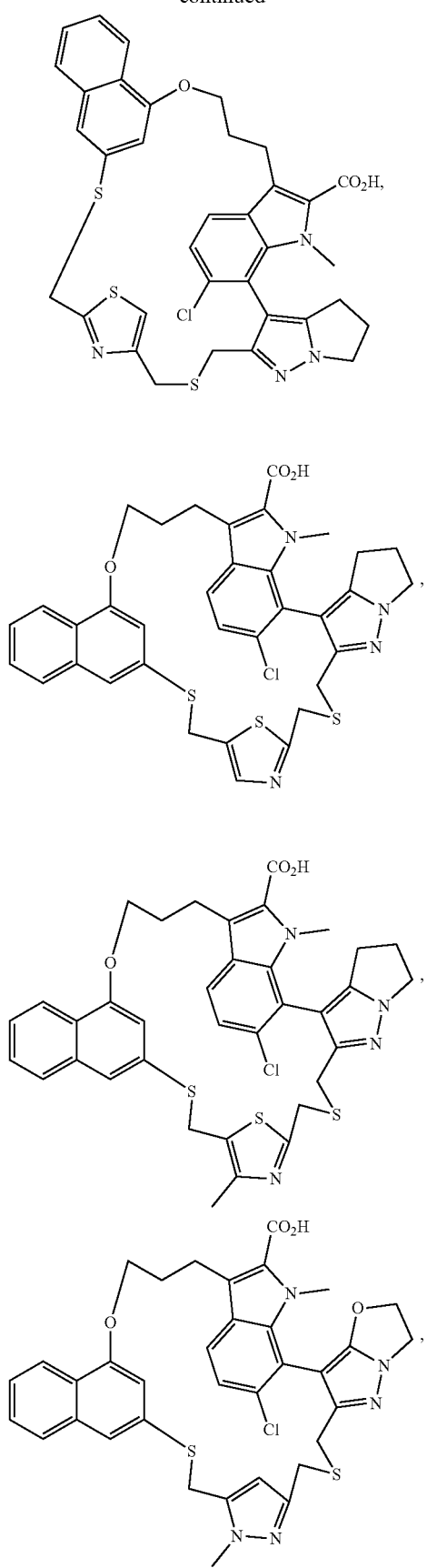
322
-continued
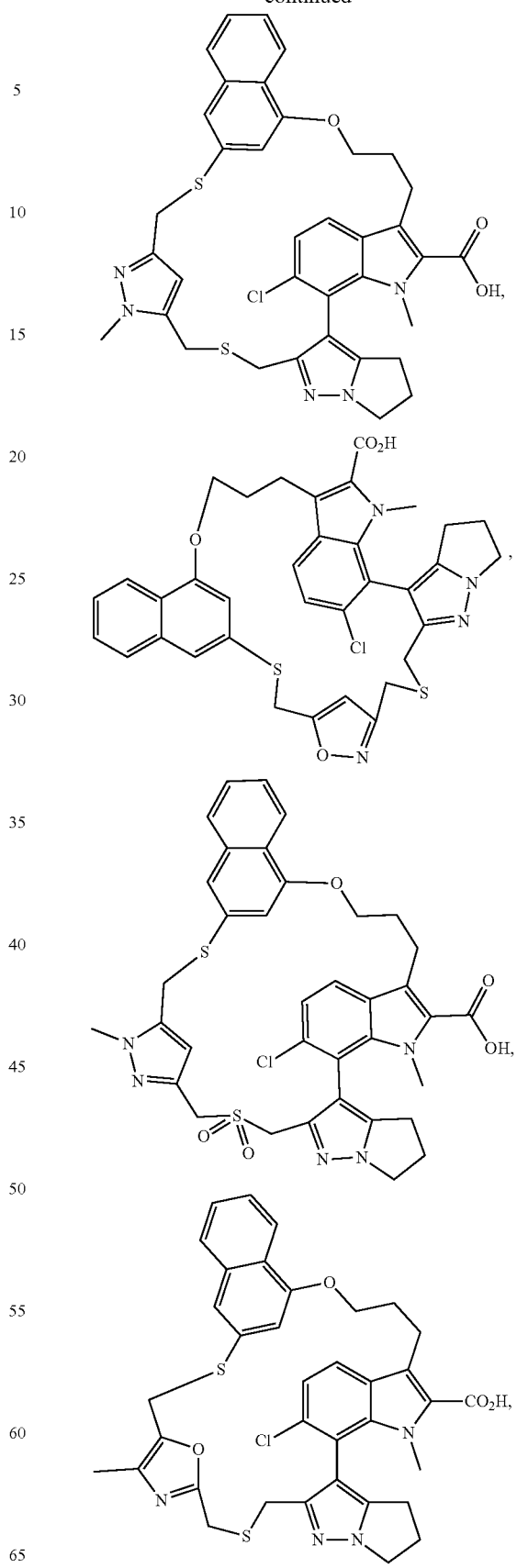

323
-continued
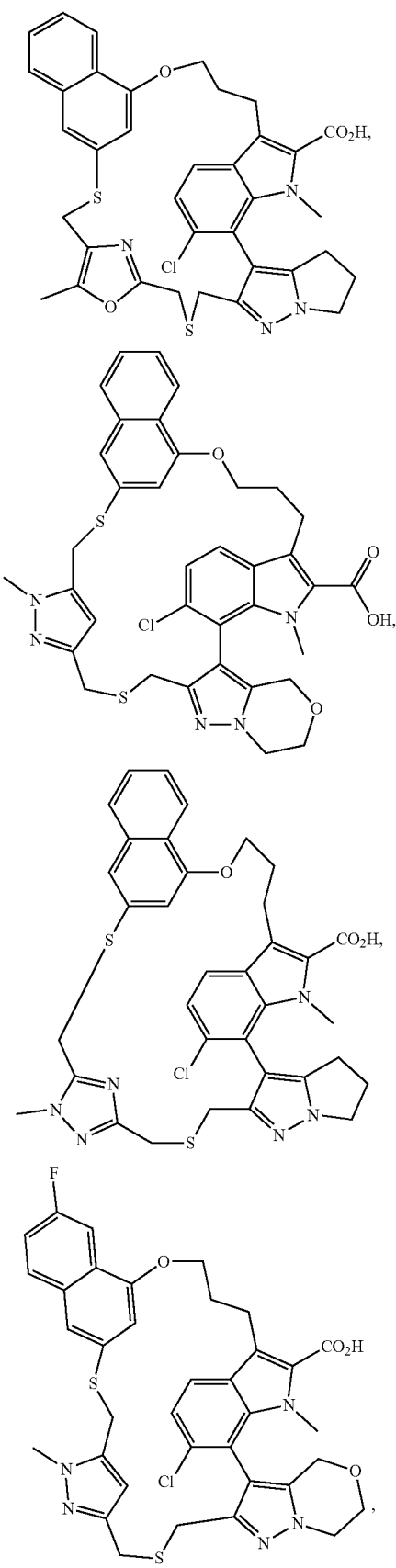
324
-continued
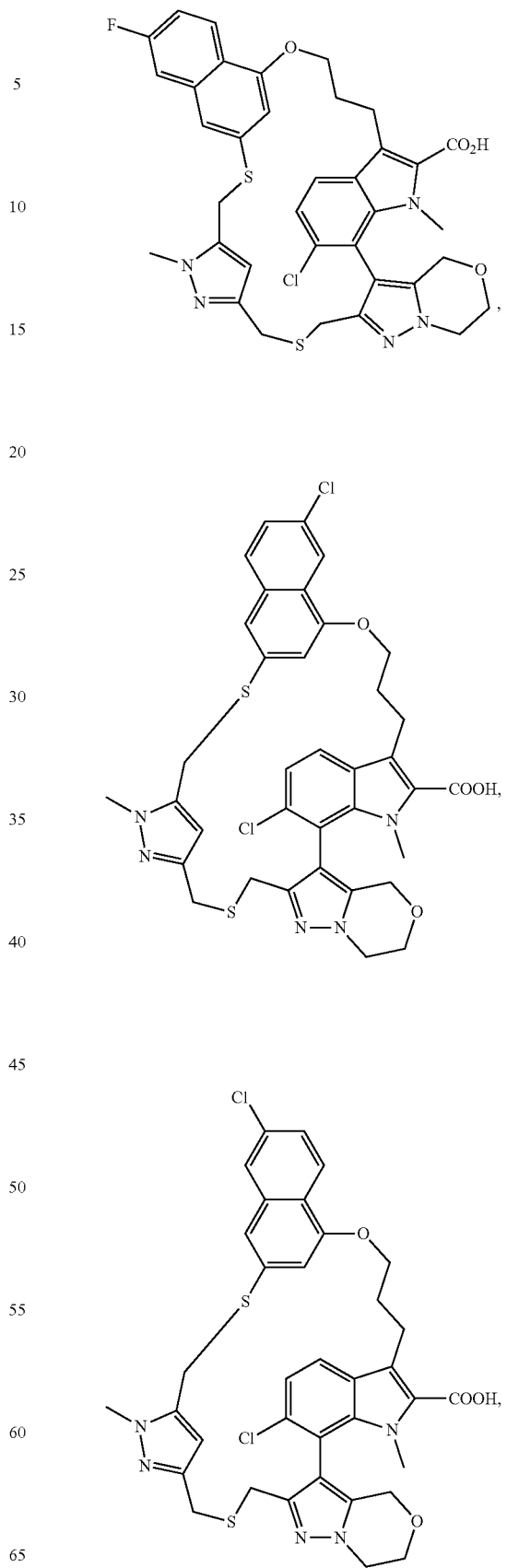

325
-continued
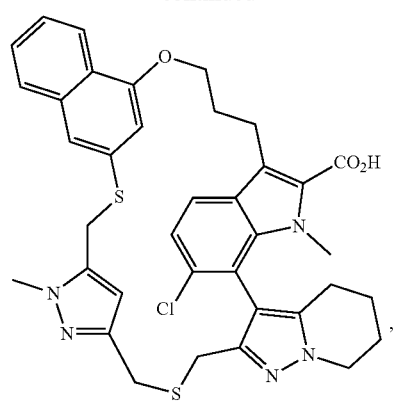
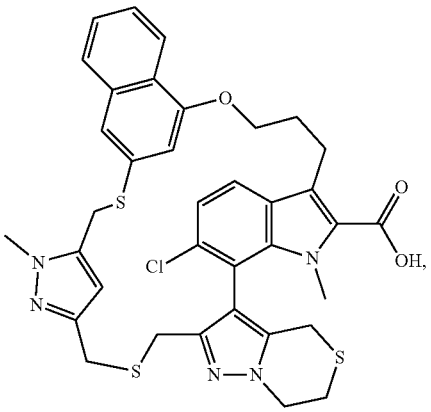
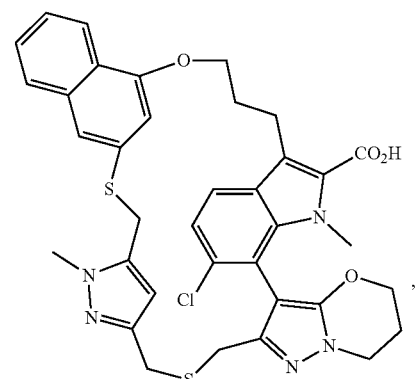
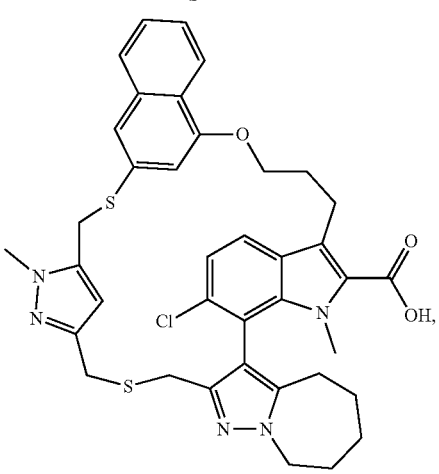
326
-continued
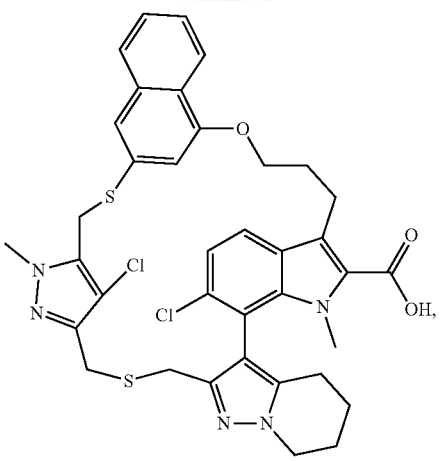
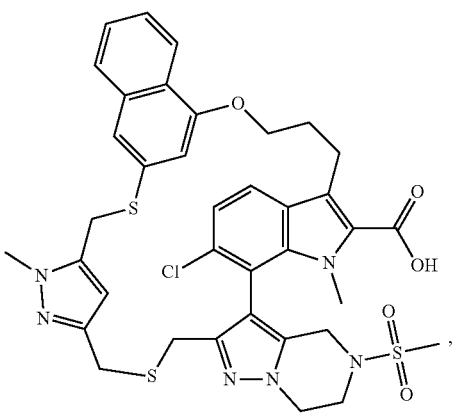
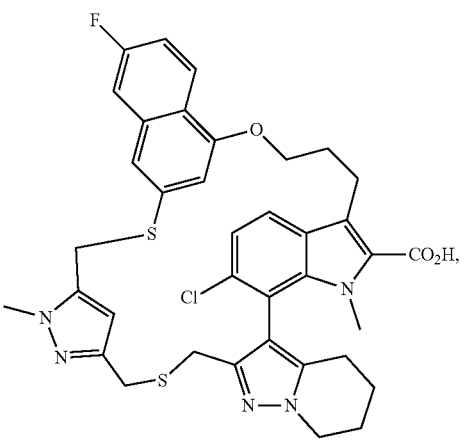
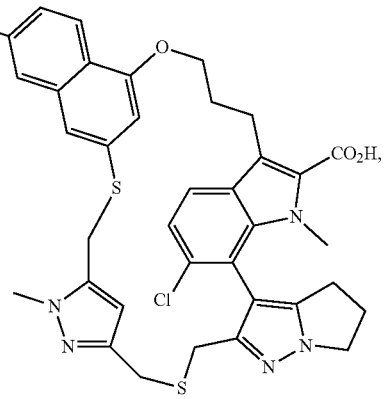

327
-continued
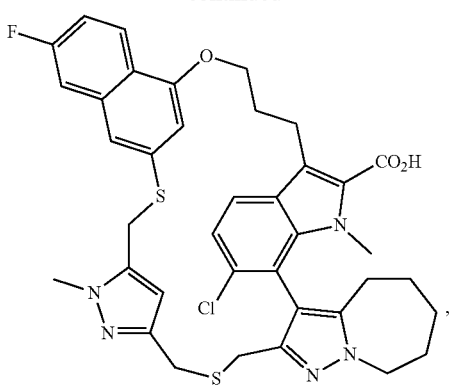
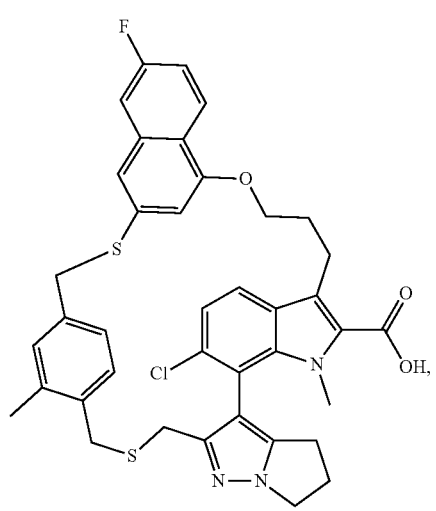
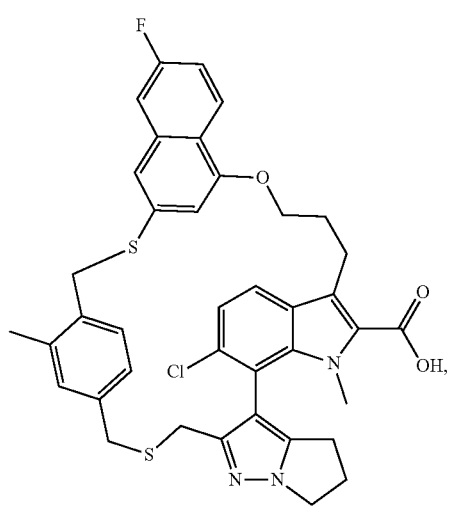
328
-continued
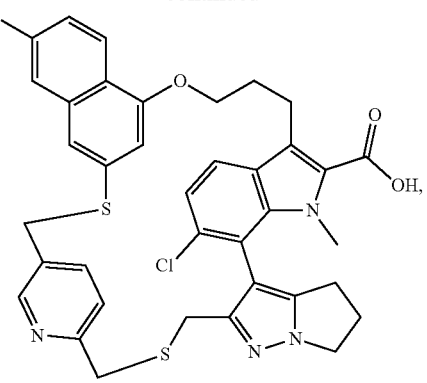
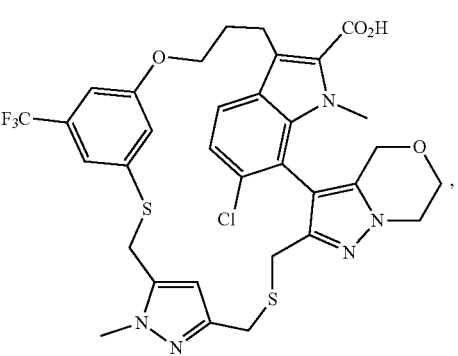

329
-continued
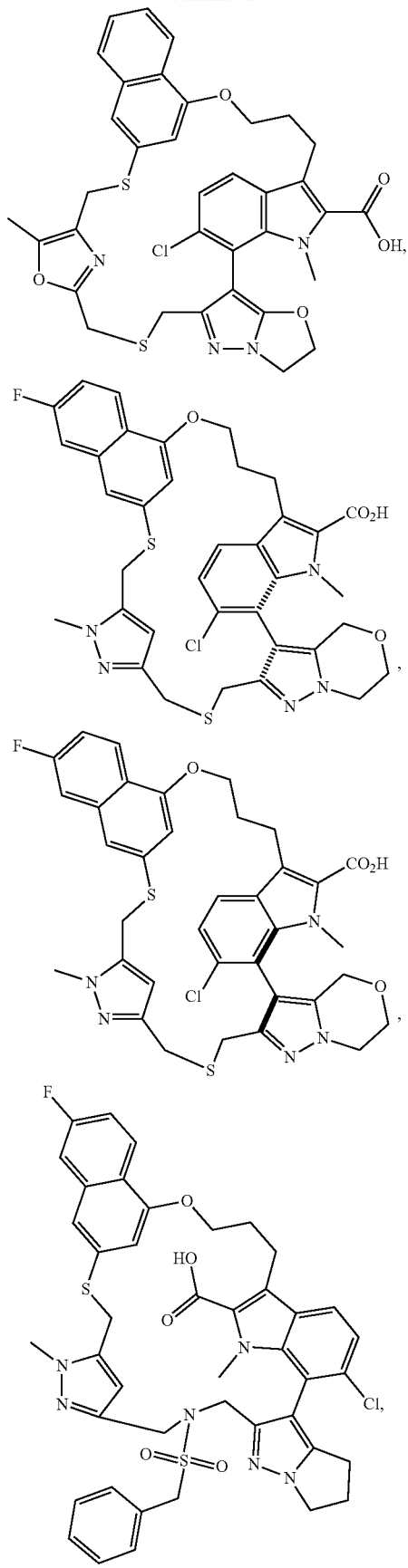
330
-continued
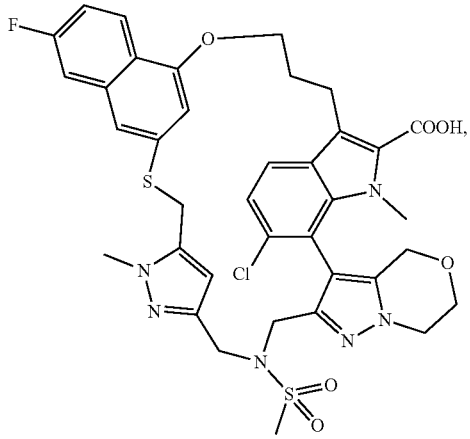
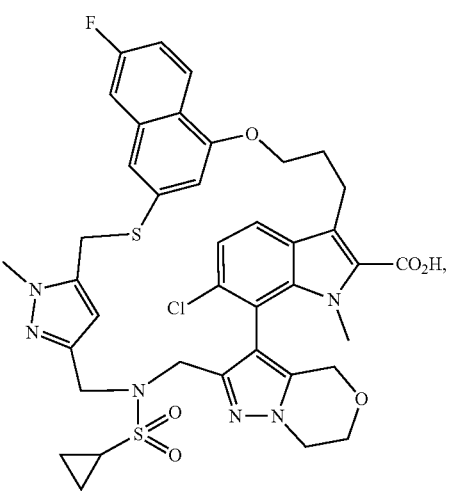
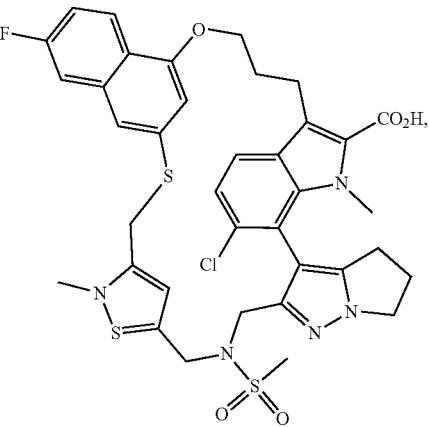

331
-continued

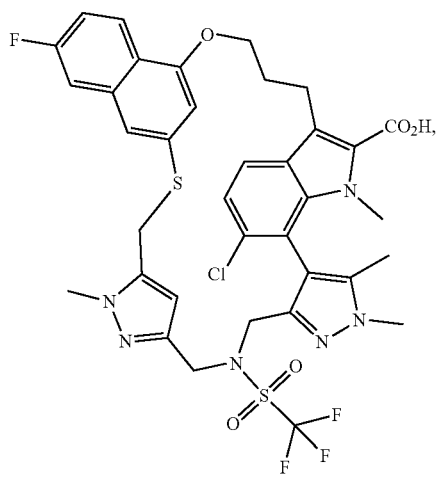

332
-continued

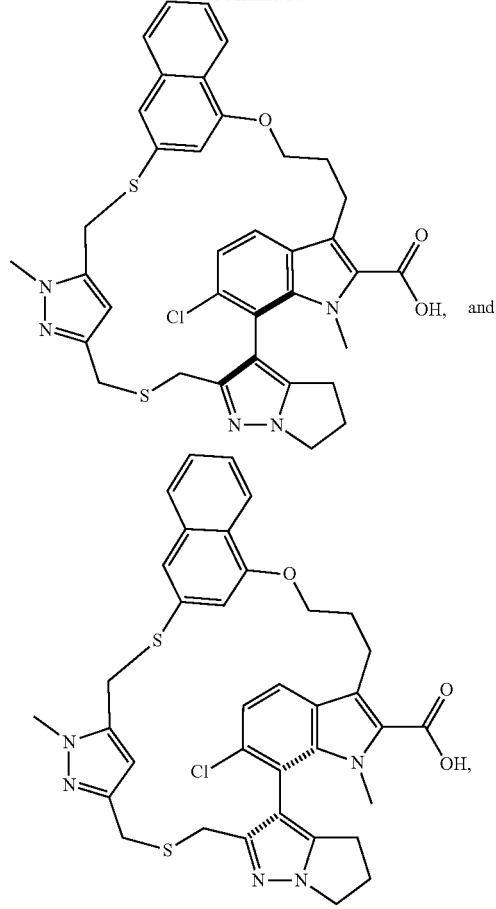

or a pharmaceutically acceptable salt thereof.

19. A pharmaceutical composition comprising the compound of claim 1, or a pharmaceutically acceptable salt thereof, and a pharmaceutically acceptable carrier.

20. A method of treating multiple myeloma, myeloid leukemia, or non-small cell lung cancer in a patient comprising administering to the patient in need thereof a therapeutically effective amount of the compound of claim 1, or a pharmaceutically acceptable salt thereof, wherein the patient has cancer, a chronic autoimmune disorder, an inflammatory condition, a proliferative disorder, sepsis, or a viral infection.

* * * * *